United States Patent
Cooper et al.

(10) Patent No.: US 11,333,672 B2
(45) Date of Patent: May 17, 2022

(54) PREECLAMPSIA BIOMARKERS AND RELATED SYSTEMS AND METHODS

(71) Applicant: PROGENITY, INC., San Diego, CA (US)

(72) Inventors: Matthew Cooper, Palo Alto, CA (US); Sharat Singh, Rancho Santa Fe, CA (US); Karen A. F. Copeland, Steamboat Springs, CO (US); Lyndal Hesterberg, Loveland, CO (US); Amin R. Mazloom, Del Mar, CA (US); Mohammad Abbasi, San Diego, CA (US); Richard Giulio Del Mastro, Norfolk, MA (US)

(73) Assignee: PROGENITY, INC., San Diego, CA (US)

( * ) Notice: Subject to any disclaimer, the term of this patent is extended or adjusted under 35 U.S.C. 154(b) by 0 days.

(21) Appl. No.: 17/234,574

(22) Filed: Apr. 19, 2021

(65) Prior Publication Data

US 2021/0293824 A1 Sep. 23, 2021

Related U.S. Application Data

(63) Continuation of application No. 16/646,552, filed as application No. PCT/US2018/050893 on Sep. 13, 2018.

(60) Provisional application No. 62/558,184, filed on Sep. 13, 2017.

(51) Int. Cl.
| | |
|---|---|
| *G01N 33/68* | (2006.01) |
| *G16B 25/10* | (2019.01) |
| *A61K 31/138* | (2006.01) |
| *A61K 31/166* | (2006.01) |
| *A61K 31/198* | (2006.01) |
| *A61K 31/277* | (2006.01) |
| *A61K 31/4168* | (2006.01) |
| *A61K 31/4422* | (2006.01) |
| *A61K 31/502* | (2006.01) |
| *A61K 31/517* | (2006.01) |
| *A61K 31/549* | (2006.01) |
| *G01N 33/543* | (2006.01) |

(52) U.S. Cl.
CPC ......... *G01N 33/689* (2013.01); *A61K 31/138* (2013.01); *A61K 31/166* (2013.01); *A61K 31/198* (2013.01); *A61K 31/277* (2013.01); *A61K 31/4168* (2013.01); *A61K 31/4422* (2013.01); *A61K 31/502* (2013.01); *A61K 31/517* (2013.01); *A61K 31/549* (2013.01); *G01N 33/54366* (2013.01); *G16B 25/10* (2019.02); *G01N 2333/471* (2013.01); *G01N 2333/4753* (2013.01); *G01N 2333/50* (2013.01); *G01N 2333/515* (2013.01); *G01N 2333/705* (2013.01); *G01N 2333/912* (2013.01); *G01N 2800/368* (2013.01)

(58) Field of Classification Search
CPC ........... G01N 33/689; G01N 33/54366; G01N 2333/471; G01N 2333/4753; G01N 2333/50; G01N 2333/515; G01N 2333/705; G01N 2333/912; G01N 2800/368; G16B 25/10; A61K 31/138; A61K 31/166; A61K 31/198; A61K 31/277; A61K 31/4168; A61K 31/4422; A61K 31/502; A61K 31/517; A61K 31/549

See application file for complete search history.

(56) References Cited

U.S. PATENT DOCUMENTS

| | | |
|---|---|---|
| 4,777,964 A | 10/1988 | Briggs et al. |
| 4,919,889 A | 4/1990 | Jones et al. |
| 5,096,830 A | 3/1992 | Senyei et al. |
| 5,223,440 A | 6/1993 | Teng et al. |
| 5,281,522 A | 1/1994 | Senyei et al. |
| 5,431,171 A | 7/1995 | Harrison et al. |
| 5,468,619 A | 11/1995 | Senyei et al. |
| 5,516,702 A | 5/1996 | Senyei et al. |
| 5,597,700 A | 1/1997 | Konstantinov et al. |
| 5,616,719 A | 4/1997 | Davalian et al. |
| 5,641,636 A | 6/1997 | Strauss, III et al. |
| 5,650,394 A | 7/1997 | Terao et al. |
| 5,698,404 A | 12/1997 | Strauss, III et al. |
| 5,783,396 A | 7/1998 | Voroteliak et al. |
| 5,807,675 A | 9/1998 | Davalian et al. |
| 5,861,319 A | 1/1999 | Lin et al. |

(Continued)

FOREIGN PATENT DOCUMENTS

| | | |
|---|---|---|
| EP | 0913405 A1 | 5/1999 |
| EP | 1804836 B1 | 11/2010 |

(Continued)

OTHER PUBLICATIONS

Stepan et al (Year: 2013).*

(Continued)

*Primary Examiner* — Jeffrey S Lundgren
*Assistant Examiner* — Ibrahim D Bori
(74) *Attorney, Agent, or Firm* — Wilson Sonsini Goodrich & Rosati

(57) ABSTRACT

Disclosed herein are methods, kits, tests, and systems for detecting, predicting, monitoring, or ruling out preeclampsia in pregnant women. Also provided herein are novel diagnostic markers, methods of data analysis, assay formats, and kits employing such markers to improve one or more characteristics of a test for identifying or ruling out preeclampsia based on biomarkers from patient samples.

15 Claims, 82 Drawing Sheets

(56) References Cited

U.S. PATENT DOCUMENTS

| | | |
|---|---|---|
| 5,877,029 A | 3/1999 | Fuks et al. |
| 5,891,722 A | 4/1999 | Fuks et al. |
| 5,898,005 A | 4/1999 | Singh et al. |
| 5,968,758 A | 10/1999 | Fuks et al. |
| 6,126,597 A | 10/2000 | Smith et al. |
| 6,126,616 A | 10/2000 | Sanyal |
| 6,140,099 A | 10/2000 | Strauss, III et al. |
| 6,149,590 A | 11/2000 | Smith et al. |
| 6,267,722 B1 | 7/2001 | Anderson et al. |
| 6,312,393 B1 | 11/2001 | Abreu et al. |
| 6,394,952 B1 | 5/2002 | Anderson et al. |
| 6,395,499 B1 | 5/2002 | Abramovitz et al. |
| 6,410,583 B1 | 6/2002 | Labelle et al. |
| 6,544,193 B2 | 4/2003 | Abreu et al. |
| 6,556,977 B1 | 4/2003 | Lapointe et al. |
| 6,605,705 B1 | 8/2003 | Oda et al. |
| 6,610,480 B1 | 8/2003 | Shimkets et al. |
| 6,678,669 B2 | 1/2004 | Lapointe et al. |
| 6,790,635 B1 | 9/2004 | Seiki et al. |
| 6,867,051 B1 | 3/2005 | Anderson et al. |
| 6,875,567 B1 | 4/2005 | Shimkets et al. |
| 6,878,522 B2 | 4/2005 | Li et al. |
| 6,884,593 B1 | 4/2005 | Hirai et al. |
| 6,936,476 B1 | 8/2005 | Anderson et al. |
| 7,041,063 B2 | 5/2006 | Abreu et al. |
| 7,109,044 B1 | 9/2006 | Oda et al. |
| 7,144,913 B2 | 12/2006 | Wang et al. |
| 7,191,068 B2 | 3/2007 | Rosenfeld et al. |
| 7,217,725 B2 | 5/2007 | Krauss et al. |
| 7,228,295 B2 | 6/2007 | Lapointe et al. |
| 7,270,970 B2 | 9/2007 | Anderson et al. |
| 7,314,727 B2 | 1/2008 | Mase et al. |
| 7,399,596 B2 | 7/2008 | Oda et al. |
| 7,403,805 B2 | 7/2008 | Abreu et al. |
| 7,407,659 B2 | 8/2008 | Karumanchi et al. |
| 7,435,419 B2 | 10/2008 | Karumanchi et al. |
| 7,445,940 B2 | 11/2008 | Caniggia et al. |
| 7,488,585 B2 | 2/2009 | Meiri et al. |
| 7,517,889 B2 | 4/2009 | Harris et al. |
| 7,524,636 B2 | 4/2009 | Bryant-Greenwood et al. |
| 7,528,133 B1 | 5/2009 | Copland, III et al. |
| 7,582,643 B2 | 9/2009 | Blake et al. |
| 7,635,571 B2 | 12/2009 | Ullman et al. |
| 7,642,249 B2 | 1/2010 | Langevin et al. |
| 7,654,957 B2 | 2/2010 | Abreu et al. |
| 7,709,272 B2 | 5/2010 | Fuks et al. |
| 7,754,495 B2 | 7/2010 | Caniggia et al. |
| 7,756,559 B2 | 7/2010 | Abreu et al. |
| 7,794,953 B2 | 9/2010 | Pentyala et al. |
| 7,809,417 B2 | 10/2010 | Abreu et al. |
| 7,811,279 B2 | 10/2010 | John et al. |
| 7,863,007 B2 | 1/2011 | Voroteliak et al. |
| 7,902,373 B2 | 3/2011 | Blake et al. |
| 7,943,294 B2 | 5/2011 | Hussa et al. |
| 7,947,449 B2 | 5/2011 | Karumanchi et al. |
| 8,060,195 B2 | 11/2011 | Gurewitsch et al. |
| 8,067,445 B2 | 11/2011 | Hutchinson et al. |
| 8,068,990 B2 | 11/2011 | Rosenfeld et al. |
| 8,071,807 B2 | 12/2011 | Hutchinson et al. |
| 8,114,610 B2 | 2/2012 | Fuks et al. |
| 8,133,859 B2 | 3/2012 | Kimura et al. |
| 8,160,692 B2 | 4/2012 | Principe et al. |
| 8,193,183 B2 | 6/2012 | Lim et al. |
| 8,242,145 B2 | 8/2012 | Hutchinson et al. |
| 8,338,484 B2 | 12/2012 | Hutchinson et al. |
| 8,362,044 B2 | 1/2013 | Hutchinson et al. |
| 8,366,640 B2 | 2/2013 | Bauer et al. |
| 8,372,581 B2 | 2/2013 | Hussa et al. |
| 8,378,107 B2 | 2/2013 | Hutchinson et al. |
| 8,383,654 B2 | 2/2013 | Hutchinson et al. |
| 8,426,449 B2 | 4/2013 | Hutchinson et al. |
| 8,497,381 B2 | 7/2013 | Hutchinson et al. |
| 8,501,688 B2 | 8/2013 | Kimura et al. |
| 8,501,959 B2 | 8/2013 | Hutchinson et al. |
| 8,517,960 B2 | 8/2013 | Bauer et al. |
| 8,524,748 B2 | 9/2013 | Hutchinson et al. |
| 8,552,364 B2 | 10/2013 | Graves et al. |
| 8,647,832 B2 | 2/2014 | Cuckle et al. |
| 8,835,183 B2 | 9/2014 | Bashirians et al. |
| 8,871,448 B2 | 10/2014 | Buhimschi et al. |
| 9,518,992 B2 | 12/2016 | Karumanchi et al. |
| 9,777,315 B2 | 10/2017 | Fredriksson et al. |
| 9,797,903 B2 | 10/2017 | Ragolia |
| 10,281,475 B2 | 5/2019 | Chaiworapongsa et al. |
| 10,413,591 B2 | 9/2019 | Karumanchi et al. |
| 2001/0023419 A1 | 9/2001 | Lapointe et al. |
| 2001/0025140 A1 | 9/2001 | Torok et al. |
| 2001/0053876 A1 | 12/2001 | Torok et al. |
| 2002/0022218 A1 | 2/2002 | Li et al. |
| 2002/0031513 A1 | 3/2002 | Leibovitz et al. |
| 2002/0046054 A1 | 4/2002 | Morand et al. |
| 2002/0049389 A1 | 4/2002 | Abreu |
| 2003/0004906 A1 | 1/2003 | Lapointe et al. |
| 2003/0027854 A1 | 2/2003 | Arimura et al. |
| 2003/0099651 A1 | 5/2003 | Leibovitz et al. |
| 2003/0105731 A1 | 6/2003 | Lapointe et al. |
| 2003/0113319 A1 | 6/2003 | Leibovitz et al. |
| 2003/0139687 A1 | 7/2003 | Abreu et al. |
| 2003/0190678 A1 | 10/2003 | Mase et al. |
| 2004/0014063 A1 | 1/2004 | Batteux et al. |
| 2004/0038314 A1 | 2/2004 | Oda et al. |
| 2004/0039297 A1 | 2/2004 | Abreu et al. |
| 2004/0039298 A1 | 2/2004 | Abreu et al. |
| 2004/0078219 A1 | 4/2004 | Kaylor et al. |
| 2004/0100376 A1 | 5/2004 | Lye et al. |
| 2004/0157222 A1 | 8/2004 | Smolyar |
| 2004/0162323 A1 | 8/2004 | Krauss et al. |
| 2004/0180934 A1 | 9/2004 | Wang et al. |
| 2004/0185509 A1 | 9/2004 | Gervais et al. |
| 2004/0197834 A1 | 10/2004 | Gervais et al. |
| 2004/0197930 A1 | 10/2004 | Rosenfeld et al. |
| 2004/0241752 A1 | 12/2004 | Anderson et al. |
| 2004/0266025 A1 | 12/2004 | Hickok et al. |
| 2005/0101841 A9 | 5/2005 | Kaylor et al. |
| 2005/0131287 A1 | 6/2005 | Kaylor et al. |
| 2005/0163771 A1 | 7/2005 | Leibovitz et al. |
| 2005/0215609 A1 | 9/2005 | Yoshikawa et al. |
| 2005/0260683 A1 | 11/2005 | Bryant-Greenwood et al. |
| 2005/0277912 A1 | 12/2005 | John et al. |
| 2006/0008923 A1 | 1/2006 | Anderson et al. |
| 2006/0014302 A1 | 1/2006 | Martinez et al. |
| 2006/0024722 A1 | 2/2006 | Fischer-Colbrie et al. |
| 2006/0024723 A1 | 2/2006 | Hussa et al. |
| 2006/0024724 A1 | 2/2006 | Hussa et al. |
| 2006/0024725 A1 | 2/2006 | Hussa et al. |
| 2006/0024757 A1 | 2/2006 | Hussa et al. |
| 2006/0040337 A1 | 2/2006 | Meiri et al. |
| 2006/0166242 A1 | 7/2006 | Pennell et al. |
| 2006/0166295 A1 | 7/2006 | Woods et al. |
| 2006/0204532 A1 | 9/2006 | John et al. |
| 2006/0240495 A1 | 10/2006 | Buhimschi et al. |
| 2006/0240498 A1 | 10/2006 | Friedman et al. |
| 2007/0003992 A1 | 1/2007 | Pentyala et al. |
| 2007/0016074 A1 | 1/2007 | Abreu et al. |
| 2007/0020609 A1 | 1/2007 | Oda et al. |
| 2007/0054951 A1 | 3/2007 | Li et al. |
| 2007/0128589 A1 | 6/2007 | Sanders et al. |
| 2007/0142718 A1 | 6/2007 | Abreu et al. |
| 2007/0161125 A1 | 7/2007 | Rosenfeld et al. |
| 2007/0196864 A1 | 8/2007 | Pentyala et al. |
| 2007/0244131 A1 | 10/2007 | Lim et al. |
| 2007/0249686 A1 | 10/2007 | Bonnert et al. |
| 2007/0265278 A1 | 11/2007 | Harris et al. |
| 2007/0265291 A1 | 11/2007 | Harris et al. |
| 2008/0009552 A1 | 1/2008 | Pennell et al. |
| 2008/0090759 A1 | 4/2008 | Kokenyesi et al. |
| 2008/0194600 A1 | 8/2008 | Langevin et al. |
| 2008/0227113 A1 | 9/2008 | Pentyala et al. |
| 2008/0233597 A1 | 9/2008 | Shiina et al. |
| 2008/0254479 A1 | 10/2008 | Kokenyesi et al. |
| 2008/0261922 A1 | 10/2008 | Carley et al. |
| 2008/0299594 A1 | 12/2008 | Rosenfeld et al. |
| 2009/0036469 A1 | 2/2009 | Stefany et al. |
| 2009/0036761 A1 | 2/2009 | Abreu et al. |

(56) References Cited

U.S. PATENT DOCUMENTS

| | | |
|---|---|---|
| 2009/0055099 A1 | 2/2009 | Rosenfeld et al. |
| 2009/0058072 A1 | 3/2009 | Weber et al. |
| 2009/0068692 A1 | 3/2009 | Voroteliak et al. |
| 2009/0081206 A1 | 3/2009 | Leibovitz et al. |
| 2009/0171234 A1 | 7/2009 | Gurewitsch et al. |
| 2009/0176804 A1 | 7/2009 | Yang et al. |
| 2009/0197959 A1 | 8/2009 | Hutchinson et al. |
| 2009/0227036 A1 | 9/2009 | Meiri et al. |
| 2009/0299212 A1 | 12/2009 | Principe et al. |
| 2010/0004331 A1 | 1/2010 | Hutchinson et al. |
| 2010/0008911 A1 | 1/2010 | Streisand et al. |
| 2010/0017143 A1 | 1/2010 | Nagalla et al. |
| 2010/0029006 A1 | 2/2010 | Rosenblatt et al. |
| 2010/0075990 A1 | 3/2010 | Endres et al. |
| 2010/0081673 A1 | 4/2010 | Hutchinson et al. |
| 2010/0093621 A1 | 4/2010 | Kimura et al. |
| 2010/0113503 A1 | 5/2010 | Hutchinson et al. |
| 2010/0130574 A1 | 5/2010 | Eggan et al. |
| 2010/0145180 A1 | 6/2010 | Abreu et al. |
| 2010/0251394 A1 | 9/2010 | Dore et al. |
| 2010/0298368 A1 | 11/2010 | Stearns et al. |
| 2010/0311190 A1 | 12/2010 | Fuks et al. |
| 2010/0318025 A1 | 12/2010 | John et al. |
| 2010/0323911 A1 | 12/2010 | Devarajan et al. |
| 2010/0330077 A1 | 12/2010 | Armer et al. |
| 2011/0002866 A1 | 1/2011 | Lubit et al. |
| 2011/0021573 A1 | 1/2011 | Hutchinson et al. |
| 2011/0021599 A1 | 1/2011 | Cotsarelis et al. |
| 2011/0028717 A1 | 2/2011 | Kugimiya et al. |
| 2011/0028807 A1 | 2/2011 | Abreu et al. |
| 2011/0034558 A1 | 2/2011 | Brittain et al. |
| 2011/0039852 A1 | 2/2011 | Hutchinson et al. |
| 2011/0040161 A1 | 2/2011 | Abreu et al. |
| 2011/0060026 A1 | 3/2011 | Hynd et al. |
| 2011/0065139 A1 | 3/2011 | Mullerad et al. |
| 2011/0071175 A1 | 3/2011 | Hynd et al. |
| 2011/0090048 A1 | 4/2011 | Li et al. |
| 2011/0098302 A1 | 4/2011 | Hutchinson et al. |
| 2011/0098352 A1 | 4/2011 | Hutchinson et al. |
| 2011/0112134 A1 | 5/2011 | Hutchinson et al. |
| 2011/0130453 A1 | 6/2011 | Hutchinson et al. |
| 2011/0144160 A1 | 6/2011 | Hutchinson et al. |
| 2011/0152338 A1 | 6/2011 | Hutchinson et al. |
| 2011/0159533 A1 | 6/2011 | Karkouche et al. |
| 2011/0166070 A1 | 7/2011 | Stewart et al. |
| 2011/0184254 A1 | 7/2011 | Grove et al. |
| 2011/0190227 A1 | 8/2011 | Hutchinson et al. |
| 2011/0237972 A1 | 9/2011 | Garfield et al. |
| 2011/0245303 A1 | 10/2011 | Hutchinson et al. |
| 2011/0301168 A1 | 12/2011 | Hutchinson et al. |
| 2011/0312927 A1 | 12/2011 | Nachaegari et al. |
| 2011/0312928 A1 | 12/2011 | Nachaegari et al. |
| 2011/0312974 A1 | 12/2011 | Hutchinson et al. |
| 2011/0318308 A1 | 12/2011 | Ragolia et al. |
| 2011/0319445 A1 | 12/2011 | Hutchinson et al. |
| 2012/0004233 A1 | 1/2012 | Stearns et al. |
| 2012/0009609 A1 | 1/2012 | Fuks et al. |
| 2012/0016029 A1 | 1/2012 | Hutchinson et al. |
| 2012/0022119 A1 | 1/2012 | Hutchinson et al. |
| 2012/0040356 A1 | 2/2012 | Hussa et al. |
| 2012/0046261 A1 | 2/2012 | Manuck et al. |
| 2012/0052595 A1 | 3/2012 | Wallace et al. |
| 2012/0058123 A1 | 3/2012 | Hutchinson et al. |
| 2012/0059055 A1 | 3/2012 | Hutchinson et al. |
| 2012/0082598 A1 | 4/2012 | Baydoun et al. |
| 2012/0157422 A1 | 6/2012 | Poston et al. |
| 2012/0196285 A1 | 8/2012 | Okamoto et al. |
| 2012/0202740 A1 | 8/2012 | Kimura et al. |
| 2012/0238469 A1 | 9/2012 | Equils et al. |
| 2012/0238894 A1 | 9/2012 | Principe et al. |
| 2012/0270747 A1 | 10/2012 | Elovitz et al. |
| 2013/0005728 A1 | 1/2013 | Harris et al. |
| 2013/0005741 A1 | 1/2013 | Harris et al. |
| 2013/0029957 A1 | 1/2013 | Giliyar et al. |
| 2013/0053670 A1 | 2/2013 | Aina-Mumuney et al. |
| 2013/0065902 A1 | 3/2013 | Aissaoui et al. |
| 2013/0071865 A1 | 3/2013 | Fuks et al. |
| 2013/0079375 A1 | 3/2013 | Endres et al. |
| 2013/0109685 A1 | 5/2013 | Aissaoui et al. |
| 2013/0158036 A1 | 6/2013 | Hutchinson et al. |
| 2013/0171672 A1 | 7/2013 | Hussa et al. |
| 2013/0177485 A1 | 7/2013 | Mullerad et al. |
| 2013/0203068 A1 | 8/2013 | Roby et al. |
| 2013/0225922 A1 | 8/2013 | Schentag et al. |
| 2013/0288249 A1 | 10/2013 | Gullberg et al. |
| 2015/0330989 A1* | 11/2015 | Burwick ............... A61K 31/609 |
| | | 435/7.92 |
| 2015/0338415 A1 | 11/2015 | Hund et al. |
| 2017/0003304 A1 | 1/2017 | Demirdjian et al. |
| 2017/0023446 A1 | 1/2017 | Rietveld et al. |
| 2018/0003713 A1 | 1/2018 | Ragolia |
| 2018/0036271 A1 | 2/2018 | Ahmed et al. |
| 2018/0114600 A1 | 4/2018 | Roberts et al. |
| 2018/0259534 A1 | 9/2018 | Chaparro Padilla et al. |
| 2019/0079097 A1 | 3/2019 | Cooper et al. |
| 2019/0227074 A1 | 7/2019 | Denk et al. |
| 2019/0317108 A1 | 10/2019 | Schuitemaker |
| 2019/0353667 A1 | 11/2019 | Anderberg et al. |
| 2020/0038354 A1 | 2/2020 | Ahmed et al. |
| 2020/0264188 A1 | 8/2020 | Cooper et al. |

FOREIGN PATENT DOCUMENTS

| | | |
|---|---|---|
| EP | 1952156 B1 | 5/2011 |
| EP | 2172220 B1 | 1/2013 |
| EP | 2434283 B1 | 3/2014 |
| EP | 2912458 A1 | 9/2015 |
| EP | 2867670 B1 | 5/2018 |
| EP | 2649454 B1 | 6/2018 |
| EP | 3097422 B1 | 7/2018 |
| WO | WO-9309432 A1 | 5/1993 |
| WO | WO-9309438 A1 | 5/1993 |
| WO | WO-9815830 A2 | 4/1998 |
| WO | WO-2006069373 A2 | 6/2006 |
| WO | WO-2009097584 A1 | 8/2009 |
| WO | WO-2011128357 A2 | 10/2011 |
| WO | WO-2013068475 A1 | 5/2013 |
| WO | WO-2013169751 A1 | 11/2013 |
| WO | WO-2014036440 A2 | 3/2014 |
| WO | WO-2014066568 A1 | 5/2014 |
| WO | WO-2014078622 A1 | 5/2014 |
| WO | WO-2014135488 A1 | 9/2014 |
| WO | WO-2015082545 A1 | 6/2015 |
| WO | WO-2016019176 A1 | 2/2016 |
| WO | WO-2016132136 A1 | 8/2016 |
| WO | WO-2019055661 A1 | 3/2019 |

OTHER PUBLICATIONS

Holets et al (Year: 2006).*
Robinson et al (Year: 2007).*
Siddqui et al (Year: 2016).*
Akolekar et al. Competing Risks Model in Early Screening for Preeclampsia by Biophysical and Biochemical Markers. Fetal Diagn Ther 33:8-15 (2013). Published online Aug. 16, 2012. DOI: 10.1159/000341264.
Akolekar et al. Prediction of early, intermediate and late pre-eclampsia from maternal factors, biophysical and biochemical markers at 11-13 weeks. Prenat Diagn 31:66-74 (2011). DOI: 10.1002/pd.2660.
Anand et al. Serum biomarkers predictive of pre-eclampsia. Biomark Med 9(6):563-575 (2015). doi: 10.2217/bmm.15.21.
Berzan et al. Treatment of Preeclampsia: Current Approach and Future Perspectives. Curr Hypertens Rep 16:473 (2014). 6 pages. DOI: https://doi.org/10.1007/s11906-014-0473-5.
Burwick et al. Complement activation and kidney injury molecule-1-associated proximal tubule injury in severe preeclampsia. Hypertension 64(4):833-8 (Oct. 2014). doi: 10.1161/HYPERTENSIONAHA.114.03456. Epub Jun. 23, 2014.
Caritis, et al. A double-blind study comparing ritodrine and terbutaline in the treatment of preterm labor. American journal of obstetrics and gynecology 150.1 (1984): 7-14. (Abstract).

(56) References Cited

OTHER PUBLICATIONS

Carty et al. Novel biomarkers for predicting preeclampsia. Trends in Cardiovascular Medicine. 18(5):186-194 (2008).

Chobanian et al. The Seventh Report of the Joint National Committee on Prevention, Detection, Evaluation, and Treatment of High Blood Pressure. JAMA 289(19):2560-2572 (May 21, 2003).doi:10.1001/jama.289.19.2560.

CLEC4A ELISA kit; 2006; retrieved from https://cdn.mybiosource.com/tds/protocol_manuals/800000-9999999/M8S7213205.pdf. 8 pages.

Co-pending U.S. Appl. No. 15/329,924, inventors Cooper; Matthew et al., filed Jan. 27, 2017.

Darmochwal-Kolarz et al. The expression of B7-H1 and B7-H4 co-stimulatory molecules on myeloid and plasmacytoid dendritic cells in pre-eclampsia and normal pregnancy. J Reprod Immunol 99 (2013) 33-38.

Dwivedi, et al. Systematic review of the role of prostaglandins. World J Pharm Pharm Sci. 3 (2). (2013): 2249-69.

Elecsys® sFlt-1/PlGF (Preeclampsia). (Website.) Roche Diagnostics. 4 pages. Accessed Oct. 30, 2018 at URL:https://diagnostics.roche.com/global/en/products/params/elecsys-sflt-1-plgf-preeclampsia.html.

EP18167167.8 Communication and Search Report dated Jun. 18, 2018.

EP18856306.8 Extended European Search Report dated Feb. 3, 2021.

EP18856306.8 Partial Supplementary European Search Report dated Oct. 5, 2020.

Fortier, et al. A postgenomic integrated view of prostaglandins in reproduction: implications for other body systems. J Physiol Pharmacol59.Suppl 1 (2008): 65-89.

Gravett, et al. Proteomic Analysis of Cervical-Vaginal Fluid: Identification of Novel Biomarkers for Detection of Intra-Amniotic Infection. J Proteome Res. Jan. 2007; 6(1): 89-96. doi:10.1021/pr060149v.

Helliwell, et al. Gestational Age-Dependent Up-Regulation of Prostaglandin D Synthase (PGDS) and Production of PGDS-Derived Antiinflammatory Prostaglandins in Human Placenta, The Journal of Clinical Endocrinology & Metabolism, vol. 91, Issue 2, Feb. 1, 2006, pp. 597-606, https://doi.org/10.1210/jc.2005-1982.

Human C. Type Lectin Domain Family 4 Member A (CLEC4A) Elisa Kit (Competitive ELISA), Catalog No. MBS7213205 (2017). 8 pages. Retrieved Jul. 10, 2020 from URL: https://cdn.mybiosource.com/tds/protocol_manuals/800000-9999999/MBS7213205.pdf.

Human Fibroblast Growth Factor-21 ELISA. Cat. No. RD191108200R, BioVendor Research and Diagnostic Products, Czech Republic. BioMedical Specimen Bank, Czech Republic. (Sep. 2013). 2 pages. Retrieved from http://npt.ir/uploads/RD191108200R.pdf.

Hund et al. Influence of the sFlt-1/PlGF ratio on clinical decision-making in women with suspected preeclampsia—the PreOS study protocol. Hypertension in Pregnancy 34(1):102-115 (Jan. 28, 2015). DOI: https://doi.org/10.3109/10641955.2014.982331.

Hund et al. Multicenter prospective clinical study to evaluate the prediction of short-term outcome in pregnant women with suspected preeclampsia (Prognosis): study protocol. BMC Pregnancy and Childbirth 14:324 (Sep. 18, 2014.) 10 pages. DOI: https://doi.org/10.1186/1471-2393-14-324.

Hypertension in pregnancy. Report of the American College of Obstetricians and Gynecologists' Task Force on Hypertension in Pregnancy. Obstet Gynecol 122(5):1122-1131 (Nov. 1, 2013). doi: 10.1097/01.AOG.0000437382.03963.88.

Khan, et al. Prostaglandins in labor—a translational approach. Front Biosci 13 (2008): 5794-5809.

Klein et al. Influence of the sFlt-1/PlGF Ratio on Clinical Decision-Making in Women with Suspected Preeclampsia. PLOS One (May 31, 2016). 19 pages. DOI:10.1371/journal.pone.0156013.

Kumar, et al. Role of Lipocalin-type prostaglandin D2 synthase (L-PGDS) and its metabolite, prostaglandin D2, in preterm birth. Prostaglandins & other lipid mediators 118 (Apr. 1, 2015): 28-33.

Lee, et al. Amniotic fluid prostaglandin concentrations increase before the onset of spontaneous labor at term. The Journal of Maternal-Fetal & Neonatal Medicine 21.2 (2008): 89-94.

Li et al. Progress in Exosome Isolation Techniques. Theranostics 7(3):789-804 (Jan. 26, 2017). doi: 10.7150/thno.18133.

Liu et al. Integrating multiple 'omics' analysis identifies serological protein biomarkers for preeclampsia. BMC Medicine 11:236 (2016). 12 pages.

Lundberg et al., Homogeneous antibody-based proximity extension assays provide sensitive and specific detection of low-abundant proteins in human blood, Nucleic Acids Res.(2011) 39(15):e102. 8 pages.

Marceau, et al. Role of nuclear receptors Peroxisome Proliferator-Activated Receptors (PPARs) and Liver X receptors (LXRs) in the human placental pathophysiology. Recent Advances in Research on the Human Placenta. IntechOpen, 2012. 379-396.

Mestecky, Jiri, et al. "Manual for collection and processing of mucosal specimens." Laboratory for Assessment of Mucosal Immune Responses Induced by AIDS Vaccines in Clinical Trial Volunteers, National Institute of Health, Division of AIDS (1999).

Molvarec et al. Circulating angiogenic factors determined by electrochemiluminescence immunoassay in relation to the clinical features and laboratory parameters in women with pre-eclampsia. Hypertension Research 33:892-898 (Jun. 10, 2010).

Myatt. Association of maternal biomarkers with obstetric outcomes. Reproductive Sciences. vol. 20, Suppl. 1, Abstract S-207 (2013). 60th Annual Meeting, Society for Gynecologic Investigation, Orlando, FL, USA, Mar. 20-23, 2013.

Myatt. Identification of different phenotypes of preeclampsia by clustering analysis of biomarker profiles. Reproductive Sciences. vol. 20, Suppl. 1, Abstract F-255 (2013). 60th Annual Meeting, Society for Gynecologic Investigation, Orlando, FL, USA, Mar. 20-23, 2013.

Nitert et al. Placental fibroblast growth factor 21 is not altered in late-onset preeclampsia. Reprod Biol Endocrinol. 2015; 13: 14. Published online Mar. 8, 2015. doi: 10.1186/s12958-015-0006-3.8 pages.

O'Gorman et al. Competing risks model in screening for preeclampsia by maternal factors and biomarkers at 11-13 weeks gestation. American Journal of Obstetrics and Gynecology 214(1):103.e1-103.e12 (Jan. 2016). DOI: https://doi.org/10.1016/j.ajog.2015.08.034.

Olson, et al. Role of the prostaglandins in labour and prostaglandin receptor inhibitors in the prevention of preterm labour. Front Biosci. Jan. 1, 2007;12:1329-43.

Park et al. Screening models using multiple markers for early detection of late-onset preeclampsia in low-risk pregnancy. BMC Pregnancy and Childbirth. 14:35 (2014). 11 pages.

Patton, et al. Proteomic analysis of the cerebrospinal fluid of patients with restless legs syndrome/Willis-Ekbom disease. Fluids and Barriers of the CNS 10.1 (2013): 20. 8 pages.

PCT/US2013/066490 Written Opinion of the International Searching Authority dated Jan. 14, 2014.

PCT/US2013/066490 International Search Report dated Jan. 14, 2014.

PCT/US2015/042976 International Search Report and Written Opinion dated Nov. 23, 2015.

PCT/US2018/050893 International Search Report and Written Opinion dated Dec. 12, 2018.

Pennings et al. Integrative data mining to identify novel candidate serum biomarkers for pre-eclampsia screening. Prenatal Diagnosis 31:1153-1159 (Sep. 22, 2011).

Pettipher, et al. Antagonism of the prostaglandin D 2 receptors DP 1 and CRTH2 as an approach to treat allergic diseases. Nature Reviews Drug Discovery 6.4 (2007): 313-325.

Phillips, et al. Genes for prostaglandin synthesis, transport and inactivation are differentially expressed in human uterine tissues, and the prostaglandin F synthase AKR1B1 is induced in myometrial cells by inflammatory cytokines. Molecular human reproduction 17.1 (Jul. 1, 2010): 1-13.

Phillips, et al. Prostaglandin pathway gene expression in human placenta, amnion and choriodecidua is differentially affected by preterm and term labour and by uterine inflammation. BMC pregnancy and childbirth 14.1 (Jan. 1, 2014): 241. 14 pages.

(56) References Cited

OTHER PUBLICATIONS

Phipps et al. Preeclampsia: Updates in Pathogenesis, Definitions, and Guidelines. Clinical Journal of the American Society of Nephrology 11(6):1102-1113 (Jun. 2016). DOI: https://doi.org/10.2215/CJN.12081115.
Pinhal-Enfield, et al. The role of macrophages in the placenta. Embryology-Updates and Highlights on Classic Topics. IntechOpen, 2012.
Pirianov, et al. The cyclopentenone 15-deoxy-delta12,14-prostaglandin J2 delays lipopolysaccharide-induced preterm delivery and reduces mortality in the newborn mouse. Endocrinology 150.2 (Epub Oct. 9, 2008): 699-706.
Poon et al. First-Trimester Prediction of Hypertensive Disorders in Pregnancy. Hypertension 53:812-818 (Mar. 9, 2009). doi: 10.1161/HYPERTENSIONAHA.108.127977.
Poon et al. First-trimester maternal factors and biomarker screening for preeclampsia. Prenatal Diagnosis 34(7):618-627 (Jul. 2014). First published Apr. 25, 2014. DOI: https://doi.org/10.1002/pd.4397.
Rinaldi, et al. Anti-inflammatory mediators as physiological and pharmacological regulators of parturition. Expert review of clinical immunology7.5 (2011): 675-696.
Romero et al. Expression of placental fibroblast growth factor 21 (FGF21) is increased in placental tissue from pregnancies with preeclampsia. Placenta, vol. 35, Issue 9, Sep. 2014, p. A84. DOI: https://doi.org/10.1016/j.placenta.2014.06.271.
Sabbisetti et al. Blood kidney injury molecule-1 is a biomarker of acute and chronic kidney injury and predicts progression to ESRD in type I diabetes. J Am Soc Nephrol 25:2177-2186 (2014).
Sano, et al. Immuno-PCR: Very sensitive antigen detection by means of specific antibody-DNA conjugates. Science. 258 (1992): 120-122.
Shiki, et al. Changes of lipocalin-type prostaglandin D synthase level during pregnancy. J Obstet Gynaecol Res. Feb. 2004;30(1):65-70.
Spencer et al. ADAM12s in maternal serum as a potential marker of pre-eclampsia. Prenatal Diagnosis 28:212-216 (Feb. 8, 2008).
Spencer et al. Low levels of maternal serum PAPP-A in the first trimester and the risk of pre-eclampsia. Prenatal Diagnosis 28(1):7-10 (Jan. 2008). First published Nov. 14, 2007. DOI: https://doi.org/10.1002/pd.1890.
Spencer et al. Screening for trisomy 21 in twin pregnancies in the first trimester: an update of the impact of chorionicity on maternal serum markers. Prenatal Diagnosis 28(1):49-52 (Jan. 2008). DOI: https://doi.org/10.1002/pd.1923.
Stepan et al. Serum levels of the adipokine fibroblast growth factor-21 are increased in preeclampsia. Cytokine, vol. 62, Issue 2, May 2013, pp. 322-326. Available online Mar. 29, 2013.
Sykes, et al. Anti-inflammatory prostaglandins for the prevention of preterm labour. Reproduction 148.2 (2014): R29-R40.
Sykes, et al. Changes in the Th1: Th2 Cytokine Bias in Pregnancy and the Effects of the Anti-Inflammatory Cyclopentenone Prostaglandin 15-Deoxy-Prostaglandin. Mediators of inflammation 2012 (2012). 12 pages.
Taylor et al. High plasma cellular fibronectin levels correlate with biochemical and clinical features of preeclampsia but cannot be attributed to hypertension alone. 165(4) Part 1, pp. 895-901 (Oct. 1991). DOI: https://doi.org/10.1016/0002-9378(91)90435-T.
Tejera et al. Preeclampsia: a bioinformatics approach through protein-protein interaction networks analysis. BMC Systems Biology 6:97 (2012). 9 pages.

Thorsen, Stine Buch et al. Detection of serological biomarkers by proximity extension assay for detection of colorectal neoplasias in symptomatic individuals. Journal of Translational Medicine 11(253): 1-13 (2013).
Tsiakkas et al. Maternal serum placental growth factor at 12, 22, 32 and 36 weeks' gestation in screening for pre-eclampsia. Ultrasound Obstet Gynecol 47:472-477 (Mar. 7, 2016). DOI: 10.1002/uog.15816.
Ullman et al. Luminescent oxygen channeling assay (LOCI): sensitive, broadly applicable homogeneous immunoassay method. Clinical Chemistry 42(9):1518-1526 (Sep. 1996).
Ullman et al. Luminescent oxygen channeling immunoassay: measurement of particle binding kinetics by chemiluminescence. PNAS 91(12):5426-5430 (Jun. 7, 1994). DOI: https://doi.org/10.1073/pnas.91.12.5426.
U.S. Appl. No. 14/438,110 Notice of Allowance dated Jun. 19, 2017.
U.S. Appl. No. 14/438,110 Office Action dated Aug. 12, 2016.
U.S. Appl. No. 14/438,110 Office Action dated Feb. 21, 2017.
U.S. Appl. No. 15/708,582 Office Action dated Sep. 4, 2018.
U.S. Appl. No. 16/141,881 Office Action dated Apr. 16, 2020.
U.S. Appl. No. 16/141,881 Office Action dated Feb. 5, 2021.
U.S. Appl. No. 16/141,881 Office Action dated Oct. 2, 2019.
Verlohren et al. New Gestational Phase-Specific Cutoff Values for the Use of the Soluble fms-Like Tyrosine Kinase-1/Placental Growth Factor Ratio as a Diagnostic Test for Preeclampsia. Hypertension 63(2):346-352 (Oct. 28, 2013).
Verlohren et al. The sFlt-1/PIGF ratio in different types of hypertensive pregnancy disorders and its prognostic potential in preeclamptic patients. American Journal of Obstetrics & Gynecology, Month 2011, pp. 1.e1-1.e8 (2011). doi: 10.1016/j.ajog.2011.07.037.
Verlohren et al. An automated method for the determination of the sFlt-1/PIGF ratio in the assessment of preeclampsia. American Journal of Obstetrics and Gynecology. 202(2):161.e1-161.e11 (Feb. 2010). DOI: https://doi.org/10.1016/j.ajog.2009.09.016.
Wang et al. Increased urinary levels of podocyte glycoproteins, matrix metallopeptidases, inflammatory cytokines, and kidney injury biomarkers in women with preeclampsia. Am J Physiol Renal Physiol 309(12):F1009-F1017 (2015). First published Oct. 14, 2015; doi:10.1152/ajprenal.00257.2015.
Warner, et al. Cyclooxygenases: new forms, new inhibitors, and lessons from the clinic. The FASEB journal 18.7 (May 1, 2004): 790-804.
Weinstein. Syndrome of hemolysis, elevated liver enzymes, and low platelet count: A severe consequence of hypertension in pregnancy. American Journal of Obstetrics and Gynecology 142(2):159-167 (Jan. 15, 1982). DOI: https://doi.org/10.1016/S0002-9378(16)32330-4.
Whelton et al. 2017 ACC/AHA/AAPA/ABC/ACPM/AGS/APhA/ASH/ASPC/NMA/PCNA Guideline for the Prevention, Detection, Evaluation, and Management of High Blood Pressure in Adults. Journal of the American College of Cardiology 71(19):e127-248 (May 2018). DOI: 10.1016/j.jacc.2017.11.006.
Xiao et al. Combined biomarkers evaluation for diagnosing kidney injury in preeclampsia. Hypertens Pregnancy 32(4):439-49 (Nov. 2013). doi: 10.3109/10641955.2013.827203. Epub Aug. 19, 2013.
Zegels, et al. Comprehensive proteomic analysis of human cervical-vaginal fluid using colposcopy samples. Proteome science 7.1 (2009): 17. 16 Pages.
Zeisler et al. Predictive Value of the sFlt-1:PIGF Ratio in Women with Suspected Preeclampsia. N Engl J Med 374:13-22 (2016). DOI: 10.1056/NEJMoa1414838.
U.S. Appl. No. 16/141,881 Office Action dated Jun. 15, 2021.

\* cited by examiner

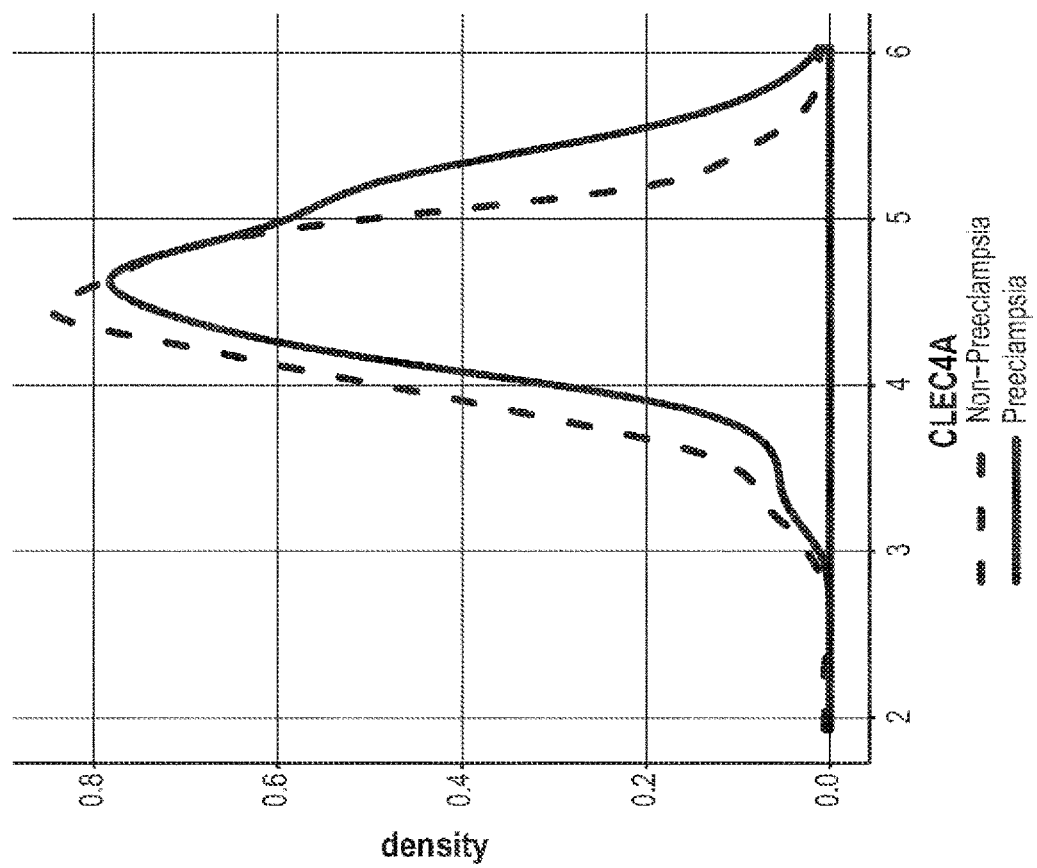
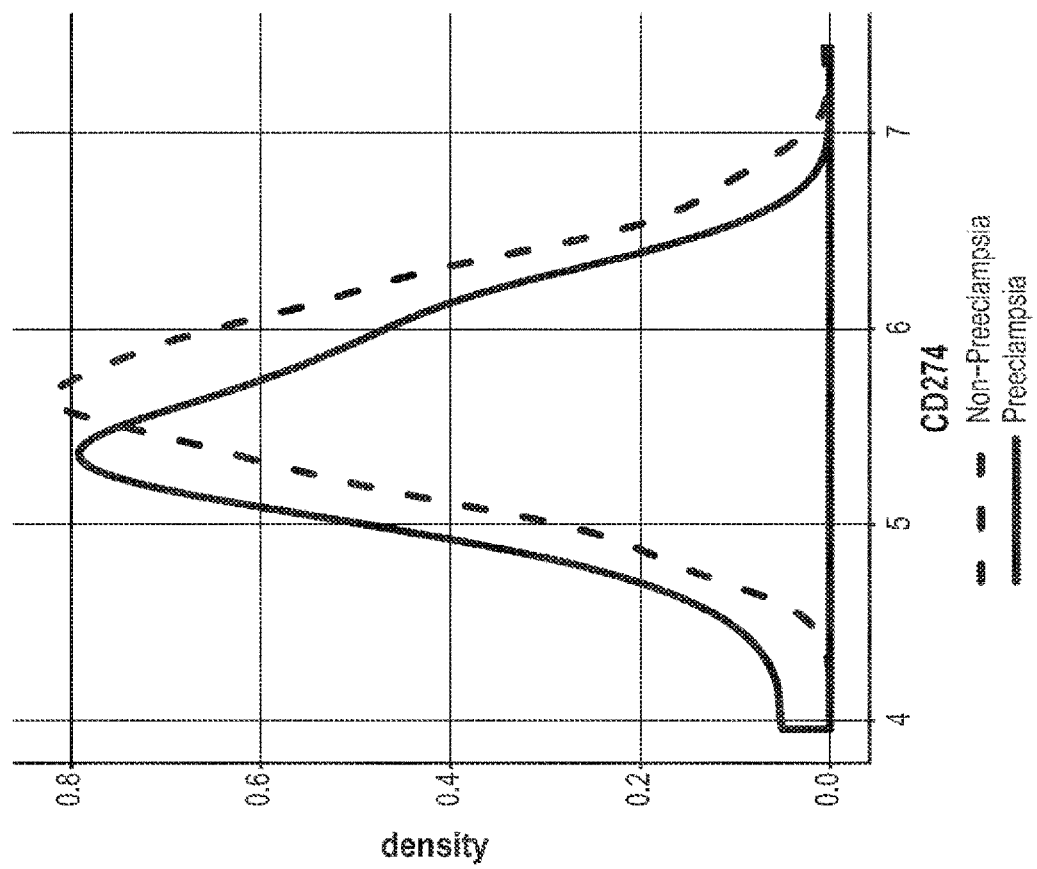
FIG. 13A
FIG. 13B

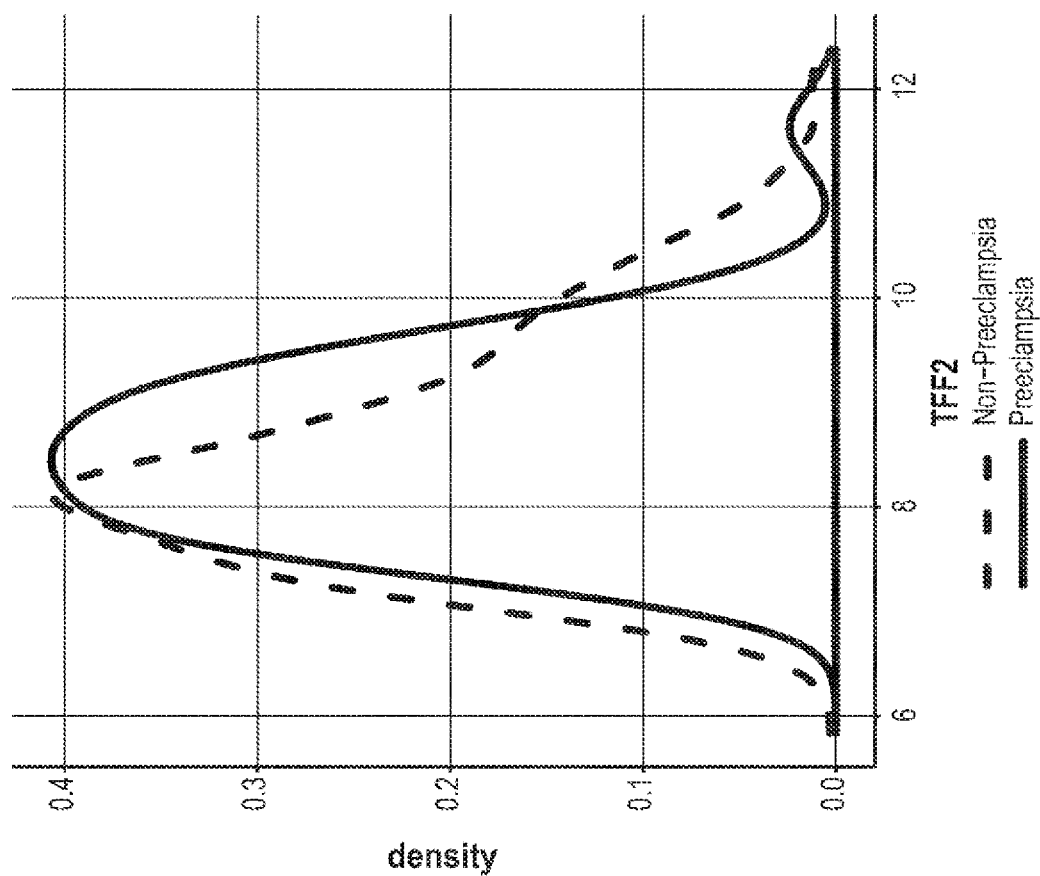

| Antigen | Company | Cat. No. | Name | Species | Reacts with | Mono- or Polyclonal | Clone # |
|---|---|---|---|---|---|---|---|
| CD274 | CST | 13684 | PD-L1 (E1L3N®) XP® Rabbit mAb | Rabbit | Human | Mono | E1L3N |
| CD274 | CST | 29122 | PD-L1 (405.9A11) Mouse mAb | Mouse | Human | Mono | 405.9A11 |
| CD274 | CST | 15165 | PD-L1 (Extracellular Domain Specific) (E1J2J™) Rabbit mAb | Rabbit | Human | Mono | E1J2J |
| CD274 | CST | 86744 | PD-L1 (Extracellular Domain Specific) (D8T4X) Rabbit mAb | Rabbit | Human | Mono | D8T4X |
| CD274 | Abcam | ab205921 | Anti-PD-L1 antibody [28-8] | Rabbit | Human | Mono | 28-8 |
| CD274 | Abcam | ab209889 | Anti-PD-L1 antibody [28-8] - Low endotoxin, Azide free | Rabbit | Human | Mono | 28-8 |

*FIG. 18*

| Antigen | Company | Cat. No. | Name | Species | Reacts with | Mono- or Polyclonal | Clone # |
|---|---|---|---|---|---|---|---|
| CD274 | Abcam | ab228415 | Anti-PD-L1 antibody [73-10]. Clone 73-10 is also known as clone MKP1A 07310. Clone 73-10 has been tested within Blueprint Phase 2 project | Rabbit | Human | Mono | 73-10 |
| CD274 | Abcam | ab226766 | Anti-PD-L1 antibody [73-10] - BSA and Azide free | Rabbit | Human | Mono | 73-10 |
| CD274 | Abcam | ab213524 | Anti-PD-L1 antibody [EPR19759] | Rabbit | Human | Mono | EPR19759 |
| CD274 | Abcam | ab221612 | Anti-PD-L1 antibody | Rabbit | Human | Mono | EPR19759 |

*FIG. 18 (Cont'd)*

| Antigen | Company | Cat. No. | Name | Species | Reacts with | Mono- or Polyclonal | Clone # |
|---|---|---|---|---|---|---|---|
| | | | [EPR19759] - BSA and Azide free | | | | |
| CD274 | Abcam | ab228462 | Anti-PD-L1 antibody [SP142] - C-terminal | Rabbit | Human | Mono | SP142 |
| CD274 | Abcam | ab236238 | Anti-PD-L1 antibody [SP142] - BSA and Azide free | Rabbit | Human | Mono | SP142 |
| CD274 | Abcam | ab210931 | Anti-PD-L1 antibody [ABM4E54] | Mouse | Human | Mono | ABM4E54 |
| CD274 | Abcam | ab233482 | Anti-PD-L1 antibody | Rabbit | Human, Mouse, Pig | Poly | NA |
| CD274 | R&D Systems | AF156 | Human PD-L1/B7-H1 Antibody | Goat | Human | Poly | NA |
| CD274 | R&D Systems | MAB1561 | Human PD-L1/B7-H1 | Mouse | Human | Mono | 130021 |

*FIG. 18 (Cont'd)*

| Antigen | Company | Cat. No. | Name | Species | Reacts with | Mono- or Polyclonal | Clone # |
|---|---|---|---|---|---|---|---|
| | | | Antibody | | | | |
| HGF | LSBio | LS-C400788 | HGF / Hepatocyte Growth Factor Antibody | Rabbit | Human, Mouse, Rat | Poly | NA |
| HGF | LSBio | LS-C404040 | HGF / Hepatocyte Growth Factor Antibody | Rabbit | Human, Mouse, Rat | Poly | NA |
| HGF | LSBio | LS-C742971 | HGF / Hepatocyte Growth Factor Antibody | Rabbit | Human | Poly | NA |
| HGF | LSBio | LS-C486536 | HGF / Hepatocyte Growth Factor Antibody | Rabbit | Human | Poly | NA |
| HGF | LSBio | LS-C486538 | HGF / Hepatocyte Growth Factor Antibody | Rabbit | Human | Poly | NA |
| HGF | LSBio | LS-C486540 | HGF / Hepatocyte Growth Factor Antibod | Rabbit | Human | Poly | NA |

*FIG. 18 (Cont'd)*

| Antigen | Company | Cat. No. | Name | Species | Reacts with | Mono- or Polyclonal | Clone # |
|---|---|---|---|---|---|---|---|
| | | | y | | | | |
| TFF2 | R&D Systems | MAB4077 | Human TFF2 Antibody Works in direct ELISA | Mouse | Human | Mono | 366508 |
| TFF2 | Novus | NBP2-50334 | TFF2 Antibody (HSP GE16C) | Mouse | Human | Mono | HSP GE16C |
| TFF2 | Novus | H00007032 | TFF2 Antibody (2A10) ELISA | Mouse | Human | Mono | 2A10 |
| TFF2 | ThermoFisher | | Only polyAbs | | | | |
| TFF2 | LSBio | LS-C669220 | TFF2 / SP Antibody (clone 4G7C3) ELISA | Mouse | Human | Mono | 4G7C3 |
| TFF2 | OriGene | TA353503L | Spasmolytic Polypeptide(TFF2) Mouse Monoclonal Antibody [Clone ID: HSP | Mouse | Human | Mono | HSP GE16C |

*FIG. 18 (Cont'd)*

| Antigen | Company | Cat. No. | Name | Species | Reacts with | Mono- or Polyclonal | Clone # |
|---|---|---|---|---|---|---|---|
| | | | GE16C] | | | | |
| Decorin (DCN) | Abcam | ab181456 | Anti-Decorin antibody [5E8E7] | Mouse | Human (Hu) | Monoclonal | 5E8E7 |
| Decorin (DCN) | Abcam | ab175404 | Anti-Decorin antibody | Rabbit | Hu, Ms, Rat | Polyclonal | na |
| Decorin (DCN) | Abcam | ab31614 | Anti-Decorin antibody | Sheep | Chk, Cow, Hu | Polyclonal | na |
| Decorin (DCN) | Abcam | ab151988 | Anti-Decorin antibody | Rabbit | Hu | Polyclonal | na |
| Decorin (DCN) | Abcam | ab35378 | Anti-Decorin antibody | Sheep | Chk, Cow, Hu | Polyclonal | na |
| Decorin (DCN) | Abcam | ab189364 | Anti-Decorin antibody | Goat | Hu | Polyclonal | na |
| Decorin (DCN) | Abcam | ab189071 | Anti-Decorin antibody - N-terminal | Sheep | Hu | Polyclonal | na |
| Decorin (DCN) | Abcam | ab137508 | Decorin antibody | Rabbit | Mouse, Human | Polyclonal | na |
| Decorin (DCN) | Abcam | ab90425 | Decorin antibody | Goat | Human | Polyclonal | na |
| Decorin (DCN) | antibodies-online | ABIN1995977 | anti-DCN (Decori | Rabbit | Human (Hu) | Monoclonal | 4 |

*FIG. 18 (Cont'd)*

| Antigen | Company | Cat. No. | Name | Species | Reacts with | Mono- or Polyclonal | Clone # |
|---|---|---|---|---|---|---|---|
| | | | n) antibody | | | | |
| Decorin (DCN) | antibodies-online | ABIN1978290 | anti-DCN (Decorin) antibody | Mouse | Human (Hu) | Monoclonal | 1G4C5 |
| Decorin (DCN) | antibodies-online | ABIN2252143 | anti-DCN (Decorin) antibody | Mouse | Human (Hu) | Monoclonal | 9j121 |
| Decorin (DCN) | Biorbyt | orb89581 | Decorin antibody | Mouse | Human (Hu) | Monoclonal | ? |
| Decorin (DCN) | Biorbyt | orb153493 | DCN antibody | Mouse | Human (Hu) | Monoclonal | 1G4C5 |
| Decorin (DCN) | Creative Diagnostics | DMABT-H13567 | Anti-DCN monoclonal antibody, clone 4I5-2G5 | Mouse | Human (Hu) | monoclonal | 4I5-2G5 |
| Decorin (DCN) | Creative Diagnostics | DCABY-4107 | Anti-DCN monoclonal antibody, clone 226535 | Mouse | Human (Hu) | monoclonal | 226535 |
| Decorin (DCN) | GeneTex | GTX52695 | Anti-Decorin antibody [6Z1] | Mouse | Human (Hu) | Monoclonal | 6Z1 |
| Decorin (DCN) | Invitrogen Antibodies | PA1-1744 | Decorin Polyclonal | Rabbit | Bovine, Human, Mouse | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | Antibody | | | | |
| Decorin (DCN) | Invitrogen Antibodies | PA5-19151 | Decorin Polyclonal Antibody | Goat | Human | Polyclonal | na |
| Decorin (DCN) | Invitrogen Antibodies | PA5-27370 | Decorin Polyclonal Antibody | Rabbit | Human | Polyclonal | na |
| Decorin (DCN) | Invitrogen Antibodies | PA5-13538 | Decorin Polyclonal Antibody | Rabbit | Human, Mouse | Polyclonal | na |
| Decorin (DCN) | Invitrogen Antibodies | PA1-85833 | Decorin Polyclonal Antibody | Sheep | Bovine, Chicken, Human | Polyclonal | na |
| Decorin (DCN) | LifeSpan BioSciences | LS-C285837-100 | Anti-DCN / Decorin Antibody (aa263-324, clone 1G4C5) | Mouse | Human (Hu) | Monoclonal | 1G4C5 |
| Decorin (DCN) | LifeSpan BioSciences | LS-C36148-500 | Anti-DCN / Decorin Antibody | Mouse | Human (Hu) | Monoclonal | ? |
| Decorin (DCN) | | LS-B4312-50 | Anti-DCN / Decorin Antibody (clone | Mouse | Human (Hu) | Monoclonal | 3H4-1F4 |

*FIG. 18 (Cont'd)*

| Antigen | Company | Cat. No. | Name | Species | Reacts with | Mono- or Polyclonal | Clone # |
|---|---|---|---|---|---|---|---|
| | LifeSpan BioSciences | | 3H4-1F4) IHC-plus™ | | | | |
| Decorin (DCN) | LifeSpan BioSciences | LS-C46802-100 | Anti-DCN / Decorin Antibody (C-Terminus) | Rabbit | Human | Polyclonal | na |
| Decorin (DCN) | LifeSpan BioSciences | LS-B33-50 | Anti-DCN / Decorin Antibody IHC-plus™ | Sheep | Chicken, Bovine, Human | Polyclonal | na |
| Decorin (DCN) | LifeSpan BioSciences | LS-C81179-50 | Anti-DCN / Decorin Antibody (C-Terminus) | Rabbit | Zebrafish, Pig, Horse, Bat, Mouse, Goat, Dog, Guinea pig, Hamster, Human, Monkey | Polyclonal | na |
| Decorin (DCN) | LifeSpan BioSciences | LS-B8177-50 | Anti-DCN / Decorin Antibody IHC-plus™ | Rabbit | Rabbit, Mouse, Rat, Pig, Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| Decorin (DCN) | LifeSpan BioSciences | LS-C99324-400 | Anti-DCN / Decorin Antibody (aa122-150) | Rabbit | Mouse, Human | Polyclonal | na |
| Decorin (DCN) | MyBioSource.com | MBS690954 | Mouse Anti-Human Decorin | Mouse | Human (Hu) | Monoclonal | (#6Z1) |
| Decorin (DCN) | MyBioSource.com | MBS2543875 | Rabbit Anti-Decorin Antibody | Rabbit | Human (Hu) | Monoclonal | ? |
| Decorin (DCN) | Novus Biologicals | NBP2-37336 | Decorin Antibody (1G4C5) | Mouse | Human (Hu) | Monoclonal | 1G4C5 |
| Decorin (DCN) | Novus Biologicals | NBP2-37333 | Decorin Antibody (5E8E7) | Mouse | Human (Hu) | Monoclonal | 5E8E7 |
| Decorin (DCN) | OriGene Technologies | AM20879PU-N | anti Decorin (full length) | Mouse | Human (Hu) | Monoclonal | 3H4-1F4 |
| Decorin (DCN) | ProSci, Inc | 51-449 | Decorin Antibody [3H4-1F4] | Mouse | Human (Hu) | Monoclonal | [3H4-1F4] |
| Decorin (DCN) | R&D Systems | MAB1432 | Decorin Antibody | Mouse | Human (Hu) | Monoclonal | 115424 |
| Decorin (DCN) | R&D Systems | MAB143 | Decorin Antibody | Mouse | Human (Hu) | Monoclonal | 115402 |
| Decorin (DCN) | R&D Systems | AF143 | Decorin Antibody | Goat | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| Decorin (DCN) | Santa Cruz Biotechnology, Inc. | sc-517271 | Decorin (1G4C5) Antibody | mouse | Human (Hu) | monoclonal | 1G4C5 |
| Decorin (DCN) | Santa Cruz Biotechnology, Inc. | sc-73896 | Decorin (9XX) | mouse | Human (Hu) | monoclonal | 9XX |
| Decorin (DCN) | Sino Biological, Inc. | 10189-R004 | Decorin / DCN / SLRR1B Antibody, Rabbit MAb | Rabbit | Human (Hu) | Monoclonal | 4 |
| Decorin (DCN) | United States Biological | D1875-06-500ug | Mouse Anti-Decorin Antibody | mouse | Human (Hu) | Monoclonal | 9j121 |
| Decorin (DCN) | United States Biological | D1875-06D-50ug | Mouse Anti-Decorin Antibody | mouse | Human (Hu) | Monoclonal | 3H4-1F4 |
| Decorin (DCN) | United States Biological | 216445-100ug | Mab Mo x human DCN (Decorin) Antibody | mouse | Human (Hu) | Monoclonal | 14L349 |
| Decorin (DCN) | ABclonal | A1669 | DCN Antibody | Rabbit | Human, Mouse, Rat | Polyclonal | na |
| Decorin (DCN) | Abnova Corporation | PAB18704 | DCN polyclonal antibody | Goat | Human | Polyclonal | na |
| Decorin | Abnova | H000016 | DCN | Mouse | Human, | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| (DCN) | Corporation | 34-B01 | MaxPab mouse polyclonal antibody (B01) | | Human, Rat | | |
| Decorin (DCN) | Abnova Corporation | PAB9509 | DCN polyclonal antibody | Rabbit | Human, Mouse, Pig, Rabbit, Rat, Human | Polyclonal | na |
| Decorin (DCN) | Abnova Corporation | PAB9510 | DCN polyclonal antibody | Rabbit | Human, Mouse, Pig, Rabbit, Rat, Human | Polyclonal | na |
| Decorin (DCN) | Abnova Corporation | H00001634-A01 | DCN polyclonal antibody (A01) | Mouse | Human | Polyclonal | na |
| Decorin (DCN) | Abnova Corporation | H00001634-B01P | DCN purified MaxPab mouse polyclonal antibody (B01P) | Mouse | Human, Human, Rat | Polyclonal | na |
| Decorin (DCN) | Abnova Corporation | H00001634-D01P | DCN purified MaxPab rabbit polyclonal antibody (D01P) | Rabbit | Human | Polyclonal | na |
| Decorin (DCN) | Abnova Corporation | PAB30851 | DCN polyclo | Rabbit | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | nal antibody | | | | |
| Decorin (DCN) | Biorbyt | orb18168 | Decorin antibody | Rabbit | Human, Rat | Polyclonal | na |
| Decorin (DCN) | Biorbyt | orb241575 | Decorin antibody | Rabbit | Human | Polyclonal | na |
| Decorin (DCN) | Biorbyt | orb86456 | Decorin antibody | Sheep | Human | Polyclonal | na |
| Decorin (DCN) | Biorbyt | orb10520 | Decorin antibody | Rabbit | Human, Mouse, Rat, Guinea Pig | Polyclonal | na |
| Decorin (DCN) | Biorbyt | orb36745 | Decorin antibody | Rabbit | Human, Mouse | Polyclonal | na |
| Decorin (DCN) | Biorbyt | orb96420 | Decorin antibody | Goat | Human, Monkey | Polyclonal | na |
| Decorin (DCN) | Biorbyt | orb386318 | DCN antibody | Rabbit | Human, Mouse | Polyclonal | na |
| Decorin (DCN) | Biorbyt | orb386292 | DCN antibody | Rabbit | Human, Mouse | Polyclonal | na |
| Decorin (DCN) | Biorbyt | orb386294 | DCN antibody | Rabbit | Human, Mouse | Polyclonal | na |
| Decorin (DCN) | Biorbyt | orb192289 | DCN antibody | Rabbit | Human, Mouse, Rat | Polyclonal | na |
| Decorin (DCN) | Biorbyt | orb215928 | DCN antibody | Rabbit | Human, Rat | Polyclonal | na |
| Decorin (DCN) | Biorbyt | orb221233 | DCN antibody | Rabbit | Human, Rat | Polyclonal | na |
| Decorin (DCN) | Biorbyt | orb375309 | DCN antibod | Rabbit | Human, Mouse, | Polyclonal | na |

FIG. 18 (Cont'd)

| Antigen | Company | Cat. No. | Name | Species | Reacts with | Mono- or Polyclonal | Clone # |
|---|---|---|---|---|---|---|---|
| | | | y | | Rat, Pig | | |
| Decorin (DCN) | Biorbyt | orb375243 | DCN antibody | Rabbit | Human, Mouse, Rat, Pig | Polyclonal | na |
| Decorin (DCN) | Biorbyt | orb48349 | DCN antibody | Rabbit | Human, Mouse, Rat | Polyclonal | na |
| Decorin (DCN) | Biorbyt | orb20265 | DCN antibody | Goat | Human | Polyclonal | na |
| Decorin (DCN) | Biorbyt | orb228678 | DCN antibody | Rabbit | Human, Mouse, Rat | Polyclonal | na |
| Decorin (DCN) | Biorbyt | orb378026 | DCN antibody | Rabbit | Human, Mouse, Rat | Polyclonal | na |
| Decorin (DCN) | LifeSpan BioSciences | LS-B8312-50 | Anti-DCN / Decorin Antibody (aa232-246) IHC-plus™ | Goat | Human, Monkey | Polyclonal | na |
| Decorin (DCN) | LifeSpan BioSciences | LS-B8745-50 | Anti-DCN / Decorin Antibody IHC-plus™ | Rabbit | Rabbit, Mouse, Rat, Pig, Human | Polyclonal | na |
| Decorin (DCN) | LifeSpan BioSciences | LS-C192752-100 | Anti-DCN / Decorin Antibody | Rabbit | Mouse, Rat, Human | Polyclonal | na |
| Decorin (DCN) | LifeSpan BioSciences | LS-C307208-50 | Anti-DCN / Decorin Antibody | Mouse | Rat, Human | Polyclonal | na |
| Decorin (DCN) | LifeSpan BioScience | LS-C310119 | Anti-DCN / | Rabbit | Human | Polyclonal | na |

FIG. 18 (Cont'd)

| Antigen | Company | Cat. No. | Name | Species | Reacts with | Mono- or Polyclonal | Clone # |
|---|---|---|---|---|---|---|---|
| | s | -100 | Decorin Antibody | | | | |
| Decorin (DCN) | LifeSpan BioSciences | LS-C331624-50 | Anti-DCN / Decorin Antibody | Rabbit | Mouse, Rat, Human | Polyclonal | na |
| Decorin (DCN) | LifeSpan BioSciences | LS-C403953-120 | Anti-DCN / Decorin Antibody | Rabbit | Hu, Ms, Rt | Polyclonal | na |
| Decorin (DCN) | LifeSpan BioSciences | LS-C331624-200 | Anti-DCN / Decorin Antibody | Rabbit | Hu, Ms, Rt | Polyclonal | na |
| Decorin (DCN) | LifeSpan BioSciences | LS-C331624-100 | Anti-DCN / Decorin Antibody | Rabbit | Hu, Ms, Rt | Polyclonal | na |
| Decorin (DCN) | LifeSpan BioSciences | LS-C393203-100 | Anti-DCN / Decorin Antibody | Rabbit | Hu, Ms, Rt | Polyclonal | na |
| Decorin (DCN) | LifeSpan BioSciences | LS-C403953-60 | Anti-DCN / Decorin Antibody | Rabbit | Hu, Ms, Rt | Polyclonal | na |
| Decorin (DCN) | LifeSpan BioSciences | LS-C403953-200 | Anti-DCN / Decorin Antibody | Rabbit | Hu, Ms, Rt | Polyclonal | na |
| Decorin (DCN) | LifeSpan BioSciences | LS-C128548-100 | Anti-DCN / Decorin Antibody (C- | Rabbit | Hu, Ms, Rt | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | Terminus) | | | | |
| Decorin (DCN) | LifeSpan BioSciences | LS-C171988-100 | Anti-DCN / Decorin Antibody (C-Terminus) | Rabbit | Hu, Ms, Rt | Polyclonal | na |
| Decorin (DCN) | LifeSpan BioSciences | LS-C403953-20 | Anti-DCN / Decorin Antibody | Rabbit | Hu, Ms, Rt | Polyclonal | na |
| Decorin (DCN) | LifeSpan BioSciences | LS-B14959-50 | Anti-DCN / Decorin Antibody (aa 20-359) IHC-plus™ | Rabbit | Human (Hu) | Polyclonal | na |
| Decorin (DCN) | LifeSpan BioSciences | LS-C344032-100 | Anti-DCN / Decorin Antibody (aa31-359) | Rabbit | Rat, Human | Polyclonal | na |
| Decorin (DCN) | LifeSpan BioSciences | LS-C293647-100 | Anti-DCN / Decorin Antibody (aa31-359) | Rabbit | Human | Polyclonal | na |
| Decorin (DCN) | LifeSpan BioSciences | LS-C293652-100 | Anti-DCN / Decorin Antibody (aa45-152) | Rabbit | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| Decorin (DCN) | LifeSpan BioSciences | LS-C485845-100 | Anti-DCN / Decorin Antibody | Rabbit | Human | Polyclonal | na |
| Decorin (DCN) | LifeSpan BioSciences | LS-C485844-400 | Anti-DCN / Decorin Antibody | Rabbit | Human | Polyclonal | na |
| Decorin (DCN) | LifeSpan BioSciences | LS-C485843-100 | Anti-DCN / Decorin Antibody | Rabbit | Human | Polyclonal | na |
| Decorin (DCN) | LifeSpan BioSciences | LS-C485843-200 | Anti-DCN / Decorin Antibody | Rabbit | Human | Polyclonal | na |
| Decorin (DCN) | LifeSpan BioSciences | LS-C485843-50 | Anti-DCN / Decorin Antibody | Rabbit | Human | Polyclonal | na |
| Decorin (DCN) | LifeSpan BioSciences | LS-C485845-50 | Anti-DCN / Decorin Antibody | Rabbit | Human | Polyclonal | na |
| Decorin (DCN) | LifeSpan BioSciences | LS-C660230-100 | Anti-DCN / Decorin Antibody | Rabbit | Human | Polyclonal | na |
| Decorin (DCN) | LifeSpan BioSciences | LS-B6704-50 | Anti-DCN / Decorin Antibody (aa36-85) IHC- | Rabbit | Rabbit, Dog, Guinea pig, Hamster, Pig, Horse, Human, | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | plus™ | | Monkey | | |
| Decorin (DCN) | LifeSpan BioSciences | LS-C22770-1000 | Anti-DCN / Decorin Antibody (aa316-329) | Sheep | Mouse, Dog, Guinea pig, Hamster, Pig, Horse, Bat, Human, Monkey | Polyclonal | na |
| Decorin (DCN) | LifeSpan BioSciences | LS-C388351-100 | Anti-DCN / Decorin Antibody (aa343-359) | Rabbit | Mouse, Dog, Guinea pig, Rat, Hamster, Pig, Horse, Bat, Human | Polyclonal | na |
| Decorin (DCN) | LifeSpan BioSciences | LS-C293647-200 | Anti-DCN / Decorin Antibody (aa31-359) | Rabbit | Human | Polyclonal | na |
| Decorin (DCN) | LifeSpan BioSciences | LS-C293652-20 | Anti-DCN / Decorin Antibody (aa45-152) | Rabbit | Human | Polyclonal | na |
| Decorin (DCN) | LifeSpan BioSciences | LS-C293647-20 | Anti-DCN / Decorin Antibody (aa31-359) | Rabbit | Human | Polyclonal | na |
| Decorin (DCN) | LifeSpan BioScience | LS-C293652 | Anti-DCN / | Rabbit | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | s | -200 | Decorin Antibody (aa45-152) | | | | |
| Decorin (DCN) | MyBioSource.com | MBS175601 | Anti-Decorin antibody | Rabbit | Human, Mouse, Rat | Polyclonal | na |
| Decorin (DCN) | MyBioSource.com | MBS177488 | Anti-Decorin Antibody | Rabbit | Human, Rat | Polyclonal | na |
| Decorin (DCN) | MyBioSource.com | MBS840859 | Decorin Antibody | Rabbit | Human, Mouse, Rat, Rabbit, Pig | Polyclonal | na |
| Decorin (DCN) | MyBioSource.com | MBS840644 | Decorin Antibody | Rabbit | Human, Mouse, Rat, Rabbit, Pig | Polyclonal | na |
| Decorin (DCN) | MyBioSource.com | MBS421985 | Goat anti-Decorin Antibody | Goat | Human, Cow, Pig, Cavia | Polyclonal | na |
| Decorin (DCN) | MyBioSource.com | MBS716239 | Rabbit anti-human decorin polyclonal Antibody | Rabbit | Human, Mouse, Rat | Polyclonal | na |
| Decorin (DCN) | MyBioSource.com | MBS1490929 | Rabbit anti-human Decorin polyclonal Antibod | Rabbit | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | y | | | | |
| Decorin (DCN) | MyBioSource.com | MBS221111 | SHEEP ANTI HUMAN DECORIN (aa36-49) | Sheep | Bovine, Chicken | Polyclonal | na |
| Decorin (DCN) | MyBioSource.com | MBS622492 | Sheep Anti-Decorin Antibody | Sheep | Bovine, Chicken, Human | Polyclonal | na |
| Decorin (DCN) | MyBioSource.com | MBS768553 | Decorin Rabbit Polyclonal | Rabbit | Human, Mouse, Rat | Polyclonal | na |
| Decorin (DCN) | MyBioSource.com | MBS244947 | Goat Polyclonal to Human DCN / Decorin | Goat | Gibbon, Chimpanzee, Gorilla, Human, Monkey | Polyclonal | na |
| Decorin (DCN) | MyBioSource.com | MBS2004983 | Polyclonal Antibody to Decorin (DCN) | Rabbit | Human | Polyclonal | na |
| Decorin (DCN) | MyBioSource.com | MBS2007005 | Polyclonal Antibody to Decorin (DCN) | Rabbit | Human | Polyclonal | na |
| Decorin (DCN) | MyBioSource.com | MBS418093 | Anti-DCN (decorin isoform d) Antibod | Rabbit | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | y | | | | |
| Decorin (DCN) | MyBioSource.com | MBS127148 | DCN Polyclonal Antibody | Rabbit | Human, Mouse, Rat | Polyclonal | na |
| Decorin (DCN) | MyBioSource.com | MBS2516635 | DCN Polyclonal Antibody | Rabbit | Human, Mouse, Rat | Polyclonal | na |
| Decorin (DCN) | MyBioSource.com | MBS625596 | Rabbit Anti-DCN Antibody | Rabbit | Human, Mouse | Polyclonal | na |
| Decorin (DCN) | MyBioSource.com | MBS9209128 | DCN Antibody (Center) | Rabbit | Human, mouse (Predicted Reactivity: Bovine, Pig) | Polyclonal | na |
| Decorin (DCN) | Novus Biologicals | NBP1-84970 | Decorin Antibody | Rabbit | Human | Polyclonal | na |
| Decorin (DCN) | Novus Biologicals | NB100-74403 | Decorin Neo Antibody | Rabbit | Human, Mouse, Bovine | Polyclonal | na |
| Decorin (DCN) | Novus Biologicals | NBP1-51962 | Decorin Antibody | Goat | Human | Polyclonal | na |
| Decorin (DCN) | Novus Biologicals | NBP1-32270 | Decorin Antibody | Rabbit | Human | Polyclonal | na |
| Decorin (DCN) | Novus Biologicals | NBP1-57923 | Decorin Antibody | Rabbit | Human | Polyclonal | na |
| Decorin (DCN) | Novus Biologicals | NBP1-57944 | Decorin Antibody | Rabbit | Human | Polyclonal | na |
| Decorin | Novus | NBP1- | Decorin | Sheep | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| (DCN) | Biologicals | 02605 | Antibody | | | | |
| Decorin (DCN) | Novus Biologicals | 2354000 2-0.1mg | Decorin Antibody | Rabbit | Human | Polyclonal | na |
| Decorin (DCN) | Novus Biologicals | NBP2-56346 | Decorin Antibody | Rabbit | Human | Polyclonal | na |
| Decorin (DCN) | Novus Biologicals | NB100-65669 | Proteoglycan 2 Precursor Antibody | Sheep | Human | Polyclonal | na |
| Decorin (DCN) | United States Biological | D1875-06C-100ug | Goat Anti-Decorin Antibody | goat | Hu | Polyclonal | na |
| Decorin (DCN) | United States Biological | 313262-100ug | Pab Rb x human Decorin Antibody | rabbit | Hu, Mo | Polyclonal | na |
| Decorin (DCN) | United States Biological | 350594-100ug | Pab Rb x human Decorin (DCN) Antibody | rabbit | Hu, Rt | Polyclonal | na |
| Decorin (DCN) | United States Biological | 313264-150ul | Pab Rb x human Decorin Antibody | rabbit | Hu, Mo, Rt | Polyclonal | na |
| Decorin (DCN) | United States Biological | 313262-50ug | Pab Rb x human Decorin | rabbit | Hu, Mo | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | Antibody | | | | |
| Decorin (DCN) | United States Biological | 313264-50ul | Pab Rb x human Decorin Antibody | rabbit | Hu, Mo, Rt | Polyclonal | na |
| Decorin (DCN) | United States Biological | 144446-100ug | Rabbit Anti-Decorin Antibody | rabbit | Hu, Mo, Rt | Polyclonal | na |
| Decorin (DCN) | United States Biological | 215275-100ug | Rabbit Anti-Decorin Antibody | rabbit | Hu, Rt | Polyclonal | na |
| Decorin (DCN) | United States Biological | 210444-100ul | Rabbit Anti-Decorin Antibody | rabbit | Hu, Mo, Rt | Polyclonal | na |
| Decorin (DCN) | United States Biological | 125752-50ug | Mouse Anti-Decorin Antibody | mouse | Hu, Rt | Polyclonal | na |
| Decorin (DCN) | United States Biological | D1875-06F-100ug | Rabbit Anti-Decorin Antibody | rabbit | Hu, Mo, Po, Rb, Rt | Polyclonal | na |
| Decorin (DCN) | United States Biological | D1875-06E-100ug | Rabbit Anti-Decorin Antibody | rabbit | Hu, Mo, Po, Rt | Polyclonal | na |
| Decorin (DCN) | United States Biological | 125753-100ug | Rabbit Anti-Decorin Antibody | rabbit | Hu | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| Decorin (DCN) | United States Biological | 140029-50ug | Rabbit Anti-Decorin Antibody | rabbit | Hu | Polyclonal | na |
| Decorin (DCN) | United States Biological | 140030-50ug | Rabbit Anti-Decorin Antibody | rabbit | Hu | Polyclonal | na |
| Decorin (DCN) | United States Biological | 140029-100ug | Rabbit Anti-Decorin Antibody | rabbit | Hu | Polyclonal | na |
| Decorin (DCN) | United States Biological | D1875-05C-50ug | Sheep Anti-Decorin Antibody | sheep | Hu | Polyclonal | na |
| Decorin (DCN) | United States Biological | D1875-05B-100ug | Rabbit Anti-Decorin Antibody | rabbit | Hu, Mo, Rt | Polyclonal | na |
| Decorin (DCN) | United States Biological | 140030-100ug | Rabbit Anti-Decorin Antibody | rabbit | Hu | Polyclonal | na |
| Decorin (DCN) | United States Biological | D1875-500ul | Sheep Anti-Decorin Antibody | sheep | Bo, Ch, Hu | Polyclonal | na |
| Decorin (DCN) | United States Biological | D1875-100ul | Sheep Anti-Decorin Antibody | sheep | Bo, Ch, Hu | Polyclonal | na |
| Decorin (DCN) | United States Biological | D1875-05-1ml | Sheep Anti-Decorin | sheep | Bo, Ch, Hu | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | , CT, aa316-329 Antibody | | | | |
| Decorin (DCN) | United States Biological | D1875-1ml | Sheep Anti-Decorin Antibody | sheep | Bo, Ch, Hu | Polyclonal | na |
| Decorin (DCN) | United States Biological | 245215-50ul | Mouse Anti-DCN Antibody | mouse | Hu | Polyclonal | na |
| Decorin (DCN) | United States Biological | 222107-100ul | Rabbit Anti-DCN Antibody | rabbit | Hu, Mo, Rt | Polyclonal | na |
| Decorin (DCN) | United States Biological | 222107-50ul | Rabbit Anti-DCN Antibody | rabbit | Hu, Mo, Rt | Polyclonal | na |
| Decorin (DCN) | United States Biological | 313103-100ul | Pab Rb x human DCN Antibody | rabbit | Hu, Mo, Rt | Polyclonal | na |
| KIM1 | R&D Systems | MAB1750 | Human TIM-1/KIM-1/HAVCR Antibody | Mouse | Human | Mono | 219211 |
| KIM1 | R&D Systems | MAB17502 | Human TIM-1/KIM-1/HAVCR | Mouse | Human | Mono | 526114R |

*FIG. 18 (Cont'd)*

| Antigen | Company | Cat. No. | Name | Species | Reacts with | Mono- or Polyclonal | Clone # |
|---|---|---|---|---|---|---|---|
| | | | Antibody | | | | |
| KIM1 | Novus | NBP2-11925 | TIM-1/KIM-1/HAVCR Antibody (MM0570-6D21) | Mouse | Human | Mono | MM0570-6D21 |
| KIM1 | Novus | H00026762 | TIM-1/KIM-1/HAVCR Antibody ELISA | Mouse | Human | Mono | 2G11 |
| KIM1 | Novus | H00026762-M02 | TIM-1/KIM-1/HAVCR Antibody ELISA | Mouse | Human | Mono | 2B9 |
| KIM1 | Novus | H00026762-M04 | TIM-1/KIM-1/HAVCR Antibody ELISA | Mouse | Human | Mono | 1G1 |
| KIM1 | Novus | NBP2-32775 | TIM-1/KIM-1/HAVCR Antibody ELISA | Mouse | Human | Mono | KIM70 |
| KIM1 | Novus | NBP2-32776 | TIM-1/KIM-1/HAVCR | Mouse | Human | Mono | KIM75 |

*FIG. 18 (Cont'd)*

| Antigen | Company | Cat. No. | Name | Species | Reacts with | Mono- or Polyclonal | Clone # |
|---|---|---|---|---|---|---|---|
| | | | Antibody ELISA | | | | |
| KIM1 | CST | 14971 | TIM-1 (E1R9N) Rabbit mAb #14971 | Rabbit | Human | Mono | E1R9N |
| KIM1 | Enzo | ADI-905-905-0100 | KIM-1 (human) monoclonal antibody (3E3) ELISA | Mouse | Human | Mono | 3E3 |
| KIM1 | Creative Diagnostics | DCAB-TJ219 | Magic™ Anti-KIM-1 monoclonal antibody, clone C2695N (DCAB-TJ219) | Mouse | Human | Mono | C2695N |
| KIM1 | Creative Diagnostics | DCAB-TJ218 | Magic™ Anti-KIM-1 monoclonal antibody, clone C2694N (DCAB-TJ218) | Mouse | Human | Mono | C2694N |
| KIM1 | Abcam | ab233714 | Anti-TIM 1 antibody | Mouse | Human | Mono | [3A12E10] |

*FIG. 18 (Cont'd)*

| Antigen | Company | Cat. No. | Name | Species | Reacts with | Mono- or Polyclonal | Clone # |
|---|---|---|---|---|---|---|---|
| | | | [3A12E10] (ab233714) | | | | |
| KIM1 | Abcam | ab233720 | Anti-TIM 1 antibody [3D9F5] (ab233720) | Mouse | Human | Mono | [3D9F5] |
| ADAM12 | Abcam | ab39155 | Anti-ADAM12 antibody - Aminoterminal end | Rabbit | Hu, Ms, Rt, Pg | Polyclonal | na |
| ADAM12 | Abcam | ab28747 | Anti-ADAM12 antibody | Goat | Human (Hu) | Polyclonal | na |
| ADAM12 | Abcam | ab115203 | Anti-ADAM12 antibody | Goat | Human (Hu) | Polyclonal | na |
| ADAM12 | Abcam | ab223476 | Anti-ADAM12 | Goat | Mouse, Rat, Human, Pig | Polyclonal | na |
| ADAM12 | Abcam | ab223745 | Anti-ADAM12 | rabbit | human | Polyclonal | na |
| ADAM12 | Abcam | ab234189 | Anti-ADAM12 | mouse | human | Monoclonal | 24F.10C12 |
| ADAM12 | Invitrogen Antibodies | MA5-24285 | ADAM12 Monocl | Mouse | Human (Hu) | Monoclonal | 632525 |

*FIG. 18 (Cont'd)*

| Antigen | Company | Cat. No. | Name | Species | Reacts with | Mono- or Polyclonal | Clone # |
|---|---|---|---|---|---|---|---|
| | | | onal Antibody (632525) | | | | |
| ADAM12 | Invitrogen Antibodies | PA5-46950 | ADAM12 Polyclonal Antibody | Sheep | Human (Hu) | Polyclonal | na |
| ADAM12 | Invitrogen Antibodies | PA1-20301 | ADAM12 Polyclonal Antibody | Rabbit | Human (Hu) | Polyclonal | na |
| ADAM12 | Invitrogen Antibodies | PA5-18314 | ADAM12 Polyclonal Antibody | Goat | Human (Hu) | Polyclonal | na |
| ADAM12 | Invitrogen Antibodies | PA5-50594 | ADAM12 Polyclonal Antibody | Rabbit | Hu, Ms | Polyclonal | na |
| ADAM12 | Invitrogen Antibodies | PA5-75796 | ADAM12 Polyclonal Antibody | Rabbit | Hu, Ms, Rt | Polyclonal | na |
| ADAM12 | MilliporeSigma | SAB2100046 | Anti-ADAM12 | rabbit | horse, rabbit, bovine, guinea pig, mouse, human, rat | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| ADAM12 | MilliporeSigma | HPA030867 | Anti-ADAM12 | rabbit | human | Polyclonal | na |
| ADAM12 | MilliporeSigma | HPA030866 | Anti-ADAM12 | rabbit | human | Polyclonal | na |
| ADAM12 | MilliporeSigma | HPA030868 | Anti-ADAM12 | rabbit | human | Polyclonal | na |
| ADAM12 | MilliporeSigma | MABT1330 | ADAM12 Antibody | Mouse | Human | mono | 8F8 |
| ADAM12 | MilliporeSigma | MABT1331 | ADAM12 Antibody | Mouse | Human | mono | 6E6 |
| ADAM12 | Novus | NB300-889 | ADAM12 Antibody | Goat | Human (Hu) | Polyclonal | na |
| ADAM12 | Novus | NBP1-82791 | ADAM12 Antibody | Rabbit | Human (Hu) | Polyclonal | na |
| ADAM12 | Novus | NBP2- | ADAM1 | Rabbit | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | 33939 | 2 Antibody | | (Hu) | | |
| ADAM12 | Novus | NBP2-33940 | ADAM12 Antibody | Rabbit | Human (Hu) | Polyclonal | na |
| ADAM12 | Novus | MAB44161 | ADAM12 Antibody | Mouse | Human (Hu) | mono | 632525 |
| ADAM12 | Novus | AF4416 | ADAM12 Antibody | Sheep | Human (Hu) | Polyclonal | na |
| ADAM12 | Novus | NBP1-59142 | ADAM12 Antibody | Rabbit | Human (Hu) | Polyclonal | na |
| ADAM12 | Novus | H00008038-D01P | ADAM12 Antibody | Rabbit | Human (Hu) | Polyclonal | na |
| ADAM12 | Novus | H00008038-M01 | ADAM12 Antibody | Mouse | Human (Hu) | mono | IG3 |
| ADAM12 | R&D Systems | MAB44161 | ADAM12 Antibody | Mouse | Human (Hu) | Monoclonal | 632525 |
| ADAM12 | R&D Systems | AF4416 | ADAM12 Antibody | Sheep | Human (Hu) | Polyclonal | na |
| ADAM12 | Raybiotech, Inc. | 119-13202 | Goat Anti-Human ADAM12 (N-Terminus) | Goat | Human (Hu) | Polyclonal | na |
| ADAM12 | Sino | 10896- | ADAM1 | Rabbit | Human | Monoclon | 737 |

*FIG. 18 (Cont'd)*

| Antigen | Company | Cat. No. | Name | Species | Reacts with | Mono- or Polyclonal | Clone # |
|---|---|---|---|---|---|---|---|
| | Biological, Inc. | R737 | 2 Antibody, Rabbit MAb | | (Hu) | al | |
| ADAM12 | Sino Biological, Inc. | 10896-MM10 | ADAM12 / MLTN Antibody, Mouse MAb | Mouse | Human (Hu) | Monoclonal | 3G1B10B9 |
| ADAM12 | Sino Biological, Inc. | 10896-RP02 | ADAM12 / MLTN Antibody, Rabbit PAb, Antigen Affinity Purified | Rabbit | Human (Hu) | Polyclonal | na |
| ADAM12 | Sino Biological, Inc. | 10896-R001 | ADAM12 / MLTN Antibody, Rabbit MAb | Rabbit | Human (Hu) | Monoclonal | 1 |
| ADAM12 | Sino Biological, Inc. | 10896-RP01 | ADAM12 / MLTN Antibody, Rabbit PAb | Rabbit | Human (Hu) | Polyclonal | na |
| ENDOGLIN (ENG) | CST | 14606 | Endoglin (3A9) Mouse mAb | Mouse | Human | Mono | 3A9 |
| ENDOGLIN (ENG) | CST | 4335 | Endoglin (3A9) Mouse | Rabbit | Human | Mono | D50G1 |

*FIG. 18 (Cont'd)*

| Antigen | Company | Cat. No. | Name | Species | Reacts with | Mono- or Polyclonal | Clone # |
|---|---|---|---|---|---|---|---|
| | | | mAb | | | | |
| ENDOGLIN (ENG) | R&D Systems | MAB1097 | Human Endoglin/CD105 Antibody | Mouse | Human | Mono | 166709 |
| ENDOGLIN (ENG) | R&D Systems | MAB10971 | Human Endoglin/CD105 Antibody | Mouse | Human | Mono | 166707 |
| ENDOGLIN (ENG) | R&D Systems | MAB10972 | Human Endoglin/CD105 Antibody | Mouse | Human | Mono | 166713 |
| ENDOGLIN (ENG) | R&D Systems | AF1097 | Human Endoglin/CD105 Antibody | Goat | Human | Poly | NA |
| ENDOGLIN (ENG) | Novus | NBP2-34493 | Endoglin/CD105 Antibody (CL1912) | Mouse | Human | Mono | CL1912 |
| ENDOGLIN (ENG) | Novus | NBP1-91212 | Endoglin/CD105 Antibody | Rabbit | Human | Poly | NA |
| ENDOGLIN (ENG) | Novus | NBP2-49516 | Endoglin/CD105 Antibody | Rabbit | Human | Poly | NA |
| ENDOGLIN | Novus | NBP2- | Endogli | Mouse | Human | Mono | ENG/132 |

*FIG. 18 (Cont'd)*

| Antigen | Company | Cat. No. | Name | Species | Reacts with | Mono- or Polyclonal | Clone # |
|---|---|---|---|---|---|---|---|
| IN (ENG) | | 53327 | n/CD105 Antibody (ENG/1326) | | | | 6 |
| ENDOGLIN (ENG) | Novus | NBP1-35471 | Endoglin/CD105 Antibody | Rabbit | Human | Poly | NA |
| ENDOGLIN (ENG) | 22 Abcam (13 mono; 9 poly) | | | | | | |
| ENDOGLIN (ENG) | Abcam | ab11414 | Anti-CD105 antibody [SN6] | Mouse | Human, Rat | Mono | SN6 |
| ENDOGLIN (ENG) | Abcam | ab169545 | Anti-CD105 antibody [EPR10145-12] | Rabbit | Human | Mono | EPR10145-12 |
| ENDOGLIN (ENG) | Abcam | ab156756 | Anti-CD105 antibody [OTI8A1] | Mouse | Mouse, Rat, Dog, Human, Monkey | Mono | OTI8A1 |
| ENDOGLIN (ENG) | Abcam | ab107595 | Anti-CD105 antibody | Rabbit | Human, Mouse, Rat* | Poly | NA |
| ENDOGLIN (ENG) | Abcam | ab2529 | Anti-CD105 antibody [MEM-226] | Mouse | Human, Rat | Mono | MEM-226 |
| ENDOGLIN (ENG) | Abcam | ab114052 | Anti-CD105 antibod | Mouse | Human | Mono | 3A9 |

*FIG. 18 (Cont'd)*

| Antigen | Company | Cat. No. | Name | Species | Reacts with | Mono- or Polyclonal | Clone # |
|---|---|---|---|---|---|---|---|
| | | | y [3A9] | | | | |
| ENDOGLIN (ENG) | Abcam | ab49228 | Anti-CD105 antibody | Rabbit | Human, Mouse* | Poly | NA |
| ENDOGLIN (ENG) | Abcam | ab44967 | Anti-CD105 antibody [105C02] | Mouse | Human | Mono | 105C02 |
| ENDOGLIN (ENG) | Abcam | ab135528 | Anti-CD105 antibody | Rabbit | Human, Mouse | Poly | NA |
| ENDOGLIN (ENG) | Abcam | ab27422 | Anti-CD105 antibody, prediluted | Rabbit | Human | Poly | NA |
| ENDOGLIN (ENG) | Abcam | ab69772 | Anti-CD105 antibody [MEM-229] | Mouse | Human, Pig | Mono | MEM-229 |
| ENDOGLIN (ENG) | Abcam | ab170943 | Anti-CD105 antibody [EPR10145-10] | Rabbit | Human | Mono | EPR10145-10 |
| ENDOGLIN (ENG) | Abcam | ab21224 | Anti-CD105 antibody | Rabbit | Human | Poly | NA |
| ENDOGLIN (ENG) | Abcam | ab206419 | Anti-CD105 antibody [EPR19911] | Rabbit | Human | Mono | EPR19911 |

*FIG. 18 (Cont'd)*

| Antigen | Company | Cat. No. | Name | Species | Reacts with | Mono- or Polyclonal | Clone # |
|---|---|---|---|---|---|---|---|
| ENDOGLIN (ENG) | Abcam | ab137389 | Anti-CD105 antibody | Rabbit | Human | Poly | NA |
| ENDOGLIN (ENG) | Abcam | ab219362 | Anti-CD105 antibody [EPR10145-12] - Low endotoxin, Azide free | Rabbit | Human | Mono | EPR10145-10 |
| ENDOGLIN (ENG) | Abcam | ab85956 | Anti-CD105 antibody | Rabbit | Human, Orangutan* | Poly | NA |
| ENDOGLIN (ENG) | Abcam | ab124610 | Anti-CD105 antibody | Rabbit | Human, Chimpanzee*, Macaque monkey*, Gorilla* | Poly | NA |
| ENDOGLIN (ENG) | Abcam | ab74462 | Anti-CD105 antibody | Rabbit | Human | Poly | NA |
| ENDOGLIN (ENG) | Abcam | ab218387 | Anti-CD105 antibody [ENG/1327] | Mouse | Human | Mono | ENG/1327 |
| ENDOGLIN (ENG) | Abcam | ab218855 | Anti-CD105 antibody [ENG/1327] - BSA and | Mouse | Human | Mono | ENG/1327 |

*FIG. 18 (Cont'd)*

| Antigen | Company | Cat. No. | Name | Species | Reacts with | Mono- or Polyclonal | Clone # |
|---|---|---|---|---|---|---|---|
| | | | Azide free | | | | |
| ENDOGLIN (ENG) | Abcam | ab171225 | Anti-CD105 antibody [SN6] - Low endotoxin, Azide free | Mouse | Human, Rat | Mono | SN6 |
| ENDOGLIN (ENG) | ThermoFisher | | | | | Mono | SN6 |
| ENDOGLIN (ENG) | ThermoFisher | | | | | Mono | SN6h |
| ENDOGLIN (ENG) | ThermoFisher | | | | | Mono | MEM-226 |
| ENDOGLIN (ENG) | ThermoFisher | | | | | Mono | MEM-229 |
| ENDOGLIN (ENG) | ThermoFisher | | | | | Mono | 3A9 |
| ENDOGLIN (ENG) | Biolegend | 323202 | Purified anti-human CD105 Antibody | Mouse | Human | Mono | 43A3 |
| ENDOGLIN (ENG) | Biolegend | 800501 | Purified anti-human CD105 Antibody | Mouse | Human | Mono | SN6h |
| ENDOGLIN (ENG) | Biolegend | 684102 | Purified anti-human CD105 Antibody | Mouse | Human | Mono | 099E5 |
| ENDOGLIN (ENG) | Hycult Biotech | HM2140 | Endoglin, Human | Mouse | Not stated | Not stated | Not stated |

*FIG. 18 (Cont'd)*

| Antigen | Company | Cat. No. | Name | Species | Reacts with | Mono- or Polyclonal | Clone # |
|---|---|---|---|---|---|---|---|
| | | | , mAb E9 | | | | |
| ENDOGLIN (ENG) | Bosterbio | M02997 | Anti-Endoglin / CD105 (Angiogenesis Marker) Monoclonal Antibody | Mouse | Human | Mono | ENG/1327 |
| PLGF | R&D Systems | MAB264 | Human plGF Antibody | Mouse | Human | Mono | IgG1 Clone # 37203 |
| PLGF | R&D Systems | MAB264R | Human plGF Antibody | Mouse | Human | Mono | IgG1 Clone # 37203R |
| PLGF | R&D Systems | MAB2642 | Human plGF Antibody | Rat | Human | Mono | IgG2A Clone # 358905 |
| PLGF | R&D Systems | AF-264-PB | Human plGF Antibody | Goat | Human | Poly | NA |
| PLGF | R&D Systems | AF6837 | Human plGF Antibody | Sheep | Human | Poly | NA |
| PLGF | R&D Systems | AB-264-PB | Human plGF Antibody | Goat | Human | Poly | NA |
| PLGF | Abcam | ab140639 | Anti-PLGF antibody [EPR2802(2)] | Rabbit | Human | Mono | EPR2802(2) |

*FIG. 18 (Cont'd)*

| Antigen | Company | Cat. No. | Name | Species | Reacts with | Mono- or Polyclonal | Clone # |
|---|---|---|---|---|---|---|---|
| PLGF | Abcam | ab10966 | Anti-PLGF antibody [37203.111] | Mouse | Human | Mono | [37203.111] |
| PLGF | Abcam | ab190717 | Anti-PLGF antibody [PLGF94] | Mouse | Human | Mono | [PLGF94] |
| PLGF | Abcam | ab212717 | Anti-PLGF antibody [PLGF/94] - BSA and Azide free | Mouse | Human | Mono | [PLGF/94] |
| PLGF | Abcam | ab9542 | Anti-PLGF antibody - N-terminal | Rabbit | Human, Mouse | Poly | NA |
| PLGF | Abcam | ab196666 | Anti-PLGF antibody | Rabbit | Human, Mouse, Rat | Poly | NA |
| PLGF | Abcam | ab99250 | Anti-PLGF antibody | Goat | Human | Poly | NA |
| PLGF | Abcam | ab11938 | Anti-PlGF Antibody | Rabbit | Human | Poly | NA |
| PLGF | Abcam | ab83906 | Anti-PLGF antibod | Rabbit | Human | Poly | NA |

*FIG. 18 (Cont'd)*

| Antigen | Company | Cat. No. | Name | Species | Reacts with | Mono- or Polyclonal | Clone # |
|---|---|---|---|---|---|---|---|
| | | | y | | | | |
| PLGF | Abcam | ab217001 | Anti-PlGF Antibody | Rabbit | Human | Poly | NA |
| PLGF | Abcam | ab214917 | Anti-PlGF Antibody | Sheep | Human | Poly | NA |
| PLGF | EMD/Millipore | MABF241 | Anti-PLGF Antibody | Mouse | Human | Mono | 216-17 |
| PLGF | LSBio | LS-C91984-100 | Anti-PLGF Antibody | Mouse | Human | Mono | Not indicated |
| PLGF | LSBio | LS-C343156-100 | PGF / PLGF Antibody (clone 3G6-F5-F4) | Mouse | Human | Mono | 3G6-F5-F4 |
| PLGF | LSBio | LS-C343158-100 | PGF / PLGF Antibody (clone 2H8-E2-G11) | Mouse | Human | Mono | 2H8-E2-G11 |
| PLGF | LSBio | LS-C343168-100 | PGF / PLGF Antibody (clone 5E9-C7-G7-F7) | Mouse | Human | Mono | 5E9-C7-G7-F7 |
| PLGF | LSBio | LS-C358022-100 | PGF / PLGF Antibody (clone | Mouse | Human | Mono | PLGF94 |

*FIG. 18 (Cont'd)*

| Antigen | Company | Cat. No. | Name | Species | Reacts with | Mono- or Polyclonal | Clone # |
|---|---|---|---|---|---|---|---|
| | | | PLGF94) | | | | |
| PLGF | LSBio | LS-C391649-100 | PGF / PLGF Antibody (clone PLGF/93) | Mouse | Human | Mono | PLGF/93 |
| PLGF | OriGene | DM3524 | PLGF(PGF) Mouse Monoclonal Antibody [Clone ID: 342/3B10] | Mouse | Human | Mono | 342/3B10 |
| PLGF | OriGene | DM3525 | PLGF(PGF) Mouse Monoclonal Antibody [Clone ID: 178/G10] | Mouse | Human | Mono | 178/G10 |
| PLGF | OriGene | DM3526 | PLGF(PGF) Mouse Monoclonal Antibody [Clone ID: 331/H12] | Mouse | Human | Mono | 331/H12 |
| PLGF | OriGene | AM50307 | PLGF( | Mouse | Human | Mono | PLGF94 |

*FIG. 18 (Cont'd)*

| Antigen | Company | Cat. No. | Name | Species | Reacts with | Mono- or Polyclonal | Clone # |
|---|---|---|---|---|---|---|---|
| | | PU-S | PGF) Mouse Monoclonal Antibody [Clone ID: PLGF94] | | | | |
| PLGF | Novus | NB110-60976 | PLGF Antibody (MM0010-2D93) | Mouse | Human | Mono | MM0010-2D93 |
| PLGF | RayBiotech | 188-10153-SAF | Mouse anti-Human PLGF Antibody [Sodium Azide Free] | Mouse | Human | Mono | Not stated |
| PLGF | ThermoFisher | MA1-188 | PGF Monoclonal Antibody (24G3) | Mouse | Human | Mono | 24G3 |
| PLGF | CreativeBio Labs | HOM-19431 | Recombinant Human Anti-Human PLGF Monoclonal Antibody | Mouse | Human | Mono | Not stated |
| PLGF | USBio | 216895 | 216895 | Mouse | Human | Mono | 14L799 |

*FIG. 18 (Cont'd)*

| Antigen | Company | Cat. No. | Name | Species | Reacts with | Mono- or Polyclonal | Clone # |
|---|---|---|---|---|---|---|---|
|  |  |  | Mouse Anti-PLGF |  |  |  |  |
| PLGF | USBio | P4273-01B | P4273-01B Mouse Anti-PLGF | Mouse | Human | Mono | 9A373 |
| PAPP-A | Novus | NB100-73060 | Pappalysin-1/PAPP-A Antibody | Mouse | Human | Monoclonal | 7A6 |
| PAPP-A | Novus | NB200-404 | Pappalysin-1/PAPP-A Antibody | Mouse | Human | Monoclonal | 10H9 |
| PAPP-A | Novus | NB120-8346 | Pappalysin-1/PAPP-A Antibody | Mouse | Human | Monoclonal | 10E1 |
| PAPP-A | Novus | NB110-8423 | Pappalysin-1/PAPP-A Antibody | Mouse | Human | Monoclonal | 5H9 |
| PAPP-A | Novus | NB100-73059 | Pappalysin-1/PAPP-A Antibody | Mouse | Human | Monoclonal | 18A10 |
| PAPP-A | R&D Systems | AF2487 | Pappalysin-1 / PAPP-A Antibod | Goat | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | y | | | | |
| FGF21 | Abbexa Ltd | abx270292 | Fibroblast Growth Factor 21 (FGF21) | Rabbit | Human (Hu) | Polyclonal | na |
| FGF21 | Abcam | ab171941 | Recombinant FGF21 [EPR8314(2)] | Rabbit | Hu, Ms, Rt | Monoclonal | na |
| FGF21 | Abcam | ab77692 | Anti-FGF21 | Goat | Human (Hu) | Polyclonal | na |
| FGF21 | Abcam | ab66564 | Anti-FGF21 | Rabbit | Hu, Ms | Polyclonal | na |
| FGF21 | Abcam | ab64857 | Anti-FGF21 | Rabbit | Human, Mouse | Polyclonal | na |
| FGF21 | Abcam | ab219368 | Anti-FGF21 | Rabbit | Human, Mouse, Rat | Monoclonal | EPR8314(2) |
| FGF21 | Abcam | ab137715 | Anti-FGF21 | Rabbit | Human | Polyclonal | na |
| FGF21 | ABclonal | A10368 | FGF21 | Rabbit | Hu, Ms | Polyclonal | na |
| FGF21 | Abnova Corporation | PAB19883 | FGF21 polyclonal | Rabbit | Human (Hu) | Polyclonal | na |
| FGF21 | antibodies-online | ABIN595091 | anti-FGF21 (Fibroblast Growth Factor 21) | Rabbit | Hu, Ms, Mu | Polyclonal | na |
| FGF21 | antibodies-online | ABIN595090 | anti-FGF21 (Fibroblast Growth Factor 21) | Sheep | Human (Hu) | Polyclonal | na |
| FGF21 | AssayPro | 13018- | Human | Rabbit | Human | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | 05011 | Fibroblast Growth Factor 21 (FGF-21) | | (Hu) | | |
| FGF21 | Atlas Antibodies | HPA061286 | Anti-FGF21 | Rabbit | Human (Hu) | Polyclonal | na |
| FGF21 | Atlas Antibodies | AMAb91421 | Anti-FGF21 | Mouse | Human (Hu) | Monoclonal | CL6491 |
| FGF21 | Biomatik | CAC07045 | FGF21 Polyclonal | Rabbit | Human (Hu) | Polyclonal | na |
| FGF21 | Biorbyt | orb76187 | FGF21 | Rabbit | Human (Hu) | Polyclonal | na |
| FGF21 | Biorbyt | orb381065 | FGF21 | Rabbit | Human (Hu) | Polyclonal | na |
| FGF21 | Bioss Inc. | bs-2318R | FGF21 | Rabbit | Hu, Rt | Polyclonal | na |
| FGF21 | BosterBio | PA1673 | Anti-FGF21 | Rabbit | Hu, Ms, Rt | Polyclonal | na |
| FGF21 | BosterBio | PB10063 | Anti-FGF21 Picoband | Rabbit | Hu, Ms, Rt | Polyclonal | na |
| FGF21 | BosterBio | M00802 | Anti-FGF21 Rabbit Monoclonal | Rabbit | Hu, Ms, Rt | Monoclonal | AG-6 |
| FGF21 | Creative Diagnostics | DPABH-24921 | Anti-FGF21 (N-terminal) polyclonal | Rabbit | Human (Hu) | polyclonal | na |
| FGF21 | Creative Diagnostics | DPABH-00759 | Anti-FGF21 (aa 99-193) polyclonal | Rabbit | Human (Hu) | polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| FGF21 | EpiGentek | A52640 | FGF21 Polyclonal | Rabbit | Human (Hu) | Polyclonal | na |
| FGF21 | Fitzgerald Industries International | 10R-4111 | FGF21 | Mouse | Human (Hu) | monoclonal | 4B4 |
| FGF21 | Fitzgerald Industries International | 10R-4112 | FGF21 | Mouse | Human (Hu) | monoclonal | 1B4 |
| FGF21 | GeneTex | GTX64384 | Anti-FGF21 | Rabbit | Hu, Ms | Polyclonal | na |
| FGF21 | GeneTex | GTX111877 | Anti-FGF21 [N3C3] | Rabbit | Human (Hu) | Polyclonal | na |
| FGF21 | Invitrogen Antibodies | PA5-18811 | FGF21 Polyclonal | Goat | Human (Hu) | Polyclonal | na |
| FGF21 | Invitrogen Antibodies | PA5-29386 | FGF21 Polyclonal | Rabbit | Human (Hu) | Polyclonal | na |
| FGF21 | Invitrogen Antibodies | PA5-44325 | FGF21 Polyclonal | Rabbit | Hu, Ms, Rb, Rt, Bv, Ca, GP, Hr | Polyclonal | na |
| FGF21 | Invitrogen Antibodies | MA5-25522 | FGF21 Monoclonal (OTI4B2) | Mouse | Human (Hu) | Monoclonal | OTI4B2 |
| FGF21 | Invitrogen Antibodies | MA5-25558 | FGF21 Monoclonal (OTI1H4) | Mouse | Human (Hu) | Monoclonal | OTI1H4 |
| FGF21 | LifeSpan BioSciences | LS-C61737-100 | Anti-FGF21 (aa103-115) | Goat | Hu, Mk | Polyclonal | na |
| FGF21 | LifeSpan BioSciences | LS-C190802-200 | Anti-FGF21 (aa184- | Rabbit | Human (Hu) | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| | | | 209) | | | | |
| FGF21 | LifeSpan BioSciences | LS-C190801-200 | Anti-FGF21 (aa26-47) | Rabbit | Human (Hu) | Polyclonal | na |
| FGF21 | MyBioSource.com | MBS9406788 | FGF21 | Rabbit | Human (Hu) | Polyclonal | na |
| FGF21 | Novus Biologicals | NBP1-31368 | FGF-21 | Rabbit | Human (Hu) | Polyclonal | na |
| FGF21 | Novus Biologicals | NBP2-00645 | FGF-21 (OTI2F10) | Mouse | Human (Hu) | Monoclonal | OTI2F10 |
| FGF21 | NSJ Bioreagents | R30758 | FGF21 | Rabbit | Hu, Ms, Rt | Polyclonal (rabbit origin) | na |
| FGF21 | NSJ Bioreagents | R32531 | FGF21 | Rabbit | Human (Hu) | Polyclonal (rabbit origin) | na |
| FGF21 | Proteintech Group Inc | 26272-1-AP | FGF21 | Rabbit | Human (Hu) | Polyclonal | na |
| FGF21 | R&D Systems | AF2539 | FGF-21 | Goat | Human (Hu) | Polyclonal | na |
| FGF21 | R&D Systems | MAB25372 | FGF-21 | Mouse | Human (Hu) | Monoclonal | 461804 |
| FGF21 | R&D Systems | MAB25371 | FGF-21 | Mouse | Hu, Ms | Monoclonal | 315901 |
| FGF21 | R&D Systems | MAB2537 | FGF-21 | Mouse | Human (Hu) | Monoclonal | 315914 |
| FGF21 | R&D Systems | MAB25373 | FGF-21 | Goat | Human (Hu) | Monoclonal | 40020A |
| FGF21 | Santa Cruz Biotechnology, Inc. | sc-81946 | FGF-21 (Y-16) | mouse | Human (Hu) | monoclonal | Y-16 |
| FGF21 | Signalway Antibody LLC | 36478 | FGF21 | Rabbit | Human (Hu) | Polyclonal | na |
| FGF21 | Signalway Antibody LLC | 42458 | Fibroblast growth factor 21 Polyclonal | Rabbit | Human (Hu) | Polyclonal | na |

*FIG. 18 (Cont'd)*

| Antigen | Company | Cat. No. | Name | Species | Reacts with | Mono- or Polyclonal | Clone # |
|---|---|---|---|---|---|---|---|
| FGF21 | St John's Laboratory | STJ112405 | Anti-FGF21 | Rabbit | Hu, Ms | Polyclonal | na |
| FGF21 | United States Biological | 126777 | Mouse Anti-FGF21 | mouse | Hu, Rt | Polyclonal | na |
| FGF21 | United States Biological | 315928 | Pab Rb x human FGF21 | rabbit | Hu, Ms | Polyclonal | na |
| SFLT1 | ThermoFisher | 14-5936-82 | VEGF Receptor 1 (Flt1) Monoclonal Antibody (7A6), eBioscience™ | Rat | Human | Mono | 7A6 |
| SFLT1 | ThermoFisher | BMS196 | VEGF Receptor 1 (Flt1) Monoclonal Antibody (Flt-19), eBioscience™ | Mouse | Human | Mono | FLT-19 |
| SFLT1 | ThermoFisher | MA5-15550 | VEGF Receptor 1 Monoclonal Antibody (3D10) | Mouse | Human | Mono | 3D10 |
| SFLT1 | ThermoFisher | 36-1100 | VEGF Receptor 1 (solubl | Rabbit | Human | Poly | NA |

*FIG. 18 (Cont'd)*

| Antigen | Company | Cat. No. | Name | Species | Reacts with | Mono- or Polyclonal | Clone # |
|---|---|---|---|---|---|---|---|
| | | | e) Polyclonal Antibody | | | | |
| SFLT1 | Abgent | AJ1814a | VEGFR-1 Antibody (N-term) Rabbit Monoclonal Antibody | Rabbit | Human, Mouse | Mono | Y103 |
| SFLT1 | LSBio | LS-B9103 | FLT1 / VEGFR1 Antibody (N-Terminus) IHC-plus™ LS-A9405 (this antibody replaces LS-C76792) | Rabbit | Human, Rat | Poly | NA |
| SFLT1 | LSBio | LS-A9405 | FLT1 / VEGFR1 Antibody (N-Terminus) IHC-plus™ LS-B9103 | Rabbit | Human, Monkey*, Dog*, Horse* | Poly | NA |

*FIG. 18 (Cont'd)*

| Antigen | Company | Cat. No. | Name | Species | Reacts with | Mono- or Polyclonal | Clone # |
|---|---|---|---|---|---|---|---|
| | | | (This antibody replaces LS-C132867) | | | | |
| SFLT1 | LSBio | LS-C144953 | FLT1 / VEGFR1 Antibody (N-Terminus) | Rabbit | Human | Poly | NA |
| SFLT1 | Epitomics/ Abcam | 1303-1; ab32152 | Anti-VEGF Receptor 1 antibody [Y103] | Rabbit | Human, Mouse, Rat, Hamster | Mono | Y103 |
| SFLT1 | Abcam | ab184784 | Anti-VEGF Receptor 1 antibody [Y103] - Low endotoxin, Azide free | Rabbit | Human, Mouse, Rat, Hamster | Mono | Y103 |
| SFLT1 | Abcam | ab56300 | Anti-VEGF Receptor 1 antibody [AP-MAB0702] | Mouse | Human, Mouse | Mono | AP-MAB0702 |
| SFLT1 | Sigma | V4262 | Monoclonal | Mouse | Human | Mono | FLT-11 |

*FIG. 18 (Cont'd)*

| Antigen | Company | Cat. No. | Name | Species | Reacts with | Mono- or Polyclonal | Clone # |
|---|---|---|---|---|---|---|---|
| | | | Anti-Vascular Endothelial Growth Factor Receptor-1 antibody produced in mouse | | | | |
| SFLT1 | Creative Biolabs | TAB-177 | Anti-Human VEGFR-1 Therapeutic Antibody (Icrucumab) | Human | Human | Mono | |
| SFLT1 | Active Bioscience | 2029.650.200 | Anti-human Flt-1 / VEGFR-1 Agonistic (MAB) | Mouse | Human | Mono | |
| SFLT1 | Cell Sciences | CMV125 | Mouse Anti-human VEGFR1 Agonistic mAb | Mouse | Human | Mono | |
| SFLT1 | Novus | NB110-60964 | VEGFR1/Flt-1 Antibody | Mouse | Human | Mono | MM0001-7G96 |

*FIG. 18 (Cont'd)*

| Antigen | Company | Cat. No. | Name | Species | Reacts with | Mono- or Polyclonal | Clone # |
|---|---|---|---|---|---|---|---|
| | | | (MM0001-7G96) | | | | |
| SFLT1 | Novus | NBP2-21963 | VEGFR1/Flt-1 Antibody (MAB0702) | Mouse | Human, Mouse | Mono | MAB0702 |
| SFLT1 | R&D Systems | AF321 | Human VEGFR1/Flt-1 Antibody | Goat | Human | Poly | |
| SFLT1 | R&D Systems | MAB321 | Human VEGFR1/Flt-1 Antibody | Mouse | Human | Mono | 49560 |
| SFLT1 | Sino | 10136-MM03 | Anti-FLT1 antibody | Mouse | Human | Mono | 5A4D2 |
| SFLT1 | Sino | 10136-R111 | Anti-FLT1 antibody | Rabbit | Human | Mono | 111 |
| SFLT1 | Sino | 10136-H08H | FLT1 Protein, Human, Recombinant (His Tag) | | | | |
| PAPP-A2 | R&D Systems | MAB1668 | Human Pappalysin-2/PAPP-A2 Antibod | Mouse | Human | Mono | 242011 |

*FIG. 18 (Cont'd)*

| Antigen | Company | Cat. No. | Name | Species | Reacts with | Mono- or Polyclonal | Clone # |
|---|---|---|---|---|---|---|---|
| | | | y | | | | |
| PAPP-A2 | Abcam | ab89899 | Anti-PAPP A2 antibody [MM0507-8M12] | Mouse | Human | Mono | [MM0507-8M12] |
| PAPP-A2 | Abcam | ab228434 | Share by email Anti-PAPP A2 antibody [ABM4C62] (ab228434) | Mouse | Human | Mono | [ABM4C62] |
| PAPP-A2 | USBiologicals | 216877 | 216877 Mouse Anti-PAPPA2 (Pappalysin-2, Pregnancy-associated Plasma Protein A2, PAPP-A2, Pregnancy-associated Plasma Protein | Mouse | Human | Mono | 14L781 |

*FIG. 18 (Cont'd)*

| Antigen | Company | Cat. No. | Name | Species | Reacts with | Mono- or Polyclonal | Clone # |
|---|---|---|---|---|---|---|---|
| | | | E1) | | | | |
| uPA | Novus | NBP2-23502 | u-Plasminogen Activator/Urokinase Antibody | Mouse | Human | Monoclonal | U-12 |
| uPA | Novus | NBP1-05160 | u-Plasminogen Activator/Urokinase Antibody | Mouse | Human | Monoclonal | U-16 |
| uPA | Sino Biological | 10815-MM05 | Anti-Urokinase / uPA Antibody | Mouse | Human | Monoclonal | 05 |
| uPA | Sino Biological | 10815-T16 | Anti-Urokinase / uPA Antibody | Rabbit | Human | Polyclonal | na |
| uPA | Sino Biological | 10815-MM03 | Anti-Urokinase / uPA Antibody | Mouse | Human | Monoclonal | 1D3F2B11 |
| uPA | Sino Biological | 10815-MM02 | Anti-Urokinase / uPA Antibody | Mouse | Human | Monoclonal | 1A2G4G11 |
| uPA | RayBiotech | MD-15-0102 | Anti-Human Urokinase (uPA) / PLAU | Rabbit | Human | ? | ? |

*FIG. 18 (Cont'd)*

| Antigen | Company | Cat. No. | Name | Species | Reacts with | Monoclonal or Polyclonal | Clone # |
|---|---|---|---|---|---|---|---|
| Fibronectin | R&D Systems | MAB1918 | Human Fibronectin Antibody | Mouse | Human | Mono | P1H11 |
| Fibronectin | R&D Systems | MAB19182 | Human Fibronectin Antibody | Mouse | Human | Mono | 960642 |
| Fibronectin | R&D Systems | MAB19181 | Human Fibronectin Antibody | Mouse | Human | Mono | P1F11 |
| Fibronectin | Novus | NBP2-22113 | Fibronectin antibody- ELISA | Mouse | Human | Mono | 2F4 |
| Fibronectin | Novus | NBP2-37509 | Fibronectin antibody- ELISA | Mouse | Human | Mono | 2F4G2 |
| Fibronectin | Novus | NBP1-05056 | Fibronectin antibody- ELISA | Mouse | Human | Mono | A35 |
| Fibronectin | Novus | NBP2-23525 | Fibronectin antibody- ELISA | Mouse | Human | Mono | A32 |
| Fibronectin | Novus | NBP2-23524 | Fibronectin antibody- ELISA | Mouse | Human | Mono | A17 |
| Fibronectin | Novus | NBP1-05068 | Fibronectin antibody- ELISA | Mouse | Human | Mono | 3D2 |
| Fibronectin | Novus | NBP1-05117 | Fibronectin antibody- ELISA | Mouse | Human | Mono | A22 |
| Fibronectin | Novus | 7 polyAbs | | | | | |
| Fibronectin | CST | No antibodies | | | | | |
| Fibronectin | Abcam | ab6328 | Not suitable ELISA | Mouse | Human | Mono | IST-9 |
| Fibronectin | Abcam | ab154210 | Anti-Fibronectin antibody [BC-1] ELIS | Mouse | Human | Mono | BC-1 |

*FIG. 18 (Cont'd)*

| Antigen | Company | Cat. No. | Name | Species | Reacts with | Monoclonal or Polyclonal | Clone # |
|---|---|---|---|---|---|---|---|
| Fibronectin | Abcam | ab206928 | Anti-Fibronectin antibody [F14] | Rabbit | Human, Mouse, rat | Mono | F14 |
| Fibronectin | Abcam | ab219366 | Anti-Fibronectin antibody [F1] - Low endotoxin, Azide free | Rabbit | Human | Mono | F1 |
| Fibronectin | Abcam | ab212371 | Anti-Fibronectin antibody [HFN7.1] | Mouse | Human | Mono | HFN7.1 |
| Fibronectin | Abcam | ab212373 | Anti-Fibronectin antibody [TV-1] | Mouse | Human | Mono | TV-1 |
| Fibronectin | Abcam | 5 polyAb | | | | | |
| Fibronectin | Thermo | | Not suitable | | The FN-3 antibody recognizes a determinant on human | | FN3 |
| Fibronectin | Thermo | MA1-12597 | Fibronectin Monoclonal Antibody (EP5) | Mouse | Human | Mono | EP5 |
| Fibronectin | Origene | CF803784 | Fibronectin(FN1) Mouse Monoclonal Antibody | Mouse | Human | Mono | OTI5C1 (formerly 5C1) |
| Fibronectin | Origene | CF803733 | Fibronectin(FN1) Mouse Monoclonal Antibody | Mouse | Human | Mono | OTI1G2 |
| Fibronectin | Origene | CF803782 | Fibronectin(FN1) Mouse Monoclonal Antibody | Mouse | Human | Mono | OTI3F9 |
| Fibronectin | Origene | AM50111PU-S | Fibronectin(FN1) Mouse Monoclonal Antibody | Mouse | Human | Mono | SPM539 |
| Fibronectin | Origene | AM50112PU-S | Fibronectin(FN1) Mouse Monoclonal Antibody | Mouse | Human, Mouse, rat, Porcine | Mono | SPM246 |
| Fibronectin | Origene | AM50272PU-S | Fibronectin(FN1) Mouse Monoclonal Antibody | Mouse | Human, Mouse, rat, Porcine | Mono | 2755-8 |
| Fibronectin | Origene | AM05755PU-N | Fibronectin(FN1) Mouse Monoclonal Antibody | Mouse | Human | Mono | 2F4-G2 |
| Fibronectin | Atlas Antibodies | AMAb91223 | Anti-FN1 antibody | Mouse | Human | Mono | CL3730 |
| Fibronectin | SinoBiological | 10314-R014 | Anti-FN1 antibody ELISA | Rabbit | Human | Mono | 014 |
| Fibronectin | SinoBiological | 10314-MM02 | Anti-FN1 antibody ELISA | Mouse | Human | Mono | 9A6D4A7 |

*FIG. 18 (End)*

PREECLAMPSIA BIOMARKERS AND RELATED SYSTEMS AND METHODS

CROSS REFERENCE

This application is a continuation of U.S. patent application Ser. No. 16/646,552, filed Mar. 11, 2020, which is a National Phase Entry of International Application No. PCT/US2018/050893, filed Sep. 13, 2018, and claims the benefit of U.S. Provisional Application No. 62/558,184, filed Sep. 13, 2017, which are hereby incorporated by reference in their entirety for all purposes.

BACKGROUND OF THE INVENTION

Preeclampsia is a serious multisystem complication of pregnancy. The incidence of the disorder is generally considered to between 2% to 8% of all pregnancies, and the disorder carries significant morbidity and mortality risks for both mothers and infants. Preeclampsia is the second largest cause of maternal/fetal deaths, and is responsible for approximately twenty billion dollars in healthcare costs annually. In the United States, approximately one million women present with classical symptoms of preeclampsia (hypertension and/or proteinuria after the $20^{th}$ month of gestation) each year.

The cause(s) and pathogenesis of preeclampsia remain uncertain, and the identification (or ruling out) of preeclampsia using the classical clinical symptoms of the disease is non-ideal. The presentation of classical clinical symptoms can be highly variable, and the symptoms can be indicative of other distinct disorders, such as chronic hypertension, gestational hypertension, temporary high blood pressure, and gestational diabetes. Current laboratories tests (e.g., tests for proteinuria) can be prone to inaccuracies, or are useful for detection of preeclampsia only during relatively late periods in the progression of the disorder. Methods for more reliably determining whether a pregnant woman does or does not have preeclampsia may, among other things, (1) lead to a more timely diagnosis, (2) improve the accuracy of a diagnosis, and/or (3) prevent the unnecessary treatment of women with preeclampsia treatments.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Features of the inventions described herein are set forth with particularity in the appended claims. A better understanding of the features and advantages of the present inventions will be obtained by reference to the following detailed description that sets forth illustrative embodiments, in which the principles of the inventions are utilized, and the accompanying drawings of which:

FIG. 13A, FIG. 13B, FIG. 13C, FIG. 13D, FIG. 13E, FIG. 13F, FIG. 13G, FIG. 13H, FIG. 13I, FIG. 13J, and FIG. 13K depict log-transforms of expression levels of the top 11 markers identified for detection of preeclampsia in both preeclampsia and non-preeclampsia samples.

FIG. 18 lists various antibodies or other antigen-binding agents for use in some embodiments disclosed herein.

DETAILED DESCRIPTION OF THE INVENTION

Figure 1A:
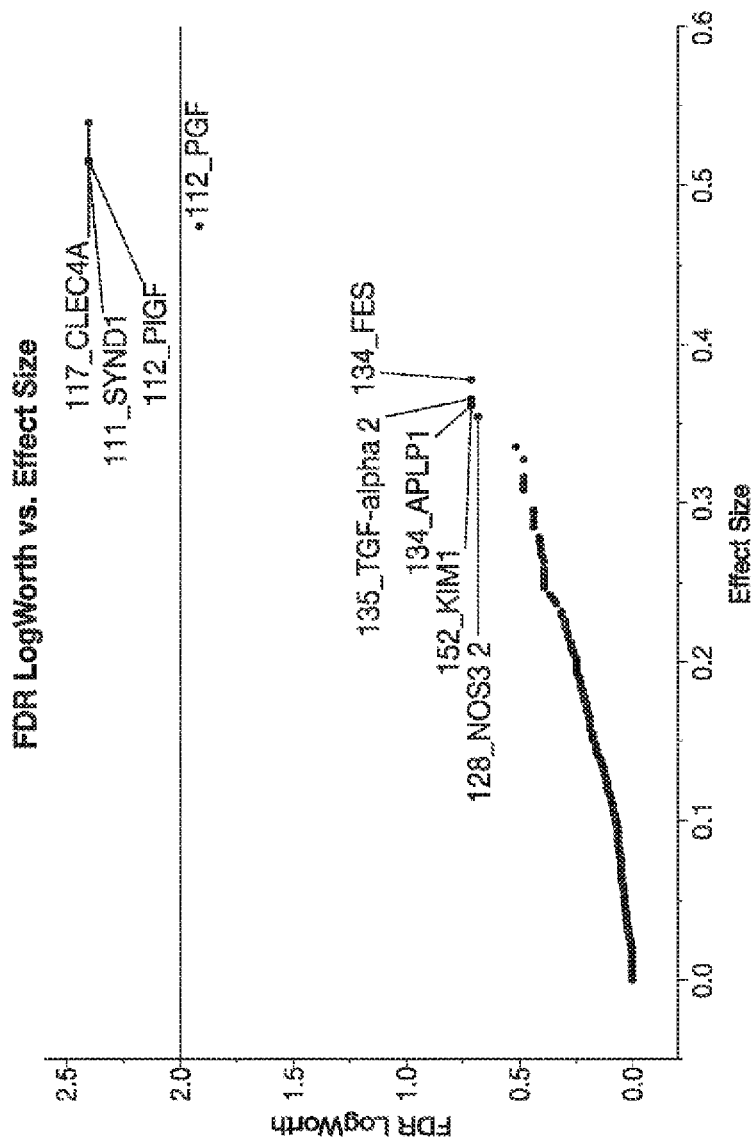
FIG. 1A shows a plot of LogWorth vs. effect size from the initial ANOVA-based screening for markers of interest presented in Example 3.

Detection of preeclampsia using the classic clinical symptoms of the disease is error prone, risking significant adverse outcome for patients and added burden to the healthcare system through misdiagnosis. Measurement of proteinuria is prone to inaccuracies (e.g., false negatives and false positives), preeclampsia complications may occur before proteinuria becomes significant, the clinical presentation of preeclampsia can be highly variable (from severe, rapidly progressing, and early-onset to late-onset and less severe), and the symptoms (hypertension, proteinuria, or both) can be indicative of other distinct disorders that could utilize a less aggressive treatment course (chronic hypertension, gestational hypertension, temporary high blood pressure, and gestational diabetes). Thus, there is significant risk for patients with only suspected preeclampsia to be over treated (e.g., delivered or induced early, thereby unnecessarily putting the infant at risk of preterm birth complications and/or unnecessarily putting the mother at risk of surgical complications), and there is risk for patients with silent or rapidly-progressing preeclampsia to be treated insufficiently aggressively (e.g., putting the infant at risk of intrauterine growth restriction or death, and the mother at risk of preeclamptic sequelae such as eclampsia seizures, renal or liver damage, pulmonary edema, placental abruption, and coma).

In other words, hypertension and proteinuria merely reflect downstream consequences of the actual preeclampsia disease process. Traditional diagnoses of preeclampsia lead to masking of the disease because the only reliable treatment is delivery. In the interest of improved detection of preeclampsia, research into the dysfunctional angiogenic processes associated with preeclampsia has been undertaken to find better and/or more direct indicators of preeclampsia. One avenue of this research has led to the use of the sFlt1/PlGF ratio in patient serum as a method for identifying preeclampsia (see e.g., Zeisler et al. NEJM 274(2017):13-22 or Verlohren et al. Hypertension. 63(2014):346-52). However, this method only has a maximal sensitivity of 80% and specificity of 78.3%; and thus involves a significant proportion of false negatives and positives, making it of limited use in ruling out a diagnosis of preeclampsia and avoiding the overtreatment/under treatment conundrum.

Accordingly, there is a need for the methods, compositions, systems and kits for improved detection or prediction of preeclampsia in pregnant patients, particularly those that enable the detection or prediction of preeclampsia with a high negative predictive value and/or allow medical professionals to rule out a diagnosis of preeclampsia for an extended period of time.

The disclosure provides for one or more tests with improved characteristics for assessing the risk of preeclampsia in a subject, wherein the test can be used to identify subjects that should not be treated for preeclampsia (e.g., in some instances identifying a subject that shows one or more signs, symptoms, or risk factors of preeclampsia, but should not be treated for preeclampsia). In some embodiments, this test is a multi-marker serum or plasma protein assay. In some embodiments, the test is a multiplexed serum/plasma protein assay. The one or more symptoms associated with preeclampsia can be diabetes (e.g. gestational, type I or type II), higher than normal glucose level, hypertension (e.g., chronic or non-chronic), excessive or sudden weight gain, higher than normal weight, obesity, higher than normal body mass index (BMI), abnormal weight gain, abnormal blood pressure, water retention, hereditary factors, abnormal proteinuria, headache, edema, abnormal protein/creatinine ratio, abnormal platelet count, stress, nulliparity, abnormal Papanicolaou test results (Pap smear), prior preeclampsia episodes (e.g., personal history of PreE), familial history of preeclampsia, preeclampsia in prior pregnancies, renal disease, thrombophilia, or any combination thereof.

The disclosure provides for tests, systems, and methods for assessing a risk of preeclampsia in a subject, such as ruling out a patient as having or needing treatment for preeclampsia. In some embodiments, a test is used to discern whether a patient having one or symptoms or risk factors associated with preeclampsia should be treated for preeclampsia. The one or more symptoms or risk factors associated with preeclampsia can be diabetes (e.g. gestational, type I or type II), higher than normal glucose level, hypertension (e.g., chronic or non-chronic), excessive or sudden weight gain, higher than normal weight, obesity, higher than normal body mass index (BMI), abnormal weight gain, abnormal blood pressure, water retention, hereditary factors, abnormal proteinuria, headache, edema, abnormal protein/creatinine ratio, abnormal platelet count, stress, nulliparity, abnormal Papanicolaou test results (Pap smear), prior preeclampsia episodes (e.g., personal history of PreE), familial history of preeclampsia, preeclampsia in prior pregnancies, renal disease, thrombophilia, or any combination thereof. Stated differently in some embodiments, the tests disclosed herein can be used to identify pregnant women who are symptomatic (and/or have one or more risk factors for preeclampsia), but do not have preeclampsia that is likely to require preterm birth. In some embodiments, the test may be used on asymptomatic patients or patients with little or no risk identified (or identifiable) risk factors.

Definitions

As used in the specification and in the claims, the singular form "a," "an," and "the" include plural referents unless the context clearly dictates otherwise.

The term "hypertension" refers to abnormally high blood pressure. Hypertension can be identified in any suitable manner, such as by reference to a sitting systolic blood pressure (sSBP) of greater than 140 mmHg or a sitting diastolic blood pressure (sDBP) of greater than 90 mmHg. Hypertension can be further classified into class 1 or class 2 hypertension, with class 1 exhibiting sSBP of 140-149 mmHg or 90-99 mmHg sDBP, and class 2 exhibiting greater than 160 mmHg sSBP or 100 mmHg sDBP. (See, e.g., The Seventh Report of the Joint National Committee on Prevention, Detection, Evaluation, and Treatment of High Blood Pressure. JAMA 2003; 289:2560-71.) Other suitable criteria may be used to identify hypertension, such as having a sitting systolic blood pressure of greater than 130 and/or a sitting diastolic blood pressure of greater than 90 mmHg. Hypertension can also be determined according to the 2017 AHA guidelines (see Whelton et al. 2017 ACC/AHA/AAPA/ABC/ACPM/AGS/APhA/ASH/ASPC/NMA/PCNA Guideline for the Prevention, Detection, Evaluation, and Management of High Blood Pressure in Adults, Journal of the American College of Cardiology (2017), doi: 10.1016/j.jacc.2017.11.006). Such guidelines identify "normal" blood pressure as less than 120/80 mmHg, "elevated" as systolic between 120-129 mmHg and diastolic less than 80 mmHg, "stage 1" as systolic between 120-139 mmHg or diastolic between 80-89 mmHg, "stage 2" as systolic at least 140 mmHg or diastolic at least 90 mmHg, and "hypertensive crisis" as systolic over 180 and/or diastolic over 120.

As used herein, the term "proteinuria" is defined as the presence of abnormal protein in the urine. A number of indicator dyes and reagents can used to measure proteinuria semi-quantitatively (e.g., bromophenol blue). In some embodiments, concentrations of protein in urine can be determined by a semi quantitative "dipstick" analysis and graded as negative, trace (10-20 mg/dL), 1+(~30 mg/dL), 2+(~100 mg/dL), 3+(~300 mg/dL), or 4+(~1,000 mg/dL), with 2+ commonly being used as the threshold for problematic proteinuria. In an alternative scheme, concentrations of protein in urine can also be measured per 24 hour urine collection, in which greater than or equal to 300 mg protein indicates proteinuria. In an alternative scheme, concentrations of protein in urine can be measured in a spot urine sample, in which 30 mg of protein per deciliter or greater indicates proteinuria. In yet an alternative scheme, proteinuria can also be expressed as the protein/creatinine ratio (Pr/Cr) in urine, in which a Pr/Cr ratio of ≥0.3 is indicative of problematic proteinuria.

As used herein, the term "antibody or fragments thereof" is used in the broadest sense and specifically encompasses intact monoclonal antibodies, polyclonal antibodies, multi-specific antibodies (e.g. bispecific antibodies) formed from at least two intact antibodies, and antibody fragments. Antibody fragments comprise a portion of an intact antibody that retains antigen-binding activity; examples include Fab, Fab', F(ab)$_2$, F(abc)$_2$, and Fv fragments as well as diabodies, linear antibodies, scFvs, and multispecific antibodies formed from antibody fragments.

As used herein, the term "aptamer" refers to an oligonucleotide that is capable of forming a complex with an intended target substance. Such complex formation is target-specific in the sense that other materials which may accompany the target do not complex to the aptamer. It is recognized that complex formation and affinity are a matter of degree; however, in this context, "target-specific" means that the aptamer binds to target with a much higher degree of affinity than it binds to contaminating or "off-target" materials.

As used herein, the term "preeclampsia" (or "PreE") refers to a pregnancy-specific disorder involving multiple organ systems thought to originate from abnormal placentation, dysfunctional trophoblast development, defective placental angiogenesis, and a heightened systemic inflammatory response in the mother. Preeclampsia, when untreated, can progress to ecclampsia, HELLP syndrome, hemorrhagic or ischenic stroke, liver damage, acute kidney injury, and acute respiratory distress syndrome (ARDS). Thus, while preeclampsia frequently presents with symptoms such as hypertension and proteinuria, it is distinct from simple vascular tension disorders and kidney dysfunction (as evidenced by the non-overlapping set of complications that result when it is untreated), and symptoms reflective of vascular tension disorders and kidney dysfunction on their own therefore have less than ideal predictive/diagnostic value for preeclampsia. Further information on the pathophysiology of preeclampsia can be found, e.g., in Phipps et al. Clin J Am Soc Nephrol 11(2016): 1102-1113. In some embodiments, a traditional diagnosis of preeclampsia is made when hypertension and proteinuria as defined above are detected at the same time. In other embodiments (see American College of Obstetricians and Gynecologists; Task Force on Hypertension in Pregnancy. Obstet Gynecol. 122 (2013):1122-31, which is explicitly incorporated by reference herein) a traditional diagnosis of preeclampsia is made upon simultaneous detection of hypertension (blood pressure greater than or equal to 140 mmHg systolic or greater than or equal to 90 mmHg diastolic on two occasions at least 4 hours apart after 20 weeks gestation in a woman with a previously normal blood pressure, or blood pressure with greater than equal to 160 mmHg systolic or greater than or equal to 110 mmHg diastolic within a short interval of minutes) and proteinuria (greater than or equal to 300 mg per 24-hour urine collection either measured or extrapolated, or protein creatinine ratio greater than or equal to 0.3, or a dipstick reading of 1+) or upon new onset hypertension in the absence of proteinurea when (a) blood platelet count is less than 100,000 per milliliter, (b) serum creatinine is greater than 1.1 mg/dL or double baseline for the patient, or (c) blood concentration of liver transaminases is twice normal or greater). In some cases, preeclampsia is made without a diagnosis of proteinurea, for instance where evidence of other end-stage organ damage is present.

The term "subject" can include human or non-human animals. Thus, the methods and described herein are applicable to both human and veterinary disease and animal models. Preferred subjects are "patients," i.e., living humans that are receiving medical care for a disease or condition. This includes persons with no defined illness who are being investigated for signs of pathology.

The term "FRET pair" refers to a pair of dye molecules where one of the dye molecules absorbs light (the acceptor or quencher dye) at a wavelength at which the other emits light (the donor dye) and the two dyes are spatially separated by a distance that permits energy transfer, with the disclosed embodiments generally being within about 100 angstroms, such as within about 50, 20 or 10 angstroms of each other (for example, because they are bonded to the same substrate moiety). Excitation of the donor dye leads to excitation of the acceptor dye through the FRET mechanism, and a lower level of fluorescence is observed from the donor dye. The efficiency of FRET depends on the distance between the dyes, the quantum yield of the donor dye, the fluorescence lifetime of the donor dye, and the overlap of the donor's emission spectrum and the acceptor's absorption spectrum.

The term "photosensitizer" refers to a photoactivatable compound, or a biological precursor of a photoactivatable compound, that produces a reactive species (for e.g., oxygen) having a photochemical effect on a biomolecule.

The term "oxygen-sensitive dye" refers a fluorescent dye that changes its fluorescence intensity or emission maximum after binding to molecular oxygen (such dyes are used for FOCI assays), or a chemiluminescent dye that emits light after binding to molecular oxygen (such dyes are used for LOCI assays).

The term "afimer" as used herein refers to small, highly stable proteins that bind to a target molecule with similar specificity and affinity to that of antibodies.

The term "unnecessary treatment of preeclampsia" can refer to treatments for preeclampsia that would be, statistically speaking, unjustified when a practitioner takes into account the results of a test or procedure described herein, such as a test based on the determination of an amount of concentration of various protein biomarkers. Such unnecessary treatment can include preterm induction based on one or more symptoms or risk factors for preeclampsia.

Subjects

In some embodiments, the methods, compositions, systems and kits provided herein are used for detecting or predicting a condition in a pregnant human subject at any stage in pregnancy. In other embodiments, the pregnant human subject is post-the 20$^{th}$ week of gestation. In other embodiments, the pregnant human subject is post-first or -second trimester of pregnancy. In some embodiments, the pregnant human subject is post-21st, 22nd, 23rd, 24th, 25th, 26th, 27th, 28th, 29th, 30th, 31st, 32nd, 33rd, 34th, 35th, 36th, 37th, 38th, 39th, 40th, 41st, or 42nd week of gestation.

The methods, compositions, systems and kits are suitable for detecting or predicting a condition of the pregnant subject such as preeclampsia (PreE) or non-preeclampsia (NonPreE). In some embodiments, preeclampsia is further divided into very early-onset (before 25 weeks gestation), early-onset (before 34 weeks gestation) and late-onset (after 34 weeks gestation) preeclampsia. Typically, when the pregnant patient does not exhibit hypertensive or renal symptoms, the patient is considered NonPreE. Further, when the pregnant patient exhibits only hypertensive symptoms alone without signs of proteinuria, the patient is generally only suspected to have preeclampsia. However, as the measurement of proteinuria is prone to inaccuracies (e.g., false negatives and false positives), preeclampsia complications may occur before proteinuria becomes significant, the clinical presentation of preeclampsia can be highly variable (from severe, rapidly progressing, and early-onset to late-onset and less severe), and the symptoms (hypertension, proteinuria, or both) can be indicative of other distinct disorders that could utilize a different treatment course. Thus, there is significant risk for patients with only suspected preeclampsia to be unnecessarily treated (e.g., delivered/induced early putting the infant at risk of preterm birth complications or the mother at risk of surgical complications), and there is risk for patients with silent or rapidly-progressing preeclampsia to be treated insufficiently aggressively (e.g., putting the infant at risk of intrauterine growth restriction or death, and the mother at risk of preeclampsia sequelae such as eclampsia seizures, renal or liver damage, pulmonary edema, placental abruption, and coma).

A subject therefore can be a pregnant female that has no known risk factors, or has one or more at-risk factors for a condition such as PreE. In some instances, hypertension and/or proteinuria can indicate a subject at risk of preeclampsia. In some instances, a subject at risk of preeclampsia can have a urine protein content measured as 2+ (100 mg/dL) or greater by dipstick assay, greater than or equal to 300 mg per 24 hour urine collection, 30 mg of protein per deciliter or greater in a spot urine sample, or a Pr/Cr ratio in urine of ≥30 mg per millimole. In some instances, a subject at risk of preeclampsia can have a sitting systolic blood pressure (sSBP) of greater than 140 mmHg or a sitting diastolic blood pressure (sDBP) of greater than 90 mmHg or both. In some instances, sFlt1/PlGF ratio can be used to identify subject at risk of preeclampsia (see, e.g., Zeisler et al. NEJM 274(2017):13-22 or Verlohren et al. Hypertension. 63(2014):346-52). In some instances both hypertension and proteinuria can be used to identify a subject at risk of preeclampsia. In some instances new onset hypertension in combination with one or more symptoms selected from (a) blood platelet count is less than 100,000 per milliliter, (b) serum creatinine is greater than 1.1 mg/dL or double baseline for the patient, or (c) blood concentration of liver transaminases is twice normal or greater can be used to identify a subject at risk of preeclampsia.

Samples

Methods for detecting molecules (e.g., nucleic acids, proteins, etc.) in a pregnant subject in order to detect, diagnose, monitor, predict, or evaluate the status or outcome of the pregnancy are described in this disclosure. In some cases, the molecules are circulating molecules (e.g. unbound to cells and freely circulating in bodily fluids such as blood, blood plasma or blood serum). In some cases, the molecules are expressed in the cytoplasm of blood, endothelial, or organ cells. In some cases, the molecules are expressed on the surface of blood, endothelial, or organ cells.

The methods, kits, and systems disclosed herein can be used to classify one or more samples from one or more subjects. A sample can be any material containing tissues, cells, nucleic acids, genes, gene fragments, expression products, proteins, polypeptides, exosomes, gene expression products, or gene expression product fragments of a subject to be tested. A sample can include but is not limited to, tissue, cells, plasma, serum, or any other biological material from cells or derived from cells of an individual. The sample can be a heterogeneous or homogeneous population of cells or tissues. The sample can be a fluid that is acellular or depleted of cells (e.g., plasma or serum). In some cases, the sample is from a single patient. In some cases, the method comprises analyzing multiple samples at once, e.g., via massively parallel multiplex expression analysis on protein arrays or the like.

The sample is preferably a bodily fluid. The bodily fluid can be saliva, urine, blood, and/or amniotic fluid. The sample can be a fraction of any of these fluids, such as plasma, serum or exosomes (exemplary exosome isolation techniques can be found, e.g. in Li et al. Theranostics. 7(2017): 789-804). In preferred embodiments, the sample is a blood sample, plasma sample, or serum sample.

The sample may be obtained using any method that can provide a sample suitable for the analytical methods described herein. The sample may be obtained by a non-invasive method such as a throat swab, buccal swab, bronchial lavage, urine collection, scraping of the cervix, cervicovaginal sample secretion collection (e.g. with an ophthalmic sponge such as a Weck-Cel sponge), saliva collection, or feces collection. The sample may be obtained by a minimally-invasive method such as a blood draw. The sample may be obtained by venipuncture.

As used herein "obtaining a sample" includes obtaining a sample directly or indirectly. In some embodiments, the sample is taken from the subject by the same party (e.g. a testing laboratory) that subsequently acquires biomarker data from the sample. In some embodiments, the sample is received. (e.g. by a testing laboratory) from another entity that collected it from the subject (e.g. a physician, nurse, phlebotomist, or medical caregiver). In some embodiments, the sample is taken from the subject by a medical professional under direction of a separate entity (e.g. a testing laboratory) and subsequently provided to said entity (e.g. the testing laboratory). In some embodiments, the sample is taken by the subject or the subject's caregiver at home and subsequently provided to the party that acquires biomarker data from the sample (e.g. a testing laboratory). A variety of kits suitable for self or home collection of biological samples have been described commercially and in the literature; see e.g., US20170023446A1 and U.S. Pat. No. 4,777,964A.

Sample Data

The methods, kits, and systems disclosed herein may comprise data pertaining to one or more samples or uses thereof. The data can be representative of an amount or concentration of one or more biomarkers, such as various proteins described herein. Stated differently, the data can be expression level data of proteins or polypeptides. The expression level data of biomarkers described herein can be determined by protein array, proteomics, expression proteomics, mass spectrometry (e.g., liquid chromatography-mass spectrometry (LC-MS), multiple reaction monitoring (MRM), selected reaction monitoring (SRM), scheduled MRM, scheduled SRM), 2D PAGE, 3D PAGE, electrophoresis, proteomic chip, proteomic microarray, Edman degradation, direct or indirect ELISA, immunosorbent assay, immuno-PCR (see, e.g., Sano et al. Science. 258(1992):120-2), proximity extension assay (see, e.g., Thorsen et al. Journal of Translational Medicine. 11(2013):253, US20130288249A1, U.S. Pat. No. 9,777,315B2), Luminex assay, or homogenous assays such as ALPHAscreen (see, e.g., Application Note. Nature Methods 5, (2008), U.S. Pat. Nos. 5,898,005A, 5,861,319A), time-resolved fluorescence resonance energy transfer (TR-FRET see e.g., US20130203068A1 and WO1998015830A2), time-resolved fluorescence (TRF), fluorescent oxygen channeling immunoassay (FOCI), or luminescent oxygen channeling immunoassay (LOCI™, see e.g. Ullman et al. Proc Natl Acad Sci USA. 91(1994):5426-5430 or Ullman et al. Clin Chem. 1996 September; 42(9):1518-26 for exemplary methods and reagents).

In some embodiments, the compositions, methods and devices described herein make use of labeled molecules in various sandwich, competitive, or non-competitive assay formats to determine expression levels of biomarkers described herein. Such methods generate a signal that is related to the presence or amount of one or more of the proteins described herein. Suitable assay formats also include chromatographic, mass spectrographic, and protein "blotting" methods. Additionally, certain methods and devices, such as biosensors, optical immunoassays, immunosorbent assays, and enzyme immunoassays, may be employed to determine the presence or amount of analytes without the need for a labeled molecule. Examples of enzyme immunoassays (EIA) include chemiluminescent enzyme immunoassay, electrochemiluminescence immunoassay (ECLIA), and enzyme-linked immunosorbent assay (ELISA), which are further described by Kuhle, Jens, et al. "Comparison of three analytical platforms for quantification of the neurofilament light chain in blood samples: ELISA, electrochemiluminescence immunoassay and Simoa." Clinical Chemistry and Laboratory Medicine (CCLM) 54.10 (2016): 1655-1661. Robotic instrumentation for performing these immunoassays are commercially available including, but not limited to Abbott AXSYM®, IMx®, or Commander® systems; Biolog 24i® or CLC480 systems; Beckman Coulter ACCESS®, ACCESS 2®, or Unicel Dxl 600/800 systems; bioMerieux VIDAS® or mini-VIDAS® systems; Chimera Biotec GmbH Imperacer® assay; Dade Behring STRATUS® system; DiaSorin LIAISON XL® or ETI-Mlax 300 systems; Dynex Agility® system; Gold Standard Diagnostics Thunderbolt® analyzer; Gyrolab xPlore/xPand® system; Hudson Robotics ELISA Workstation; Ortho Clinical Diagnostics Vitros® ECL or 3600 systems; Hamiltorn Robotics ELISA NIMBUS or STARlet systems; Luminex xMAP® system; PerkinElmer ALPHAscreen® or AlphaLISA®; Phadia Laboratory System 100E, 250, 1000, 2500, or 5000; Quanterix SIMOA® system; Quidel Sofia®2 POC systems; Radiometer AQT90 Flex system; Roche Diagnostics ElecSys® 2010, Cobas® 4000/6000/8000 Analyzers, or Integra® 400 Plus; c111, c311, c501, c502 family of analyzers; Seikisui Diagnostics FastPack® IP automated system; Siemens Dimension Vista® 1500 System, DPC Immulite 1000/2000 system, or DCA Vantage® Analyzer; Singulex Single Molecule Counting (SMC™) assay; Stratus® CS Acute Care Diagnostic System; Sysmex Eurolyser®; ThermoFisher MGC 240 Benchtop Analyzer; Tosoh Bioscience AIA®-360 or AIA-60011 systems; UniCel Dxl 860i Synchron Access Clinical System, UniCel DxC 680i Synchron Access Clinical System, Access/Access 2 Immunoassay System, 600 Access Immunoassay System, 600i Synchron Access Clinical System, Dxl 800 Access Immunoassay System, DxC 880i Synchron Access Clinical System; and Vital Diagnostics PathFast® point-of-care chemiluminescence immunoassay analyzer. But any suitable immunoassay may be utilized, for example, enzyme-linked immunoassays (ELISA), radioimmunoassays (RIAs), competitive binding assays, and the like.

Other exemplary analytical systems include assay systems, such as, for example, optical systems containing one or more sources of radiation and/or one more detectors. Such systems may use, for example, a light source that illuminates and a sample and a detector configured to detect light that is emitted by the sample (e.g., fluorescence spectroscopy), optical density (e.g., the portion of light that passes through the sample), and/or light that is diffracted by sample (e.g., diffraction optics). An analytical system may use, for example, ELISA (enzyme-linked immunosorbent assay). An analytical system may use, for example, LOCI (luminescent oxygen channeling), FOCI (fluorescent oxygen channeling), or ALPHAscreen. An analytical technique may involve incubating and/or diluting a sample before or during the analysis/assaying of the sample.

In some embodiments, the compositions, methods and devices described herein make use of fluorescent oxygen channeling immunoassay (FOCI) compositions and methods. FOCI is generally described in U.S. Pat. Nos. 5,807,675; 5,616,719; and 7,635,571, the entire contents of which are expressly incorporated herein by reference. In some embodiments, a first analyte-binding agent that is capable of binding to an analyte and comprises a photosensitizer is used in combination with a second analyte-binding agent comprising a fluorogenic dye. In some embodiments, the photosensitizer of the first analyte-binding agent generates singlet oxygen in an excited state thereby causing the fluorogenic dye of the second analyte-binding agent to emit fluorescence upon reacting with the singlet oxygen. In some embodiments, the emitted fluorescence can be detected to, e.g., determine the presence and/or absence of the analyte and/or to quantitate and/or analyze the analyte in a sample. In some embodiments, the first and the second analyte-binding agents bind to the same region (e.g., epitope) of the analyte (e.g., a protein). For example, in some embodiments, the first and the second analyte-binding agents comprise the same type of analyte-binding moiety or reagent (e.g., the same antibody). In some embodiments, the first and the second analyte-binding agents bind to separate regions (e.g., epitopes) of the analyte (e.g., a protein). In some embodiments, the first and the second analyte-binding agents bind to the separate regions of the analyte (e.g., a protein) that do not spatially overlap. In some embodiments, the first analyte-binding agent and the second analyte-binding agent are configured such that when both analyte-binding agents are bound to the analyte, the singlet oxygen generated by photosensitizer of the first analyte-binding agent is in close proximity to the fluorogenic dye of the second analyte-binding agent. In some embodiments, the first and/or second analyte binding agent(s) is an antigen-binding agent (e.g., an antibody). In some embodiments, the first and/or second analyte binding agent(s) is an affimer. In some embodiments, the first and/or second analyte binding agent(s) is an antigen-binding agent is an aptamer. In some embodiments, both the photosensitizer and fluorogenic dye are provided in the form of beads.

In some cases, arrays can use different probes (e.g., antibodies, scFvs, Fab fragments) attached to different particles or beads. In such arrays, the identity of which probe is attached to which particle or beads may be determinable from an encoding system. The probes can be antibodies or antigen-binding fragments or derivatives thereof.

The data pertaining to the sample can be compared to data pertaining to one or more control samples. In some cases, control samples can be samples from the same patient at different times. In some cases, the one or more control samples can comprise one or more samples from healthy subjects, unhealthy subjects, or a combination thereof. The one or more control samples can comprise one or more samples from healthy subjects, subjects suffering from pregnancy-associated conditions other than preeclampsia, subjects suffering chronic conditions along with pregnancy associated conditions, or subjects suffering from chronic conditions alone.

In some instances, the expression level data for various samples is used to develop or train an algorithm or classifier provided herein. In some instances, where the subject is a patient, such as a pregnant female; gene expression levels are measured in a sample from the patient and a classifier or algorithm (e.g., trained algorithm) is applied to the resulting data in order to detect, predict, monitor, rule out, or estimate the risk of a pregnancy-associated condition such as preeclampsia.

In some cases, analysis of expression levels initially provides a measurement of the expression level of each of several individual biomarkers. The expression level can be absolute in terms of a concentration of a biomarker, or relative in terms of a relative concentration of an expression product of interest to another biomarker in the sample. For example, relative expression levels of proteins can be expressed with respect to the expression level of a housekeeping or structural protein in the sample. Relative expression levels can also be determined by simultaneously analyzing differentially labeled samples bound to the same array. Expression levels can also be expressed in arbitrary units, for example, related to signal intensity.

Classifiers and Classifier Probe Sets

Disclosed herein is the use of a classification system comprising one or more classifiers. In some instances, the classifier is a 2-way classifier. In some instances, a two-way classifier can classify a sample from a pregnant patient into one of two classes comprising preeclampsia (PreE) and non-preeclampsia (nonPreE). In some instances, the classifier may be used classify a subject as not needing treatment for preeclampsia. In some instances, a multi-way classifier may be used (e.g., preeclampsia, non-preeclampsia, and indeterminate).

Classifiers and/or classifier probe sets (e.g., antibody sets) can be used to either rule-in or rule-out a sample as from a patient to be treated for preeclampsia. For example, a classifier can be used to classify a sample as being from a healthy subject. Alternatively, a classifier can be used to classify a sample as being from an unhealthy subject. Alternatively, or additionally, classifiers can be used to either rule-in or rule-out a sample as being from a subject who should be treated for preeclampsia.

Data Analysis Systems and Methods

The methods, kits, and systems disclosed herein can comprise algorithms or uses thereof. The one or more algorithms can be used to classify one or more samples from one or more subjects. The one or more algorithms can be applied to data from one or more samples. The data can comprise biomarker expression data.

The methods disclosed herein can comprise assigning a classification to one or more samples from one or more subjects. Assigning the classification to the sample can comprise applying an algorithm to the expression level. In some cases, the gene expression levels are inputted to a data analysis system comprising a trained algorithm for classifying the sample as one of the conditions comprising preeclampsia, eclampsia, non-preeclampsia, chronic hypertension, gestational hypertension, or HELLP (Hemolysis, Elevated Liver enzymes, and Low Platelet count-see e.g., Weinstein et al. Am J Obstet Gynecol. 142(1982):159-67) syndrome. In some embodiments the algorithm can, as part of its execution, calculate an index for a sample and compare the sample index to a threshold value; the predefined relationship can be indicative of a likelihood of the sample belonging to a particular classification.

The algorithm can provide a record of its output including a classification of a sample and/or a confidence level. In some instances, the output of the algorithm can be the possibility of the subject of having a condition comprising preeclampsia, eclampsia, chronic hypertension, gestational hypertension, or HELLP syndrome.

A data analysis system can be a trained algorithm. The algorithm can comprise a linear classifier. In some instances, the linear classifier comprises one or more of linear discriminant analysis, Fisher's linear discriminant, Naïve Bayes classifier, Logistic regression, Perceptron, Support vector machine, or a combination thereof. The linear classifier can be a support vector machine (SVM) algorithm. The algorithm can comprise a two-way classifier. The two-way classifier can comprise one or more decision tree, random forest, Bayesian network, support vector machine, neural network, or logistic regression algorithms.

The algorithm can comprise one or more linear discriminant analysis (LDA), Basic perceptron, Elastic Net, logistic regression, (Kernel) Support Vector Machines (SVM), Diagonal Linear Discriminant Analysis (DLDA), Golub Classifier, Parzen-based, (kernel) Fisher Discriminant Classifier, k-nearest neighbor, Iterative RELIEF, Classification Tree, Maximum Likelihood Classifier, Random Forest, Nearest Centroid, Prediction Analysis of Microarrays (PAM), k-medians clustering, Fuzzy C-Means Clustering, Gaussian mixture models, graded response (GR), Gradient Boosting Method (GBM), Elastic-net logistic regression, logistic regression, or a combination thereof. The algorithm can comprise a Diagonal Linear Discriminant Analysis (DLDA) algorithm. The algorithm can comprise a Nearest Centroid algorithm. The algorithm can comprise a Random Forest algorithm. In some embodiments, for discrimination of preeclampsia and non-preeclampsia, the performance of logistic regression, random forest, and gradient boosting method (GBM) is superior to that of linear discriminant analysis (LDA), neural network, and support vector machine (SVM).

Biomarkers Gene Expression Products

The term "biomarker" refers to a measurable indicator of some biological state or condition. In some instances, a biomarker can be a substance found in a subject, a quantity of the substance, or some other indicator. For example, a biomarker can be the amount of a protein and/or other gene expression products in a sample. In some embodiments, a biomarker is a full-length, unmodified protein. In other embodiments, a biomarker is an alternatively spliced, post-translationally cleaved, or post-translationally chemically modified (e.g., methylated, phosphorylated, glycosylated, formylated, etc) protein.

The methods, compositions and systems as described here also relate to the use of biomarker panels and/or gene expression products for purposes of identification, diagnosis, classification, treatment or to otherwise characterize various conditions of pregnant patients comprising Non-PreE, PreE, chronic hypertension, gestational hypertension, or HELLP syndrome. Sets of biomarkers and/or gene expression products useful for classifying biological samples are provided, as well as methods of obtaining such sets of biomarkers. Often, the pattern of levels of gene expression biomarkers in a panel (also known as a signature) is determined from one or more references samples and then used to evaluate the signature of the same panel of biomarkers in a test sample, such as by a measure of similarity between the test sample signature and the reference sample signature.

Figure 16:
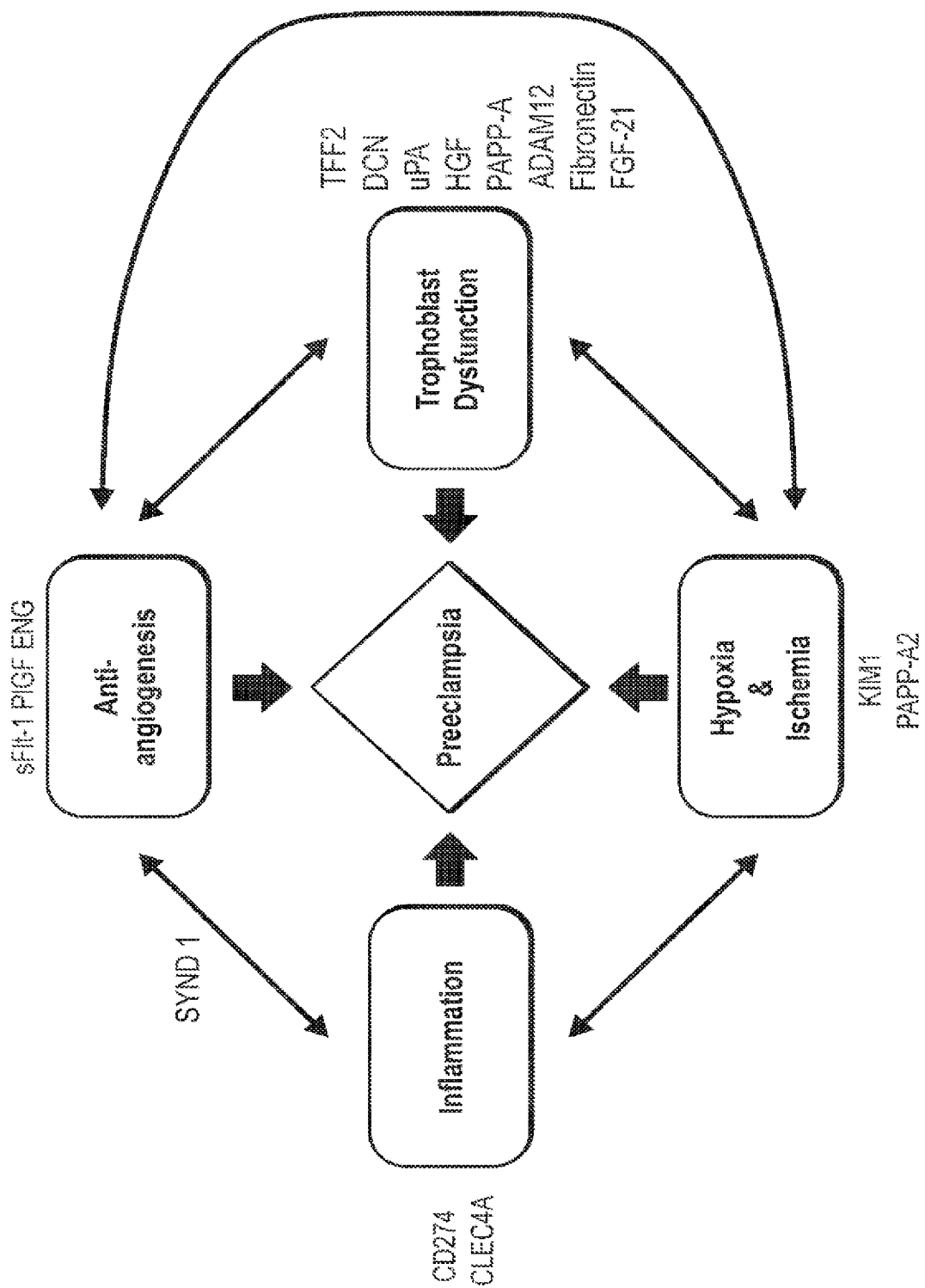
FIG. 16 is a diagram showing exemplary functional roles for various markers in the pathophysiology of preeclampsia.

In some embodiments, the methods, compositions, and systems described herein may involve the detection of one or more biomarker belonging to a particular functional class of biomarkers with a connection to one or more pathophysiological features of preeclampsia (see FIG. 16, which shows various pathophysiological features or preeclampsia). While FIG. 16 shows various pathophysiological features, and associated biomarkers, that are thought to be associated with preeclampsia, numerous other methods for describing the pathophysiology and relationship between the markers is possible. For instance, KIM-1, CD274, and decorin can be considered as kidney damage associated proteins. Similarly, sFlt1, endoglin, pappalysin 2, and decorin can be considered as angiogenesis-associated proteins. A person of skill in the art will recognize that various other classification schemes could be similarly used.

Without wishing to be limited by theory, preeclampsia is thought to originate in abnormal trophoblast invasion, which results in incomplete spiral artery remodeling and hypoperfusion of the placenta, and that this hypoperfusion of the placenta triggers dysfunction in multiple body systems causing the signs and symptoms of preeclampsia. Such dysfunctional systems can include, as a result of placental hypoperfusion, angiogenesis and endothelial function, as evidenced e.g. by imbalances in pro-and-anti-angiogenic factors, many of which are released by the placenta in response to the abnormal physiology of preeclampsia, and which disrupt vascular homeostasis in the mother's body. SFLT1 (Soluble FMS-like tyrosine kinase 1, a tyrosine-protein kinase that acts as a cell-surface receptor for VEGFA, VEGFB and PIGF and decreases towards term, and plays an essential role in the development of embryonic vasculature), PIGF (Placental growth factor, a proangiogenic protein peaking at 30 weeks of gestation that stimulates endothelial cell growth, proliferation, and migration), DCN (Decorin, which is a functional component of the extracellular matrix and plays a role in tissue repair and regulation of cell adhesion and migration by binding to ECM molecules), ENG (Endoglin, which in its soluble form, sENG is a powerful antiangiogenic molecule, and acts by inhibiting TGF-β1 binding), and FGF21 (Fibroblast growth factor 21, which has been demonstrated to be expressed in placental syncytiotrophoblasts, and is both an adipokine and a regulator of glucose transport) are considered to be markers of angiogenesis dysfunction in preeclampsia. Another such dysfunctional system is oxygen signaling, which results from hypoperfusion of the placenta, and leads to upregulation of oxidative stress factors. KIM-1 (Kidney Injury Molecule-1) is considered to be a marker of dysfunction in oxygen signaling in preeclampsia, as its expression is known to increase in response to local hypoxia/ischemia in proximal renal tubule cells. Another such dysfunctional system is altered immune response, which may result from inflammation of placental tissues as a result of their hypoperfusion. CLEC4A (C-type Lectin domain family member A, which maintains the balance of polarization of naïve Th cells into Th1 and Th2 effector cells), TFF2 (Trefoil factor 2, which is upregulated on mucosal surfaces during inflammation), and CD274/PD-L1 (cluster of differentiation 274 or programmed-death ligand 1) are considered to be markers of the dysfunctional immune response in preeclampsia. These systems are thought to interact and amplify each other, resulting in the widespread maternal vascular dysfunction and organ damage that can result from preeclampsia.

The methods herein can comprise identifying or ruling out a condition (e.g. preeclampsia) from one or more biomarkers recited in the following table (Table A).

TABLE A

High Priority Biomarkers for Identifying or Ruling Out Preeclampsia

| | Biomarker |
|---|---|
| 1 | PlGF |
| 2 | SFLT.1 |
| 3 | KIM1 |
| 4 | CLEC4A |

The methods herein can comprise identifying or ruling out a condition (e.g. preeclampsia) from one or more biomarkers recited in the following table (Table B).

TABLE B

High Priority Biomarkers for Identifying or Ruling Out Preeclampsia

| | Biomarker |
|---|---|
| 5 | FGF21 |
| 6 | ENDOGLIN |
| 7 | DECORIN |
| 8 | CD274 |
| 9 | HGF |
| 10 | TFF2 |
| 11 | PAPP.A2 |

The methods provided herein can comprise identifying or ruling out a condition (e.g. preeclampsia) from (e.g., based on analysis from) one or more biomarkers selected from Table A and Table B. In some cases, the methods provided herein can comprise identifying or ruling out a condition (e.g. preeclampsia) from two or more biomarkers selected from Table A and Table B. In some cases, the methods provided herein can comprise identifying or ruling out a condition (e.g. preeclampsia) from three or more biomarkers selected from Table A and Table B. In some cases, the methods provided herein can comprise identifying or ruling out a condition (e.g. preeclampsia) from one biomarker selected from Table A and Table B. In some cases, the methods provided herein can comprise identifying or ruling out a condition (e.g. preeclampsia) from two biomarkers selected from Table A and Table B In some cases, the methods provided herein can comprise identifying or ruling out a condition (e.g. preeclampsia) from three biomarkers selected from Table A and Table B. In some cases, the methods provided herein can comprise identifying or ruling out a condition (e.g. preeclampsia) from four biomarkers selected from Table A and Table B. In some cases, the methods provided herein can comprise identifying or ruling out a condition (e.g. preeclampsia) from five biomarkers selected from Table A and Table B. In some cases, the methods provided herein can comprise identifying or ruling out a condition (e.g. preeclampsia) from all the biomarkers identified in Table A and Table B. In some cases, the methods provided herein can comprise identifying or ruling out a condition (e.g. preeclampsia) from no more than 3 biomarkers selected from Table A and Table B. In some cases, the methods provided herein can comprise identifying or ruling out a condition (e.g. preeclampsia) from no more than 4 biomarkers selected from Table A and Table B. In some cases, the methods provided herein can comprise identifying or ruling out a condition (e.g. preeclampsia) from no more than 5 biomarkers selected from Table A and Table B. In some cases, the methods provided herein can comprise identifying or ruling out a condition (e.g. preeclampsia) from no more than 6 biomarkers selected from Table A and Table B. In some cases, the methods provided herein can comprise identifying or ruling out a condition (e.g. preeclampsia) from no more than 7 biomarkers selected from Table A and Table B. In some cases, the methods provided herein can comprise identifying or ruling out a condition (e.g. preeclampsia) from no more than 8 biomarkers selected from Table A and Table B. In some cases, the methods provided herein can comprise identifying or ruling out a condition (e.g. preeclampsia) from no more than 9 biomarkers selected from Table A and Table B. In some cases, the methods provided herein can comprise identifying or ruling out a condition (e.g. preeclampsia) from no more than 10 biomarkers selected from Table A and Table B. In some cases, the methods provided herein can comprise identifying or ruling out a condition (e.g. preeclampsia) from no more than 11 biomarkers selected from Table A and Table B.

The methods provided herein can comprise identifying or ruling out a condition (e.g. preeclampsia) from one or more biomarkers selected from Table A and one or more biomarkers selected from Table B. In some cases, the methods provided herein can comprise identifying or ruling out a condition (e.g. preeclampsia) from 2 or more biomarkers selected from Table A and one or more biomarkers selected from Table B. In some cases, the methods provided herein can comprise identifying or ruling out a condition (e.g. preeclampsia) from 3 or more biomarkers selected from Table A and one or more biomarkers selected from Table B. In some cases, the methods provided herein can comprise identifying or ruling out a condition (e.g. preeclampsia) from 4 biomarkers selected from Table A and one or more biomarkers selected from Table B. In some cases, the methods provided herein can comprise identifying or ruling out a condition (e.g. preeclampsia) from 3 biomarkers selected from Table A and one or more biomarkers selected from Table B. In some cases, the methods provided herein can comprise identifying or ruling out a condition (e.g. preeclampsia) from 3 biomarkers selected from Table A and two or more biomarkers selected from Table B. In some cases, the methods provided herein can comprise identifying or ruling out a condition (e.g. preeclampsia) from 3 biomarkers selected from Table A and three or more biomarkers selected from Table B. In some cases, the methods provided herein can comprise identifying or ruling out a condition (e.g. preeclampsia) from 3 biomarkers selected from Table A and four or more biomarkers selected from Table B. In some cases, the methods provided herein can comprise identifying or ruling out a condition (e.g. preeclampsia) from 3 biomarkers selected from Table A and five or more biomarkers selected from Table B. In some cases, the methods provided herein can comprise identifying or ruling out a condition (e.g. preeclampsia) from 3 biomarkers selected from Table A and six or more biomarkers selected from Table B. In some cases, the methods provided herein can comprise identifying or ruling out a condition (e.g. preeclampsia) from 3 biomarkers selected from Table A and one biomarker selected from Table B. In some cases, the methods provided herein can comprise identifying or ruling out a condition (e.g. preeclampsia) from 3 biomarkers selected from Table A and two biomarkers selected from Table B. In some cases, the methods provided herein can comprise identifying or ruling out a condition (e.g. preeclampsia) from 3 biomarkers selected from Table A and three biomarkers selected from Table B. In some cases, the methods provided herein can comprise identifying or ruling out a condition (e.g. preeclampsia) from 3 biomarkers selected from Table A and four biomarkers selected from Table B. In some cases, the methods provided herein can comprise identifying or ruling out a condition (e.g. preeclampsia) from 3 biomarkers selected from Table A and five biomarkers selected from Table B. In some cases, the methods provided herein can comprise identifying or ruling out a condition (e.g. preeclampsia) from 3 biomarkers selected from Table A and six biomarkers selected from Table B. In some cases, the methods provided herein can comprise identifying or ruling out a condition (e.g. preeclampsia) from 3 biomarkers selected from Table A and seven biomarkers selected from Table B. The methods provided herein can comprise identifying or ruling out a condition (e.g. preeclampsia) from no more than one biomarker selected from Table A and no more than 2 biomarkers selected from Table B. The methods provided herein can comprise identifying or ruling out a condition (e.g. preeclampsia) from no more than two biomarkers selected from Table A and no more than 2 biomarkers selected from Table B. The methods provided herein can comprise identifying or ruling out a condition (e.g. preeclampsia) from no more than three biomarkers selected from Table A and no more than 2 biomarkers selected from Table B. The methods provided herein can comprise identifying or ruling out a condition (e.g. preeclampsia) from no more than one biomarker selected from Table A and no more than 2 biomarkers selected from Table B. The methods provided herein can comprise identifying or ruling out a condition (e.g. preeclampsia) from no more than one biomarker selected from Table A and no more than 3 biomarkers selected from Table B. The methods provided herein can comprise identifying or ruling out a condition (e.g. preeclampsia) from no more than two biomarkers selected from Table A and no more than 3 biomarkers selected from Table B. The methods provided herein can comprise identifying or ruling out a condition (e.g. preeclampsia) from no more than three biomarkers selected from Table A and no more than 3 biomarkers selected from Table B. The methods provided herein can comprise identifying or ruling out a condition (e.g. preeclampsia) from no more than one biomarker selected from Table A and no more than 3 biomarkers selected from Table B. The methods provided herein can comprise identifying or ruling out a condition (e.g. preeclampsia) from no more than one biomarker selected from Table A and no more than 4 biomarkers selected from Table B. The methods provided herein can comprise identifying or ruling out a condition (e.g. preeclampsia) from no more than two biomarkers selected from Table A and no more than 4 biomarkers selected from Table B. The methods provided herein can comprise identifying or ruling out a condition (e.g. preeclampsia) from no more than three biomarkers selected from Table A and no more than 4 biomarkers selected from Table B. The methods provided herein can comprise identifying or ruling out a condition (e.g. preeclampsia) from no more than one biomarker selected from Table A and no more than 4 biomarkers selected from Table B.

In some embodiments, the methods provided herein can comprises identifying or ruling out a condition (e.g. preeclampsia) from a panel of markers comprising sFLT-1, PIGF, FGF21, CLEC4a, endoglin, CD274, and decorin.

The methods provided herein can comprise identifying or ruling out a condition (e.g. preeclampsia) from (e.g., based on analysis from) sFlt.1, PIGF, KIM1, and CLEC4A; sFlt.1, PIGF, KIM1, CLEC4A, and FGF21; sFlt.1, PIGF, KIM1, CLEC4A, and CD274; sFlt.1, PIGF, KIM1, CLEC4A, and ENDOGLIN; sFlt.1, PIGF, KIM1, CLEC4A, and DECORIN; sFlt.1, PIGF, KIM1, CLEC4A, FGF21, and ENDOG- LIN; sFlt.1, PlGF, KIM1, CLEC4A, FGF21, and CD274; sFlt.1, PlGF, KIM1, CLEC4A, ENDOGLIN, and CD274; sFlt.1, PlGF, KIM1, CLEC4A, ENDOGLIN, and DECORIN; sFlt.1, PlGF, KIM1, CLEC4A, FGF21, ENDOGLIN, and CD274; sFlt.1, PlGF, KIM1, CLEC4A, FGF21, ENDOGLIN, CD274, and DECORIN; PlGF, KIM1, CLEC4A, and ENDOGLIN; PlGF, KIM1, CLEC4A, ENDOGLIN, and DECORIN; sFlt.1, PlGF, KIM1, TFF2, FGF21, and DECORIN; sFlt.1, PlGF, KIM1, CLEC4A, CD2741, and ENDOGLIN, or HGF, SYND1, CLEC4A, sFlt.1, PlGF, KIM1, CLEC4A, and FGF21.

The methods provided herein can comprise identifying or ruling out a condition (e.g. preeclampsia) from (e.g., based on analysis from) the following sets of four biomarkers optionally in combination with PlGF:SFLT1, KIM1, CLEC4A, FGF21; SFLT1, KIM1, CLEC4A, endoglin; SFLT1, KIM1, CLEC4A, decorin; SFLT1, KIM1, CLEC4A, CD274; SFLT1, KIM1, CLEC4A, HGF; SFLT1, KIM1, CLEC4A, TFF2; SFLT1, KIM1, CLEC4A, PAPP.A2; SFLT1, KIM1, FGF21, endoglin; SFLT1, KIM1, FGF21, decorin; SFLT1, KIM1, FGF21, CD274; SFLT1, KIM1, FGF21, HGF; SFLT1, KIM1, FGF21, TFF2; SFLT1, KIM1, FGF21, PAPP.A2; SFLT1, KIM1, endoglin, decorin; SFLT1, KIM1, endoglin, CD274; SFLT1, KIM1, endoglin, HGF; SFLT1, KIM1, endoglin, TFF2; SFLT1, KIM1, endoglin, PAPP.A2; SFLT1, KIM1, decorin, CD274; SFLT1, KIM1, decorin, HGF; SFLT1, KIM1, decorin, TFF2; SFLT1, KIM1, decorin, PAPP.A2; SFLT1, KIM1, CD274, HGF; SFLT1, KIM1, CD274, TFF2; SFLT1, KIM1, CD274, PAPP.A2; SFLT1, KIM1, HGF, TFF2; SFLT1, KIM1, HGF, PAPP.A2; SFLT1, KIM1, TFF2, PAPP.A2; SFLT1, CLEC4A, FGF21, endoglin; SFLT1, CLEC4A, FGF21, decorin; SFLT1, CLEC4A, FGF21, CD274; SFLT1, CLEC4A, FGF21, HGF; SFLT1, CLEC4A, FGF21, TFF2; SFLT1, CLEC4A, FGF21, PAPP.A2; SFLT1, CLEC4A, endoglin, decorin; SFLT1, CLEC4A, endoglin, CD274; SFLT1, CLEC4A, endoglin, HGF; SFLT1, CLEC4A, endoglin, TFF2; SFLT1, CLEC4A, endoglin, PAPP.A2; SFLT1, CLEC4A, decorin, CD274; SFLT1, CLEC4A, decorin, HGF; SFLT1, CLEC4A, decorin, TFF2; SFLT1, CLEC4A, decorin, PAPP.A2; SFLT1, CLEC4A, CD274, HGF; SFLT1, CLEC4A, CD274, TFF2; SFLT1, CLEC4A, CD274, PAPP.A2; SFLT1, CLEC4A, HGF, TFF2; SFLT1, CLEC4A, HGF, PAPP.A2; SFLT1, CLEC4A, TFF2, PAPP.A2; SFLT1, FGF21, endoglin, decorin; SFLT1, FGF21, endoglin, CD274; SFLT1, FGF21, endoglin, HGF; SFLT1, FGF21, endoglin, TFF2; SFLT1, FGF21, endoglin, PAPP.A2; SFLT1, FGF21, decorin, CD274; SFLT1, FGF21, decorin, HGF; SFLT1, FGF21, decorin, TFF2; SFLT1, FGF21, decorin, PAPP.A2; SFLT1, FGF21, CD274, HGF; SFLT1, FGF21, CD274, TFF2; SFLT1, FGF21, CD274, PAPP.A2; SFLT1, FGF21, HGF, TFF2; SFLT1, FGF21, HGF, PAPP.A2; SFLT1, FGF21, TFF2, PAPP.A2; SFLT1, endoglin, decorin, CD274; SFLT1, endoglin, decorin, HGF; SFLT1, endoglin, decorin, TFF2; SFLT1, endoglin, decorin, PAPP.A2; SFLT1, endoglin, CD274, HGF; SFLT1, endoglin, CD274, TFF2; SFLT1, endoglin, CD274, PAPP.A2; SFLT1, endoglin, HGF, TFF2; SFLT1, endoglin, HGF, PAPP.A2; SFLT1, endoglin, TFF2, PAPP.A2; SFLT1, decorin, CD274, HGF; SFLT1, decorin, CD274, TFF2; SFLT1, decorin, CD274, PAPP.A2; SFLT1, decorin, HGF, TFF2; SFLT1, decorin, HGF, PAPP.A2; SFLT1, decorin, TFF2, PAPP.A2; SFLT1, CD274, HGF, TFF2; SFLT1, CD274, HGF, PAPP.A2; SFLT1, CD274, TFF2, PAPP.A2; SFLT1, HGF, TFF2, PAPP.A2; KIM1, CLEC4A, FGF21, endoglin; KIM1, CLEC4A, FGF21, decorin; KIM1, CLEC4A, FGF21, CD274; KIM1, CLEC4A, FGF21, HGF; KIM1, CLEC4A, FGF21, TFF2; KIM1, CLEC4A, FGF21, PAPP.A2; KIM1, CLEC4A, endoglin, decorin; KIM1, CLEC4A, endoglin, CD274; KIM1, CLEC4A, endoglin, HGF; KIM1, CLEC4A, endoglin, TFF2; KIM1, CLEC4A, endoglin, PAPP.A2; KIM1, CLEC4A, decorin, CD274; KIM1, CLEC4A, decorin, HGF; KIM1, CLEC4A, decorin, TFF2; KIM1, CLEC4A, decorin, PAPP.A2; KIM1, CLEC4A, CD274, HGF; KIM1, CLEC4A, CD274, TFF2; KIM1, CLEC4A, CD274, PAPP.A2, KIM1, CLEC4A, HGF, TFF2; KIM1, CLEC4A, HGF, PAPP.A2; KIM1, CLEC4A, TFF2, PAPP.A2; KIM1, FGF21, endoglin, decorin; KIM1, FGF21, endoglin, CD274; KIM1, FGF21, endoglin, HGF; KIM1, FGF21, endoglin, TFF2; KIM1, FGF21, endoglin, PAPP.A2; KIM1, FGF21, decorin, CD274; KIM1, FGF21, decorin, HGF; KIM1, FGF21, decorin, TFF2; KIM1, FGF21, decorin, PAPP.A2; KIM1, FGF21, CD274, HGF; KIM1, FGF21, CD274, TFF2; KIM1, FGF21, CD274, PAPP.A2; KIM1, FGF21, HGF, TFF2; KIM1, FGF21, HGF, PAPP.A2; KIM1, FGF21, TFF2, PAPP.A2; KIM1, endoglin, decorin, CD274; KIM1, endoglin, decorin, HGF; KIM1, endoglin, decorin, TFF2; KIM1, endoglin, decorin, PAPP.A2; KIM1, endoglin, CD274, HGF; KIM1, endoglin, CD274, TFF2; KIM1, endoglin, CD274, PAPP.A2; KIM1, endoglin, HGF, TFF2; KIM1, endoglin, HGF, PAPP.A2; KIM1, endoglin, TFF2, PAPP.A2; KIM1, decorin, CD274, HGF; KIM1, decorin, CD274, TFF2; KIM1, decorin, CD274, PAPP.A2; KIM1, decorin, HGF, TFF2; KIM1, decorin, HGF, PAPP.A2; KIM1, decorin, TFF2, PAPP.A2; KIM1, CD274, HGF, TFF2; KIM1, CD274, HGF, PAPP.A2; KIM1, CD274, TFF2, PAPP.A2; KIM1, HGF, TFF2, PAPP.A2; CLEC4A, FGF21, endoglin, decorin; CLEC4A, FGF21, endoglin, CD274; CLEC4A, FGF21, endoglin, HGF; CLEC4A, FGF21, endoglin, TFF2; CLEC4A, FGF21, endoglin, PAPP.A2; CLEC4A, FGF21, decorin, CD274; CLEC4A, FGF21, decorin, HGF; CLEC4A, FGF21, decorin, TFF2; CLEC4A, FGF21, decorin, PAPP.A2; CLEC4A, FGF21, CD274, HGF; CLEC4A, FGF21, CD274, TFF2; CLEC4A, FGF21, CD274, PAPP.A2; CLEC4A, FGF21, HGF, TFF2; CLEC4A, FGF21, HGF, PAPP.A2; CLEC4A, FGF21, TFF2, PAPP.A2; CLEC4A, endoglin, decorin, CD274; CLEC4A, endoglin, decorin, HGF; CLEC4A, endoglin, decorin, TFF2; CLEC4A, endoglin, decorin, PAPP.A2; CLEC4A, endoglin, CD274, HGF; CLEC4A, endoglin, CD274, TFF2; CLEC4A, endoglin, CD274, PAPP.A2; CLEC4A, endoglin, HGF, TFF2; CLEC4A, endoglin, HGF, PAPP.A2; CLEC4A, endoglin, TFF2, PAPP.A2; CLEC4A, decorin, CD274, HGF; CLEC4A, decorin, CD274, TFF2; CLEC4A, decorin, CD274, PAPP.A2; CLEC4A, decorin, HGF, TFF2; CLEC4A, decorin, HGF, PAPP.A2; CLEC4A, decorin, TFF2, PAPP.A2; CLEC4A, CD274, HGF, TFF2; CLEC4A, CD274, HGF, PAPP.A2; CLEC4A, CD274, TFF2, PAPP.A2; CLEC4A, HGF, TFF2, PAPP.A2; FGF21, endoglin, decorin, CD274; FGF21, endoglin, decorin, HGF; FGF21, endoglin, decorin, TFF2; FGF21, endoglin, decorin, PAPP.A2; FGF21, endoglin, CD274, HGF; FGF21, endoglin, CD274, TFF2; FGF21, endoglin, CD274, PAPP.A2; FGF21, endoglin, HGF, TFF2; FGF21, endoglin, HGF, PAPP.A2; FGF21, endoglin, TFF2, PAPP.A2; FGF21, decorin, CD274, HGF; FGF21, decorin, CD274, TFF2; FGF21, decorin, CD274, PAPP.A2; FGF21, decorin, HGF, TFF2; FGF21, decorin, HGF, PAPP.A2; FGF21, decorin, TFF2, PAPP.A2; FGF21, CD274, HGF, TFF2; FGF21, CD274, HGF, PAPP.A2; FGF21, CD274, TFF2, PAPP.A2; FGF21, HGF, TFF2, PAPP.A2; endoglin, decorin, CD274, HGF; endoglin, decorin, CD274, TFF2; endoglin, decorin, CD274, PAPP.A2; endoglin, decorin, HGF, TFF2; endoglin, decorin, HGF, PAPP.A2; endoglin, decorin, TFF2, PAPP.A2; endoglin, CD274, HGF, TFF2; endoglin, CD274, HGF, PAPP.A2; endoglin, CD274, TFF2, PAPP.A2; endoglin, HGF, TFF2, PAPP.A2; decorin, CD274, HGF, TFF2; decorin, CD274, HGF, PAPP.A2; decorin, CD274, TFF2, PAPP.A2; or decorin, HGF, TFF2, PAPP.A2; CD274, HGF, TFF2, PAPP.A2

The methods provided herein can comprise identifying or ruling out a condition (e.g. preeclampsia) from (e.g., based on analysis from) the following sets of three biomarkers optionally in combination with PlGF: SFLT1, KIM1, CLEC4A; SFLT1, KIM1, FGF21; SFLT1, KIM1, endoglin; SFLT1, KIM1, decorin; SFLT1, KIM1, CD274; SFLT1, KIM1, HGF; SFLT1, KIM1, TFF2; SFLT1, KIM1, PAPP.A2; SFLT1, CLEC4A, FGF21; SFLT1, CLEC4A, endoglin; SFLT1, CLEC4A, decorin; SFLT1, CLEC4A, CD274; SFLT1, CLEC4A, HGF; SFLT1, CLEC4A, TFF2; SFLT1, CLEC4A, PAPP.A2; SFLT1, FGF21, endoglin; SFLT1, FGF21, decorin; SFLT1, FGF21, CD274; SFLT1, FGF21, HGF; SFLT1, FGF21, TFF2; SFLT1, FGF21, PAPP.A2; SFLT1, endoglin, decorin: SFLT1, endoglin, CD274; SFLT1, endoglin, HGF; SFLT1, endoglin, TFF2; SFLT1, endoglin, PAPP.A2; SFLT1, decorin, CD274; SFLT1, decorin, HGF; SFLT1, decorin, TFF2; SFLT1, decorin, PAPP.A2; SFLT1, CD274, HGF; SFLT1, CD274, TFF2; SFLT1, CD274, PAPP.A2; SFLT1, HGF, TFF2; SFLT1, HGF, PAPP.A2; SFLT1, TFF2, PAPP.A2; KIM1, CLEC4A, FGF21; KIM1, CLEC4A, endoglin; KIM1, CLEC4A, decorin; KIM1, CLEC4A, CD274; KIM1, CLEC4A, HGF; KIM1, CLEC4A, TFF2; KIM1, CLEC4A, PAPP.A2; KIM1, FGF21, endoglin; KIM1, FGF21, decorin; KIM1, FGF21, CD274; KIM1, FGF21, HGF; KIM1, FGF21, TFF2; KIM1, FGF21, PAPP.A2; KIM1, endoglin, decorin; KIM1, endoglin, CD274; KIM1, endoglin, HGF; KIM1, endoglin, TFF2; KIM1, endoglin, PAPP.A2; KIM1, decorin, CD274; KIM1, decorin, HGF; KIM1, decorin, TFF2; KIM1, decorin, PAPP.A2; KIM1, CD274, HGF; KIM1, CD274, TFF2; KIM1, CD274, PAPP.A2; KIM1, HGF, TFF2; KIM1, HGF, PAPP.A2; KIM1, TFF2, PAPP.A2; CLEC4A, FGF21, endoglin; CLEC4A. FGF21, decorin; CLEC4A, FGF21, CD274; CLEC4A, FGF21, HGF; CLEC4A, FGF21, TFF2; CLEC4A, FGF21, PAPP.A2; CLEC4A, endoglin, decorin; CLEC4A, endoglin, CD274; CLEC4A, endoglin, HGF, CLEC4A, endoglin, TFF2; CLEC4A, endoglin, PAPP.A2; CLEC4A, decorin, CD274; CLEC4A, decorin, HGF; CLEC4A, decorin, TFF2; CLEC4A, decorin, PAPP.A2; CLEC4A, CD274, HGF; CLEC4A, CD274, TFF2; CLEC4A, CD274, PAPP.A2; CLEC4A, HGF, TFF2; CLEC4A, HGF, PAPP.A2; CLEC4A, TFF2, PAPP.A2; FGF21, endoglin, decorin; FGF21, endoglin, CD274; FGF21, endoglin, HGF; FGF21, endoglin, TFF2; FGF21, endoglin, PAPP.A2; FGF21, decorin, CD274; FGF21, decorin, HGF; FGF21, decorin, TFF2; FGF21, decorin, PAPP.A2; FGF21, CD274, HGF; FGF21, CD274, TFF2; FGF21, CD274, PAPP.A2; FGF21, HGF, TFF2; FGF21, HGF, PAPP.A2; FGF21, TFF2, PAPP.A2; endoglin, decorin, CD274; endoglin, decorin, HGF; endoglin, decorin, TFF2; endoglin, decorin, PAPP.A2; endoglin, CD274, HGF; endoglin, CD274, TFF2; endoglin, CD274, PAPP.A2; endoglin, HOF, TFF2; endoglin, HGF, PAPP.A2; endoglin, TFF2, PAPP.A2; decorin, CD274, HGF; decorin, CD274, TFF2; decorin, CD274, PAPP.A2; decorin, HGF, TFF2; decorin, HGF, PAPP.A2; decorin, TFF2, PAPP.A2; CD274, HGF, TFF2; CD274, HGF, PAPP.A2; CD274, TFF2, PAPP.A2; or HGF, TFF2, PAPP.A2.

The methods provided herein can comprise identifying or ruling out a condition (e.g. preeclampsia) from (e.g., based on analysis from) the following sets of three biomarkers optionally in combination with PIGF: SFLT1, KIM1; SFLT1, CLEC4A; SFLT1, FGF21; SFLT1, endoglin; SFLT1, decorin; SFLT1, CD274; SFLT1, HGF; SFLT1, TFF2; SFLT1, PAPP.A2; KIM1, CLEC4A; KIM1, FGF21; KIM1, endoglin; KIM1, decorin; KIM1, CD274; KIM1, HGF; KIM1, TFF2; KIM1, PAPP.A2; CLEC4A, FGF21; CLEC4A, endoglin; CLEC4A, decorin; CLEC4A, CD274; CLEC4A, HGF; CLEC4A, TFF2; CLEC4A, PAPP.A2; FGF21, endoglin; FGF21, decorin; FGF21, CD274; FGF21, HGF; FGF21, TFF2; FGF21, PAPP.A2; endoglin, decorin; endoglin, CD274; endoglin, HGF; endoglin, TFF2; endoglin, PAPP.A2; decorin, CD274; decorin, HGF; decorin, TFF2; decorin, PAPP.A2; CD274, HGF; CD274, TFF2; CD274, PAPP.A2; HGF, TFF2; HGF, PAPP.A2; TFF2, PAPP.A2.

The methods provided herein can comprise identifying or ruling out a condition (e.g. preeclampsia) from (e.g., based on analysis from) the following sets of biomarkers: PIGF, sFLT1, KIM1; PIGF, sFLT1, CLEC4A; PIGF, sFLT1, FGF21; PIGF, sFLT1, Decorin; PIGF, sFLT1, CD274; PIGF, sFL.T1, HGF; PIGF, sFLT1, TFF2; PIGF, sFLT1, PAPP-A2; PIGF, Endoglin, KIM1; PIGF, Endoglin, CLEC4A; PIGF, Endoglin, FGF21; PIGF, Endoglin, Decorin; PIGF, Endoglin, CD274; PIGF, Endoglin, HGF; PIGF, Endoglin, TFF2; PIGF, Endoglin, PAPP-A2; PIGF, KIM1, CLEC4A; PIGF, KIM1, FGF21; PIGF, KIM1, Decorin; PIGF, KIM1, CD274; PIGF, KIM1, HGF; PIGF, KIM1, TFF2; PIGF, KIM1, PAPP-A2; PIGF, CLEC4A, FGF21; PIGF, CLEC4A, Decorin; PIGF, CLEC4A, CD274; PIGF, CLEC4A, HGF: PIGF, CLEC4A, TFF2; PIGF, CLEC4A, PAPP-A2; PIGF, CD274, CLEC4A; PIGF, CD274, FGF21; PIGF, CD274, HGF; PIGF, CD274, TFF2; PIGF, CD274, PAPP-A2; PIGF, Decorin, CLEC4A; PIGF, Decorin, FGF21; PIGF, Decorin, HGF; PIGF, Decorin, TFF2; PIGF, Decorin, PAPP-A2; PIGF, FGF21, TFF2, Decorin; PIGF, FGF21, TFF2, CD274; PIGF, FGF21, TFF2, HGF; PIGF, FGF21, TFF2; PIGF, FGF21, TFF2, PAPP-A2; PIGF, Endoglin, PAPP-A2, DECORIN, KIM1; PIGF, Endoglin, PAPP-A2, DECORIN, CLEC4A; PIGF, Endoglin, PAPP-A2, DECORIN, FGF21; PIGF, Endoglin, PAPP-A2, DECORIN, CD274; PIGF, Endoglin, PAPP-A2, DECORIN, HGF; PIGF, Endoglin, PAPP-A2, DECORIN, TFF2.

The methods provided herein can comprise identifying or ruling out a condition from one or more biomarkers selected from Table 2, Table 3, Table 4, Table 5, CCL2 (chemokine C-C motif ligand 2), CD134 (cluster of differentiation 134), DCN, HGF (hepatocyte growth factor), NOS3 (nitric oxide synthase 3), PIGF, CD274, CDCP1 (cub domain containing protein 1), FGF-21, TGFa (transforming growth factor alpha), UPA (urokinase-type plasminogen activator), CLEC4A, CLEC4C (C-type lectin domain family 4 member C), ZBTB16 (Zinc Finger And BTB Domain Containing 16), APLP1 (Amyloid Beta Precursor Like Protein 1), DPP7 (Dipeptidyl Peptidase 7), GRAP2 (GRB2 Related Adaptor Protein 2), ITGB7 (Integrin Subunit Beta 7), PAG1 (Phosphoprotein Membrane Anchor With Glycosphingolipid Microdomains 1), TFF2, AMN (Amnion Associated Transmembrane Protein), CAPG (Capping Actin Protein, Gelsolin Like), CLEC1A5, FES (Tyrosine-protein kinase Fes/Fps), KIM1, PGF (Placental Growth Factor), ERBB4 (Erb-B2 Receptor Tyrosine Kinase 4), GPNMB (Glycoprotein Nmb), PPY (Pancreatic Polypeptide), or SYND1 (Syndecan 1), and any combination thereof ("Group 1"). In some cases, preeclampsia of a pregnant patient can be detected from one or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from two or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from three or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from four or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from five or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from six or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from seven or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from eight or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from nine or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from ten or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from eleven or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from twelve or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from thirteen or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from fourteen or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from fifteen or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from sixteen or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from seventeen or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from eighteen or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from nineteen or more biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than twenty biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than nineteen biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than eighteen biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than seventeen biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than sixteen biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than fifteen biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than fourteen biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than thirteen biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than twelve biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than eleven biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than ten biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than nine biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, ITS, KIM1, PGF, ERBB4, GPNMB, PPY, or SYND1, and any combination thereof. In some cases, preeclampsia of a pregnant patient can be detected from no more than eight biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than seven biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than six biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than five biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than four biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than three biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from 1, 2, 3, 4, 5, 6, 7, 8, 9, 10, 11, 12, 13, 14, 15, 16, 17, 18, 19, or 20 biomarkers selected from Table 2, Table 3, Table 4, Table 5, CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof.

The methods provided herein can comprise identifying or ruling out a condition (e.g. preeclampsia) from one or more biomarkers selected from Table 2, Table 3, Table 4, or Table 5, and any combination thereof ("Group 2"). In some cases, preeclampsia of a pregnant patient can be detected from one or more biomarkers selected from Table 2, Table 3, Table 4, or Table 5, and any combination thereof. In some cases, preeclampsia of a pregnant patient can be detected from two or more biomarkers selected from Table 2, Table 3, Table 4, or Table 5, and any combination thereof. In some cases, preeclampsia of a pregnant patient can be detected from three or more biomarkers selected from Table 2, Table 3, Table 4, or Table 5, and any combination thereof. In some cases, preeclampsia of a pregnant patient can be detected from four or more biomarkers selected from Table 2, Table 3, Table 4, or Table 5, and any combination thereof. In some cases, preeclampsia of a pregnant patient can be detected from five or more biomarkers selected from Table 2, Table 3, Table 4, or Table 5, and any combination thereof. In some cases, preeclampsia of a pregnant patient can be detected from six or more biomarkers selected from Table 2, Table 3, Table 4, or Table 5, and any combination thereof. In some cases, preeclampsia of a pregnant patient can be detected from seven or more biomarkers selected from Table 2, Table 3, Table 4, Table 5, and any combination thereof. In some cases, preeclampsia of a pregnant patient can be detected from eight or more biomarkers selected from Table 2, Table 3, Table 4, or Table 5, and any combination thereof. In some cases, preeclampsia of a pregnant patient can be detected from nine or more biomarkers selected from Table 2, Table 3, Table 4, or Table 5, and any combination thereof. In some cases, preeclampsia of a pregnant patient can be detected from ten or more biomarkers selected from Table 2, Table 3, Table 4, or Table 5, and any combination thereof. In some cases, preeclampsia of a pregnant patient can be detected from eleven or more biomarkers selected from Table 2, Table 3, Table 4, or Table 5, and any combination thereof. In some cases, preeclampsia of a pregnant patient can be detected from twelve or more biomarkers selected from Table 2, Table 3, Table 4, or Table 5, and any combination thereof. In some cases, preeclampsia of a pregnant patient can be detected from thirteen or more biomarkers selected from Table 2, Table 3, Table 4, or Table 5, and any combination thereof. In some cases, preeclampsia of a pregnant patient can be detected from fourteen or more biomarkers selected from Table 2, Table 3, Table 4, or Table 5, and any combination thereof. In some cases, preeclampsia of a pregnant patient can be detected from fifteen or more biomarkers selected from Table 2, Table 3, Table 4, or Table 5, and any combination thereof. In some cases, preeclampsia of a pregnant patient can be detected from sixteen or more biomarkers selected from Table 2, Table 3, Table 4, or Table 5, and any combination thereof. In some cases, preeclampsia of a pregnant patient can be detected from seventeen or more biomarkers selected from Table 2, Table 3, Table 4, or Table 5, and any combination thereof. In some cases, preeclampsia of a pregnant patient can be detected from eighteen or more biomarkers selected from Table 2, Table 3, Table 4, or Table 5, and any combination thereof. In some cases, preeclampsia of a pregnant patient can be detected from nineteen or more biomarkers selected from Table 2, Table 3, Table 4, or Table 5, and any combination thereof. In some cases, preeclampsia of a pregnant patient can be detected from no more than twenty biomarkers selected from Table 2, Table 3, Table 4, or Table 5, and any combination thereof. In some cases, preeclampsia of a pregnant patient can be detected from no more than nineteen biomarkers selected from Table 2, Table 3, Table 4, or Table 5, and any combination thereof. In some cases, preeclampsia of a pregnant patient can be detected from no more than eighteen biomarkers selected from Table 2, Table 3, Table 4, or Table 5, and any combination thereof. In some cases, preeclampsia of a pregnant patient can be detected from no more than seventeen biomarkers selected from Table 2, Table 3, Table 4, or Table 5, and any combination thereof. In some cases, preeclampsia of a pregnant patient can be detected from no more than sixteen biomarkers selected from Table 2, Table 3, Table 4, or Table 5, and any combination thereof. In some cases, preeclampsia of a pregnant patient can be detected from no more than fifteen biomarkers selected from Table 2, Table 3, Table 4, or Table 5, and any combination thereof. In some cases, preeclampsia of a pregnant patient can be detected from no more than fourteen biomarkers selected from Table 2, Table 3, Table 4, or Table 5, and any combination thereof. In some cases, preeclampsia of a pregnant patient can be detected from no more than thirteen biomarkers selected from Table 2, Table 3, Table 4, or Table 5, and any combination thereof. In some cases, preeclampsia of a pregnant patient can be detected from no more than twelve biomarkers selected from Table 2, Table 3, Table 4, or Table 5, and any combination thereof. In some cases, preeclampsia of a pregnant patient can be detected from no more than eleven biomarkers selected from Table 2, Table 3, Table 4, or Table 5, and any combination thereof. In some cases, preeclampsia of a pregnant patient can be detected from no more than ten biomarkers selected from Table 2, Table 3, Table 4, or Table 5, and any combination thereof. In some cases, preeclampsia of a pregnant patient can be detected from no more than nine biomarkers selected from Table 2, Table 3, Table 4, or Table 5, and any combination thereof. In some cases, preeclampsia of a pregnant patient can be detected from no more than eight biomarkers selected from Table 2, Table 3, Table 4, or Table 5, and any combination thereof. In some cases, preeclampsia of a pregnant patient can be detected from no more than seven biomarkers selected from Table 2, Table 3, Table 4, or Table 5, and any combination thereof. In some cases, preeclampsia of a pregnant patient can be detected from no more than six biomarkers selected from Table 2, Table 3, Table 4, or Table 5, and any combination thereof. In some cases, preeclampsia of a pregnant patient can be detected from no more than five biomarkers selected from Table 2, Table 3, Table 4, or Table 5, and any combination thereof. In some cases, preeclampsia of a pregnant patient can be detected from no more than four biomarkers selected from Table 2, Table 3, Table 4, or Table 5, and any combination thereof. In some cases, preeclampsia of a pregnant patient can be detected from no more than three biomarkers selected from Table 2, Table 3, Table 4, or Table 5, and any combination thereof. In some cases, preeclampsia of a pregnant patient can be detected from 1, 2, 3, 4, 5, 6, 7, 8, 9, 10, 11, 12, 13, 14, 15, 16, 17, 18, 19, or 20 biomarkers selected from Table 2, Table 3, Table 4, or Table 5, and any combination thereof.

The methods provided herein can comprise identifying or ruling out a condition (e.g. preeclampsia) from one or more biomarkers selected from Table 2, Table 3, or Table 5, and any combination thereof ("Group 3"). In some cases, preeclampsia of a pregnant patient can be detected from one or more biomarkers selected from Table 2, Table 3, or Table 5, and any combination thereof. In some cases, preeclampsia of a pregnant patient can be detected from two or more biomarkers selected from Table 2, Table 3, or Table 5, and any combination thereof. In some cases, preeclampsia of a pregnant patient can be detected from three or more biomarkers selected from Table 2, Table 3, or Table 5, and any combination thereof. In some cases, preeclampsia of a pregnant patient can be detected from four or more biomarkers selected from Table 2, Table 3, or Table 5, and any combination thereof. In some cases, preeclampsia of a pregnant patient can be detected from five or more biomarkers selected from Table 2, Table 3, or Table 5, and any combination thereof. In some cases, preeclampsia of a pregnant patient can be detected from six or more biomarkers selected from Table 2, Table 3, or Table 5, and any combination thereof. In some cases, preeclampsia of a pregnant patient can be detected from seven or more biomarkers selected from Table 2, Table 3, or Table 4, and any combination thereof. In some cases, preeclampsia of a pregnant patient can be detected from eight or more biomarkers selected from Table 2, Table 3, or Table 4, and any combination thereof. In some cases, preeclampsia of a pregnant patient can be detected from nine or more biomarkers selected from Table 2, Table 3, or Table 4, and any combination thereof. In some cases, preeclampsia of a pregnant patient can be detected from ten or more biomarkers selected from Table 2, Table 3, or Table 4, and any combination thereof. In some cases, preeclampsia of a pregnant patient can be detected from eleven or more biomarkers selected from Table 2, Table 3, or Table 4, and any combination thereof. In some cases, preeclampsia of a pregnant patient can be detected from twelve or more biomarkers selected from Table 2, Table 3, or Table 4, and any combination thereof. In some cases, preeclampsia of a pregnant patient can be detected from thirteen or more biomarkers selected from Table 2, Table 3, or Table 4, and any combination thereof. In some cases, preeclampsia of a pregnant patient can be detected from fourteen or more biomarkers selected from Table 2, Table 3, or Table 4, and any combination thereof. In some cases, preeclampsia of a pregnant patient can be detected from fifteen or more biomarkers selected from Table 2, Table 3, or Table 4, and any combination thereof. In some cases, preeclampsia of a pregnant patient can be detected from sixteen or more biomarkers selected from Table 2, Table 3, or Table 4, and any combination thereof. In some cases, preeclampsia of a pregnant patient can be detected from seventeen or more biomarkers selected from Table 2, Table 3, or Table 4, and any combination thereof. In some cases, preeclampsia of a pregnant patient can be detected from eighteen or more biomarkers selected from Table 2, Table 3, or Table 4, and any combination thereof. In some cases, preeclampsia of a pregnant patient can be detected from nineteen or more biomarkers selected from Table 2, Table 3, or Table 4, and any combination thereof. In some cases, preeclampsia of a pregnant patient can be detected from no more than twenty biomarkers selected from Table 2, Table 3, or Table 4, and any combination thereof. In some cases, preeclampsia of a pregnant patient can be detected from no more than nineteen biomarkers selected from Table 2, Table 3, or Table 4, and any combination thereof. In some cases, preeclampsia of a pregnant patient can be detected from no more than eighteen biomarkers selected from Table 2, Table 3, or Table 4, and any combination thereof. In some cases, preeclampsia of a pregnant patient can be detected from no more than seventeen biomarkers selected from Table 2, Table 3, or Table 4, and any combination thereof. In some cases, preeclampsia of a pregnant patient can be detected from no more than sixteen biomarkers selected from Table 2, Table 3, or Table 4, and any combination thereof. In some cases, preeclampsia of a pregnant patient can be detected from no more than fifteen biomarkers selected from Table 2, Table 3, or Table 4, and any combination thereof. In some cases, preeclampsia of a pregnant patient can be detected from no more than fourteen biomarkers selected from Table 2, Table 3, or Table 4, and any combination thereof. In some cases, preeclampsia of a pregnant patient can be detected from no more than thirteen biomarkers selected from Table 2, Table 3, or Table 4, and any combination thereof. In some cases, preeclampsia of a pregnant patient can be detected from no more than twelve biomarkers selected from Table 2, Table 3, or Table 4, and any combination thereof. In some cases, preeclampsia of a pregnant patient can be detected from no more than eleven biomarkers selected from Table 2, Table 3, or Table 4, and any combination thereof. In some cases, preeclampsia of a pregnant patient can be detected from no more than ten biomarkers selected from Table 2, Table 3, or Table 5, and any combination thereof. In some cases, preeclampsia of a pregnant patient can be detected from no more than nine biomarkers selected from Table 2, Table 3, or Table 5, and any combination thereof. In some cases, preeclampsia of a pregnant patient can be detected from no more than eight biomarkers selected from Table 2, Table 3, or Table 5, and any combination thereof. In some cases, preeclampsia of a pregnant patient can be detected from no more than seven biomarkers selected from Table 2, Table 3, or Table 5, and any combination thereof. In some cases, preeclampsia of a pregnant patient can be detected from no more than six biomarkers selected from Table 2, Table 3, or Table 5, and any combination thereof. In some cases, preeclampsia of a pregnant patient can be detected from no more than five biomarkers selected from Table 2, Table 3, or Table 5, and any combination thereof. In some cases, preeclampsia of a pregnant patient can be detected from no more than four biomarkers selected from Table 2, Table 3, or Table 5, and any combination thereof. In some cases, preeclampsia of a pregnant patient can be detected from no more than three biomarkers selected from Table 2, Table 3, or Table 5, and any combination thereof. In some cases, preeclampsia of a pregnant patient can be detected from 1, 2, 3, 4, 5, 6, 7, 8, 9, 10, 11, 12, 13, 14, 15, 16, 17, 18, 19, or 20 biomarkers selected from Table 2, Table 3, or Table 5, and any combination thereof.

The methods provided herein can comprise identifying or ruling out a condition (e.g. preeclampsia) from one or more biomarkers selected from Table 2 or Table 5, and any combination thereof ("Group 4"). In some cases, preeclampsia of a pregnant patient can be detected from one or more biomarkers selected from Table 2 or Table 5, and any combination thereof. In some cases, preeclampsia of a pregnant patient can be detected from two or more biomarkers selected from Table 2 or Table 5, and any combination thereof. In some cases, preeclampsia of a pregnant patient can be detected from three or more biomarkers selected from Table 2 or Table 5, and any combination thereof. In some cases, preeclampsia of a pregnant patient can be detected from four or more biomarkers selected from Table 2 or Table 5, and any combination thereof. In some cases, preeclampsia of a pregnant patient can be detected from five or more biomarkers selected from Table 2 or Table 5, and any combination thereof. In some cases, preeclampsia of a pregnant patient can be detected from six or more biomarkers selected from Table 2 or Table 5, and any combination thereof. In some cases, preeclampsia of a pregnant patient can be detected from seven or more biomarkers selected from Table 2 or Table 5, and any combination thereof. In some cases, preeclampsia of a pregnant patient can be detected from eight or more biomarkers selected from Table 2 or Table 5, and any combination thereof. In some cases, preeclampsia of a pregnant patient can be detected from nine or more biomarkers selected from Table 2 or Table 5, and any combination thereof. In some cases, preeclampsia of a pregnant patient can be detected from ten or more biomarkers selected from Table 2 or Table 5, and any combination thereof. In some cases, preeclampsia of a pregnant patient can be detected from 11, 12, 13, 14, 15, 16, 17, 18, or 19 or more biomarkers selected from Table 2 or Table 5, and any combination thereof. In some cases, preeclampsia of a pregnant patient can be detected from no more than 20, 19, 18, 17, 16, 15, 14, 13, 12, or 11 biomarkers selected from Table 2 or Table 5, and any combination thereof. In some cases, preeclampsia of a pregnant patient can be detected from no more than ten biomarkers selected from Table 2 or Table 5, and any combination thereof. In some cases, preeclampsia of a pregnant patient can be detected from no more than nine biomarkers selected from Table 2 or Table 5, and any combination thereof. In some cases, preeclampsia of a pregnant patient can be detected from no more than eight biomarkers selected from Table 2 or Table 5, and any combination thereof. In some cases, preeclampsia of a pregnant patient can be detected from no more than seven biomarkers selected from Table 2 or Table 5, and any combination thereof. In some cases, preeclampsia of a pregnant patient can be detected from no more than six biomarkers selected from Table 2 or Table 5, and any combination thereof. In some cases, preeclampsia of a pregnant patient can be detected from no more than five biomarkers selected from Table 2 or Table 5, and any combination thereof. In some cases, preeclampsia of a pregnant patient can be detected from no more than four biomarkers selected from Table 2 or Table 5, and any combination thereof. In some cases, preeclampsia of a pregnant patient can be detected from no more than three biomarkers selected from Table 2 or Table 5, and any combination thereof. In some cases, preeclampsia of a pregnant patient can be detected from 1, 2, 3, 4, 5, 6, 7, 8, 9, 10, 11, 12, 13, 14, 15, 16, 17, 18, 19, or 20 biomarkers selected from Table 2 or Table 5, and any combination thereof.

The methods provided herein can comprise identifying or ruling out a condition (e.g. preeclampsia) from one or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof ("Group 5"). In some cases, preeclampsia of a pregnant patient can be detected from one or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from two or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from three or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from four or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from five or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from six or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from seven or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from eight or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from nine or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from ten or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from 11, 12, 13, 14, 15, 16, 17, 18, or 19 or more biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than 20, 19, 18, 17, 16, 15, 14, 13, 12, or 11 biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than ten biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than nine biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than eight biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than seven biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than six biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than five biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than four biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from no more than three biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof. In some cases, preeclampsia of a pregnant patient can be detected from 1, 2, 3, 4, 5, 6, 7, 8, 9, 10, 11, 12, 13, 14, 15, 16, 17, 18, 19, or 20 biomarkers selected from CCL2, CD134, DCN, HGF, NOS3, PIGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, or SYND1, and any combination thereof.

The methods provided herein can comprise identifying or ruling out a condition (e.g. preeclampsia) from one or more biomarkers selected from Table 5. In some cases, preeclampsia of a pregnant patient can be detected from one or more biomarkers selected from Table 5. In some cases, preeclampsia of a pregnant patient can be detected from two or more biomarkers selected from Table 5. In some cases, preeclampsia of a pregnant patient can be detected from three or more biomarkers selected from Table 5. In some cases, preeclampsia of a pregnant patient can be detected from four or more biomarkers selected from Table 5. In some cases, preeclampsia of a pregnant patient can be detected from five or more biomarkers selected from Table 5. In some cases, preeclampsia of a pregnant patient can be detected from six or more biomarkers selected from Table 5. In some cases, preeclampsia of a pregnant patient can be detected from nine biomarkers selected from Table 5. In some cases, preeclampsia of a pregnant patient can be detected from no more than eight biomarkers selected from Table 5. In some cases, preeclampsia of a pregnant patient can be detected from no more than seven biomarkers selected from Table 5. In some cases, preeclampsia of a pregnant patient can be detected from no more than six biomarkers selected from Table 5. In some cases, preeclampsia of a pregnant patient can be detected from no more than five biomarkers selected from Table 5. In some cases, preeclampsia of a pregnant patient can be detected from no more than four biomarkers selected from Table 5. In some cases, preeclampsia of a pregnant patient can be detected from no more than three biomarkers selected from Table 5. In some cases, preeclampsia of a pregnant patient can be detected from 1, 2, 3, 4, 5, 6, 7, 8, or 9 biomarkers selected from Table 5.

The methods provided herein can comprise identifying or ruling out a condition (e.g. preeclampsia) from one or more biomarkers selected from Table 2. In some cases, preeclampsia of a pregnant patient can be detected from one or more biomarkers selected from Table 2. In some cases, preeclampsia of a pregnant patient can be detected from two or more biomarkers selected from Table 2. In some cases, preeclampsia of a pregnant patient can be detected from three or more biomarkers selected from Table 2. In some cases, preeclampsia of a pregnant patient can be detected from four or more biomarkers selected from Table 2. In some cases, preeclampsia of a pregnant patient can be detected from five or more biomarkers selected from Table 2. In some cases, preeclampsia of a pregnant patient can be detected from six or more biomarkers selected from Table 2. In some cases, preeclampsia of a pregnant patient can be detected from nine biomarkers selected from Table 2. In some cases, preeclampsia of a pregnant patient can be detected from no more than eight biomarkers selected from Table 2. In some cases, preeclampsia of a pregnant patient can be detected from no more than seven biomarkers selected from Table 2. In some cases, preeclampsia of a pregnant patient can be detected from no more than six biomarkers selected from Table 2. In some cases, preeclampsia of a pregnant patient can be detected from no more than five biomarkers selected from Table 2. In some cases, preeclampsia of a pregnant patient can be detected from no more than four biomarkers selected from Table 2. In some cases, preeclampsia of a pregnant patient can be detected from no more than three biomarkers selected from Table 2. In some cases, preeclampsia of a pregnant patient can be detected from 1, 2, 3, 4, 5, 6, 7, 8, or 9 biomarkers selected from Table 2.

The methods provided herein can comprise identifying or ruling out a condition (e.g. preeclampsia) from one or more biomarkers selected from Table 3. In some cases, preeclampsia of a pregnant patient can be detected from one or more biomarkers selected from 4. In some cases, preeclampsia of a pregnant patient can be detected from two or more biomarkers selected from 4. In some cases, preeclampsia of a pregnant patient can be detected from three or more biomarkers selected from 4. In some cases, preeclampsia of a pregnant patient can be detected from four or more biomarkers selected from Table 3. In some cases, preeclampsia of a pregnant patient can be detected from five or more biomarkers selected from Table 3. In some cases, preeclampsia of a pregnant patient can be detected from six or more biomarkers selected from Table 3. In some cases, preeclampsia of a pregnant patient can be detected from seven or more biomarkers selected from Table 3. In some cases, preeclampsia of a pregnant patient can be detected from eight or more biomarkers selected from Table 3. In some cases, preeclampsia of a pregnant patient can be detected from nine or more biomarkers selected from Table 3. In some cases, preeclampsia of a pregnant patient can be detected from ten or more biomarkers selected from Table 3. In some cases, preeclampsia of a pregnant patient can be detected from 11, 12, 13, 14, 15, 16, 17, 18, or 19 or more biomarkers selected from Table 3. In some cases, preeclampsia of a pregnant patient can be detected from no more than 20, 19, 18, 17, 16, 15, 14, 13, 12, or 11 biomarkers selected from Table 3. In some cases, preeclampsia of a pregnant patient can be detected from no more than ten biomarkers selected from Table 3. In some cases, preeclampsia of a pregnant patient can be detected from no more than nine biomarkers selected from Table 3. In some cases, preeclampsia of a pregnant patient can be detected from no more than eight biomarkers selected from Table 3. In some cases, preeclampsia of a pregnant patient can be detected from no more than seven biomarkers selected from Table 3. In some cases, preeclampsia of a pregnant patient can be detected from no more than six biomarkers selected from Table 3. In some cases, preeclampsia of a pregnant patient can be detected from no more than five biomarkers selected from Table 3. In some cases, preeclampsia of a pregnant patient can be detected from no more than four biomarkers selected from Table 3. In some cases, preeclampsia of a pregnant patient can be detected from no more than three biomarkers selected from Table 3. In some cases, preeclampsia of a pregnant patient can be detected from 1, 2, 3, 4, 5, 6, 7, 8, 9, 10, 11, 12, 13, 14, 15, 16, 17, 18, 19, or 20 biomarkers selected from Table 3.

The methods provided herein can comprise identifying or ruling out a condition (e.g. preeclampsia) from one or more biomarkers selected from Table 4. In some cases, preeclampsia of a pregnant patient can be detected from one or more biomarkers selected from 5. In some cases, preeclampsia of a pregnant patient can be detected from two or more biomarkers selected from 5. In some cases, preeclampsia of a pregnant patient can be detected from three or more biomarkers selected from 5. In some cases, preeclampsia of a pregnant patient can be detected from four or more biomarkers selected from Table 4. In some cases, preeclampsia of a pregnant patient can be detected from five or more biomarkers selected from Table 4. In some cases, preeclampsia of a pregnant patient can be detected from six or more biomarkers selected from Table 4. In some cases, preeclampsia of a pregnant patient can be detected from seven or more biomarkers selected from Table 4. In some cases, preeclampsia of a pregnant patient can be detected from eight or more biomarkers selected from Table 4. In some cases, preeclampsia of a pregnant patient can be detected from nine or more biomarkers selected from Table 4. In some cases, preeclampsia of a pregnant patient can be detected from ten or more biomarkers selected from Table 4. In some cases, preeclampsia of a pregnant patient can be detected from 11, 12, 13, 14, 15, 16, 17, 18, or 19 or more biomarkers selected from Table 4. In some cases, preeclampsia of a pregnant patient can be detected from no more than ten biomarkers selected from Table 4. In some cases, preeclampsia of a pregnant patient can be detected from no more than nine biomarkers selected from Table 4. In some cases, preeclampsia of a pregnant patient can be detected from no more than eight biomarkers selected from Table 4. In some cases, preeclampsia of a pregnant patient can be detected from no more than seven biomarkers selected from Table 4. In some cases, preeclampsia of a pregnant patient can be detected from no more than six biomarkers selected from Table 4. In some cases, preeclampsia of a pregnant patient can be detected from no more than five biomarkers selected from Table 4. In some cases, preeclampsia of a pregnant patient can be detected from no more than four biomarkers selected from Table 4. In some cases, preeclampsia of a pregnant patient can be detected from no more than three biomarkers selected from Table 4. In some cases, preeclampsia of a pregnant patient can be detected from 1, 2, 3, 4, 5, 6, 7, 8, 9, 10, 11, 12, 13, 14, 15, 16, 17, 18, 19, or 20 biomarkers selected from Table 4.

In some embodiments, the methods provided herein can comprise detecting a condition (such as preeclampsia) from one or more biomarkers selected from (a) known preeclampsia candidate biomarkers reported in the literature (such as PAPP-A, sFlt1, PlGF, or Fibronectin), (b) preeclampsia biomarkers specifically identified herein (such as those selected from Group 1, Group 2, Group 3, Group 4, Group 5, Table 2, Table 3, Table 4, or Table 5), or (c) any combination of (a) and (b). In other embodiments, the methods provided herein can comprise detecting a condition (such as preeclampsia) from two or more, three or more, four or more, five or more, six or more, or seven or more biomarkers selected from (a), (b), or (c). In other embodiments, the methods provided herein can comprise detecting a condition (such as preeclampsia) from no more than ten, no more than 9, no more than 8, no more than 7, no more than 6, no more than 5, no more than 4, or no more than 3 biomarkers selected from (a), (b), or (c). In other embodiments, the methods provided herein can comprise detecting a condition (such as preeclampsia) from 1, 2, 3, 4, 5, 6, 7, 8, 9, 10, 11, 12, 13, 14, 15, 16, 17, 18, 19, or 20 biomarkers selected from (a), (b), or (c).

Clinical/Therapeutic Applications

The methods, compositions, systems and kits provided herein can be used to detect, diagnose, predict or monitor a condition of a pregnant patient. In some instances, the methods, compositions, systems and kits described herein provide information to a medical practitioner that can be useful in making a clinical therapeutic decision. Clinical and therapeutic decisions can include decisions to: continue with a particular therapy, modify a particular therapy, alter the dosage of a particular therapy, stop or terminate a particular therapy, altering the frequency of a therapy, introduce a new therapy, introduce a new therapy to be used in combination with a current therapy, or any combination of the above. In some instances, medical action taken may comprise watchful waiting or the administration of one or more additional diagnostic tests of the same or different nature. In some cases, a clinical decision may be made to not induce labor, or to proceed with ambulant monitoring of the subject. In some cases, the methods provided herein can be applied in an experimental setting, e.g., clinical trial. In some instances, the methods provided herein can be used to monitor a pregnant patient who is being treated with an experimental agent such as an angiogenic/antiangiogenic drug, compound, or therapeutic cell type. In some instances, the methods provided herein can be useful to determine whether a subject can be administered an experimental agent (e.g., an agonist, antagonist, peptidomimetic, protein, peptide, nucleic acid, therapeutic cell, small molecule, or other drug candidate) to reduce the risk of preeclampsia. Thus, the methods described herein can be useful in determining if a subject can be effectively treated with an experimental agent and for monitoring the subject for risk of preeclampsia.

Detecting-Diagnosing a Condition of a Pregnant Patient

The methods, compositions, systems and kits provided herein are particularly useful for detecting, diagnosing, or ruling out a condition of a pregnant patient such as a condition the pregnant patient has at the time of testing. An exemplary condition that can be detected, diagnosed, or ruled out with the present method includes preeclampsia. The methods, compositions, systems, and kits provided herein can also be useful, in combination with other standard clinical data collected for pregnant patients, for ruling in or ruling out a diagnosis of preeclampsia, hypertension, gestational hypertension, or HELLP syndrome. The methods provided herein are particularly useful for pregnant patients who have exhibited one or more new-onset symptoms associated with preeclampsia prior to testing (e.g., hypertension, proteinuria, low platelet count, elevated serum creatinine levels, elevated liver enzymes, pulmonary edema, or cerebral/visual symptoms), such that the patients are suspected of having preeclampsia.

In some embodiments, the methods, compositions, systems and kits provided herein can rule out a diagnosis of preeclampsia for a specified number of days in the future. In some instances, the specified number of days in the future is 1 to 30 days. In some instances the specified number of days in the future is at least 1 day. In some instances the specified number of days in the future is at most 30 days. In some instances the specified number of days in the future is 1 day to 5 days, 1 day to 10 days, 1 day to 30 days, 5 days to 10 days, 5 days to 30 days, or 10 days to 30 days. In some instances the specified number of days in the future is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In some preferred embodiments, the specified number of days in the future is 5 days to 10 days. In other preferred embodiments, the specified number of days in the future is 5, 6, 7, 8, 9, or 10 days. In some embodiments, the methods, compositions, systems and kits provided herein can rule-out mothers for hospital admission and preterm delivery. In some embodiments, the methods, compositions, systems and kits provided herein can rule out a diagnosis of preeclampsia for a specified number of weeks in the future. In some instances the specified number of weeks is at least 1 week. In some instances the specified number of weeks is at least 2 weeks. In some instances the specified number of weeks is at least 3 weeks. In some instances the specified number of weeks is at least 4 weeks. In some instances the specified number of weeks is at least 5 weeks. In some instances the specified number of weeks is at least 6 weeks. In some instances the specified number of weeks is at most 1 week. In some instances the specified number of weeks is at most 2 weeks. In some instances the specified number of weeks is at most 3 weeks. In some instances the specified number of weeks is at most 4 weeks. In some instances the specified number of weeks is at most 5 weeks. In some instances the specified number of weeks is at most 6 weeks.

In some embodiments, the methods, compositions, systems and kits provided herein can rule out a diagnosis of preeclampsia for a specified number of weeks in the future with a particular PPV. In some cases the positive predictive value (PPV) is at least about 300%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, or 57%, or any range in between these values.

In some embodiments, the methods, compositions, systems and kits provided herein can rule out a diagnosis of preeclampsia for a specified number of weeks in the future with a particular NPV. The NPV can be at least about 80%, 81%, 82%, 83%, 84%, 85%, 86%, 87%, 88%, 89%, 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9% N, or any range in between these values.

In some embodiments, the methods, compositions, systems and kits provided herein can rule out a diagnosis of preeclampsia for a specified number of weeks in the future with a particular AUC. In some cases, the AUC of can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

In some embodiments, the methods, compositions, systems and kits provided herein can rule out a diagnosis of preeclampsia for a specified number of weeks in the future with a particular AUP. The AUP can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

The diagnosis, detection, or ruling out of a condition of the pregnant patient can be particularly useful in limiting the number of unnecessary invasive medical interventions that are administered to the patient, and/or indicating alternative less-invasive therapeutic interventions such as pharmacological therapies (anticonvulsants, antihypertensives, central alpha agonists, alpha-blockers, beta-blockers, calcium-channel blockers, vasodilators, cyclooxygenase inhibitors). For example, the methods provided herein can limit, delay, or eliminate the use of preterm cesarean delivery or labor induction in patients suspected of having preeclampsia via high-confidence ruling out of a diagnosis of preeclampsia in the pregnant patient (e.g., via a high negative predictive value of the methods, compositions, systems, and kits provided herein).

In a further embodiment, the methods, compositions, systems and kits provided herein can be used alone or in combination with other standard diagnosis methods currently used to detect, diagnose, or rule out a condition of a pregnant patient, such as but not limited to blood pressure measurement, urine protein measurement, blood platelet counting, serum creatinine level measurement, creatinine clearance measurement, urine protein/creatinine ratio measurement, serum transaminase level measurement, serum LDH level measurement, serum bilirubin level measurement, or Doppler ultrasound indices (e.g., uterine artery indices). For example, hypertension in a pregnant patient can be indicative of conditions such as chronic hypertension, gestational hypertension, or preeclampsia; ruling out the diagnosis of preeclampsia via the methods, compositions, systems and kits provided herein allows for the patient to be correctly diagnosed with chronic hypertension or gestational hypertension.

Predicting a Condition of a Pregnant Patient

In some embodiments, the methods provided herein can predict preeclampsia prior to actual onset of the condition or symptoms associated with the condition (e.g., hypertension or proteinuria). In some instances, the methods provided herein can predict preeclampsia or other disorders in a pregnant patient at least 1 day, 1 week, 2 weeks, 3 weeks, 1 month, 2 months prior to onset of the condition or symptoms associated with the condition. In other instances, the methods provided herein can predict preeclampsia or other disorders in a pregnant patient at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days prior to onset. In other instances, the methods provided herein can predict preeclampsia or other disorders in a pregnant patient at least 1, 2, 3, or 4 months prior to onset.

Monitoring a Condition of a Pregnant Patient

Provided herein are methods, systems, kits and compositions for monitoring a condition of a pregnant patient. Often, the monitoring is conducted by serial testing, such as serial non-invasive tests, serial minimally-invasive tests (e.g., blood draws), or some combination thereof. Preferably, the monitoring is conducted by administering serial non-invasive tests or serial minimally-invasive tests (e.g., blood draws).

In some instances, the pregnant patient is monitored as needed (e.g., on an as-needed basis) using the methods described herein. Additionally or alternatively the pregnant patient can be monitored weekly, monthly, or at any pre-specified intervals. In some instances, the pregnant patient is monitored at least once every 24 hours. In some instances the pregnant patient is monitored at least once every 1 day to 30 days. In some instances the pregnant patient is monitored at least once every at least 1 day. In some instances the pregnant patient is monitored at least once every at most 30 days. In some instances the pregnant patient is monitored at least (optionally on average) once every 1 day to 5 days, 1 day to 10 days, 1 day to 15 days, 1 day to 20 days, 1 day to 25 days, 1 day to 30 days, 5 days to 10 days, 5 days to 15 days, 5 days to 20 days, 5 days to 25 days, 5 days to 30 days, 10 days to 15 days, 10 days to 20 days, 10 days to 25 days, 10 days to 30 days, 15 days to 20 days, 15 days to 25 days, 15 days to 30 days, 20 days to 25 days, 20 days to 30 days, or 25 days to 30 days. In some instances the pregnant patient is monitored at least once every 1, 2, 3, 4, 5, 6, 7, 8, 9, 10, 11, 12, 13, 14, 15, 16, 17, 18, 19, 20, 21, 28, 29, 30 or 31 days. In some instances, the pregnant patient is monitored at least once every 1, 2, or 3 months. In some instances, the pregnant patient is monitored via the methods described herein no more frequently than one week, 10 days, two weeks, three weeks, or one month. In other words, the predictive value of the some of the methods described herein can be of clinical use for at least one week, at least 10 days, at least two week, at least three weeks, or at least one month.

In some instances, biomarker expression levels in the patients can be measured, for example, within, one week, two weeks, three weeks, or four weeks after detection of one or more symptoms associated with preeclampsia (e.g., hypertension or proteinuria). In some methods, biomarker expression levels are determined at regular intervals, e.g., every 1 week, 2 weeks, 3 weeks, 1 month, 2 months or 3 months post-conception, after the beginning of the $2^{nd}$ trimester, after the beginning of the $3^{rd}$ trimester, or after week 20 of the pregnancy, either indefinitely, or until evidence of a condition is observed. In some methods, biomarker expression levels are determined at regular intervals after week 20, 21, 22, 23, 24, 25, 26, 27, 28, 29, 30, 31, 32, 33, 34, 35, 36, 37, 38, 39, 40, 41, or 42 weeks. Where evidence of a condition is observed, the frequency of monitoring is sometimes increased. In some methods, baseline values of expression levels are determined in a subject before detection of one or more symptoms associated with preeclampsia (e.g., hypertension or proteinuria) in combination with determining expression levels after onset of symptoms.

Therapeutic Decision/Regimens

The results of diagnosing, predicting, ruling out, or monitoring a condition of the pregnant patient can be useful for informing a clinical or therapeutic decision such as determining or monitoring a therapeutic regimen.

In some embodiments, an entity that acquires sample data and/or classifies a sample from a patient as having preeclampsia is other than the physician, caregiver, or medical institution performing the treatment. In some embodiments, the entity acquiring sample data (e.g. levels of levels of two or more proteins from Tables A, B, 2, 3, 4, and 5), calculating an index based (at least in part) on the levels of the plurality of the protein biomarkers, and/or determining risk of preeclampsia is a third-party testing service. Thus, in some embodiments, determining or monitoring a therapeutic regimen first comprises receiving information from a third-party testing service, which can comprise, for example (but not limited to), classification of a sample as being at risk or not of preeclampsia, risk of a pregnant patient having preeclampsia, levels of a plurality of protein biomarkers from the sample associated with preeclampsia (e.g. levels of two or more proteins from Tables A, B, 2, 3, 4, and 5), or the likelihood a pregnant patient will deliver preterm.

In some embodiments, an entity that acquires sample data, determines the risk of preterm birth of the patient from the sample, and/or classifies a sample from a patient as having a significant risk of preterm birth is the same entity that performing the treatment.

In some instances, determining a therapeutic regimen can comprise administering a therapeutic drug. In some instances, determining a therapeutic regimen comprises modifying, continuing, initiating or stopping a therapeutic regimen. In some instances, determining a therapeutic regimen comprises treating the disease or condition (e.g., preeclampsia, eclampsia, gestational hypertension, hypertension, or HELLP syndrome). In some instances, the therapy is an anti-hypertensive therapy. In some instances, the therapy is an anti-cyclooxygenase (COX) therapy. In some instances, the therapy is an anti-convulsant therapy.

Modifying the therapeutic regimen can comprise terminating a therapy. Modifying the therapeutic regimen can comprise altering a dosage of a therapy. Modifying the therapeutic regimen can comprise altering a frequency of a therapy. Modifying the therapeutic regimen can comprise administering a different therapy. In some instances, the results of diagnosing, predicting, or monitoring a condition of the pregnant patient can be useful for informing a therapeutic decision such as caesarean delivery. Other examples of therapeutic decisions can be cervical ripening and/or labor induction. Examples of agents that can be used for cervical ripening and/or labor induction include prostaglandins, misoprostol, mifepristone, relaxin, and oxytocin. Other examples of therapeutic decisions can be cesarean delivery.

Examples of a therapeutic regimen can include administering compounds or agents having anti-hypertensive properties (e.g., central alpha agonists such as methyldopa, vasodilators such as clonidine, diazoxide, hydralazine and prazosin, calcium-channel blockers such as nifedipine and verapamil, alpha-blockers such as labetalol, or beta-blockers such as oxprenolol), compounds or agents having anti-cyclooxygenase activity (e.g., acetylsalicylic acid), or compounds having anti-convulsant activity (e.g., phenytoin or magnesium sulfate). These compounds can be used alone or in combination.

In some cases, modifying the therapeutic regimen can comprise proceeding with treatment of said pregnant human in a manner that avoids unnecessary treatment of preeclampsia. For instance, in some embodiments, managing the pregnant human subject identified not as at risk for preeclampsia comprises ambulant monitoring, or refraining from the administration of any drug for treating preeclampsia. In some instances, in patients that are identified as not patients that should not be treated for preeclampsia, antihypertensive drugs (rather than delivery) may be prescribed and/or administered to the patient.

Sensitivity, Specificity, NPV, PPV, AUC, AUP, and Accuracy

The methods, kits, and systems disclosed herein for use in identifying, classifying (or ruling out a classification) or characterizing a sample can be characterized by having a specificity of at least about 80% using the methods disclosed herein. In some embodiments, the specificity of the methods is at least about 85%. In some embodiments, the specificity of the methods is at least about 90%. In some embodiments, the specificity of the methods is at least about 95%. The specificity of the method can be at least about 80%, 81%, 82%, 83%, 84%, 85%, 86%, 87%, 88%, 89%, 90%, 91%, 92%, 93%, 94%, 95%, 96%, 97%, 98%, or 99%, or any range in between these values.

In some embodiments, the present invention provides a method of identifying, classifying (or ruling out a classification) or characterizing a sample that gives a sensitivity of at least about 80% using the methods disclosed herein. In some embodiments, the sensitivity of the methods is at least 85%. In some embodiments, the sensitivity of the methods is at least 90%. In some embodiments, the sensitivity of the methods is at least 95%. The sensitivity of the method can be at least about 80%, 81%, 82%, 83%, 84%, 85%, 86%, 87%, 88%, 89%, 90%, 91%, 92%, 93%, 94%, 95%, 96%, 97%, 98%, or 99%, or any range in between these values.

The methods, kits and systems disclosed herein can improve upon the accuracy of current methods of monitoring or predicting a status or outcome of a pregnancy (e.g. preeclampsia) or identifying or ruling out a classification of a sample. The accuracy of the methods, kits, and systems disclosed herein can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

The methods, kits, and systems for use in identifying, classifying (or ruling out a classification) or characterizing a sample can be characterized by having a negative predictive value (NPV) greater than or equal to 90%. The NPV can be at least about 80%, 81%, 82%, 83%. 84%, 85%, 86%. 87%, 88%, 89%, 90%, 91%. 92%, 93%, 94%. 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. The NPV can be greater than or equal to 95%. The NPV can be greater than or equal to 96%. The NPV can be greater than or equal to 97%. The NPV can be greater than or equal to 98%.

The methods, kits, and/or systems disclosed herein for use in identifying, classifying (or ruling out a classification) or characterizing a sample (e.g. for preeclampsia) can be characterized by having a positive predictive value (PPV) of at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, or 57%, or any range in between these values using the methods disclosed herein.

The methods, kits and systems disclosed herein can improve upon the AUC of current methods of monitoring or predicting a status or outcome of a pregnancy (e.g. preeclampsia) or identifying or ruling out a classification of a sample. The AUC of the methods, kits, and systems disclosed herein can be at least about 50%, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

The methods, kits and systems disclosed herein can improve upon the AUP of current methods of monitoring or predicting a status or outcome of a pregnancy (e.g. preeclampsia) or identifying or ruling out a classification of a sample. The AUP of the methods, kits, and systems disclosed herein can be at least about 50% 0, 53%, 55%, 57%, 60%, 63%, 65%, 67%, 70%, 72%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range in between these values.

The methods, kits, and systems disclosed herein for use in diagnosing, prognosing, and/or monitoring a status or outcome of a pregnancy in a subject in need thereof can be characterized by having an accuracy of at least about 80%, 82%, 85%, 87%, 90%, 92%, 95%, or 97% or any range in between these values.

The methods, kits, and systems disclosed herein for use in diagnosing, prognosing, and/or monitoring a status or outcome of a pregnancy in a subject in need thereof can be characterized by having a specificity of at least about 80%, 82%, 85%, 87%, 90%, 92%, 95%, or 97%, or any range in between these values.

The methods, kits, and systems disclosed herein for use in diagnosing, prognosing, and/or monitoring a status or outcome of a pregnancy in a subject in need thereof can be characterized by having a sensitivity of at least about 80%, 82%, 85%, 87%, 90%, 92%, 95%, or 97%, or any range in between these values.

The methods, kits, and systems disclosed herein for use in diagnosing, prognosing, and/or monitoring a status or outcome of a pregnancy in a subject in need thereof can be characterized by having a negative predictive value (NPV) greater than or equal to 90%. The NPV can be at least about 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. The NPV can be greater than or equal to 95%. The NPV can be greater than or equal to 96%. The NPV can be greater than or equal to 97%. The NPV can be greater than or equal to 98%.

The methods, kits, and systems disclosed herein for use in diagnosing, prognosing, and/or monitoring a status or outcome of a pregnancy in a subject in need thereof can be characterized by having a positive predictive value (PPV) of at least about 80%. In some embodiments, the methods, kits, and systems disclosed herein for use in diagnosing, prognosing, and/or monitoring a status or outcome of a pregnancy in a subject in need thereof can be characterized by having a positive predictive value (PPV) of at least about 85%. In some embodiments, the methods, kits, and systems disclosed herein for use in diagnosing, prognosing, and/or monitoring a status or outcome of a pregnancy in a subject in need thereof can be characterized by having a positive predictive value (PPV) of at least about 90%. The PPV can be at least about 80%, 85%, 90%/0, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. The PPV can be greater than or equal to 95%. The PPV can be greater than or equal to 98%.

In some embodiments, disclosure provides a test for confirming preeclampsia in a subject, preferably a pregnant subject, wherein the test is able to discern subjects not having preeclampsia but having one or more symptoms associated with preeclampsia from subjects having by preeclampsia with an NPV of at least about 90%, 91%, 92%, 93%, 94%, 95%, 95.2%, 95.5%, 95.7%, 96%, 96.2%, 96.5%, 96.7%, 97%, 97.2%, 97.5%, 97.7%, 98%, 98.2%, 98.5%, 98.7%, 99%, 99.2%, 99.5%, 99.7%, or 99.9%, or any range in between these values. The one or more symptoms associated with preeclampsia can be diabetes (e.g. gestational, type I or type II), higher than normal glucose level, hypertension (e.g. chronic or non-chronic), excessive or sudden weight gain, higher than normal weight, obesity, higher than normal body mass index (BMI), abnormal weight gain, abnormal blood pressure, water retention, hereditary factors, abnormal proteinuria, headache, edema, abnormal protein/creatinine ratio, abnormal platelet count, stress, nulliparity, abnormal Papanicolaou test results (Pap smear), prior preeclampsia episodes (e.g., personal history of PreE), familial history of preeclampsia, preeclampsia in prior pregnancies, renal disease, thrombophilia, or any combination thereof. Gestational age may also be used in tests, such as tests for ruling out preeclampsia.

In some embodiments, disclosure provides for a method, kit, system, or test that has a sensitivity of at least 79% and a specificity of at least 94%. In some embodiments, a method, kit, system, or test has a sensitivity of at least 82% and a specificity of at least 80%. In some embodiments, a method, kit, system of test has a sensitivity of at least 90% and a specificity of at least 80%.

Computer Program

The methods, kits, and systems disclosed herein can include at least one computer program, or use of the same. A computer program can include a sequence of instructions, executable in the digital processing device's CPU (i.e. processor), written to perform a specified task. Computer readable instructions can be implemented as program modules, such as functions, objects, Application Programming Interfaces (APIs), data structures, and the like, that perform particular tasks or implement particular abstract data types. In light of the disclosure provided herein, those of skill in the art will recognize that a computer program can be written in various versions of various languages.

The functionality of the computer readable instructions can be combined or distributed as desired in various environments. The computer program will normally provide a sequence of instructions from one location or a plurality of locations.

Further disclosed herein are systems for classifying (or ruling out a classification) one or more samples and uses thereof. The system can comprise (a) a digital processing device comprising an operating system configured to perform executable instructions and a memory device; (b) a computer program including instructions executable by the digital processing device to classify a sample from a subject comprising: (i) a first software module configured to receive a biomarker expression profile of one or more biomarkers from the sample from the subject; (ii) a second software module configured to analyze the biomarker expression profile from the subject; and (iii) a third software module configured to classify the sample from the subject based on a classification system. In some embodiments, the classification system comprises two classes. In other embodiments, the classification system comprises two or more classes. At least two of the classes can be selected from preeclampsia, non-preeclampsia (e.g., for at least a period of time), normal pregnancy, complicated pregnancy, and gestational hypertension. Analyzing the biomarker expression profile from the subject can comprise applying an algorithm. Analyzing the biomarker expression profile can comprise normalizing the biomarker expression profile from the subject.

Figure 6:
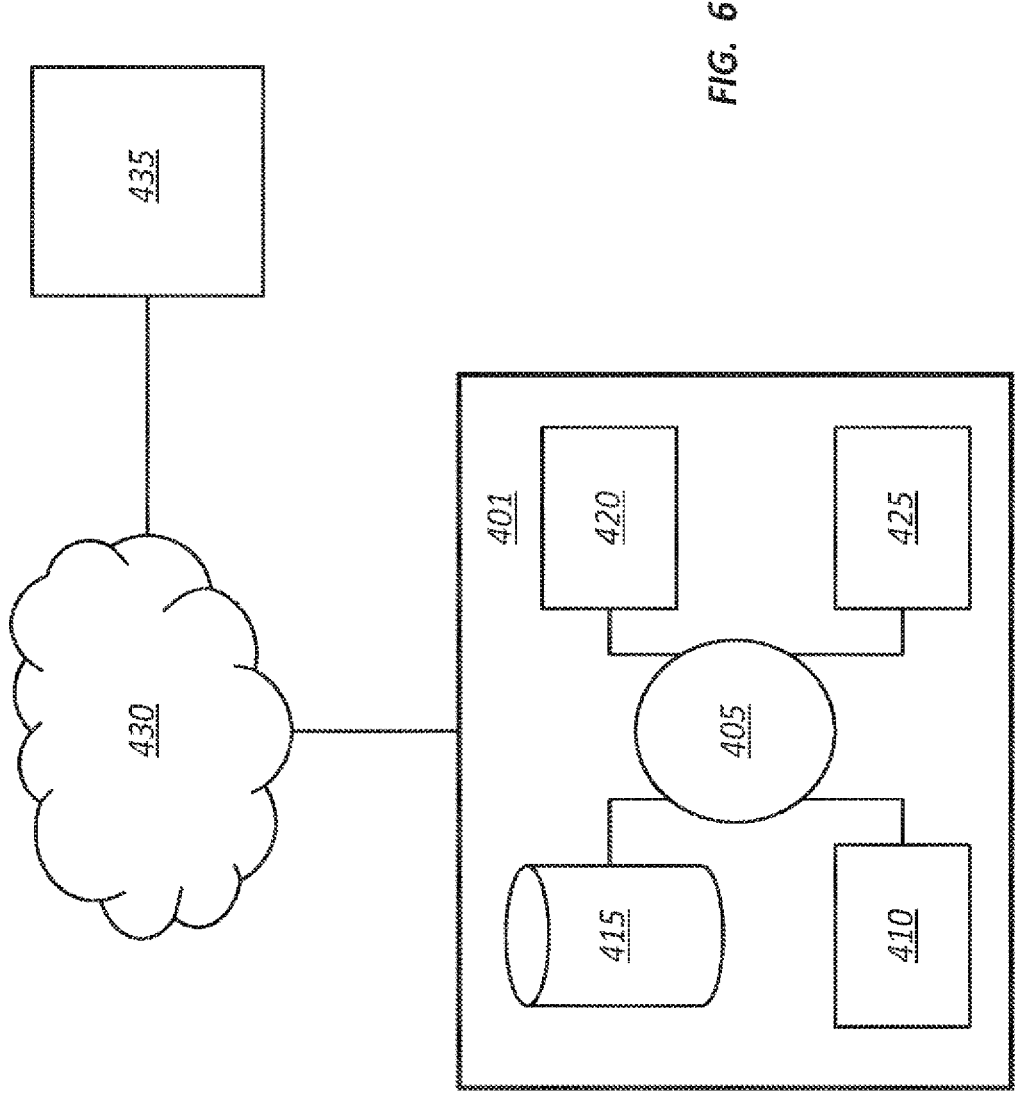
FIG. 6 shows a system for implementing the methods of the disclosure.
Figure 7:
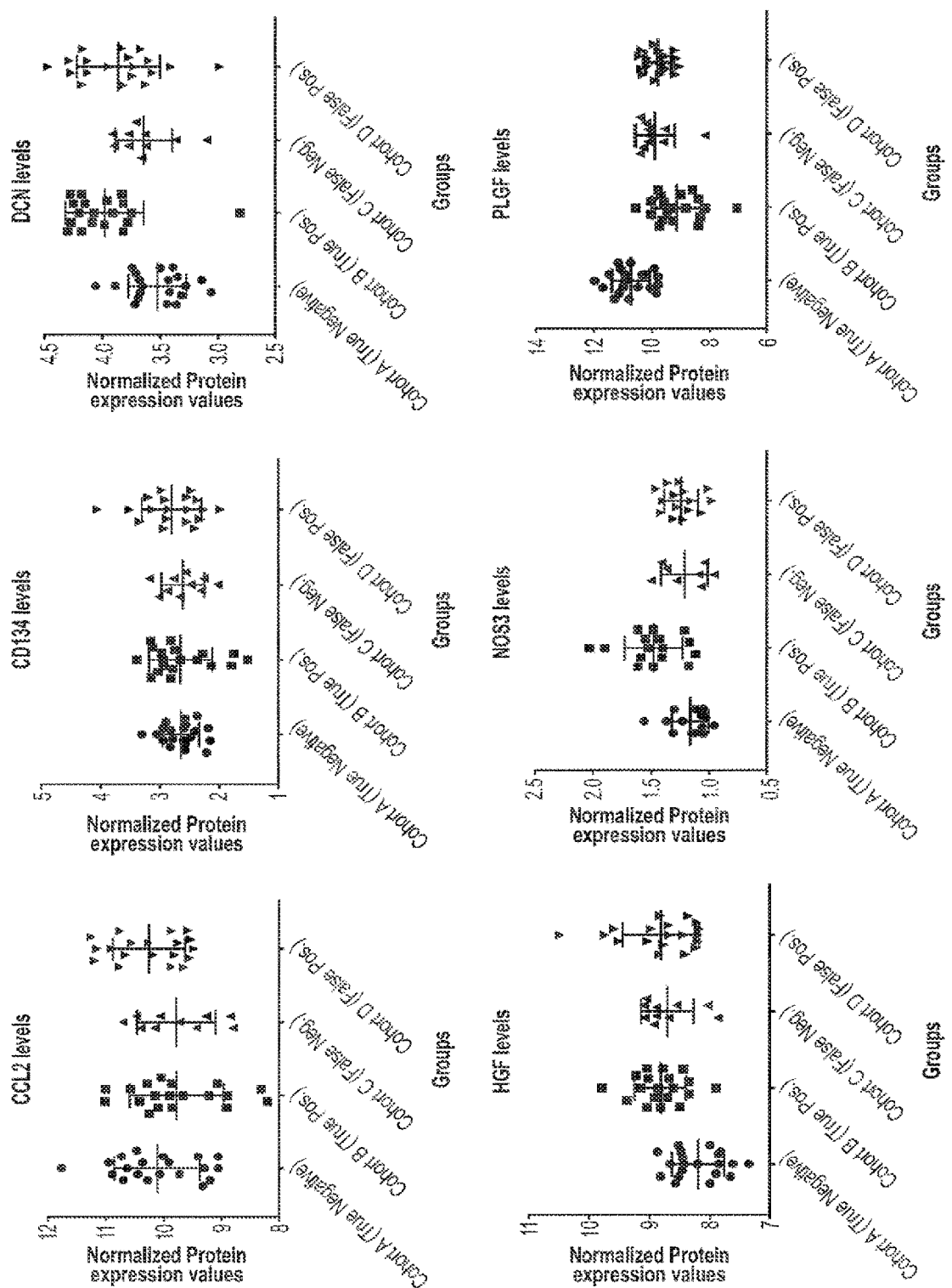
FIG. 7, FIG. 8, FIG. 9, FIG. 10, FIG. 11, and FIG. 12 show single-plex analysis of additional candidate biomarkers by AlphaScreen™, with the expression level presented by subcohort (A=nonPreE/true negatives, B=PreE/true positive, C=PreE/false negative, D=nonPreE/false positive).
Figure 8:
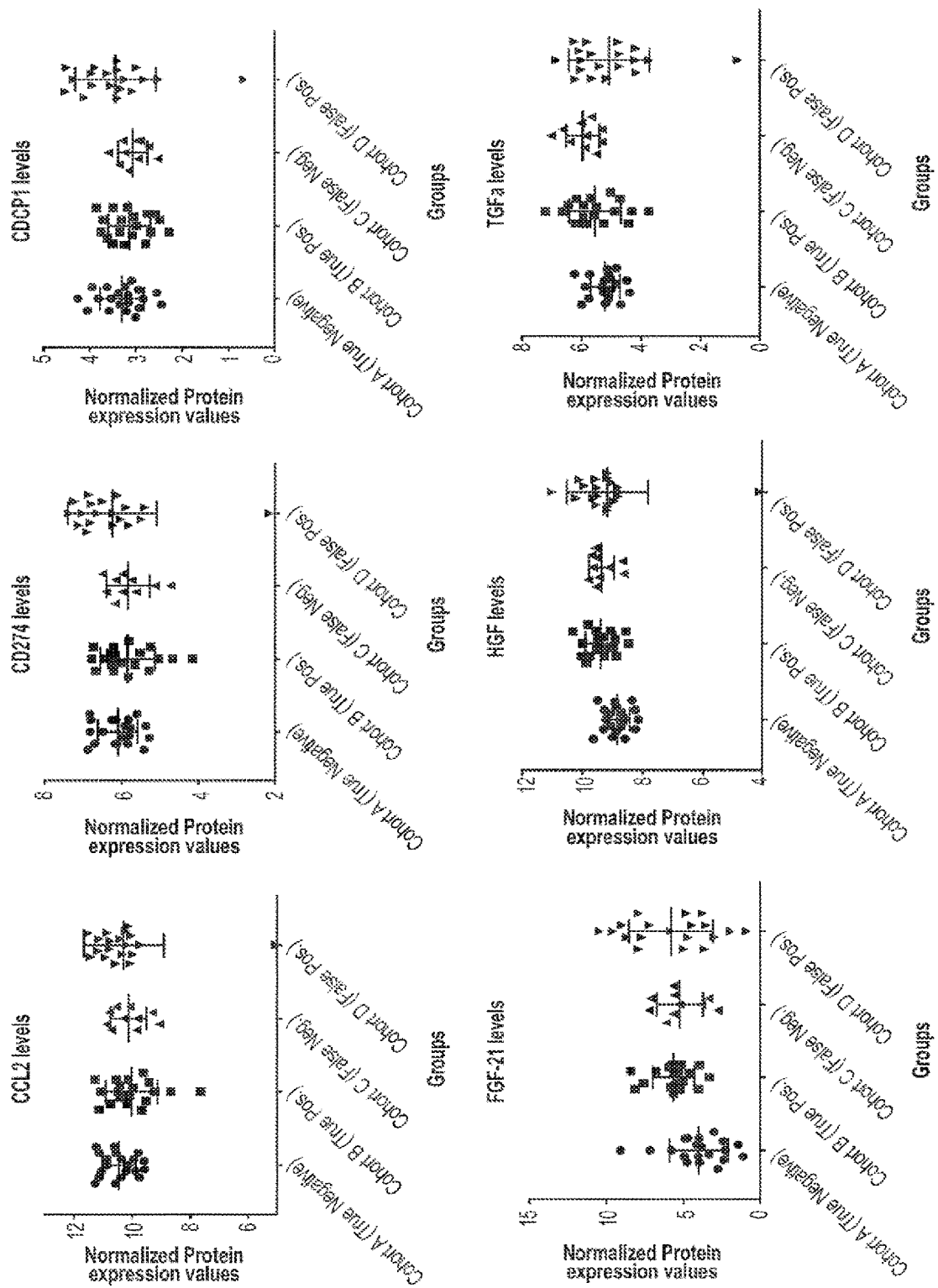
Figure 9:
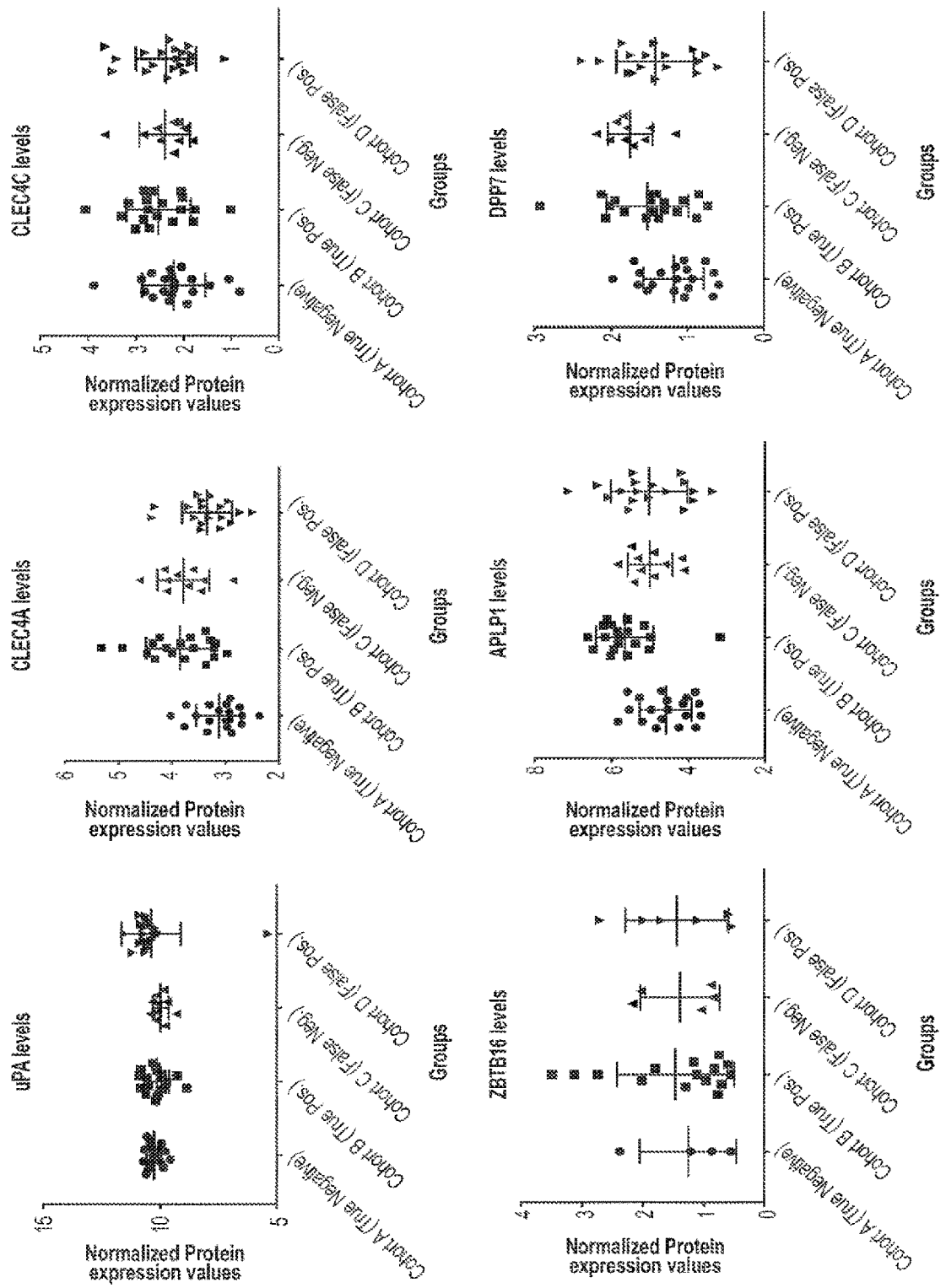
Figure 10:
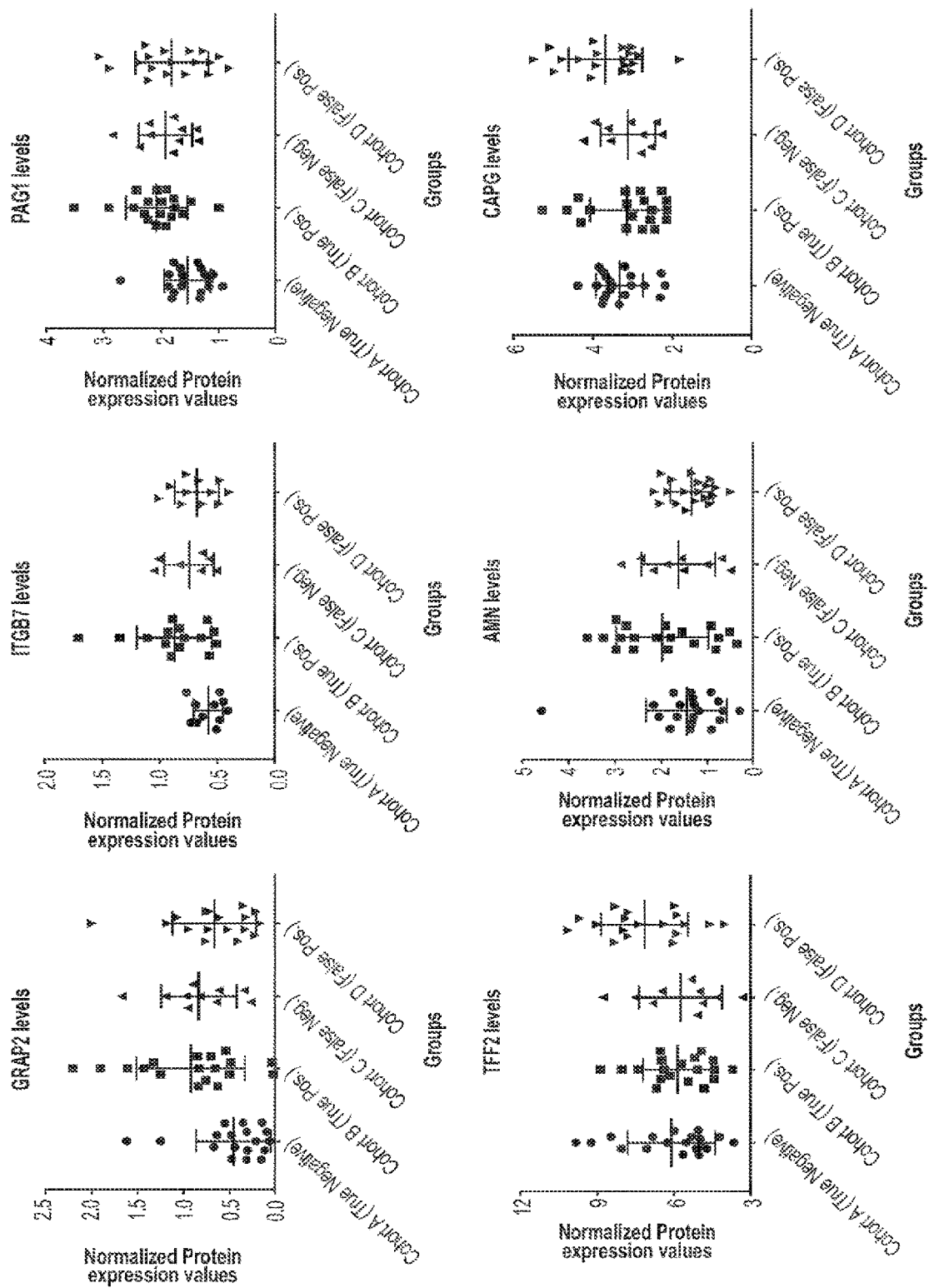
Figure 11:
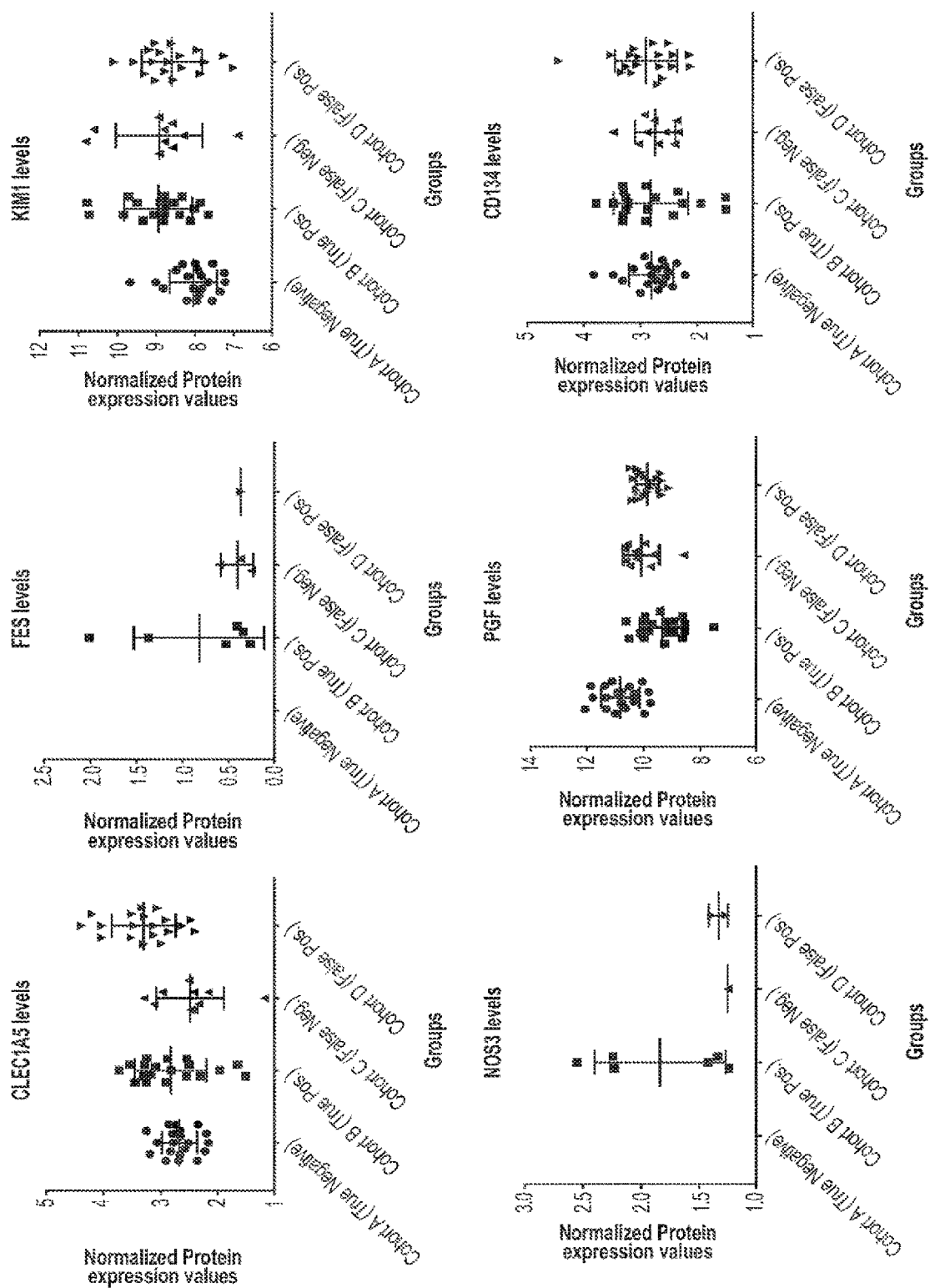
Figure 12:
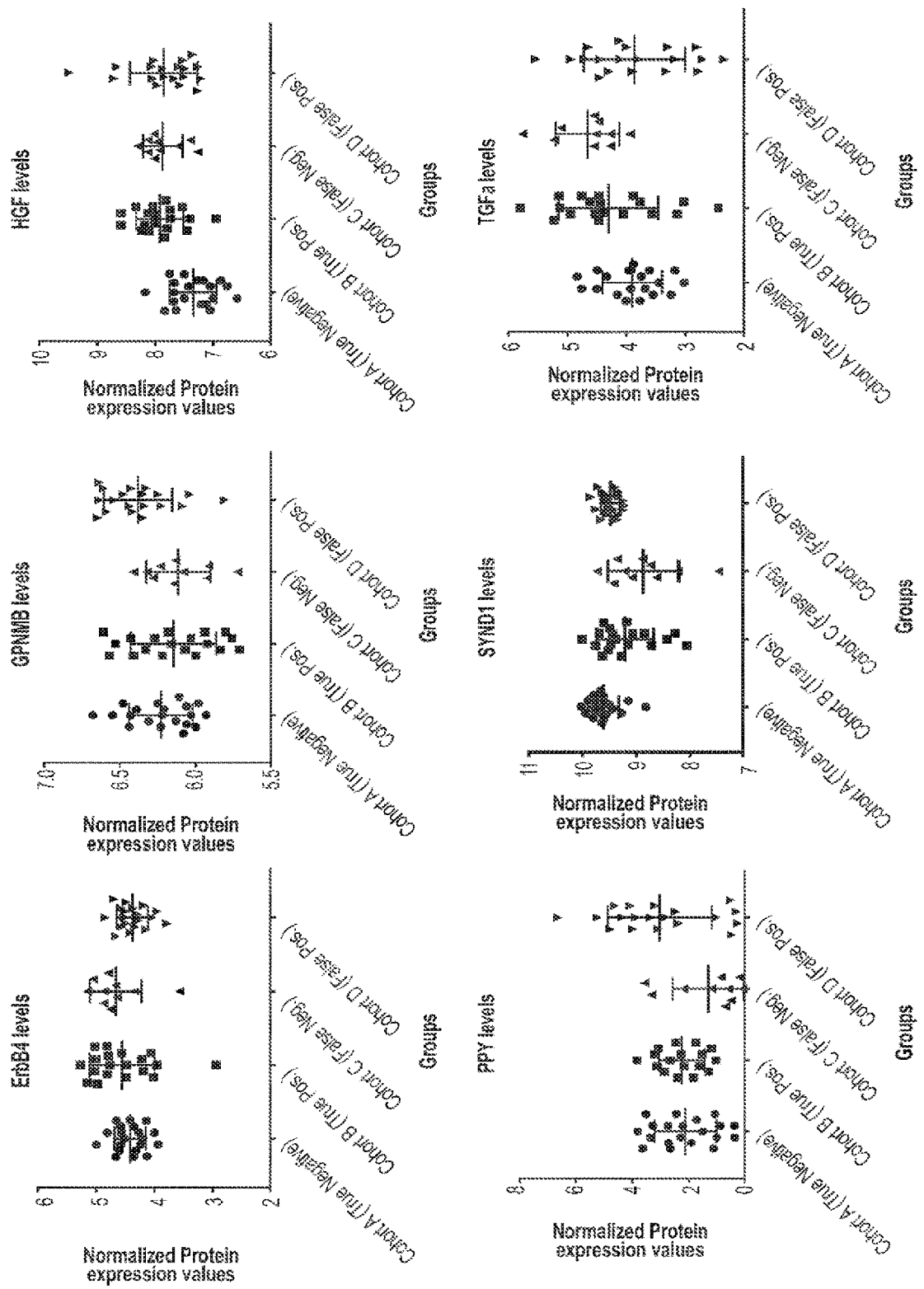
Figure 13D:
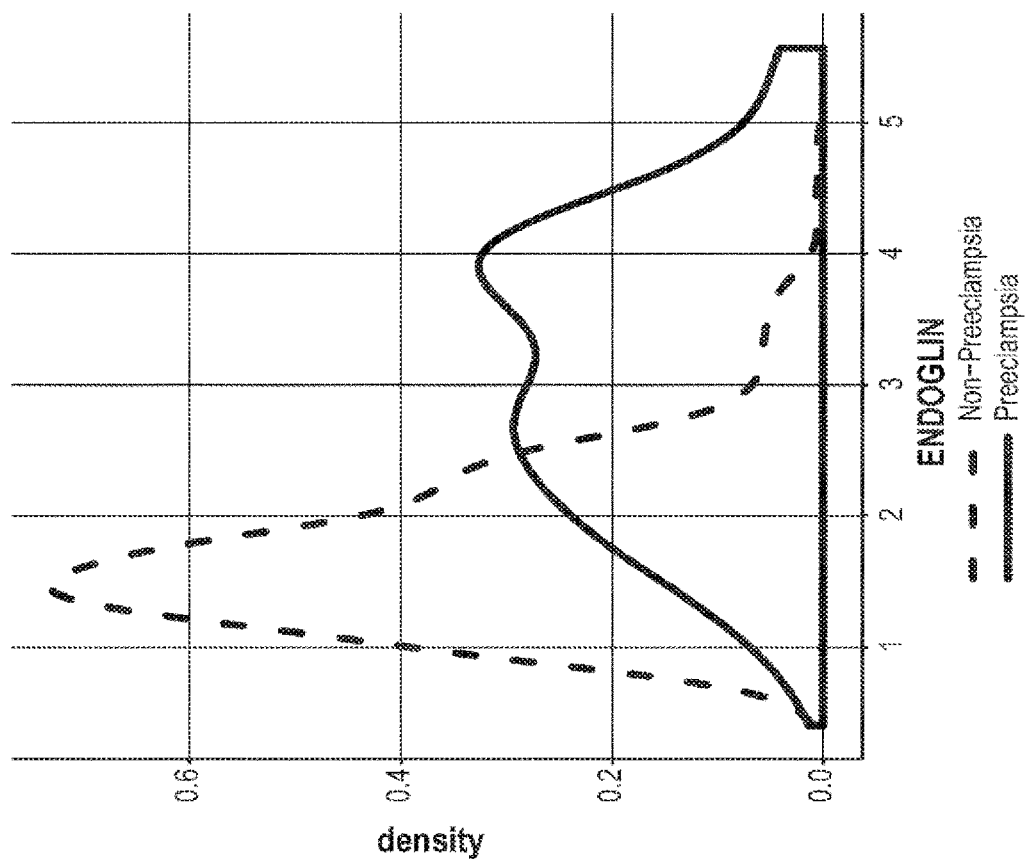
Figure 13C:
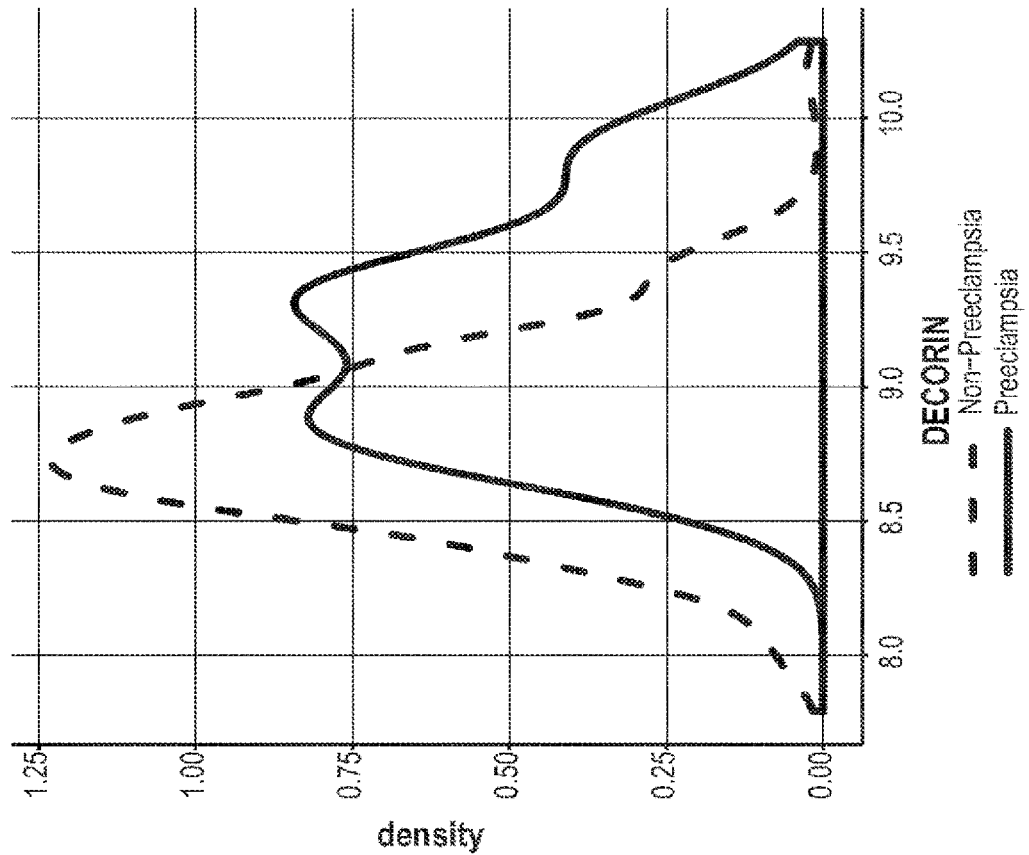
Figure 13F:
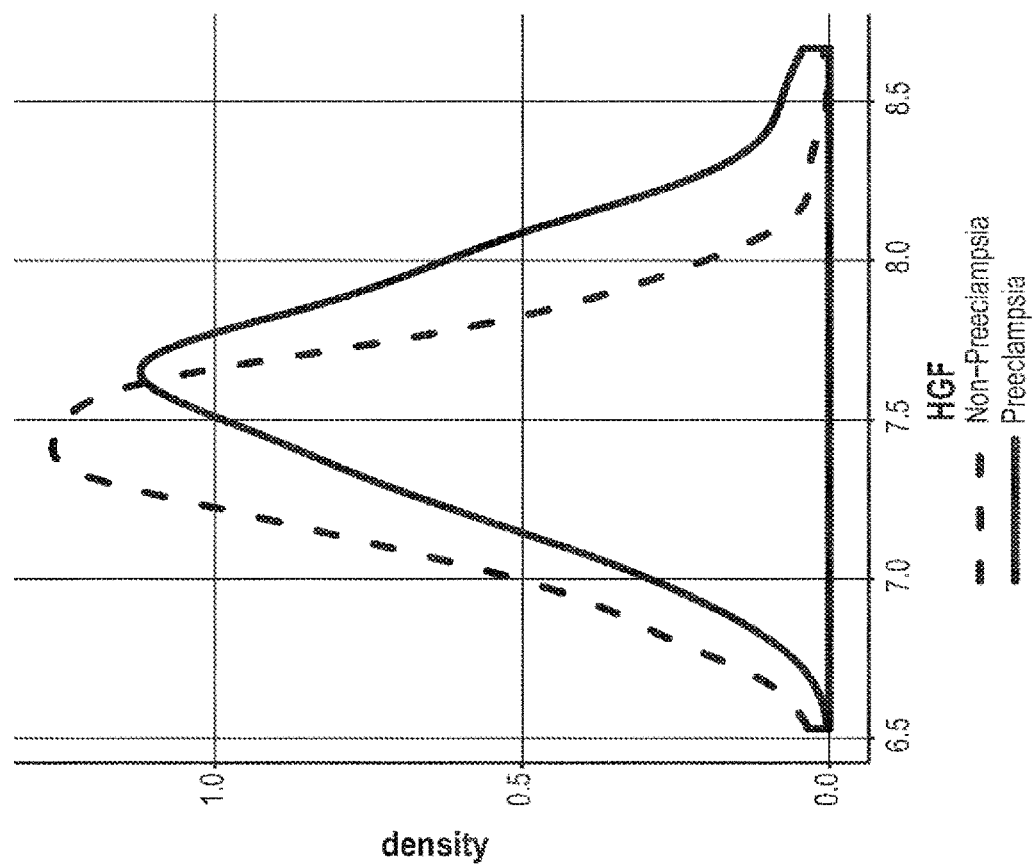
Figure 13E:
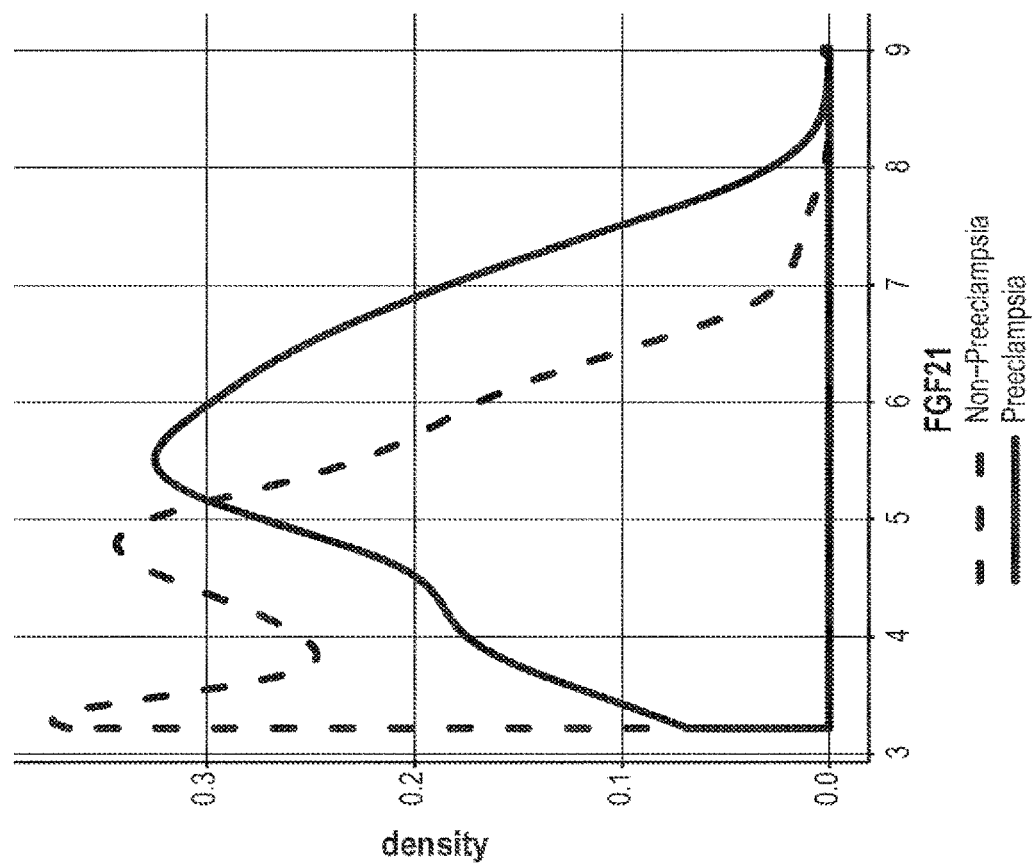
Figure 13H:
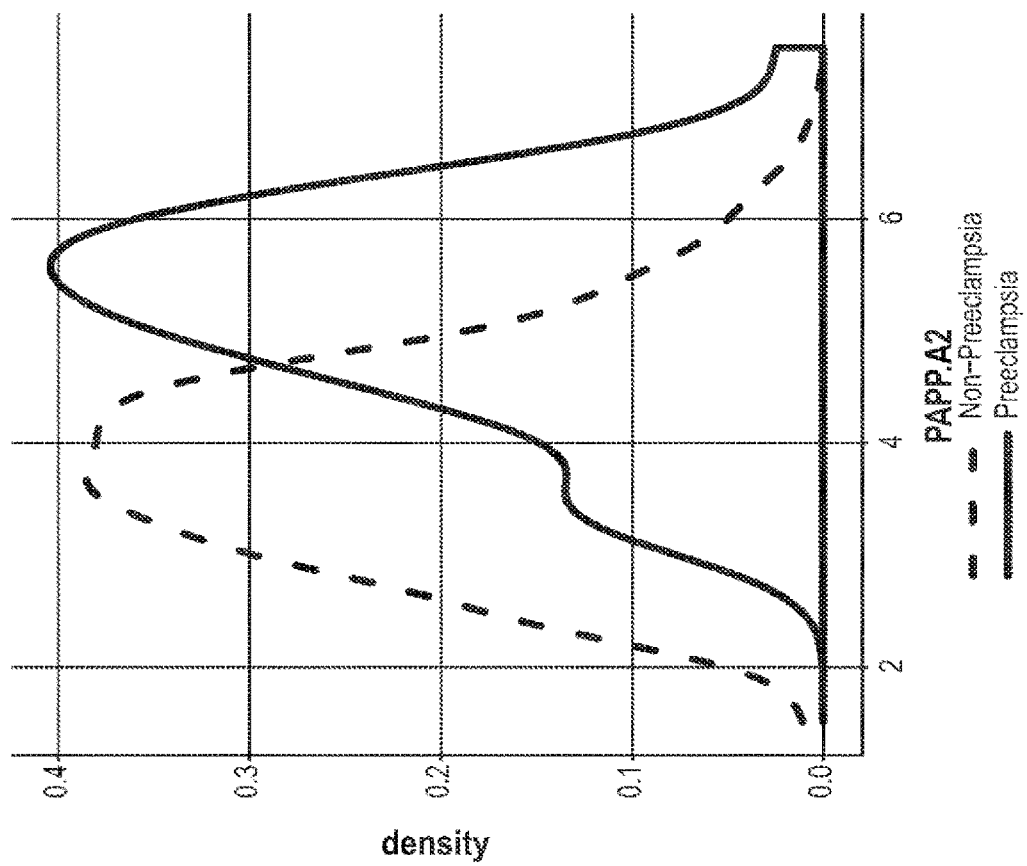
Figure 13G:
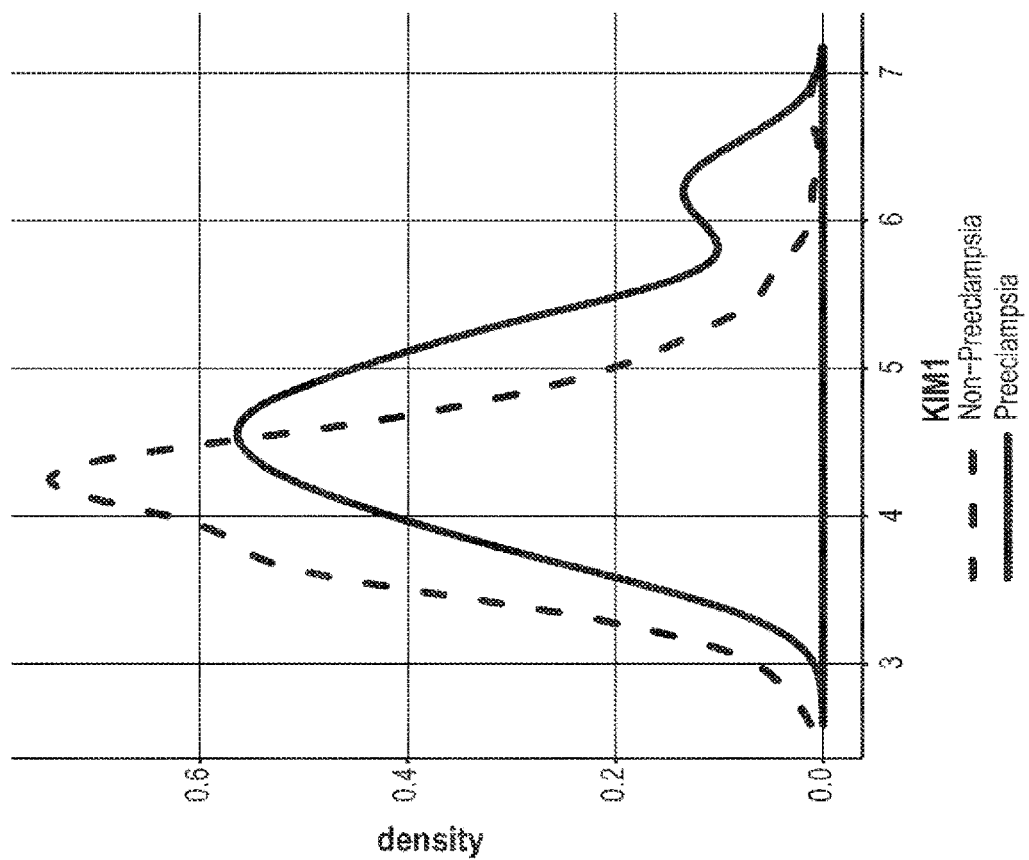
Figure 13J:
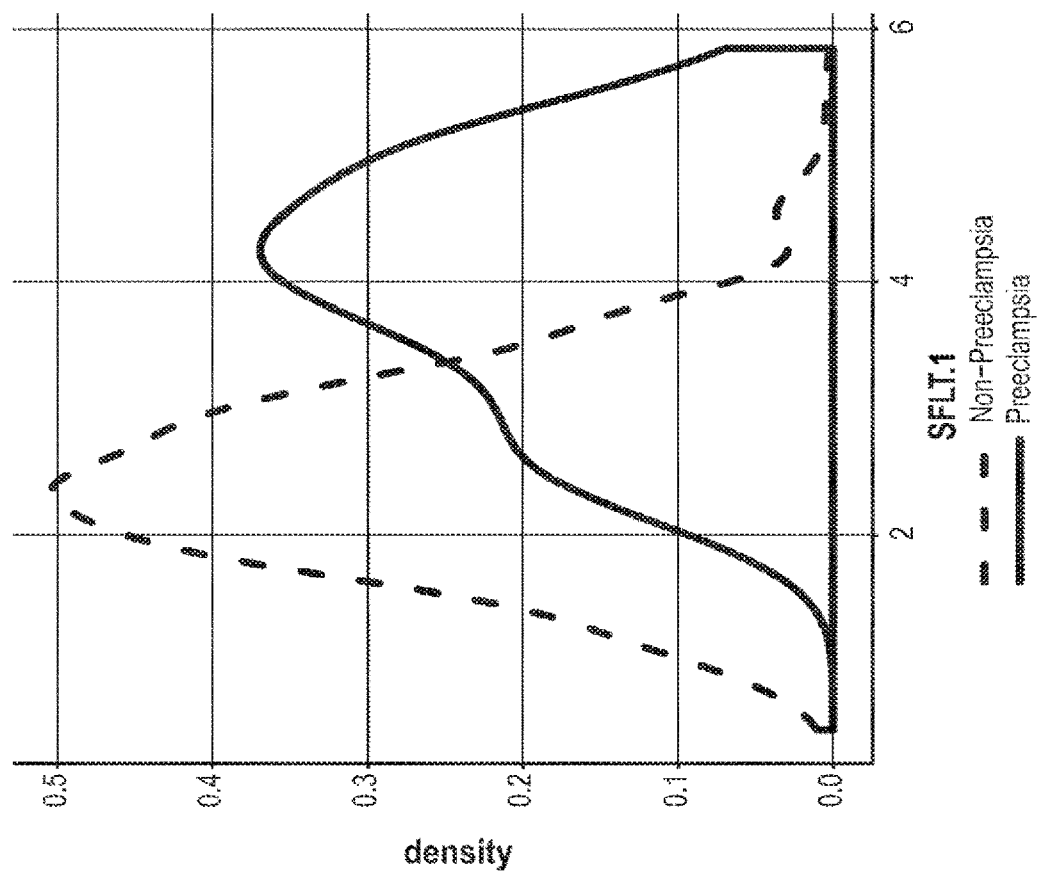
Figure 13I:
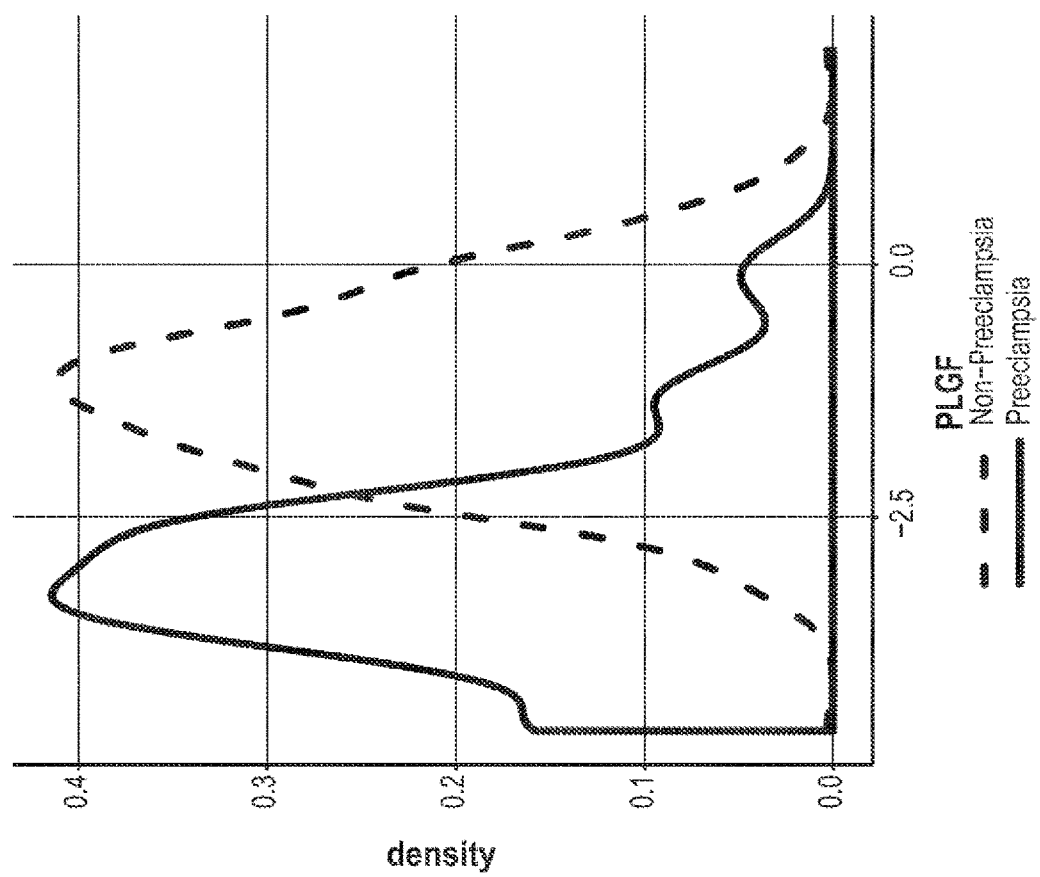

FIG. 6 shows a computer system (also "system" herein) 401 programmed or otherwise configured for implementing the methods of the disclosure, such as producing a selector set and/or for data analysis. The system 401 includes a central processing unit (CPU, also "processor" and "computer processor" herein) 405, which can be a single core or multi core processor, or a plurality of processors for parallel processing. The system 401 also includes memory 410 (e.g., random-access memory, read-only memory, flash memory), electronic storage unit 415 (e.g., hard disk), communications interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communications bus (solid lines), such as a motherboard. The storage unit 415 can be a data storage unit (or data repository) for storing data. The system 401 is operatively coupled to a computer network ("network") 430 with the aid of the communications interface 420. The network 430 can be the Internet, an internet and/or extranet, or an intranet and/or extranet that is in communication with the Internet. The network 430 in some instances is a telecommunication and/or data network. The network 430 can include one or more computer servers, which can enable distributed computing, such as cloud computing. The network 430 in some instances, with the aid of the system 401, can implement a peer-to-peer network, which can enable devices coupled to the system 401 to behave as a client or a server.

The system 401 is in communication with a processing system 435. The processing system 435 can be configured to implement the methods disclosed herein. In some examples, the processing system 435 is a microfluidic qPCR system. In other examples, the processing system 435 is an ALPHA screen or other plate reader. In other examples, the processing system 435 is a FACS sorter or analyzer. The processing system 435 can be in communication with the system 401 through the network 430, or by direct (e.g., wired, wireless) connection. In some embodiments, raw data from the processing system (e.g. a biomarker expression profile) is uploaded through the network to the system for processing (e.g. sample classification or determination of a probability of a certain classification). This data transfer may be direct (e.g. FTP, TCP, or other direct network connection between the processing system 435 and the system 401), or indirect (e.g. transfer to a cloud storage system which can be accessed by the system 401).

Methods as described herein can be implemented by way of machine (or computer processor) executable code (or software) stored on an electronic storage location of the system 401, such as, for example, on the memory 410 or electronic storage unit 415. During use, the code can be executed by the processor 405. In some examples, the code can be retrieved from the storage unit 415 and stored on the memory 410 for ready access by the processor 405. In some situations, the electronic storage unit 415 can be precluded, and machine-executable instructions are stored on memory 410.

Digital Processing Device

The methods, kits, and systems disclosed herein can include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

The digital processing device will normally include an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

The device generally includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

A display to send visual information to a user will normally be initialized. Examples of displays include a cathode ray tube (CRT, a liquid crystal display (LCD), a thin film transistor liquid crystal display (TFT-LCD, an organic light emitting diode (OLED) display. In various further embodiments, on OLED display is a passive-matrix OLED (PMOLED) or active-matrix OLED (AMOLED) display. In some embodiments, the display can be a plasma display, a video projector or a combination of devices such as those disclosed herein.

The digital processing device would normally include an input device to receive information from a user. The input device can be, for example, a keyboard, a pointing device including, by way of non-limiting examples, a mouse, trackball, track pad, joystick, game controller, or stylus; a touch screen, or a multi-touch screen, a microphone to capture voice or other sound input, a video camera to capture motion or visual input or a combination of devices such as those disclosed herein.

Non-Transitory Computer Readable Storage Medium

The methods, kits, and systems disclosed herein can include one or more non-transitory computer readable storage media encoded with a program including instructions executable by the operating system to perform and analyze the test described herein; preferably connected to a networked digital processing device. The computer readable storage medium is a tangible component of a digital device that is optionally removable from the digital processing device. The computer readable storage medium includes, by way of non-limiting examples, CD-ROMs, DVDs, flash memory devices, solid state memory, magnetic disk drives, magnetic tape drives, optical disk drives, cloud computing systems and services, and the like. In some instances, the program and instructions are permanently, substantially permanently, semi-permanently, or non-transitorily encoded on the media.

A non-transitory computer-readable storage media can be encoded with a computer program including instructions executable by a processor to create or use a classification system. The storage media can comprise (a) a database, in a computer memory, of one or more clinical features of two or more control samples, wherein (i) the two or more control samples can be from two or more subjects; and (ii) the two or more control samples can be differentially classified based on a classification system comprising two or more classes; (b) a first software module configured to compare the one or more clinical features of the two or more control samples; and (c) a second software module configured to produce a classifier set based on the comparison of the one or more clinical features. At least two of the classes can be selected from preeclampsia, non-preeclampsia, normal pregnancy, complicated pregnancy, and gestational hypertension.

Antigen Detection (E.g., Antibodies)

In some embodiments, at least one antigen binding reagent is used to detect any of the biomarkers identified herein. In some embodiments, the antigen binding reagent can be an antibody (monoclonal or polyclonal), antigen-binding fragment (e.g. Fab, Fab', F(ab)2, F(abc)2, or Fv fragment) of an antibody, or an antibody derivative (e.g. diabody, linear antibody, or scFv). In some embodiments, the at least one antigen detection moiety is an antibody from FIG. 18. In some embodiments, the antigen binding reagent is an antigen-binding fragment (e.g. Fab, Fab', F(ab)2, F(abc)2, or Fv fragment) or antibody derivative (e.g. diabody, linear antibody, or scFv) of any of the antibodies provided in FIG. 18.

Kits

In some embodiments, the disclosure provides assay kits for analysis of any of the sets of biomarkers included herein for the detection of preeclampsia. In some cases, the assay kits comprise one or more antigen-binding reagents (e.g. monoclonal or polyclonal antibodies provided in FIG. 18, or antigen-binding fragments or antibody derivatives of antibodies provided in FIG. 18). In some embodiments, the one or more antigen-binding reagents comprise combinations of antigen-binding reagents with specificities for the antigens/biomarkers presented below.

In some embodiments, the assay kit provided comprises at least one antibody, antibody fragment, or antibody derivative specific for each biomarker in one of the following sets: sFlt.1, PIGF, KIM1, and CLEC4A; sFlt.1, PIGF, KIM1, CLEC4A, and FGF21; sFlt.1, PIGF, KIM1, CLEC4A, and CD274; sFlt.1, PIGF, KIM1, CLEC4A, and ENDOGLIN; sFlt.1, PIGF, KIM1, CLEC4A, and DECORIN; sFlt.1, PIGF, KIM1, CLEC4A, FGF21, and ENDOGLIN; sFlt.1, PIGF, KIM1, CLEC4A, FGF21, and CD274; sFlt.1, PIGF, KIM1, CLEC4A, ENDOGLIN, and CD274; sFlt.1, PIGF, KIM1, CLEC4A, ENDOGLIN, and DECORIN; sFlt.1, PIGF, KIM1, CLEC4A, FGF21, ENDOGLIN, and CD274; sFlt.1, PIGF, KIM1, CLEC4A, FGF21, ENDOGLIN, CD274, and DECORIN; PIGF, KIM1, CLEC4A, and ENDOGLIN; PIGF, KIM1, CLEC4A, ENDOGLIN, and DECORIN; sFlt.1, PIGF, KIM1, TFF2, FGF21, and DECORIN; sFlt.1, PIGF, KIM1, CLEC4A, CD2741, and ENDOGLIN; or HGF, SYND1, CLEC4A, sFlt1, PIGF, KIM1, CLEC4A, and FGF21.

In some embodiments, the assay kit provided comprises at least one antibody, antibody fragment, or antibody derivative specific for each biomarker in one of the following sets of four optionally in combination with PIGF:SFLT1, KIM1, CLEC4A, FGF21; SFLT1, KIM1, CLEC4A, endoglin; SFLT1, KIM1, CLEC4A, decorin; SFLT1, KIM1, CLEC4A, CD274; SFLT1, KIM1, CLEC4A, HGF; SFLT1, KIM1, CLEC4A, TFF2; SFLT1, KIM1, CLEC4A, PAPP.A2; SFLT1, KIM1, FGF21, endoglin; SFLT1, KIM1, FGF21, decorin; SFLT1, KIM1, FGF21, CD274; SFLT1, KIM1, FGF21, HGF; SFLT1, KIM1, FGF21, TFF2; SFLT1, KIM1, FGF21, PAPP.A2; SFLT1, KIM1, endoglin, decorin; SFLT1, KIM1, endoglin, CD274; SFLT1, KIM1, endoglin, HGF; SFLT1, KIM1, endoglin, TFF2; SFLT1, KIM1, endoglin, PAPP.A2; SFLT1, KIM1, decorin, CD274; SFLT1, KIM1, decorin, HGF; SFLT1, KIM1, decorin, TFF2; SFLT1, KIM1, decorin, PAPP.A2; SFLT1, KIM1, CD274, HGF; SFLT1, KIM1, CD274, TFF2; SFLT1, KIM1, CD274, PAPP.A2; SFLT1, KIM1, HGF, TFF2; SFLT1, KIM1, HGF, PAPP.A2; SFLT1, KIM1, TFF2, PAPP.A2; SFLT1, CLEC4A, FGF21, endoglin; SFLT1, CLEC4A, FGF21, decorin; SFLT1, CLEC4A, FGF21, CD274; SFLT1, CLEC4A, FGF21, HGF; SFLT1, CLEC4A, FGF21, TFF2; SFLT1, CLEC4A, FGF21, PAPP.A2; SFLT1, CLEC4A, endoglin, decorin; SFLT1, CLEC4A, endoglin, CD274; SFLT1, CLEC4A, endoglin, HGF; SFLT1, CLEC4A, endoglin, TFF2; SFLT1, CLEC4A, endoglin, PAPP.A2; SFLT1, CLEC4A, decorin, CD274; SFLT1, CLEC4A, decorin, HGF; SFLT1, CLEC4A, decorin, TFF2; SFLT1, CLEC4A, decorin, PAPP.A2; SFLT1, CLEC4A, CD274, HGF; SFLT1, CLEC4A, CD274, TFF2; SFLT1, CLEC4A, CD274, PAPP.A2; SFLT1, CLEC4A, HGF, TFF2; SFLT1, CLEC4A, HGF, PAPP.A2; SFLT1, CLEC4A, TFF2, PAPP.A2; SFLT1, FGF21, endoglin, decorin; SFLT1, FGF21, endoglin, CD274; SFLT1, FGF21, endoglin, HGF; SFLT1, FGF21, endoglin, TFF2; SFLT1, FGF21, endoglin, PAPP.A2; SFLT1, FGF21, decorin, CD274; SFLT1, FGF21, decorin, HGF; SFLT1, FGF21, decorin, TFF2; SFLT1, FGF21, decorin, PAPP.A2; SFLT1, FGF21, CD274, HGF; SFLT1, FGF21, CD274, TFF2; SFLT1, FGF21, CD274, PAPP.A2; SFLT1, FGF21, HGF, TFF2; SFLT1, FGF21, HGF, PAPP.A2; SFLT1, FGF21, TFF2, PAPP.A2; SFLT1, endoglin, decorin, CD274; SFLT1, endoglin, decorin, HGF; SFLT1, endoglin, decorin, TFF2; SFLT1, endoglin, decorin, PAPP.A2; SFLT1, endoglin, CD274, HGF; SFLT1, endoglin, CD274, TFF2; SFLT1, endoglin, CD274, PAPP.A2; SFLT1, endoglin, HGF, TFF2; SFLT1, endoglin, HGF, PAPP.A2; SFLT1, endoglin, TFF2, PAPP.A2; SFLT1, decorin, CD274, HGF; SFLT1, decorin, CD274, TFF2; SFLT1, decorin, CD274, PAPP.A2; SFLT1, decorin, HGF, TFF2; SFLT1, decorin, HGF, PAPP.A2; SFLT1, decorin, TFF2, PAPP.A2; SFLT1, CD274, HGF, TFF2; SFLT1, CD274, HGF, PAPP.A2; SFLT1, CD274, TFF2, PAPP.A2; SFLT1, HGF, TFF2, PAPP.A2; KIM1, CLEC4A, FGF21, endoglin; KIM1, CLEC4A, FGF21, decorin; KIM1, CLEC4A, FGF21, CD274; KIM1, CLEC4A, FGF21, HGF; KIM1, CLEC4A, FGF21, TFF2; KIM1, CLEC4A, FGF21, PAPP.A2; KIM1, CLEC4A, endoglin, decorin; KIM1, CLEC4A, endoglin, CD274; KIM1, CLEC4A, endoglin, HGF; KIM1, CLEC4A, endoglin, TFF2; KIM1, CLEC4A, endoglin, PAPP.A2; KIM1, CLEC4A, decorin, CD274; KIM1, CLEC4A, decorin, HGF; KIM1, CLEC4A, decorin, TFF2; KIM1, CLEC4A, decorin, PAPP.A2; KIM1, CLEC4A, CD274, HGF; KIM1, CLEC4A, CD274, TFF2; KIM1, CLEC4A, CD274, PAPP.A2; KIM1, CLEC4A, HGF, TFF2; KIM1, CLEC4A, HGF, PAPP.A2; KIM1, CLEC4A, TFF2, PAPP.A2; KIM1, FGF21, endoglin, decorin; KIM1, FGF21, endoglin, CD274; KIM1. FGF21, endoglin, HGF; KIM1, FGF21, endoglin, TFF2; KIM1, FGF21, endoglin, PAPP.A2; KIM1, FGF21, decorin, CD274; KIM1, FGF21, decorin, HGF; KIM1, FGF21, decorin, TFF2; KIM1, FGF21, decorin, PAPP.A2; KIM1, FGF21, CD274, HGF; KIM1, FGF21, CD274, TFF2; KIM1, FGF21, CD274, PAPP.A2; KIM1, FGF21, HGF, TFF2; KIM1, FGF21, HGF, PAPP.A2; KIM1, FGF21, TFF2, PAPP.A2; KIM1, endoglin, decorin, CD274; KIM1, endoglin, decorin, HGF; KIM1, endoglin, decorin, TFF2; KIM1, endoglin, decorin, PAPP.A2; KIM1, endoglin, CD274, HGF; KIM1, endoglin, CD274, TFF2; KIM1, endoglin, CD274, PAPP.A2; KIM1, endoglin, HGF, TFF2; KIM1, endoglin, HGF, PAPP.A2; KIM1, endoglin, TFF2, PAPP.A2; KIM1, decorin, CD274, HGF; KIM1, decorin, CD274, PAPP.A2; KIM1, decorin, HGF, TFF2; KIM1, decorin, HGF, PAPP.A2; KIM1, decorin, TFF2, PAPP.A2; KIM1, CD274, HGF, TFF2; KIM1, CD274, HGF, PAPP.A2; KIM1, CD274, TFF2, PAPP.A2; KIM1, HGF, TFF2, PAPP.A2; CLEC4A, FGF21, endoglin, decorin; CLEC4A, FGF21, endoglin, CD274; CLEC4A, FGF21, endoglin, HGF; CLEC4A, FGF21, endoglin, TFF2; CLEC4A, FGF21, endoglin, PAPP.A2; CLEC4A, FGF21, decorin, CD274; CLEC4A, FGF21, decorin, HGF; CLEC4A, FGF21, decorin, TFF2; CLEC4A, FGF21, decorin, PAPP.A2; CLEC4A, FGF21, CD274, HGF; CLEC4A, FGF21, CD274, TFF2; CLEC4A, FGF21, CD274, PAPP.A2; CLEC4A, FGF21, HGF, TFF2; CLEC4A, FGF21, HGF, PAPP.A2; CLEC4A, FGF21, TFF2, PAPP.A2; CLEC4A, endoglin, decorin, CD274; CLEC4A, endoglin, decorin, HGF; CLEC4A, endoglin, decorin, TFF2; CLEC4A, endoglin, decorin, PAPP.A2; CLEC4A, endoglin, CD274, HGF; CLEC4A, endoglin, CD274, TFF2; CLEC4A, endoglin, CD274, PAPP.A2; CLEC4A, endoglin, HGF, TFF2; CLEC4A, endoglin, HGF, PAPP.A2; CLEC4A, endoglin, TFF2, PAPP.A2; CLEC4A, decorin, CD274, HGF; CLEC4A, decorin, CD274, TFF2; CLEC4A, decorin, CD274, PAPP.A2; CLEC4A, decorin, HGF, TFF2; CLEC4A, decorin, HGF, PAPP.A2; CLEC4A, decorin, TFF2, PAPP.A2; CLEC4A, CD274, HGF, TFF2; CLEC4A, CD274, HGF, PAPP.A2; CLEC4A, CD274, TFF2, PAPP.A2; CLEC4A, HGF, TFF2, PAPP.A2; FGF21, endoglin, decorin, CD274; FGF21, endoglin, decorin, HGF; FGF21, endoglin, decorin, TFF2; FGF21, endoglin, decorin, PAPP.A2; FGF21, endoglin, CD274, HGF; FGF21, endoglin, CD274, TFF2; FGF21, endoglin, CD274, PAPP.A2; FGF21, endoglin, HGF, TFF2; FGF21, endoglin, HGF, PAPP.A2; FGF21, endoglin, TFF2, PAPP.A2; FGF21, decorin, CD274, HGF; FGF21, decorin, CD274, TFF2; FGF21, decorin, CD274, PAPP.A2; FGF21, decorin, HGF, TFF2; FGF21, decorin, HGF, PAPP.A2; FGF21, decorin, TFF2, PAPP.A2; FGF21. CD274, HGF, TFF2; FGF21, CD274, HGF, PAPP.A2; FGF21, CD274, TFF2, PAPP.A2; FGF21, HGF, TFF2, PAPP.A2; endoglin, decorin, CD274. HGF; endoglin, decorin, CD274, TFF2; endoglin, decorin, CD274, PAPP.A2; endoglin, decorin, HGF, TFF2; endoglin, decorin, HGF, PAPP.A2; endoglin, decorin, TFF2, PAPP.A2; endoglin, CD274, HGF, TFF2; endoglin, CD274, HGF, PAPP.A2; endoglin, CD274, TFF2, PAPP.A2; endoglin, HGF, TFF2, PAPP.A2; decorin, CD274, HGF, TFF2; decorin, CD274, HGF, PAPP.A2; decorin, CD274, TFF2, PAPP.A2; or decorin, HGF, TFF2, PAPP.A2; CD274, HGF, TFF2, PAPP.A2.

In some embodiments, the assay kit provided comprises at least one antibody, antibody fragment, or antibody derivative specific for each biomarker in one of the following sets of three optionally in combination with PIGF: SFLT1, KIM1, CLEC4A; SFLT1, KIM1, FGF21; SFLT1, KIM1, endoglin; SFLT1, KIM1, decorin; SFLT1, KIM1, CD274; SFLT1, KIM1, HGF; SFLT1, KIM1, TFF2; SFLT1, KIM1, PAPP.A2; SFLT1, CLEC4A, FGF21; SFLT1, CLEC4A, endoglin; SFLT1, CLEC4A, decorin; SFLT1, CLEC4A, CD274; SFLT1, CLEC4A, HGF; SFLT1, CLEC4A, TFF2; SFLT1, CLEC4A, PAPP.A2; SFLT1, FGF21, endoglin; SFLT1, FGF21, decorin; SFLT1, FGF21, CD274; SFLT1, FGF21, HGF; SFLT1, FGF21, TFF2; SFLT1, FGF21, PAPP.A2; SFLT1, endoglin, decorin; SFLT1, endoglin, CD274; SFLT1, endoglin, HGF; SFLT1, endoglin, TFF2; SFLT1, endoglin, PAPP.A2; SFLT1, decorin, CD274; SFLT1, decorin, HGF; SFLT1, decorin, TFF2; SFLT1, decorin, PAPP.A2; SFLT1, CD274, HGF; SFLT1, CD274, TFF2; SFLT1, CD274, PAPP.A2; SFLT1, HGF, TFF2; SFLT1, HGF, PAPP.A2; SFLT1, TFF2, PAPP.A2; KIM1, CLEC4A, FGF21; KIM1, CLEC4A, endoglin; KIM1, CLEC4A, decorin; KIM1, CLEC4A, CD274; KIM1, CLEC4A, HGF; KIM1, CLEC4A, TFF2; KIM1, CLEC4A, PAPP.A2; KIM1, FGF21, endoglin; KIM1, FGF21, decorin; KIM1, FGF21, CD274; KIM1, FGF21, HGF; KIM1, FGF21, TFF2; KIM1, FGF21, PAPP.A2; KIM1, endoglin, decorin; KIM1, endoglin, CD274; KIM1, endoglin, HGF; KIM1, endoglin, TFF2; KIM1, endoglin, PAPP.A2; KIM1, decorin, CD274; KIM1, decorin, HGF; KIM1, decorin, TFF2; KIM1, decorin, PAPP.A2; KIM1, CD274, HGF; KIM1, CD274, TFF2; KIM1, CD274, PAPP.A2; KIM1, HGF, TFF2; KIM1, HGF, PAPP.A2; KIM1, TFF2, PAPP.A2; CLEC4A, FGF21, endoglin; CLEC4A, FGF21, decorin; CLEC4A, FGF21, CD274; CLEC4A, FGF21, HGF; CLEC4A, FGF21, TFF2; CLEC4A, FGF21, PAPP.A2; CLEC4A, endoglin, decorin; CLEC4A, endoglin, CD274; CLEC4A, endoglin, HGF; CLEC4A, endoglin, TFF2; CLEC4A, endoglin, PAPP.A2; CLEC4A, decorin, CD274; CLEC4A, decorin, HGF; CLEC4A, decorin, TFF2; CLEC4A, decorin, PAPP.A2; CLEC4A, CD274, HGF; CLEC4A, CD274, TFF2; CLEC4A, CD274, PAPP.A2; CLEC4A, HGF, TFF2; CLEC4A, HGF, PAPP.A2; CLEC4A, TFF2, PAPP.A2; FGF21, endoglin, decorin; FGF21, endoglin, CD274; FGF21, endoglin, HGF; FGF21, endoglin, TFF2; FGF21, endoglin, PAPP.A2; FGF21, decorin, CD274; FGF21, decorin, HGF; FGF21, decorin, TFF2; FGF21, decorin, PAPP.A2; FGF21, CD274, HGF; FGF21, CD274, TFF2; FGF21, CD274, PAPP.A2; FGF21, HGF, TFF2; FGF21, HGF, PAPP.A2; FGF21, TFF2, PAPP.A2; endoglin, decorin, CD274; endoglin, decorin, HGF; endoglin, decorin, TFF2; endoglin, decorin, PAPP.A2; endoglin, CD274, HGF; endoglin, CD274, TFF2; endoglin, CD274, PAPP.A2; endoglin, HGF, TFF2; endoglin, HGF, PAPP.A2; endoglin, TFF2, PAPP.A2; decorin, CD274, HGF; decorin, CD274, TFF2; decorin, CD274, PAPP.A2; decorin, HGF, TFF2; decorin, HGF, PAPP.A2; decorin, TFF2, PAPP.A2; CD274, HGF, TFF2; CD274, HGF, PAPP.A2; CD274, TFF2, PAPP.A2; or HGF, TFF2, PAPP.A2.

In some embodiments, the assay kit provided comprises at least one antibody, antibody fragment, or antibody derivative specific for each biomarker in one of the following sets of two optionally in combination with PIGF: SFLT1, KIM1; SFLT1, CLEC4A; SFLT1, FGF21; SFLT1, endoglin; SFLT1, decorin; SFLT1, CD274; SFLT1, HGF; SFLT1, TFF2; SFLT1, PAPP.A2; KIM1, CLEC4A; KIM1, FGF21; KIM1, endoglin; KIM1, decorin; KIM1, CD274; KIM1, HGF; KIM1, TFF2; KIM1, PAPP.A2; CLEC4A, FGF21; CLEC4A, endoglin; CLEC4A, decorin; CLEC4A, CD274; CLEC4A, HGF; CLEC4A, TFF2; CLEC4A, PAPP.A2; FGF21, endoglin; FGF21, decorin; FGF21, CD274; FGF21, HGF; FGF21, TFF2; FGF21, PAPP.A2; endoglin, decorin; endoglin, CD274; endoglin, HGF; endoglin, TFF2; endoglin, PAPP.A2; decorin, CD274; decorin, HGF; decorin, TFF2; decorin, PAPP.A2; CD274, HGF; CD274, TFF2; CD274, PAPP.A2; HGF, TFF2; HGF, PAPP.A2; TFF2, PAPP.A2.

In some embodiments, the assay kit provided comprises at least one antibody, antibody fragment, or antibody derivative specific for each biomarker in one of the following sets: PIGF, sFLT1, KIM1; PIGF, sFLT1, CLEC4A; PIGF, sFLT1, FGF21; PIGF, sFLT1, Decorin; PIGF, sFLT1, CD274; PIGF, sFLT1, HGF; PIGF, sFLT1, TFF2; PIGF, sFLT1, PAPP-A2; PIGF, Endoglin, KIM1; PIGF, Endoglin, CLEC4A; PIGF, Endoglin, FGF21; PIGF, Endoglin, Decorin; PIGF, Endoglin, CD274; PIGF, Endoglin, HGF; PIGF, Endoglin, TFF2; PIGF, Endoglin, PAPP-A2; PIGF, KIM1, CLEC4A; PIGF, KIM1, FGF21; PIGF, KIM1, Decorin; PIGF, KIM1, CD274; PIGF, KIM1, HGF; PIGF, KIM1, TFF2; PIGF, KIM1, PAPP-A2; PlGF, CLEC4A, FGF21; PlGF, CLEC4A, Decorin; PlGF, CLEC4A, CD274; PlGF, CLEC4A, HGF; PlGF, CLEC4A, TFF2; PlGF, CLEC4A, PAPP-A2; PlGF, CD274, CLEC4A; PlGF, CD274, FGF21; PlGF, CD274, HGF; PlGF, CD274, TFF2; PlGF, CD274, PAPP-A2; PlGF, Decorin, CLEC4A; PlGF, Decorin, FGF21; PlGF, Decorin, HGF; PlGF, Decorin, TFF2; PlGF, Decorin, PAPP-A2; PlGF, FGF21, TFF2, Decorin; PlGF, FGF21, TFF2, CD274; PlGF, FGF21, TFF2, HGF; PlGF, FGF21, TFF2; PlGF, FGF21, TFF2, PAPP-A2; PlGF, Endoglin, PAPP-A2, DECORIN, KIM1; PlGF, Endoglin, PAPP-A2, DECORIN, CLEC4A; PlGF, Endoglin, PAPP-A2, DECORIN, FGF21; PlGF, Endoglin, PAPP-A2, DECORIN, CD274; PlGF, Endoglin, PAPP-A2, DECORIN, HGF; PlGF, Endoglin, PAPP-A2, DECORIN, TFF2.

In some embodiments, the assay kit provided is suitable for a multiplex homogenous biomarker assay, suitable for detection of all the analytes in a single reaction (e.g. in the same solution compartment). In such assays, multiple antibodies or antigen detection reagents that bind to separate epitopes are provided against the same analyte/biomarker, and detection of coincident binding/interaction of both antibodies to the same molecule of analyte/biomarker serves to detect the analyte/biomarker in the sample. Thus, such kits provide two antibodies or antigen-binding reagents against each analyte.

In the case of a multiplex homogenous biomarker assay detectable by TR-FRET, such kits provide a pair of antibodies or antigen-binding reagents for each analyte conjugated to a complementary pair of FRET dyes, wherein one antibody or antigen-binding reagent of the pair is conjugated to a FRET donor and the other is conjugated to a FRET acceptor. In the case of a multiplex homogenous biomarker assay detectable by LOCI, such kits provide a pair of antibodies or antigen-binding reagents wherein one antibody or antigen-binding reagent of the pair is conjugated to a photosensitizer and the other antibody or antigen-binding reagent of the pair is conjugated to an oxygen sensitive dye.

In some embodiments, the assay kit provided is suitable for a multiplex non-homogenous biomarker assay suitable for detection of all the analytes in separate reactions (e.g. in separate solution compartments). In some embodiments of such assays (e.g. sandwich ELISA), antibodies or antigen binding reagents against the relevant set of biomarkers are provided attached to a substrate (e.g. in a well of a multiwell plate, or in a lateral flow assay lane). A second free antibody against each of the biomarkers provided attached to the substrate is also provided; this antibody can be labeled (e.g. with a fluorescent dye, with a chemiluminescent enzyme, or a luminescent enzyme) or unlabeled. In the case where an unlabeled antibody is provided, a secondary labeled (e.g. with a fluorescent dye, with a chemiluminescent enzyme, or a luminescent enzyme) antibody or antigen-binding reagent is provided which has binding specificity against the second free antibody.

In some embodiments, the kit is for use as an in vitro diagnostic kit that includes one or more cartridges with reagents for testing on third-party platforms. Data collected from third-parties could be uploaded to a server (the cloud), put through a model/algorithm, and results can be shared with a doctor or other medical practitioner. Kits may also include instructions for use.

Exemplary Embodiments

In some aspects, the present disclosure provides for a method for avoiding unnecessary treatment of preeclampsia, the method comprising: (a) contacting a biological sample that has been collected from a pregnant human female with a plurality of different probes, wherein the plurality of different probes comprises probes with specific affinity for four or more proteins selected from proteins listed in Table A or Table B; (b) determining, based on binding of the plurality of different probes to corresponding proteins, an amount or concentration for each of the four or more proteins; and (c) proceeding with treatment of said pregnant human in a manner that avoids unnecessary treatment of preeclampsia based at least in part on the amounts or concentrations of the four or more proteins determined in step (b). In some embodiments, the four or more proteins comprise: (a) placental growth factor (PlGF); (b) one or more angiogenesis-associated proteins selected from the group consisting of soluble fms-like tyrosine kinase 1 (sFlt1), endoglin, pappalysin 2 (PAPP-A2), and decorin; and (c) one or more kidney damage associated-proteins selected from the group consisting of (1) kidney injury molecule-1 (KIM1), (2) programmed cell death 1 ligand 1 (CD274), and decorin. In some embodiments, the four or more proteins further comprise one or more proteins selected from the group consisting of C-type lectin domain family 4 member A (CLEC4A), fibroblast growth factor 21 (FGF21), trefoil factor 2 (TFF2), and hepatocyte growth factor (HGF). In some embodiments, the four or more proteins comprise PlGF, sFlt1, KIM1, and CLEC4A. In some embodiments, the plurality of different probes comprises probes with specific affinity to fibroblast growth factor 21 (FGF21), and the four or more proteins comprise FGF21. In some embodiments, the plurality of different probes comprises probes with specific affinity for endoglin, and the four or more proteins comprise endoglin. In some embodiments, the plurality of different probes comprises probes with specific affinity for decorin, and the four or more proteins comprise decorin. In some embodiments, the plurality of different probes comprises probes with specific affinity for cluster of differentiation 274 (CD274), and the four or more proteins comprise CD274. In some embodiments, the plurality of different probes comprises probes with specific affinity for hepatocyte growth factor (HGF), and the four or more proteins comprise HGF. In some embodiments, the plurality of different probes comprises probes with specific affinity for trefoil factor 2 (TFF2), and the four or more proteins comprises TFF2. In some embodiments, the plurality of different probes comprises probes with specific affinity for pappalysin-2 (PAPP-A2), and the four or more proteins comprise PAPP-A2. In some embodiments, the biological sample is obtained from the pregnant female after gestational week 20. In some embodiments, the biological sample has been collected from the pregnant female prior to gestational week 30. In some embodiments, the method further comprises: applying a classifier algorithm to an expression profile of the four or more proteins, wherein the classifier algorithm calculates an index; and comparing the index to a reference value to determine whether to avoid the unnecessary treatment of preeclampsia. In some embodiments, the classifier algorithm further comprises a correction for gestational age. In some embodiments, the correction for gestational age comprises a LOESS correction. In some embodiments, the classifier algorithm comprises a logistic regression. In some embodiments, the classifier algorithm comprises a logistic regression with elastic-net regularization. In some embodiments, the classifier algorithm comprises a Random Forest. In some embodiments, the biological sample is a urine, blood, amniotic fluid, exosome, plasma, or serum sample. In some embodiments, the biological sample is from blood of the pregnant human female. In some embodiments, the amount or concentration of no more than 20, no more than 15, nor more than 10, nor more than 9, no more than 8, no more than 7, no more than 6, nor more than 5, or no more than 4 proteins is determined. In some embodiments, one or more of the plurality of different probes are antibodies, antibody fragments, or antibody derivatives. In some embodiments, each of the plurality of different probes are antibodies, antibody fragments, or antibody derivatives. In some embodiments, the amount or concentration of at least one of (or all of (e.g., SYND1 and/or CLEC4A)) the four or more proteins is determined using a luminescent oxygen channeling immunoassay. In some embodiments, the amount or concentration of at least one of (or all of) the four or more proteins is determined using a time-resolved fluorescence resonance energy transfer (TR-FRET) assay. In some embodiments, the amount or concentration of at least one of (or all of) the four or more proteins is determined using a proximity extension assay. In some embodiments, the amount or concentration of at least one of (or all of) the four or more proteins is determined using an enzyme-linked immunosorbent assay (ELISA). In some embodiments, the amount or concentration of at least one of (or all of) the four or more proteins is determined using an amplified luminescent proximity homogenous assay. In some embodiments, the amount or concentration of at least one of (or all of) the four or more proteins is determined using a lateral flow assay. In some embodiments, the biological sample is obtained from the pregnant human while in a perinatologist's office, a labor and delivery room, or triage (ER). In some embodiments, the method further comprises separating the biological sample into a plurality of different reaction vessels, the plurality of reaction vessels comprising a first reaction vessel, a second reaction vessel, a third reaction vessel, and a fourth reaction vessel, wherein contacting the biological sample with the plurality of different probes comprises delivering probes with specific affinity for PlGF in a first reaction vessel, delivering probes with specific affinity to sFlt1 to a second reaction vessel, delivering probes with specific affinity to KIM1 to a third reaction vessel, and delivering probes with specific affinity to CLEC4A to a fourth reaction vessel. In some embodiments, the step of contacting the biological sample with the plurality of different probes occurs in a single reaction vessel. In some embodiments, the biological sample was obtained from the pregnant female after the pregnant female has shown one or more symptoms of preeclampsia, wherein the symptoms of preeclampsia are selected from (1) high blood pressure and (2) proteinuria. In some embodiments, the sample was obtained from the pregnant female after the pregnant female has shown both (1) high blood pressure and (2) proteinuria. In some embodiments, the plurality of different probes comprises two sets of probes with specific affinity for each of the four or more proteins, wherein each set of the two sets of probes binds to different epitopes.

In some aspects, the present disclosure provides for a method, such as a laboratory method, for detecting and/or quantifying a plurality of proteins in a sample from a pregnant human female, the method comprising: contacting a biological sample from a pregnant human female with a plurality of probes, wherein the plurality of probes comprises probes with specific affinity for four or more proteins selected from the proteins listed in Table A or Table B and detecting the presence and/or quantity of the four or more proteins based on binding of the plurality of different probes to corresponding proteins. In some embodiments, the four or more proteins comprise: (a) placental growth factor, (b) one or more angiogenesis-associated proteins selected from the group consisting of soluble fms-like tyrosine kinase 1 (sFlt1), endoglin, pappalysin 2 (PAPP-A2), and decorin; and (c) one or more kidney damage associated-proteins selected from the group consisting of (1) kidney injury molecule-1 (KIM1), (2) programmed cell death 1 ligand 1 (CD274), and decorin. In some embodiments, the four or more proteins further comprise one or more proteins selected from the group consisting of C-type lectin domain family 4 member A (CLEC4A), fibroblast growth factor 21 (FGF21), trefoil factor 2 (TFF2), and hepatocyte growth factor (HGF). In some embodiments, the four or more proteins comprise PlGF, sFlt1, KIM1, and CLEC4A. In some embodiments, the plurality of different probes comprises probes with specific affinity to fibroblast growth factor 21 (FGF21), and the four or more proteins comprise FGF21. In some embodiments, the plurality of different probes comprises probes with specific affinity for endoglin, and the four or more proteins comprise endoglin. In some embodiments, the plurality of different probes comprises probes with specific affinity for decorin, and the four or more proteins comprise decorin. In some embodiments, the plurality of different probes comprises probes with specific affinity for cluster of differentiation 274 (CD274), and the four or more proteins comprise CD274. In some embodiments, the plurality of different probes comprises probes with specific affinity for hepatocyte growth factor (HGF), and the four or more proteins comprise HGF. In some embodiments, the plurality of different probes comprises probes with specific affinity for trefoil factor 2 (TFF2), and the four or more proteins comprises TFF2. In some embodiments, the plurality of different probes comprises probes with specific affinity for pappalysin-2 (PAPP-A2), and the four or more proteins comprise PAPP-A2. In some embodiments, the biological sample has been collected from the pregnant human female after gestational week 20. In some embodiments, the biological sample has been collected from the pregnant female prior to gestational week 30. In some embodiments, the biological sample is a urine, blood, amniotic fluid, exosome, plasma, or serum sample. In some embodiments, the biological sample is from blood of the pregnant human female. In some embodiments, the amount or concentration of no more than 20, no more than 15, nor more than 10, nor more than 9, no more than 8, no more than 7, no more than 6, nor more than 5, or no more than 4 proteins is determined. In some embodiments, one or more of the plurality of different probes are antibodies, antibody fragments, or antibody derivatives. In some embodiments, each of the plurality of different probes are antibodies, antibody fragments, or antibody derivatives. In some embodiments, the plurality of probes contact the biological sample or a fraction thereof in a single reaction vessel. In some embodiments, the plurality of probes contact the biological sample or a fraction thereof in separate reaction vessels for each protein of the four or more proteins. In some embodiments, the method further comprises a second plurality of probes, wherein the second plurality of probes comprises a probe set that is specific for binding to PlGF, a probe set that is specific for binding to sFlt1, a probe set that is specific for binding to KIM1, and a probe set that is specific for binding to CLEC4A, wherein the second plurality of probes binds to its corresponding protein at an epitope that differs from the epitope to which each of the first plurality of probes binds. In some embodiments, coincident binding of at least one pair of the first and the second plurality of probes to the same protein molecules in the sample is detected by a luminescent oxygen channeling immunoassay (LOCI), a time-resolved fluorescence resonance energy transfer (TR-FRET) assay, an amplified luminescent proximity homogenous assay, an enzyme-linked immunosorbent assay, a proximity extension assay, or a lateral flow assay.

In some aspects, the present disclosure provides for a method for managing a pregnant human subject and identifying the pregnant human subject as not at risk for preeclampsia for a specified period of time, the method comprising: (a) identifying, via a test having (1) a specificity of greater than 80% and (2) a sensitivity of greater than 85%, the pregnant subject as not at risk for developing preeclampsia within the specified period of time, wherein the specified period of time is between one week and six weeks; and (b) managing the pregnant human subject identified as not at risk for developing preeclampsia within the specified period of time by proceeding with ambulant monitoring treatment of said pregnant patient without treating the patient for preeclampsia. In some embodiments, the test has a specificity of at least 82.0%, at least 84.0%, at least 85.0%, at least 87.0%, at least 88.0%, at least 89.0%, at least 90.0%, at least 90.5%, at least 91.0%, or at least 91.5%. In some embodiments, the test has a sensitivity of at least 86%, at least 87%, at least 88%, at least 89%, at least 90%, at least 91%, at least 92%, at least 93%, at least 94%, or at least 95%. In some embodiments, the test has a negative predictive value of at least about 95.0%, 96.0%, 97.0%, 98.0%, 98.2%, 98.4%, 98.5%, 98.7%, 99%, 99.2%, or 99.5% when applied to a random population of ethnically diverse pregnant women after gestational week 20 that exhibit one or more of (1) high blood pressure and (2) proteinuria. In some embodiments, the test has a positive predictive value of at least about 30%, at least about 32%, at least about 35%, at least about 37%; at least about 40%, at least about 42%, at least about 45%, at least about 50%, at least about 55%, or at least about 57% when applied to a random population of ethnically diverse pregnant women after gestational week 20 that exhibit one or more of (1) high blood pressure and (2) proteinuria. In some embodiments, the negative predictive value of the test is higher than the positive predictive value of the test. In some embodiments, the specified period of time is between one week and four weeks, one week and three weeks, or one week and two weeks. In some embodiments, the test comprises determining an amount or concentration of each of four or more proteins selected from proteins listed in Table A or Table B. In some embodiments, the four or more proteins comprise PIGF, sFlt-1, KIM1, and CLEC4A. In some embodiments, the four or more proteins further comprise FGF21.

In some aspects, the present disclosure provides for a method of treating a pregnant human subject, the method comprising: obtaining an indicium generated, at least in part, from a determination of levels for four or more proteins listed in Table A or Table B; and changing a clinical regimen for the pregnant human subject based, at least in part, on the obtained indicium. In some embodiments, obtaining the indicium comprises: determining the levels for PIGF, sFlt1, KIM1, and CLEC4A, wherein the levels are determined from binding of each of PIGF, sFlt1, KIM1, and CLEC4A to corresponding probes. In some embodiments, the obtaining the indicium further comprises determining the level for FGF21, wherein the level of FGF21 is determined from binding of FGF21 to corresponding probes. In some embodiments, the method further comprises classifying (or ruling out a classification) the pregnant subject as having a low risk of having preeclampsia or developing preeclampsia within a specified period of time. In some embodiments, the pregnant subject is classified by any method described herein. In some embodiments, the method further comprises administering an antihypertensive drug to the patient. In some embodiments, the antihypertensive drug is a central alpha agonist, a vasodilator, a calcium-channel blocker, an alpha-blocker or a beta-blocker. In some embodiments, the antihypertensive drug is methyldopa, labetalol, nifedipine, verapamil, clonidine, hydralazine, diazoxide, prazosin, or oxprenolol.

In some aspects, the present disclosure provides for a mixture comprising: a fluid sample from a pregnant female subject; a first plurality of different probes, wherein the first plurality of different probes comprises different probes, each with specific affinity for four or more proteins selected from proteins listed in Table A or Table B. In some embodiments, the four or more proteins comprise: (a) placental growth factor (PIGF) (b) one or more angiogenesis-associated proteins selected from the group consisting of soluble fms-like tyrosine kinase 1 (sFlt1), endoglin, pappalysin 2 (PAPP-A2), and decorin; and (c) one or more kidney damage associated-proteins selected from the group consisting of (1) kidney injury molecule-1 (KIM1), (2) programmed cell death 1 ligand 1 (CD274), and decorin. In some embodiments, the four or more proteins further comprise one or more proteins selected from the group consisting of C-type lectin domain family 4 member A (CLEC4A), fibroblast growth factor 21 (FGF21), trefoil factor 2 (TFF2), and hepatocyte growth factor (HGF). In some embodiments, the four or more proteins comprise PIGF, sFlt1, KIM1, and CLEC4A. In some embodiments, the four or more proteins comprise FGF 21. In some embodiments, the four or more proteins comprise endoglin. In some embodiments, the four or more proteins comprise decorin. In some embodiments, the four or more proteins comprise CD274. In some embodiments, the four or more proteins comprise HGF. In some embodiments, the four or more proteins comprise TFF2. In some embodiments, the four or more proteins comprise PAPP-A2. In some embodiments, the fluid sample has been collected after gestational week 20. In some embodiments, the fluid sample has been collected from the pregnant female prior to gestational week 30. In some embodiments, the mixture includes no more than 20, no more than 16, no more than 14, no more than 12, no more than 10, no more than eight, no more than seven, no more than 6, no more than 5, or nor more than 4 sets of probes that are designed to bind to different proteins in the fluid sample. In some embodiments, the fluid sample is from a blood, plasma, serum, or exosome sample. In some embodiments, the fluid sample was obtained from the subject after the subject has shown one or more symptoms of preeclampsia, wherein the symptoms of preeclampsia are selected from (1) high blood pressure and (2) proteinuria. In some embodiments, the fluid sample was obtained from the subject after the subject has shown both (1) high blood pressure and (2) proteinuria. In some embodiments, the first plurality of different probes comprises a first set of probes with specific affinity for each of the four or more proteins and a second set of probes with specific affinity for each of the four or more proteins, wherein each set of the two sets of probes binds to different epitopes. In some embodiments, the first set of probes and the second set of probes are conjugated to pairs of oligonucleotides containing complementary hybridization regions for each protein-specific probe pair. In some embodiments, the first set of probes and the second set of probes are conjugated to unique FRET pairs of fluorophores for each protein-specific probe pair. In some embodiments, for each protein-specific probe pair, one probe is conjugated to biotin or a streptavidin-binding analog thereof. In some embodiments, the mixture further comprises (a) a photosensitizer; and (b) an oxygen-sensitive dye, wherein one of (a) and (b) is capable of binding the first set of probes, and the other is capable of binding the second set of probes. In some embodiments, one or more of the first plurality of different probes are antibodies, antibody fragments, or antibody derivatives. In some embodiments, each of the first plurality of different probes are antibodies, antibody fragments, or antibody derivatives.

In some aspects, the present disclosure provides for a reaction plate comprising a plurality of reaction wells, wherein the plurality of reaction wells comprises: a first well comprising (1) a first portion of a biological sample from a pregnant human subject, wherein the biological sample was obtained from a pregnant human subject after 20 weeks of gestation, and (2) a first set of probes for binding to PIGF; a second well comprising (1) a second portion of the biological sample from the pregnant human subject, and (2) a second set of probes for binding to sFlt1, endoglin, pappalysin 2 (PAPP-A2), or decorin; a third well comprising (1) a third portion of the biological sample from the pregnant human subject, and (2) a third set of probes for binding to KIM1, (2) programmed cell death 1 ligand 1 (CD274), or decorin; and a fourth well comprising (1) a fourth portion of the biological sample from the pregnant human subject, and (2) a fourth set of probes for binding to CLEC4A, FGF21, TFF2, or HGF. In some embodiments, the second set of probes in the second well are configured to bind to sFlt1. In some embodiments, the third set of probes in the third well are configured to bind to KIM1. In some embodiments, the fourth set of probes in the fourth well are configured to bind to CLEC4A. In some embodiments, the plurality of wells comprises a fifth well, the fifth well comprising (1) a fifth portion of the biological sample from the pregnant human subject and (2) a fifth set of probes for binding to FGF21. In some embodiments, the plurality of reaction wells comprises a well, the well comprising a portion of the biological sample and a set of probes for binding to endoglin. In some embodiments, the plurality of reaction wells comprises a well, the well comprising a portion of the biological sample and a set of probes for binding to decorin. In some embodiments, the plurality of reaction wells comprises a well, the well comprising a portion of the biological sample and a set of probes for binding to CD274. In some embodiments, the plurality of reaction wells comprises a well, the well comprising a portion of the biological sample and a set of probes for binding to HGF. In some embodiments, the plurality of reaction wells comprises a well, the well comprising a portion of the biological sample and a set of probes for binding to TFF2. In some embodiments, the plurality of reaction wells comprises a well, the well comprising a portion of the biological sample and a set of probes for binding to PAPP-A2. In some embodiments, the biological sample has been collected from the pregnant female prior to gestational week 30. In some embodiments, the biological sample is from blood of the pregnant human female. In some embodiments, the plurality of wells of the reaction include probes for specific binding to no more than 20, no more than 15, no more than 12, no more than 10, no more than 8, no more than 7, no more than 6, no more than 5, or no more than 4 proteins. In some embodiments, the probes comprise antibodies, antibody fragments, or antibody derivatives. In some embodiments, the biological sample is from the subject after the subject has shown one or more symptoms of preeclampsia, wherein the symptoms of preeclampsia are selected from (1) high blood pressure and (2) proteinuria. In some embodiments, the sample is from the subject after the subject has shown both (1) high blood pressure and (2) proteinuria. In some embodiments, each set of probes comprises probes that specifically bind to different epitopes.

In some aspects, the present disclosure provides for a kit for ruling out preeclampsia in a pregnant female subject, the kit comprising: (a) probes for determining the levels of four or more proteins selected from the proteins listed in Tables A and B; (b) wherein the kit is designed to measure the levels of no more than 20, no more than 15, no more than 10, nor more than 8, no more than 7, no more than 6, nor more than 5, or no more than 4 proteins. In some embodiments, the four or more proteins comprises: (a) placental growth factor (PIGF); (b) one or more angiogenesis-associated proteins selected from the group consisting of soluble fms-like tyrosine kinase 1 (sFlt1), endoglin, pappalysin 2 (PAPP-A2), and decorin; and (c) one or more kidney damage associated-proteins selected from the group consisting of (1) kidney injury molecule-1 (KIM1), (2) programmed cell death 1 ligand 1 (CD274), and decorin. In some embodiments, the four or more proteins comprise one or more proteins selected from the group consisting of C-type lectin domain family 4 member A (CLEC4A), fibroblast growth factor 21 (FGF21), trefoil factor 2 (TFF2), and hepatocyte growth factor (HGF). In some embodiments, the four or more proteins comprise PIGF, sFlt1, KIM1, and CLEC4A. In some embodiments, four or more proteins comprise FGF21. In some embodiments, the four or more proteins comprise endoglin. In some embodiments, the four or more proteins comprise decorin. In some embodiments, the four or more proteins comprise CD274. In some embodiments, the four or more proteins comprise HGF. In some embodiments, the four or more proteins comprise TFF2. In some embodiments, the four or more proteins comprise PAPP-A2. In some embodiments, the kit further comprises instructions for carrying out an immunoassay. In some embodiments, the kit is an enzyme-linked immunosorbent assay kit. In some embodiments, one or more of the probes are attached to substrate. In some embodiments, kit is for a lateral flow immunoassay.

In some aspects, the present disclosure provides for a system for ruling out preeclampsia in a pregnant female subject for a specified period of time, the system comprising: a processor; an input module for inputting levels of at least four proteins in a biological sample, wherein the at least four proteins are selected from Tables A and B; a computer readable medium containing instructions that, when executed by the processor, perform a first algorithm on the input levels of the at least four proteins; and an output module providing one or more indicia based on the input levels of the at least four proteins, wherein the one or more indicia are indicative of the subject not having preeclampsia for at least a specified period of time. In some embodiments, the system further comprises probes to each the at least four proteins. In some embodiments, the system is designed to output the one or more indicia based on input levels for no more than 15, no more than 10, no more than 8, no more than 7, nor more than 6, no more than 5, or no more than 4 proteins. In some embodiments, the at least four proteins comprise: (a) placental growth factor (PIGF); (b) one or more angiogenesis-associated proteins selected from the group consisting of soluble fms-like tyrosine kinase 1 (sFlt1), endoglin, pappalysin 2 (PAPP-A2), and decorin; and (c) one or more kidney damage associated-proteins selected from the group consisting of (1) kidney injury molecule-1 (KIM1), (2) programmed cell death 1 ligand 1 (CD274), and decorin. In some embodiments, the at least four proteins comprise one or more proteins selected from the group consisting of C-type lectin domain family 4 member A (CLEC4A), fibroblast growth factor 21 (FGF21), trefoil factor 2 (TFF2), and hepatocyte growth factor (HGF). In some embodiments, the at least four proteins comprise PlGF, sFlt1, KIM1, and CLEC4A. In some embodiments, the at least four proteins comprise FGF21. In some embodiments, the at least four proteins comprise decorin. In some embodiments, the at least four proteins comprise CD274. In some embodiments, the at least four proteins comprise HGF. In some embodiments, the at least four proteins comprise TFF2. In some embodiments, the at least four proteins comprise PAPP-A2. In some embodiments, the algorithm comprises a correction based on gestational age. In some embodiments, the algorithm comprises a logistic regression.

In one aspect, the disclosure provides for a method for assessing a risk of a female subject having or developing preeclampsia within a specified time period, the method comprising: (a) obtaining a sample from a pregnant female subject; (b) measuring the levels of a plurality of proteins from the sample derived from a pregnant female subject, wherein at least two of the plurality of proteins is selected from the group ("Group 2") consisting of Tables 2, 3, 4, and 5; (c) calculating an index based, at least in part, on the levels of the plurality of proteins; and (d) determining a risk of having or developing preeclampsia in the female subject based on the index; wherein the specified period of time is at least one week. In some embodiments, the sample is a urine, blood, amniotic fluid, cervical-vaginal, exosome, plasma, or serum sample. In some embodiments, the sample is a blood sample. In some embodiments, the sample is a serum sample. In some embodiments, the sample is a plasma sample. In some embodiments, measuring the levels of a plurality of proteins from the sample comprises contacting the proteins with a plurality of probes specific for each protein. In some embodiments, the probes may comprise antibodies. In some embodiments, at least two of the plurality of proteins are selected from Group 2. In some embodiments, at least three of the plurality of proteins are selected from Group 2. In some embodiments, at least four of the plurality of proteins are selected from Group 2. In some embodiments, at least five of the plurality of proteins are selected from Group 2. In some embodiments, at least six of the plurality of proteins are selected from Group 2. In some embodiments, at least seven of the plurality of proteins are selected from Group 2. In some embodiments, levels are measured for no more than ten proteins. In some embodiments, levels are measured for no more than nine proteins. In some embodiments, levels are measured for no more than eight proteins. In some embodiments, levels are measured for no more than seven proteins. In some embodiments, levels are measured for no more than six proteins. In some embodiments, levels are measured for no more than five proteins. In some embodiments, levels are measured for no more than four proteins. In some embodiments, levels are measured for no more than three proteins. In some embodiments, the sample was obtained from the subject after the subject has shown one or more symptoms of preeclampsia, wherein the symptoms of preeclampsia are selected from (1) high blood pressure and (2) proteinuria. In some embodiments, the sample was obtained from the subject after the subject has shown both (1) high blood pressure and (2) proteinuria. In some embodiments, the sample is obtained from the subject after week 20 of the pregnancy. In some embodiments, determining the risk of preeclampsia in the female subject comprises comparing the index to a threshold value. In some embodiments, a predefined relationship between the index and the threshold value is indicative, with a negative predictive value of at least 80%, at least 85%, at least 90%, at least 91%, at least 92%, at least 93%, at least 94%, at least 95%, at least 96%, at least 97%, at least 97.5%, at least 98%, at least 98.5%, or at least 99%, of the subject not having or developing preeclampsia when used on an unbiased population of pregnant women that have both high blood pressure and proteinuria. In some embodiments, a predefined relationship between the index and the threshold value is indicative, with a negative predictive value of at least 90%, of the subject not having or developing preeclampsia. In some embodiments, the negative predictive value is higher than any negative predictive value of any test that measures only one or more of sFLT-1, PlGF, endoglin, and PAPP-A. In some embodiments, the plurality of proteins comprises soluble fms-like tyrosine kinase-1 ("sFLT-1"), and the index is calculated, in part, based on the level of sFLT-1 in the sample. In some embodiments, the plurality of proteins comprises placental growth factor ("PlGF"), and the index is calculated, in part, based on the level of PlGF in the sample. In some embodiments, the index is calculated, at least in part, based on the levels of both sFLT-1 and PlGF. In some embodiments, the plurality of proteins comprises pregnancy-associated plasma protein A (PAPP-A), and the index is calculated, in part, based on the levels of PAPP-A in the sample. In some embodiments, the index is calculated based on the levels of no protein some than the proteins of Group 1, sFLT-1, PlGF, endoglin, and PAPP-A. In some embodiments, the levels of the plurality of proteins are determined via an immunoassay. In some embodiments, the levels of the at least two proteins are determined by one or more enzyme-linked immunosorbent assays. In some embodiments, the levels of the at least two proteins are determined by one or more luminescent oxygen channeling immunoassays (LOCI). In some embodiments, the levels of the at least two proteins are determined by one or more of mass spectrometry, ELISPOT, nanoparticles, or radioimmunoassays. In some embodiments, the sample is obtained from the subject in a perinatologist's office, a labor and delivery room, or triage (ER).

In a further aspect, the disclosure provides for a method for assessing whether or not a pregnant female subject currently has or will develop (or will not develop) preeclampsia within a specified period of time, the method comprising: performing a binary classification test on a first sample derived from a pregnant female subject who has both high blood pressure and proteinuria, wherein the test comprises measuring the levels of one or more proteins in the first sample, wherein the one or more proteins are selected from the group consisting of Tables 2, 3, 4, and 5; wherein the specified time period is between one week and six weeks; and wherein the test has a negative predictive value of greater than 90% when used on an unbiased population of pregnant women that have both high blood pressure and proteinuria. In some embodiments, the binary classification test is a computer implemented two-way classification algorithm. In some embodiments, the binary classification test is a decision tree, random forest, Bayesian network, support vector machine, neural network, linear discriminant analysis (LDA), gradient boosting method (GBM), elastic-net logistic regression, or logistic regression test. In some embodiments, the method further comprises obtaining a sample from the subject. In some embodiments, the sample is a urine, blood, amniotic fluid, exosome, plasma, or serum sample. In some embodiments, the sample is a serum sample. In some embodiments, the sample is a plasma sample. In some embodiments, the binary classification test has a positive predictive power of at least 85% when used on an unbiased population of pregnant women that have both high blood pressure and proteinuria. In some embodiments, the binary classification test has a negative predictive value that is greater than its positive predictive value. In some embodiments, the binary classification test has a specificity of at least 85%. In some embodiments, the binary classification test has a sensitivity of at least 85%. In some embodiments, the specified time period is between 10 days and three weeks.

In another aspect, the disclosure provides for a method of classifying a pregnant human subject as having a low risk of having or developing preeclampsia within a specified time period, the method comprising: (a) obtaining a sample from a pregnant human subject who has been identified as having high blood pressure or proteinuria; (b) running a test to obtain a protein expression profile, wherein the protein expression profile includes levels of two or more proteins from Tables 2, 3, 4, and 5; (c) applying a classifier algorithm to the expression profile, wherein the classifier algorithm calculates an index; and comparing the index to a reference value to determine whether the pregnant human subject has a low risk of having or developing preeclampsia.

In another aspect, the disclosure provides for a method of treatment comprising: (a) classifying a pregnant subject as having a low risk of having or developing preeclampsia according to any method described herein; and (b) changing a therapeutic regimen for the subject based on the classification. In some embodiments, the method further comprises administering an antihypertensive drug to the patient if the test indicates that the pregnant female subject will not develop preeclampsia within the specified time period. In some embodiments, the antihypertensive drug is a central alpha agonist, a vasodilator, a calcium-channel blocker, an alpha-blocker or a beta-blocker. In some embodiments, the antihypertensive drug is methyldopa, labetalol, nifedipine, verapamil, clonidine, hydralazine, diazoxide, prazosin, or oxprenolol.

In yet another aspect, the disclosure provides for a kit for confirming the presence or absence of preeclampsia in a female subject, the kit comprising. (a) reagents for detecting one or more protein selected from the group consisting of Tables 2, 3, 4, and 5; and optionally (b) reagents for detecting PlGF and/or sFLT-1, wherein the kit is designed to measure the levels of not more than 10 proteins. In some embodiments, the kit further comprises reagents for measuring the levels of PAPP-A. In some embodiments, the kit is an enzyme-linked immunosorbent assay kit.

In another aspect, the disclosure provides for a system for assessing the likelihood that a pregnant subject has or will develop preeclampsia within a specified period of time, the system comprising: (a) a first agent that selectively binds to the one or more proteins in a sample from a pregnant subject, wherein the one or more proteins are selected from the group consisting of Group 2; (b) optionally a second agent that selectively binds to placental growth factor (PlGF); (c) optionally a third agent that selectively bind to soluble fms-like tyrosine kinase 1 (sFlt-1); (d) an input module for inputting levels of optionally PlGF, optionally sFlt-1, and the one or more proteins from the group consisting of Tables 2, 3, 4, and 5; (d) a processor; (e) a computer readable medium containing instructions which, when executed by the processor, performs a first algorithm on the input levels of optionally PlGF, optionally sFlt-1 and the one or more protein from Group 2; (f) an output module providing one or more indicia based on the input levels of optionally PlGF, optionally sFlt-1 and the one or more proteins from Group 2, wherein the one or more indicia represent the presence or absence of preeclampsia in the pregnant subject. In one embodiment, the first and second agents do not bind to the same protein. In another embodiment, the system is designed to output the one or more indicia based on input levels for no more than ten proteins.

In another aspect, the disclosure provides for a computer-implemented method of assessing the likelihood a pregnant subject has or will develop preeclampsia within a specified period of time, comprising: (a) receiving, at a computer, expression level data derived from a plasma or serum sample from the pregnant subject; (b) applying, by the computer, a classifier algorithm to the expression level data derived from the plasma or serum sample from the pregnant subject using a classification rule or a class probability equation; and (c) using, by the computer, the classification rule or class probability equation to output a classification for the sample, wherein the classification classifies the sample as a having a probability of having preeclampsia with a negative predictive value of greater than 80 percent, wherein the pregnant subject has hypertension or proteinuria. In some embodiments, the expression level data comprises levels of proteins selected from the group consisting of Tables 2, 3, 4, and 5. In some embodiments, the classifier algorithm is logistic regression. In some embodiments, the classifier algorithm is a decision tree, random forest, Bayesian network, support vector machine, neural network, or logistic regression algorithm.

EXAMPLES

Examples 1-7 describe an initial, smaller study design to identify markers that can be used to rule out the need for treatment of preeclampsia. Examples 8-16 describe follow-on, larger studies that provided additional information regarding the discriminatory of biomarkers and combinations of biomarkers in the context of assessing risks associated with, for example, women with one or more symptoms of preeclampsia.

Example 1—Initial Preliminary Study Design

Samples of serum and urine for biomarker analysis were obtained from a Progenity Multicenter specimen procurement study, which was designed to, inter alia, identify biomarkers that improve the detection or ruling out of preeclampsia with improved performance relative to the sFlt/PlGF ratio method described by Zeisler et al. (NEJM 274(2017):13-22). More particularly, pregnant women who were 18 years or older (20 weeks to 39 weeks of gestation at first visit) with suspected preeclampsia (based on new onset symptoms, elevated blood pressure, proteinuria, edema or others) were selected for participation. Baseline procedures were performed, including collection of demographic, medical and obstetric histories, list of concomitant medications, weight, height, blood pressure, and other clinical information, as well as obtaining blood and urine samples for use in biomarker assays. After discharge, all patients in the study were followed by interim research visits every 14 days (+/−3 days). For patients who developed PreE, the time (in days) from baseline sampling, the gestational age at diagnosis, and the severity of the disease was recorded. Patients who did not develop preeclampsia before or at delivery were included in the NEGATIVE-PRE-E CONTROL (NonPreE) group. For these NEGATIVE PRE-E CONTROLS, the time from baseline sampling (in days) to either delivery or loss to follow-up was recorded.

The interim study visits occurred every 14 days [+/−3 days] and continued until the subject either: 1) reached 37 weeks' gestation, 2) developed PreE, 3) delivered, or 4) was lost to follow-up.

Delivery outcomes (maternal and neonatal clinical information) were collected on all subjects enrolled in the study. Additionally, if possible during admission for delivery, blood and urine samples were collected for analysis at delivery.

The discovery set of samples for further analysis consisted of a total of 70 samples that were separated into non-preeclampsia or preeclampsia based on whether they delivered pre-37 weeks gestation: 40 non-preeclampsia (NonPreE) and 30 with preeclampsia (PreE). The 70 samples were grouped into four further subcohorts based on preeclampsia status and whether or not sFlt/PlGF ratio was predictive: (A) control patients who delivered at term and were not diagnosed with preeclampsia. (true negatives and false positives, n=20); (B) patients clinically diagnosed with preeclampsia with sFlt/PlGF ratio of 38 or higher (true positives, n=20); (C) patients clinically diagnosed with preeclampsia with sFlt/PlGF ratio of less than 38 (false negatives, n=10); and (D) patients who delivered at term and were not diagnosed with preeclampsia with sFlt/PlGF ratio of 38 or higher (false positives, n=20).

A comparison of the subcohort statistics for the current study is provided in Table 1. As in the Zeisler study, a high degree of false classification based on the sFt1/PGF ratio criterion was observed: a significant proportion of the patients identified by the ratio as having preeclampsia are false positives, and a significant proportion of the patients who actually developed preeclampsia were not detected by the ratio (false negatives).

of protein per 24-hour urine collection, ≥30 mg of protein per deciliter in a spot urine sample, or a ratio of protein to creatinine of ≥30 mg per millimole). sFlt/PlGF criteria for suspected preeclampsia were an sFlt/PlGF ratio greater than or equal to 38. For the purposes of analysis, patients diagnosed with suspected preeclampsia who delivered preterm were classified as actual preeclampsia (true positive). For the purposes of analysis, patients diagnosed with suspected preeclampsia who did not deliver preterm were classified as complicated pregnancy (false positive).

Exclusion criteria for patients from the study included male, not pregnant, age less than 18 or greater than 45 years, pregnancy with multiple gestation, pregnancy with gestational age less than 20 or greater than 39 weeks, or pregnancy with known fetal abnormalities.

Example 2—Quantification of Protein Biomarkers

Serum samples collected according to a standard procedure from 68 patients (one non-preeclampsia and one preeclampsia sample failed quality control checks) were analyzed retrospectively. Briefly, filled red top blood collection tubes were allowed to clot at room temperature for 30-60 minutes, were centrifuged 20 minutes at 1300 g to remove the clot, and were then aliquoted for long term storage below −80° C. Hemolysis, date and time of blood collection, and date and time of freezing were recorded. Both single analyte analysis of suspected biomarkers (of Fibronectin, PlGF, sFlt1, and PAPP-A) and unbiased panel analyses of proteins associated with inflammation, immune response, oncology, organ damage, immunooncology, and metabolism (containing 92 biomarkers in each panel) were performed. PlGF was repre-

TABLE 1

Sub-cohort statistics for this study and comparison to Zeisler et al.

| Cohort | Description | N (Zeisler study) | N (current study) | sFlt1/PlGF predictive status | Prevalence (current study) | Prevalence (Zeisler study) | Avg sFlt/PlGF (current study) |
|---|---|---|---|---|---|---|---|
| A | Control - Complicated Pregnancy diagnosis, No PREECLAMPSIA Delivered 37 weeks or later | 253 | 20 | True Negatives or False Positives | 28.50% | 77% | 33 (0.5-150) |
| B | True Positives - PREECLAMPSIA Delivered before 37 weeks (sFlt/PlGF >/= 38) | 21 | 20 | True Positives | 28.50% | 6.40% | 337 (66-1123) |
| C | False Negatives - PREECLAMPSIA Delivered before 37 weeks (sFlt/PlGF < 38) | 10 | 10 | False Negatives | 14.30% | 3% | 15 (3-33) |
| D | False Positives - Complicated Pregnancy, No PREECLAMPSIA Delivered 37 weeks or later, (sFlt/PlGF >/= 38) | 43 | 20 | False Positives | 28.50% | 13.10% | 112 (66-1123) |

Diagnostic Criteria

Patients were diagnosed with suspected preeclampsia based on new onset of hypertension (sSBP>140 mmHg or sDBP>90 mmHg or both) with accompanying proteinuria (defined with the cutoffs of 2+ protein by dipstick, ≥300 mg sented in both single analyte analysis and the unbiased panel analysis, whereas sFlt1, PAPP-A, and Fibronectin were not.

Single Candidate Analyte Analysis sFlt1, PAPP-A, PlGF, and Fibronectin single analytes were measured by a biotin/fluorescein-based AlphaScreen™ assay. Antibodies labeled with biotin and fluorescein was prepared fresh each time by combining 2.5 Antibody mix with 125 µl dilution buffer and placing the mixture on ice. This proximity mix was placed in a single well of a standard white 96 well plate (Biorad, Hemel Hempstead, UK) followed by 2 µl of target antigen or sample, which was appropriately diluted with 1× serum dilution buffer (SDB II, 4483013, Life Technologies) if needed. No protein controls (NPC) consisted of 2 µl of proximity mix and 2 µl of 1×SDB II. The plate was sealed using an optically clear heat seal with a PX1 PCR plate sealer (Biorad, Hemel Hempstead, UK), centrifuged at 780 g for 2 min (Rotina 380R Hettich Zentrifuge, Germany) and incubated for 1 h at 20° C. Following removal of the seal, 16 µl of anti-fluorescein acceptor beads (10 µgs) and St/.AV sensitizer beads (2 µgs) (Perkin Elmer) was added to each well, the plate was sealed again, spun as before and the incubation was performed at 37° C. for 60 min. The assay was read on a standard ALPHA screen reader.

Unbiased Multiplex Analyte Analysis

For unbiased discovery of biomarkers, proximity extension assays were used. A pair of oligonucleotide-conjugated antibodies specific to each panel protein was added to 1 µL of serum. Antibody-protein antibody sandwiches were detected by the hybridization of the nucleotide pairs in close proximity, followed by an extension reaction to generate a unique sequence product. These sequences were then quantitated by microfluidic qPCR. A total of 552 distinct marker levels including markers implicated in inflammation, immune response, oncology, organ damage, immuno-oncology, and metabolism were measured in this assay.

Figure 1B:
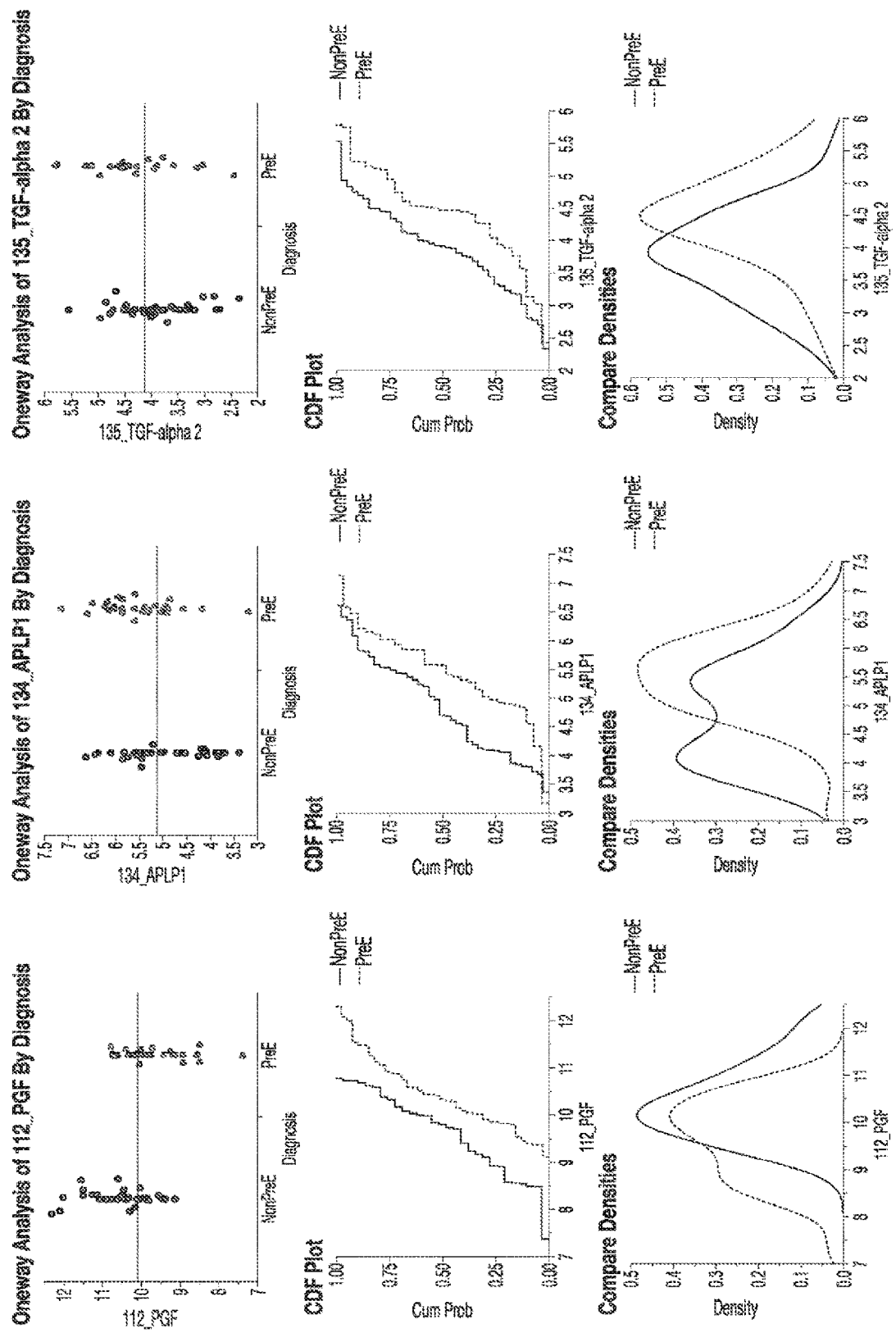
FIG. 1B provides illustrations of data spread for markers for distinguishing between preeclampsia and non-preeclampsia.

Example 3—Single Protein Screening for Distinguishing Nonpreeclampsia from Preeclampsia A response screening of non-preeclampsia vs preeclampsia using ANOVA for each of the 552 markers was performed, defining a FDR Log Worth >2 as significance. A plot of FDR Log Worth vs Effect Size (FIG. 1A) was generated to analyze the value of single biomarkers for distinguishing Nonpreeclampsia vs PreE. Three biomarkers (CLEC4A, SYND1, and PIGF) meet the FDR Log Worth criteria for significance (>2), while 6 additional biomarkers (PGF, FES, TGF-alpha 2, APLP1, KIM1, and NOS32) show an FDR Log Worth more significant than most of the biomarkers. A summary of these top distinguishing markers is provided in Table 2; while visual representations of the data spread for each of the top 3 biomarkers for non-preeclampsia vs preeclampsia is shown in FIG. 1B.

TABLE 2

Top Nine Biomarkers from Nonpreeclampsia vs Preeclampsia Response Screening

| Marker | PValue | FDR PValue | FDR LogWorth |
|---|---|---|---|
| CLEC4A | <.0001 | 0.0040 | 2.40 |
| SYND1 | <.0001 | 0.0040 | 2.40 |
| PlGF | <.0001 | 0.0040 | 2.40 |
| PGF | <.0001 | 0.0123 | 1.91 |
| APLP1 | 0.0028 | 0.1948 | 0.71 |
| TGF-alpha 2 | 0.0025 | 0.1948 | 0.71 |
| FES | 0.0018 | 0.1948 | 0.71 |
| KIM1 | 0.0028 | 0.1948 | 0.71 |
| NOS3 2 | 0.0034 | 0.2084 | 0.68 |

Example 4—Subcohort Analysis of Nine Biomarkers from Example 3

Figure 2:
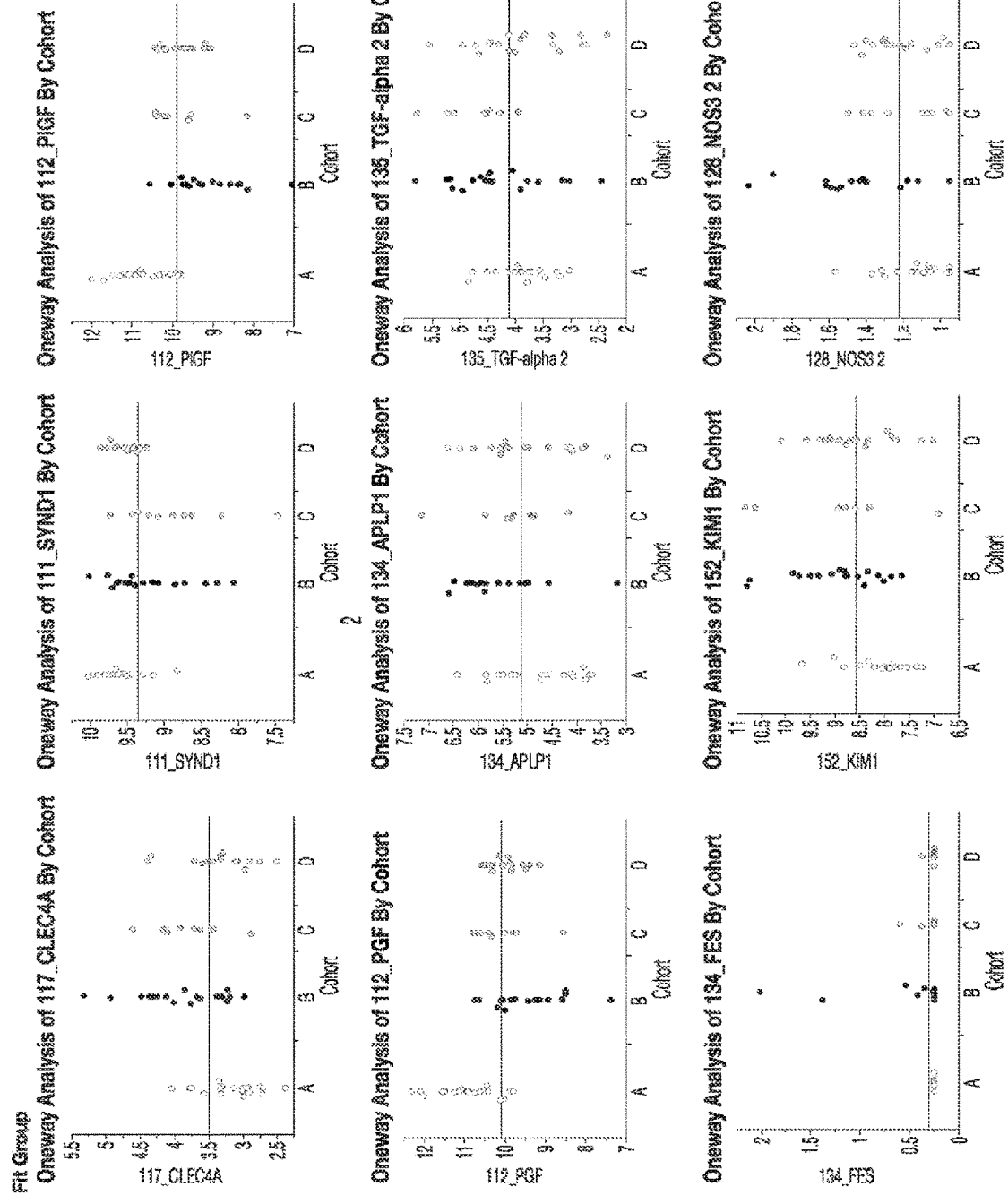
FIG. 2 shows scatter plots of the top nine biomarkers identified in Example 3 split into 4 subcohorts based on the predictive utility of the sFlt1/PlGF ratio for the subcohort (A=nonPreE/true negatives, B=PreE/true positive, C=PreE/false negative, D=nonPreE/false positive).

The expression levels of each of the top nine biomarkers identified in Example 3 were further analyzed with respect to their expression levels in each subcohort identified in Example 1 (A=nonPreE/true negatives, B=PreE/true positive, C=PreE/false negative, D=nonPreE/false positive). The results are graphically presented in FIG. 2. Consistent with the high false positive/negative rate of the sFlt1/PIGF ratio assay, PIGF (FIG. 2, top right panel) shows poor discrimination power for the C and D groups, even though it distinguishes A from B. However, other biomarkers (CLEC4A, FIG. 2, top left and SYND1, FIG. 2, middle), show the capability to distinguish between A and B cohorts as well as C and D cohorts.

Example 5—Random Bootstrap Forest Identification of Predictive Biomarkers

As an alternative to the method of Example 3 random bootstrap forest predictor screening was run on the expression level data from the 552 unbiased biomarkers assessed in multiplex screening. The top 20 predictors discovered by this method ranked by contribution are shown in Table 3.

TABLE 3

Top 20 Nonpreeclampsia vs Preeclampsia Predictors Resulting from Random Bootstrap Forest Analysis

| Predictor | Contribution | Portion | Rank |
|---|---|---|---|
| SYND1 | 4.03 | 0.1013 | 1 |
| UPA | 1.63 | 0.0410 | 2 |
| AMN | 1.24 | 0.0313 | 3 |
| ZBTB16 | 1.24 | 0.0312 | 4 |
| PGF | 1.15 | 0.0290 | 5 |
| TGFalpha2 | 1.10 | 0.0278 | 6 |
| PlGF | 1.09 | 0.0275 | 7 |
| NOS3_2 | 1.08 | 0.0271 | 8 |
| ERBB4 | 1.01 | 0.0254 | 9 |
| HGF2 | 0.71 | 0.0179 | 10 |
| CXCL6 | 0.66 | 0.0167 | 11 |
| ALDH3A1 | 0.65 | 0.0165 | 12 |
| GDNF | 0.64 | 0.0163 | 13 |
| GLB1 | 0.63 | 0.0159 | 14 |
| CALCA | 0.57 | 0.0145 | 15 |
| CCL20 | 0.56 | 0.0141 | 16 |
| CD70 | 0.55 | 0.0140 | 17 |
| CLEC4A | 0.52 | 0.0132 | 18 |
| CAPG | 0.52 | 0.0131 | 19 |
| APLP1 | 0.51 | 0.0129 | 20 |

Example 6—Four-Cohort Analysis of Single Candidate Analytes

Figure 3:
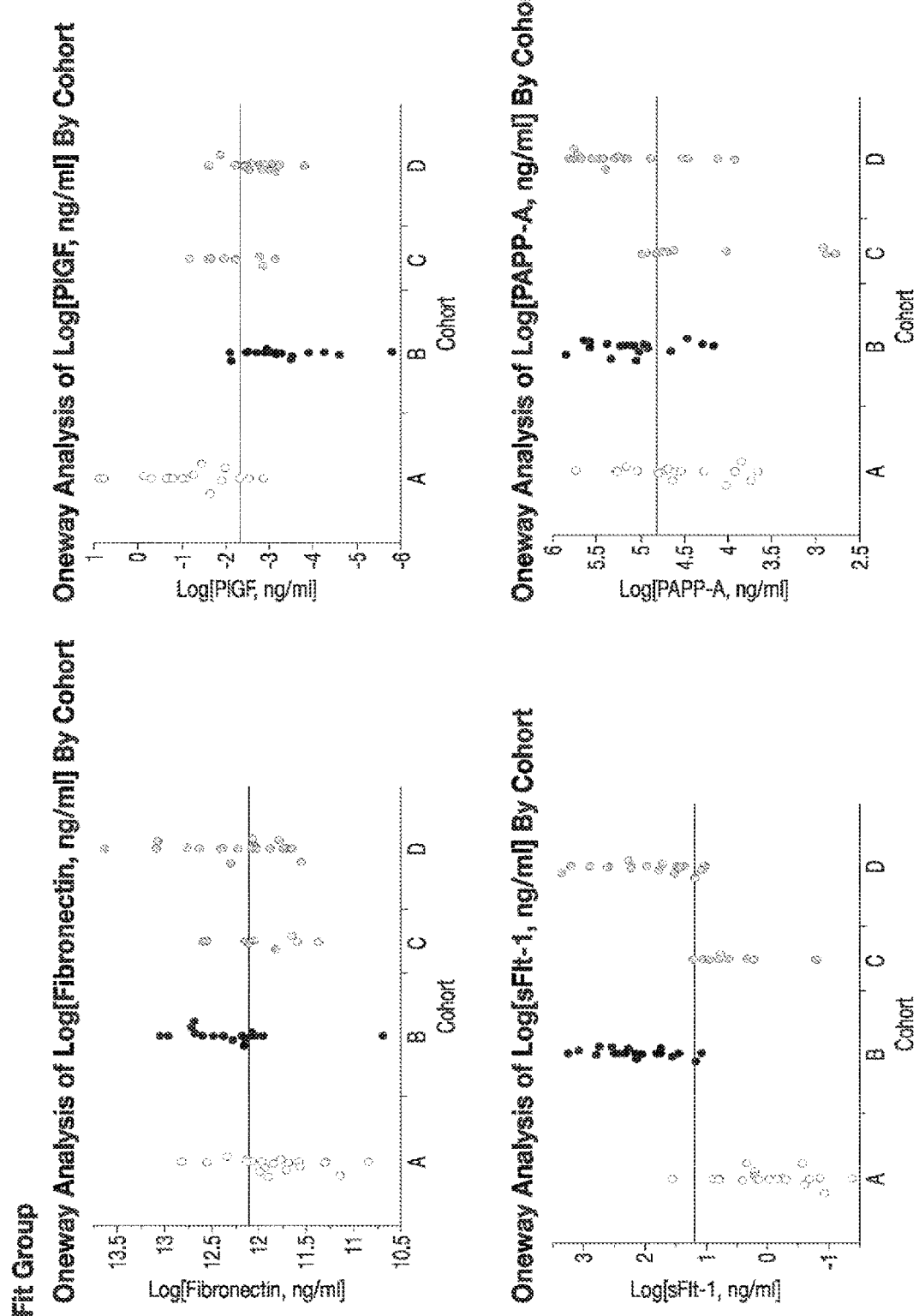
FIG. 3 shows a four-subcohort analysis that is similar to the four-subcohort analysis of FIG. 2 for the literature-identified candidate analytes Fibronectin, sFlt1, PlGF, and PAPP-A.

Candidate analytes identified in previous work: sFlt1, PIGF (e.g., Zeisler et al. NEJM 274(2017):13-22), PAPP-A (see, e.g., Spencer et al. Prenat Diagn. 28(2008):7-10), and Fibronectin (see, e.g., Taylor et al. Am J Obstet Gynecol. 165(1991):895-901) were measured and analyzed by the four-cohort analysis as above. Scatter plots of the analysis are shown in FIG. 3. While all show ability to discriminate non-preeclampsia vs preeclampsia (A vs B), all show cohort confusion as the pairs of A and C, B and D are more similar (when the ideal relationship should be A-B, C-D).

Example 7—Development of Multi-Predictor Models for Preeclampsia

Random bootstrap forest predictor screening (10 rounds) was applied to the 552 biomarkers expression levels analyzed in the multiplex analysis combined with the four candidate biomarker expression levels into a single comprehensive data set (556 markers). The top 50 markers resulting from this analysis are displayed in Table 3 by median rank, where the top row represents the top 10 markers; the second row represents the second 10 markers, and so on.

TABLE 4

Top 50 Markers from Random Bootstrap Predictor Screening of 556 Markers by Median Rank

| | | | | |
|---|---|---|---|---|
| 111_SYND1 | 117_CLEC4A | 155_ERBB4 | 112_uPA | 111_AMN |
| 195_NT-proBNP | 135_TGF-alpha 2 | 170_DCN | 159_SOST | 148_ENTPD2 |
| 102_GLB1 | 156_HGF 2 | 192_WIF-1 | 128_S100A4 | Log[PlGF, ng/ml] |
| 162_IL-10 | 117_CXCL11 | 102_VEGF-A | 105_MCP-3 | 190_CCL20 |
| 107_CDCP1 | 103_BDNF | 115_MCP-1 | 122_CXCL9 | 113_IL-6 |
| 112_PlGF | 112_PGF | 128_NOS3 2 | 105_ZBTB16 | 144_FGF-21 |
| 125_CAPG | 134_APLP1 | 148_SEZ6L | 115_CLEC4C | Log[Fibronectin, ng/ml] |
| 189_CEACAM5 | 168_CXCL6 | 130_Gal-9 | 182_SIT1 | 156_HGF |
| 106_GDNF | Log[PAPP-A, ng/ml] | 101_IL-8 | Log[sFlt-1, ng/ml] | 108_CD244 |
| 116_IL-17A | 114_IL-17C | 109_IL-7 | 111_LAP TGF-beta-1 | 110_OPG |

To identify likely components of a logistic model in an unbiased fashion, the top 19 of these markers were then fit to a graded response (GR) model, followed by 250 bootstrap fits. This resulted in nine markers (CAPG, ZBTB16, SYND1, CLEC4C, TGF alpha 2, uPA, CLEC4A, PGF, and AMN) that had a p-value <1 (meaning they had non-zero coefficients in >50% of the 250 models built from bootstrapped samples). These markers are presented in Table 5.

TABLE 5

Top 9 Markers Resulting from Multivariate Analysis Using Graded Response Model

| | | |
|---|---|---|
| 125_CAPG | 105_ZBTB16 | 111_SYND1 |
| 115_CLEC4C | 135_TGF-alpha 2 | 112_uPA |
| 117_CLEC4A | 112_PGF | 111_AMN |

Figure 4:
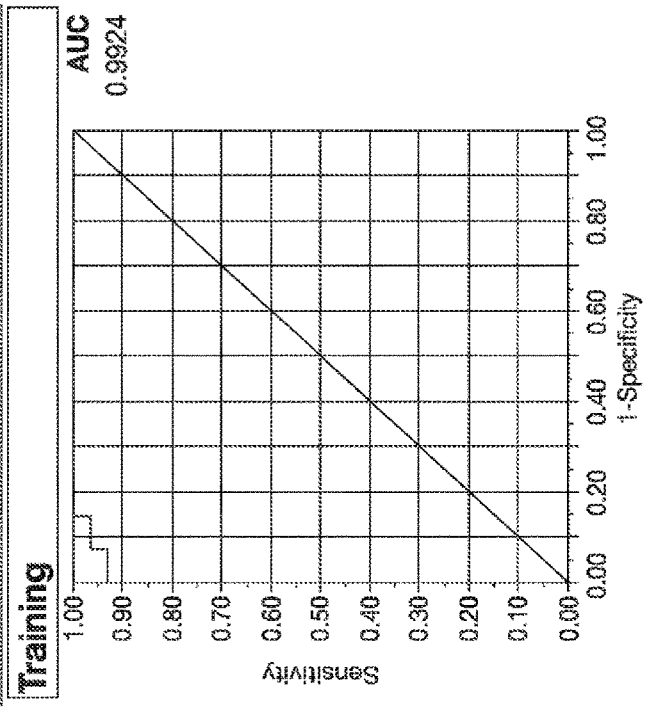
FIG. 4 shows a ROC curve and summary statistics for logistic regression model for non-preeclampsia vs preeclampsia built from the top nine predictors identified in a multivariate graded-response-based analysis in Example 7.

Summary statistics and a ROC curve for a logistic regression model built for distinguishing non-preeclampsia from preeclampsia using the nine predictors of Table 5 are presented in FIG. 4. When applied to the data generated in this study, the model had an AUC of 0.992. A preliminary estimate from the ROC curve of this data gives a specificity of approximately 90% for a specificity value of 95%.

Figure 5:
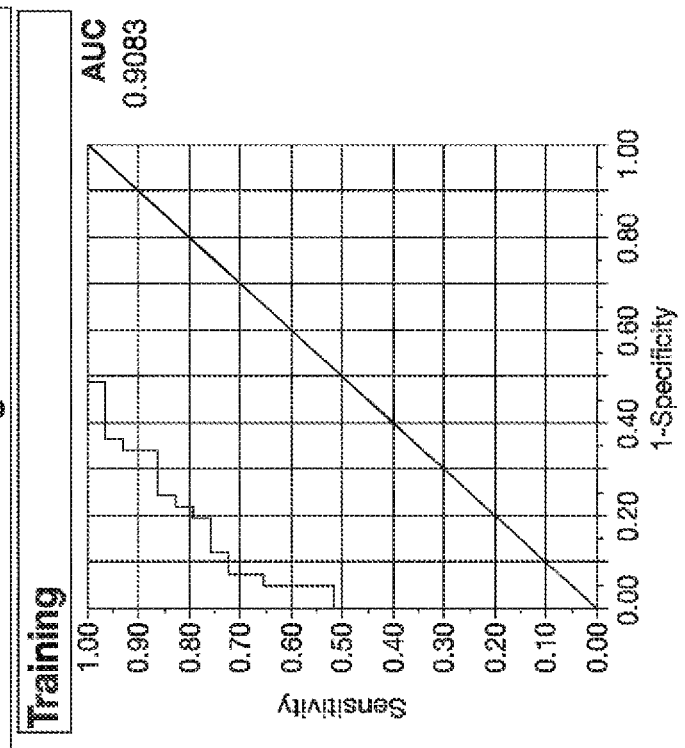
FIG. 5 shows a ROC curve and summary statistics for logistic regression model built in Example 7 for non-preeclampsia (nonPreE) vs preeclampsia (PreE) built from sFlt1 and PGF plus the top 2 predictors identified in Example 3.

For comparison, an additional logistic regression model was run using the two candidate markers (sFlt1, PlGF) from Zeisler et al., along with the addition of CLEC4A and SYND1 (the top 2 single markers identified in Example 3). Summary statistics and a ROC curve for a logistic regression model built for distinguishing non-preeclampsia from preeclampsia using these four markers are presented in FIG. 5. When applied to the data generated in this study, the model had an AUC of 0.908.

Example 8—Additional Biomarker Analysis

Additional single-plex analysis of additional candidate biomarkers CCL2, CD134, DCN, HGF, NOS3, PlGF, CD274, CDCP1, FGF-21, TGFa, UPA, CLEC4A, CLEC4C, ZBTB16, APLP1, DPP7, GRAP2, ITGB7, PAG1, TFF2, AMN, CAPG, CLEC1A5, FES, KIM1, PGF, ERBB4, GPNMB, PPY, and SYND1 was performed on the serum samples using an AlphaScreen™ assay as in Example 2, and the expression levels presented by subcohort as in Example 4. Scatter plots of the biomarker expression levels are presented in FIGS. 7-12.

Example 9—Expanded Study Design

An expanded study using the same inclusion/exclusion criteria as Example 1 was conducted to further identify and validate biomarkers for preeclampsia. An overview of the process used is set forth in the flow diagram of FIG. 17, which shows a method 100, in which the levels of biomarkers are determined 101, the resulting data undergoes a log transformation 102 and a Loess correction for gestational age 103. Then machine learning 104 is used to determine an algorithm suitable for identifying a subject who does not need to be treated for preeclampsia. A breakdown of the samples collected from patients is detailed in Table 6. After filtering (samples with duplication were removed) bona fide (−) and bona fide (+) samples collected from the study were further separated into training and test sets according to a 75/25 ratio, while preserving the ratio of (−) to (+) samples. Bona fide PreE positive (+) samples were from patients diagnosed clinically using 2013 ACOG criteria who delivered preterm (i.e. in less than 37 weeks gestational age), where the sample was collected after clinical diagnosis and before labor, and where the sample was collected within 2 weeks of preeclampsia diagnosis. Bona fide PreE negative (−) samples were from patients having at least one of the preeclampsia symptoms as defined by the ACOG 2013 guidelines who gave birth at full-term (i.e. delivery at 37 weeks gestational age or later), who had no clinical diagnostics of preeclampsia in the current pregnancy, and wherein the sample was collected before week 38 of gestational age.

TABLE 6

Breakdown of Patient Samples for Expanded Preeclampsia Study

| | Bonafide (+) for PreE | Bonafide (−) for PreE | PreE (delivered term) | PreE negative (delivered preterm) | Other | Excluded | Total |
|---|---|---|---|---|---|---|---|
| Study | 56 | 534 | 44 | 64 | 167 | 45 | 921 |
| Training | 41 | 400 | — | — | — | — | 441 |
| Test | 13 | 133 | — | — | — | — | 146 |

Bona fide PreE positive (+) samples were from patients diagnosed clinically using 2013 ACOG criteria who delivered preterm. Bona fide PreE negative (−) samples displayed at least 1 symptom according to the 2013 ACOG criteria but who delivered at term. Samples that did not fit into (+) or (−) categories were excluded from algorithm development and testing. Ethnicity/race information for this cohort is provided in Table 6A.

TABLE 6A

Breakdown of Ethnicity/Race for Expanded Preeclampsia Study

| | Non-preeclampsia | Preeclampsia | Total |
|---|---|---|---|
| Race | | | |
| AMERICAN INDIAN/ALASKA NATIVE | 1 | 1 | 2 |
| ASIAN | 3 | 0 | 3 |
| BLACK/AFRICAN AMERICAN | 242 | 21 | 263 |
| NATIVE HAWAIIAN/OTHER PACIFIC ISLANDER | 1 | 0 | 1 |
| WHITE | 276 | 24 | 300 |
| UNKNOWN | 17 | 0 | 17 |
| Total | 540 | 46 | 586 |
| Ethnicity | | | |
| HISPANIC OR LATINO | 12 | 2 | 14 |
| NOT HISPANIC OR LATINO | 295 | 39 | 334 |
| Unknown | 233 | 5 | 238 |
| Total | 540 | 46 | 586 |

Example 10: Development of Naïve Multivariate Models for Preeclampsia

A series of 16 markers (CLEC4A, HGF, PIGF, KIM1, FGF-21, FN, DCN, SYND1, CD-274, TFF-2, PAPP-A, ADAM-12, sFLT1, PAPP-A2, ENG, and UPA) was selected by hierarchical clustering of high-throughput protein expression on the bona fide (+) and (−) samples of Example 9 (wherein the bona fide criteria are the same as in Example 9). Following selection, assays for protein level of each analyte were developed and log (protein level) or ratios of log (protein level) with and without their bivariate interaction terms were used for these markers as features to build naïve multivariate models predicting preeclampsia. Starting from the set of log-transformed expression data in the "training" set described in Example 9, the models were built Random Forest using (RF), GBM (gradient boosting machine), and Electric Net Logistic Regression ("Enet LR") algorithms. The following procedure was used in connection with the full set of 16 expression markers:

1) Samples were randomly segregated into further "training" and "test" subsets at a 10:1 ratio;
2) Training sets were downsampled to balance classes,
3) 10-fold cross validation to optimize for sensitivity was performed;
4) Steps 2-3 were repeated 25×;
5) Steps 1-4 were repeated 40×, and
6) NPV, PPV, sensitivity, specificity, AUC, and AUP (area under the precision-recall curve) was reported for each algorithmic approach compared to a "baseline" model that just uses an sFlt1/PIGF expression ratio of 58 to detect preeclampsia. The features for each naïve algorithm and their contribution that resulted from this procedure are shown in Table 7, and the performance characteristics are presented in Table 8.

TABLE 7

Features of Naïve RF/GBM/EnetLR models

| RF log Baseline | | GBM log Baseline | | Enet_LR log Baseline | |
|---|---|---|---|---|---|
| f | score | f | score | f | score |
| PIGF | 296.7181 | PIGF | 738.0964 | (Intercept) | 69.7385 |
| SFLT.1 | 129.3988 | SFLT.1 | 226.7236 | FGF21 | 45.17518 |
| PIGF:SFLT.1 | 100.9284 | FGF21 | 202.6028 | CLEC4A | 36.41802 |
| FGF21 | 53.55566 | PAPP.A2 | 116.983 | SFLT.1 | 22.44577 |
| ENDOGLIN:PIGF | 53.2343 | PIGF:SFLT.1 | 94.02904 | KIM1:TFF2 | 21.95812 |
| PAPP.A2 | 40.6594 | KIM1 | 75.38029 | KIM1 | 20.85404 |
| PAPP.A2:PIGF | 39.38708 | ENDOGLIN:PIGF | 71.08517 | UPA:CLEC4A | 14.30922 |
| ENDOGLIN | 30.33046 | ENDOGLIN:PAPP.A | 66.06796 | TFF2:CLEC4A | 14.13368 |
| ENDOGLIN:SFLT.1 | 28.51433 | DECORIN | 61.41614 | PIGF | 13.17691 |
| KIM1 | 25.61497 | ENDOGLIN | 61.34832 | CD274:PAPP.A | 12.55998 |
| DECORIN | 23.96056 | UPA:CLEC4A | 61.05637 | PAPP.A2 | 12.20951 |
| ENDOGLIN:PAPP.A | 19.88032 | PAPP.A2:PIGF | 60.14436 | KIM1:SYND1 | 10.9187 |
| PAPP.A2:UPA | 14.54226 | CD274:SFLT.1 | 55.89387 | DECORIN | 10.79185 |
| KIM1:SYND1 | 14.35827 | HGF:PIGF | 55.10297 | CD274 | 10.5466 |
| CLEC4A | 14.07216 | FIBRONECTIN | 50.98952 | FGF21:TFF2 | 9.898555 |
| PAPP.A:PAPP.A2 | 13.34582 | ENDOGLIN:UPA | 34.46373 | SYND1 | 9.032184 |
| HGF:PIGF | 12.48165 | CD274:PIGF | 33.72928 | PIGF:SYND1 | 8.146656 |

TABLE 7-continued

Features of Naïve RF/GBM/EnetLR models

| RF log Baseline | | GBM log Baseline | | Enet_LR log Baseline | |
|---|---|---|---|---|---|
| f | score | f | score | f | score |
| UPA:CLEC4A | 12.32938 | CD274 | 29.81524 | UPA:SYND1 | 8.03418 |
| CD274:SFLT.1 | 11.19453 | PAPP.A:PAPP.A2 | 29.62774 | ADAM.12:FGF21 | 7.866035 |
| PAPP.A:SFLT.1 | 9.771549 | CD274:PAPP.A2 | 28.26661 | ADAM.12:CD274 | 7.849305 |

TABLE 8

Performance of Naïve RF/GBM/EnetLR Models Against Baseline sFLT1/PlGF Model and Improved Embodiments

| | NPV | PPV | Specificity | Sensitivity | AUP | AUC |
|---|---|---|---|---|---|---|
| RF (naïve) | 96.62% | 32.1% | 84.83% | 69.42% | 0.6001 | 0.8527 |
| GBM (naïve) | 96.89% | 28.4% | 81.79% | 72.88% | 0.5756 | 0.8555 |
| Enet LR (naïve) | 96.89% | 27.26% | 80.26% | 73.46% | 0.5167 | 0.8429 |
| sFlt1/PlGF | 97.32% | 17.7% | 64.80 | 81.52% | 0.6462 | 0.8553 |
| Stacked (Enet LR/RF) | 97.77% | 25.29% | 75.41% | 81.92% | 0.4993 | 0.8627 |
| Enet LR (KIM1/FGF21/CLEC4A features) | 95.88% | 17.46% | 67.33% | 70.19% | 28.02% | 76.58% |
| Stacked (Enet LR/RF) (KIM1/FGF21/CLEC4A features) | 98.28% | 17.70% | 64.80% | 88.65% | 39.22% | 84.23% |

The new models all showed improvements in specificity and PPV.

To improve false negative detection (NPV/sensitivity), algorithm optimization was first performed. The performance of each algorithm was examined in individual samples from the "false negative" category. 10/20 samples were classified as negative by RF/GBM/LR; 7/20 samples were classified as negative by GBM/LR; and only 2/20 samples were classified as negative by LR.

Figure 19:
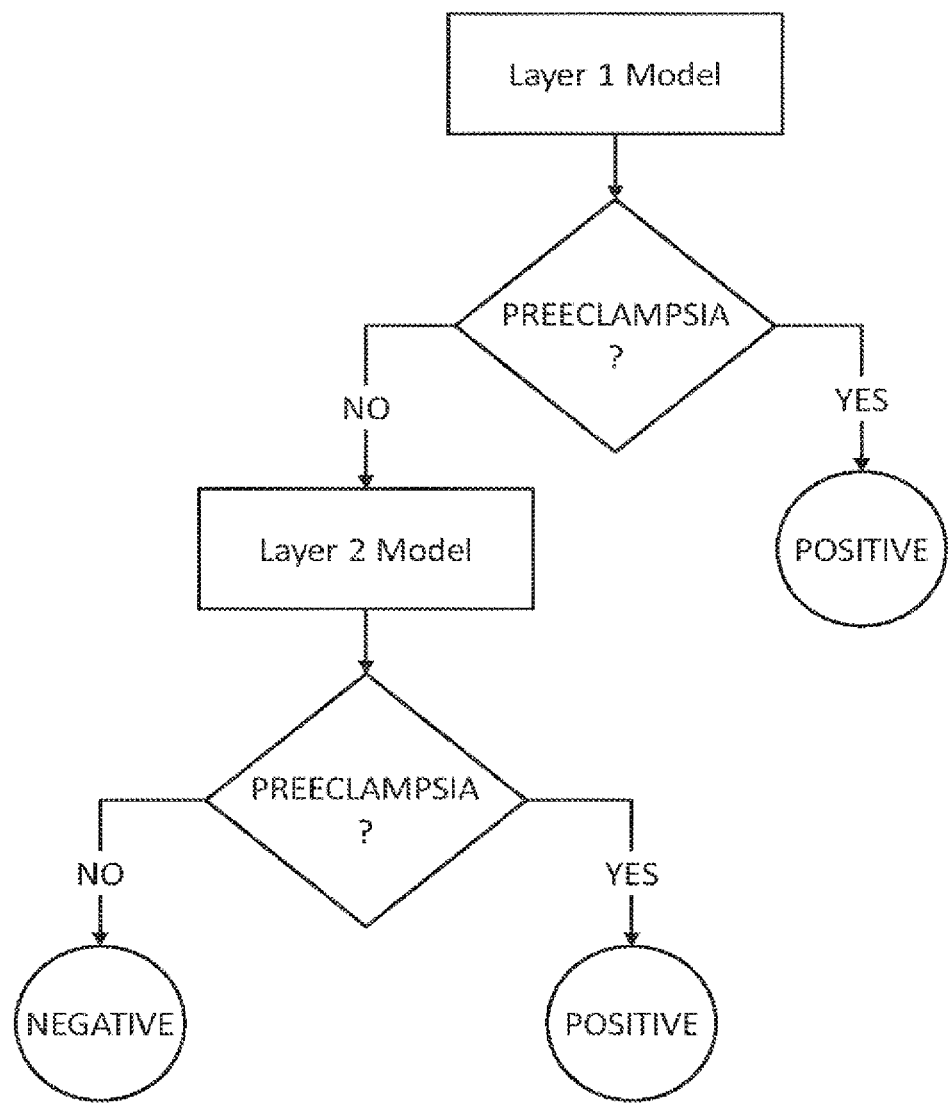
FIG. 19 provides a flow diagram for a "stacked" decision structure for ruling out preeclampsia.

Accordingly, a "stacked" structure involving a combination of Elastic net logistic regression and Random forest was investigated as a method to reduce false negatives. The performance of the stacked model is shown in Table 8. An exemplary description of a stacked model for use in diagnosing or ruling out preeclampsia is shown in FIG. 19. As hypothesized, the stacked model structure improved sensitivity, NPV, and AUC versus the individual models and the sFlt1/PlGF model.

To further improve optimization of the model performance characteristics, feature optimization was next performed.

I. Feature Selection Using Rational Selection and Clustering

Figure 20:
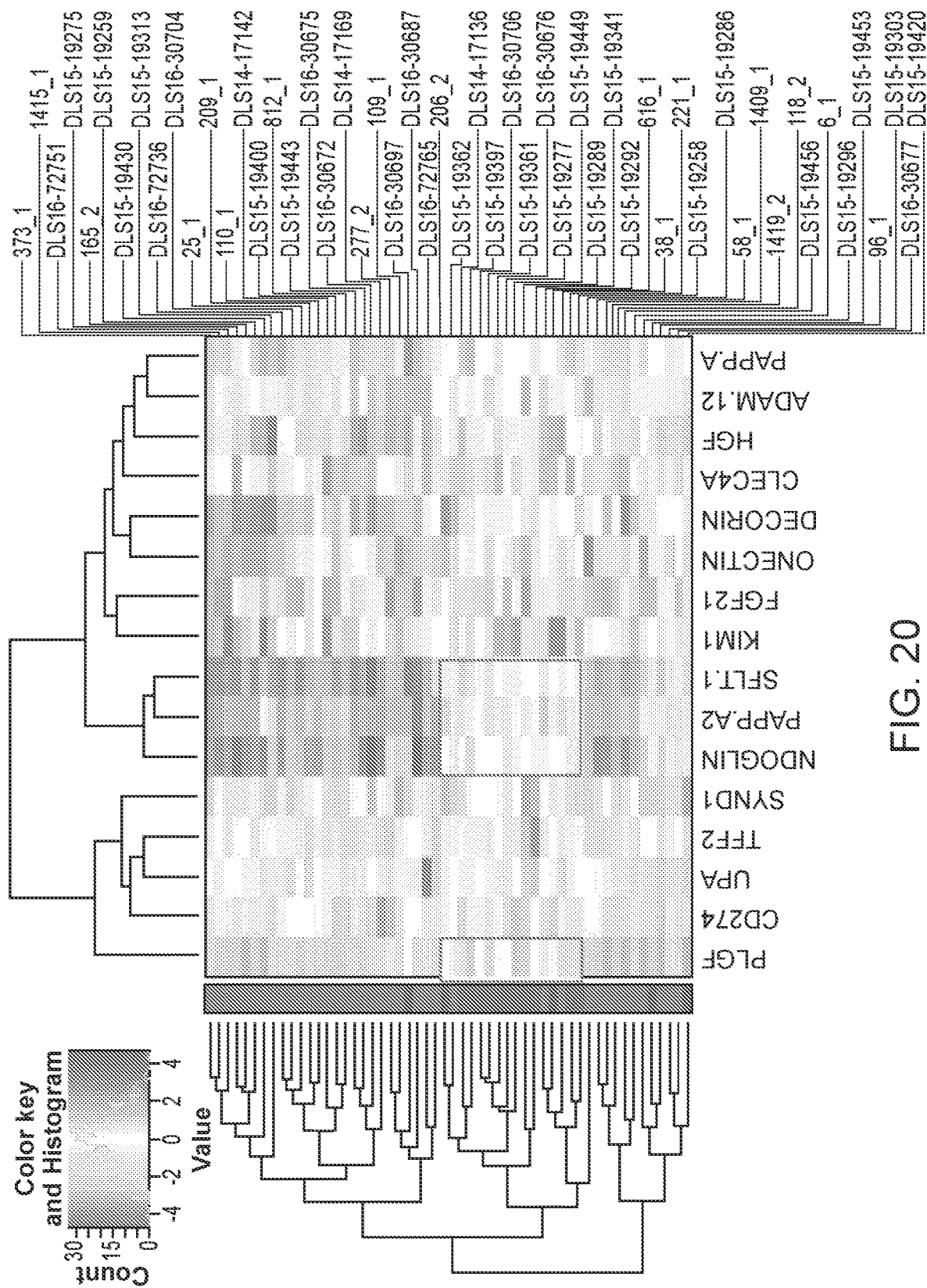
FIG. 20 is a figure showing, via color, the extent to which various markers reveal orthogonal information for ruling out preeclampsia.

The first applied approach sought to more rationally choose genes as features to improve detection. The fold upregulation/downregulation of each biomarker feature was analyzed graphically in the "false negative samples". This analysis is illustrated in FIG. 20. For these samples, PlGF, END, PAPP-A2, and sFlt1 all had low signal (in terms of changes of fold expression), suggesting that they are insufficient for the detection of a subset of preeclampsia samples. However, KIM-1, FGF-21, and CLEC4A had signal in both false negative and true negative samples, suggesting they may broadly improve detection of all subsets of preeclampsia samples. Accordingly, both a regular Enet and "stacked" RF/Enet model was constructed using just KIM-1, FGF-21, and CLEC4A as features (see Table 8). This model had marked improvements in NPV and some improvement in sensitivity versus the sFlt1/PlGF baseline model, confirming that models using KIM-1, FGF-21, and CLEC4A improve sensitivity of detection of preeclampsia.

II. Feature Selection Using Principal Component Analysis

The second applied approach examined principal components (from a PCA performed on the expression data) as features, and examined the signal of each principal component in the bona fide positive samples (wherein the bona fide criteria are the same as in Example 9). This analysis showed that the first 4 principal components (PC1, PC2, PC4, and PC9) explain 61.5% of the variance; and that PC4 in particular showed signal in the false negative samples PC1 and PC2 did not. Most of this signal appeared to originate from CLEC4A, HGF, FGF21, KIM1, and TFF2, which are contributors to PC4. Based on the assumption the four principal components form a minimal set for classification, models was generated using the top four principal components using the same algorithms used above. The performance of models built using these algorithms is presented in Table 9. The stacked model using the top four principal components as features showed improved characteristics versus the sFlt1/PlGF model in NPV, PPV, specificity, sensitivity, and AUC.

TABLE 9

Performance of models using principal components as features

| | NPV | PPV | Specificity | Sensitivity | AUP | AUC |
|---|---|---|---|---|---|---|
| RF (top 4 PC) | 97.81% | 29.57% | 80.66% | 81.15% | 0.6022 | 0.8865 |
| Enet LR (top 4 PC) | 97.63% | 32.99% | 83.50% | 79.04% | 0.6155 | 0.8838 |
| Stacked Enet LR/RF (top 4 PC) | 97.94% | 27.18% | 77.24% | 83.08% | 0.6137 | 0.8882 |
| Stacked Enet LR/RF (naïve) | 97.77% | 25.29% | 75.41% | 81.92% | 0.4993 | 0.8627 |
| sFlt1/PlGF | 97.32% | 17.7% | 64.80% | 81.52% | 0.6462 | 0.8553 |

III. Feature Selection Using Lasso-LR

Figure 21:
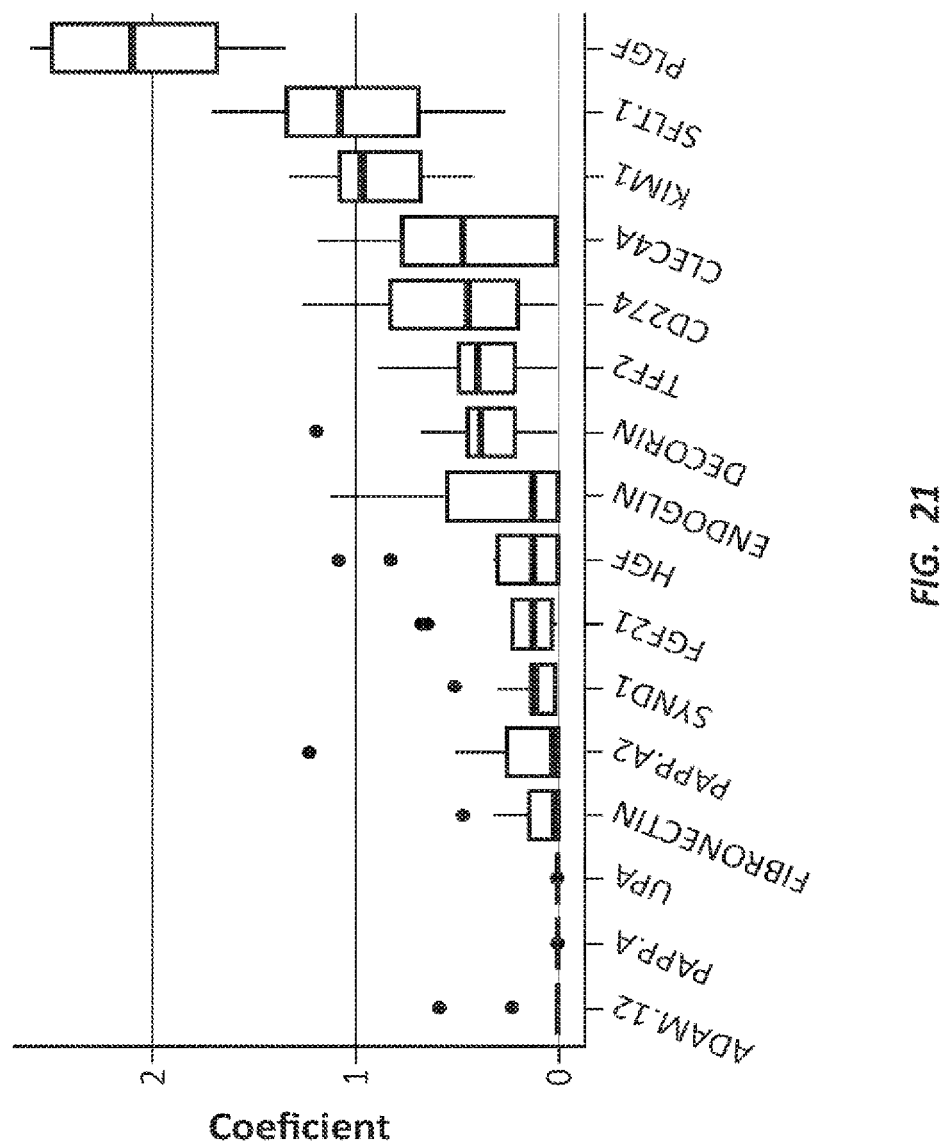
FIG. 21 is a diagram that shows the relative predictive weights of various individual biomarkers for ruling out preeclampsia.

The third approach utilized Lasso-LR on the full set of sample expression data after removal of universal false negatives and false positives to identify a set of biomarker features that optimizes performance (a sample is designated as Universal False Negative if the frequency of sample is reported as False Negative by a minimum of two prediction methods is >=0.9, and Universal False Positive if the frequency of the sample is reported as False Positive by a minimum of 3 prediction methods is >=0.8). Lasso-LR was run (using alpha=1, lambda=0.01) with 10-fold cross validation repeated 500 times for 10 different seeds to generate the feature ranking presented in FIG. 21. Graphs of expression level in preeclampsia versus non-preeclampsia samples for the top 11 of these markers is presented in FIG. 13. The top 2-10 features from this ranking were used to generate LR models, the performance of which are presented in Table 10.

TABLE 10

Performance of models using 2-10 biomarkers as features identified by Lasso-LR

|  | NPV | PPV | Spec | Sen | AUP | AUC |
| --- | --- | --- | --- | --- | --- | --- |
| Lasso_2_Features_LR | 98.62% | 40.30% | 89.04% | 84.55% | 79.24% | 92.89% |
| Lasso_3_Features_LR | 98.91% | 41.67% | 89.52% | 87.73% | 80.52% | 93.64% |
| Lasso_4_Features_LR | 99.10% | 40.43% | 88.70% | 90.00% | 81.41% | 94.21% |
| Lasso_5_Features_LR | 99.09% | 39.60% | 88.30% | 90.00% | 81.14% | 94.04% |
| Lasso_6_Features_LR | 99.01% | 37.94% | 87.61% | 89.09% | 78.30% | 94.00% |
| Lasso_7_Features_LR | 98.99% | 37.52% | 87.44% | 88.86% | 78.31% | 93.95% |
| Lasso_8_Features_LR | 99.03% | 37.67% | 87.56% | 89.32% | 78.08% | 93.70% |
| Lasso_9_Features_LR | 98.97% | 37.73% | 87.65% | 88.64% | 77.42% | 93.46% |
| Lasso_10_Features_LR | 98.95% | 37.41% | 87.41% | 88.41% | 76.63% | 93.93% |

Sensitivity was maximized using 4-5 features (PIGF/sFLT1/KIM1/CLEC4A or PIGF/sFLT1/KIM1/CLEC4A/CD274), after which additional protein marker features caused decreases in sensitivity. To estimate which, if any, of the 5$^{th}$ markers contribute most to sensitivity and other parameters in a model, models using the 4-marker combination (PIGF/sFLT1/KIM1/CLEC4A) plus all combinations of 5$^{th}$ markers (CD274 or TFF2 or ADAM12 or DCN or END or HGF or FGF21 or PAPP-A1 or FN or SYND1 or UPA or PAPP-A) were generated and their performance characteristics were compared (Table 11).

TABLE 11

Performance of models with top 4 markers + one additional marker

|  | NPV | PPV | Spec | Sen | AUP | AUC |
| --- | --- | --- | --- | --- | --- | --- |
| 4_Feature_SPKC ("sFLT1/PlGF/KIM1/CLEC4A") | 99.10% | 40.43% | 88.70% | 90.00% | 81.41% | 94.21% |
| 5_Feature_SPKC + FGF21 | 99.10% | 40.97% | 88.65% | 90.00% | 79.95% | 94.58% |
| 5_Feature_SPKC + PAPPA | 99.05% | 39.97% | 88.56% | 89.55% | 81.27% | 94.14% |
| 5_Feature_SPKC + CD274 | 99.09% | 39.60% | 88.30% | 90.00% | 81.14% | 94.04% |
| 5_Feature_SPKC + TFF2 | 98.99% | 38.20% | 87.83% | 88.86% | 78.89% | 94.11% |
| 5_Feature_SPKC + DECORIN | 99.11% | 40.24% | 88.57% | 90.23% | 81.05% | 94.08% |
| 5_Feature_SPKC + ENDOGLIN | 99.10% | 40.86% | 88.91% | 90.00% | 81.11% | 94.04% |
| 5_Feature_SPKC + ADAM12 | 99.09% | 40.24% | 88.43% | 90.00% | 80.84% | 93.92% |
| 5_Feature_SPKC + HGF | 99.04% | 40.08% | 88.61% | 89.32% | 80.25% | 94.02% |
| 5_Feature_SPKC + UPA | 99.09% | 39.59% | 88.39% | 90.00% | 80.18% | 94.03% |
| 5_Feature_SPKC + FIBRONECTIN | 99.01% | 39.52% | 88.24% | 89.09% | 80.61% | 93.88% |
| 5_Feature_SPKC + SYND1 | 99.09% | 39.87% | 88.44% | 90.00% | 80.38% | 93.69% |
| 5_Feature_SPKC + PAPPA2 | 99.07% | 39.92% | 88.39% | 89.77% | 80.33% | 94.07% |

Figure 14:
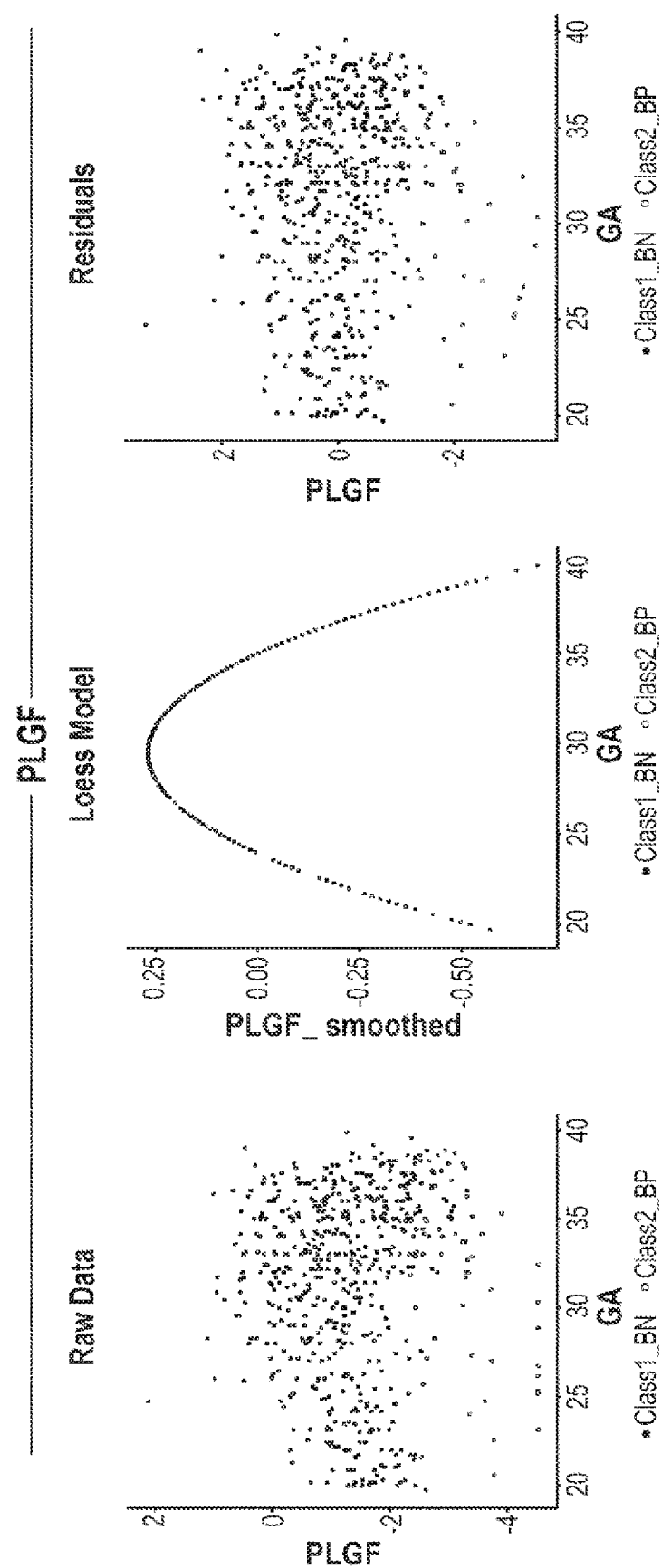
FIG. 14 depicts an exemplary procedure wherein a Loess model is used to perform gestational-age correction of biomarker (PlGF) expression levels.
Figure 15:
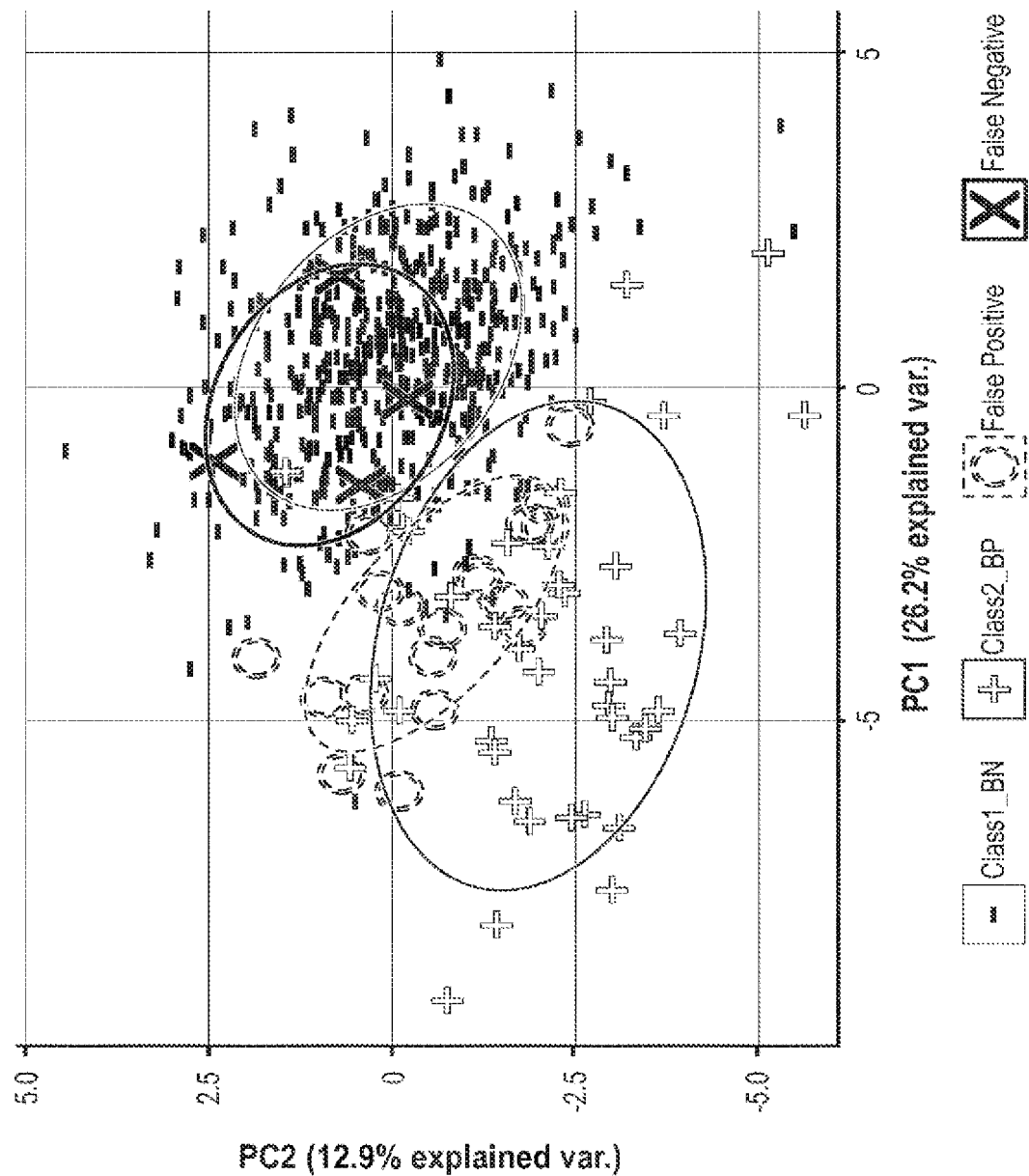
FIG. 15 depicts a graph of a principal component analysis of non-preeclampsia (−), preeclampsia (+), false positive (O) and false negative (X) samples, showing that false negative samples cluster with non-preeclampsia samples.
Figure 17:
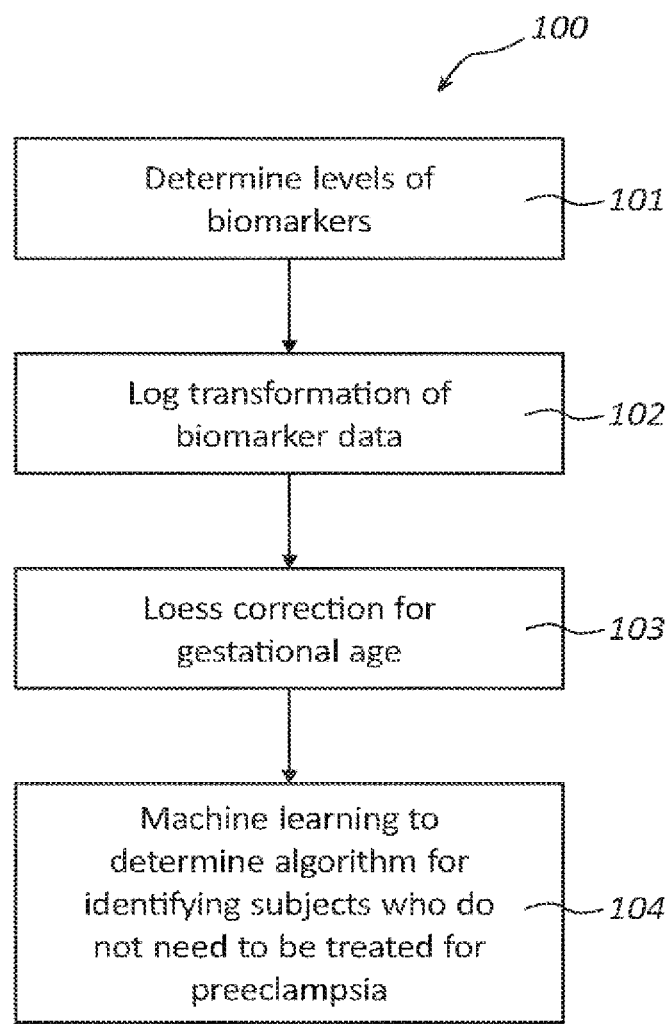
FIG. 17 provides a flow diagram of a method for building biomarker models suitable for identification of preeclampsia.

Example 11: Correction of Optimized Multivariate Model for Gestational Age-Dependent Expression The models developed and evaluated in Example 10 were next tested to see if the inclusion of gestational age, via the addition of a Loess model adjustment of biomarker expression levels prior to application of the logistic regression, would improve the performance parameters of the models. FIG. 14 depicts an exemplary procedure wherein a Loess model is used to perform gestational-age correction of biomarker (PIGF) expression levels, and FIG. 17 illustrates a procedure where this can be incorporated into the model-building workflow. Table 12 depicts performance parameters of the models with and without the Loess gestational age (GA) correction, wherein "Loess GA Removal" corresponds to models that account for a gestational age and "No GA Removal" corresponds to models that do not account for gestational age. Table 12 demonstrates that for the 5- and 4-biomarker models, gestational age correction improves the performance parameters of the models.

TABLE 12

Performance of Models With Top 5 or 4 Markers With and Without Gestational Age Correction

|  | NPV | PPV | Spec | Sen | AUP | AUC |
| --- | --- | --- | --- | --- | --- | --- |
| 5_Features_SFLT, PlGF, KIM1, FGF21, CLEC4A_LR_Loess GA Removal | 99.14% | 48.79% | 91.91% | 90.23% | 82.77% | 94.95% |
| 5_Features_SFLT, PlGF, KIM1, FGF21, CLEC4A_LR_No GA Removal | 98.78% | 31.92% | 84.26% | 87.05% | 69.49% | 93.20% |
| 4_Features_SFLT, PlGF, KIM1, CLEC4A_LR_Loess GA Removal | 99.20% | 48.85% | 91.78% | 90.91% | 83.47% | 94.70% |
| 4_Features_SFLT, PlGF, KIM1, CLEC4A_LR_No GA Removal | 98.88% | 32.05% | 84.39% | 87.27% | 72.35% | 93.03% |

Example 12: Performance of Optimized Multivariate Models Upon Reclassification of Hard-to-Classify Samples (Adjudication)

In the model building/analysis up through Example 12, several of the samples from the preeclampsia study were classified by the models as negative or positive for preeclampsia despite having the opposite clinical label. Thirty of these samples were reassessed for preeclampsia in a blinded manner by clinicians, and 9 of the 30 samples changed labels. A group of independent-specialist physicians were employed to adjudicate and affirm or modify the initial expanded study classification status of bona fide PreE positive and PreE negative samples (wherein the bona fide criteria are the same as in Example 9). The review was performed according to pre-set criteria based upon ACOG (American College of Obstetricians and Gynecologists) guidelines applied to the available clinical data. The performance parameters of the models trained upon this updated patient population were calculated and are shown in Table 13.

TABLE 13

Performance of models with top 5 or 4 markers with Patient Population having Diagnostic Labels Corrected

| | NPV | PPV | Spec | Sen | AUP | AUC |
|---|---|---|---|---|---|---|
| 5_Features_SFLT, PlGF, KIM1, FGF21, CLEC4A_LR_Loess | 99.14% | 48.79% | 91.91% | 90.23% | 82.77% | 94.95% |
| 5_Features_SFLT, PlGF, KIM1, FGF21, CLEC4A_RF_Loess | 98.92% | 42.62% | 89.61% | 87.95% | 76.34% | 94.35% |
| 5_Features_SFLT, PlGF, KIM1, FGF21, CLEC4A_Stacked_LRRF_Loess | 99.09% | 41.20% | 88.61% | 90.00% | 81.64% | 95.11% |
| 4_Features_SFLT, PlGF, KIM1, CLEC4A_LR_Loess | 99.20% | 48.85% | 91.78% | 90.91% | 83.47% | 94.70% |
| 4_Features_SFLT, PlGF, KIM1, CLEC4A_RF_Loess | 98.73% | 43.05% | 89.94% | 85.68% | 75.78% | 94.49% |
| 4_Features_SFLT, PlGF, KIM1, CLEC4A_Stacked_LRRF_Loess | 98.77% | 43.15% | 89.78% | 86.14% | 73.44% | 93.93% |
| SFLT/PlGF > 58 | 98.49% | 18.12% | 65.74% | 88.29% | 71.58% | 90.70% |

After adjudication by clinicians, four samples nonetheless continued to be classified with high frequency as false negatives. The models were again rebuilt by training on an updated patient population lacking these four high-frequency false-negatives (a sample was designated as Universal False Negative if the frequency of sample is reported as False Negative by a minimum of two prediction methods is >=0.9). The performance parameters for these updated models are presented in Table 14, and suggest that the exclusion of these false negative samples from the training paradigm improves model performance in terms of AUP and AUC.

TABLE 14

Performance of Models With Top 5 or 4 Markers With Patient Population Having Diagnostic Labels Corrected and 4 Top False Negatives Removed

| | NPV | PPV | Spec | Sen | AUP | AUC |
|---|---|---|---|---|---|---|
| 5_Features_SFLT, PlGF, KIM1, FGF21, CLEC4A_LR_Loess | 99.14% | 48.79% | 91.91% | 90.23% | 82.77% | 94.95% |
| 5_Features_SFLT, PlGF, KIM1, FGF21, CLEC4A_LR_Loess top 4 FNs removed | 99.78% | 48.35% | 91.91% | 97.36% | 93.84% | 98.82% |
| 4_Features_SFLT, PlGF, KIM1, CLEC4A_LR_Loess | 99.20% | 48.85% | 91.78% | 90.91% | 83.47% | 94.70% |
| 4_Features_SFLT, PlGF, KIM1, CLEC4A_LR_Loess top 4 FNs removed | 99.84% | 48.42% | 91.78% | 98.09% | 89.19% | 98.92% |

Example 13: Performance of Optimized Multivariate Models Upon Threshold Adjustment Next, the sensitivity threshold was adjusted using several values to see if the specificity threshold of the top-performing models could be optimized. The results of the model with several different threshold values are presented in Table 15. The results demonstrate that specificity can be traded down to 81.7% to increase sensitivity up to 94.77%.

TABLE 15

Sensitivity/Specificity Threshold Optimization for Top Performing Models

| | NPV | PPV | Spec | Sen | AUP | AUC |
|---|---|---|---|---|---|---|
| 5_Features_SFLT, PlGF, KIM1, FGF21, CLEC4A_LR_Loess (Threshold = .5) | 99.14% | 48.79% | 91.91% | 90.23% | 82.77% | 94.95% |
| 5_Features_SFLT, PlGF, KIM1, FGF21, CLEC4A_LR_Loess (Threshold = .45) | 99.20% | 46.52% | 91.06% | 90.91% | 82.77% | 94.95% |
| 5_Features_SFLT, PlGF, KIM1, FGF21, CLEC4A_LR_Loess (Threshold = .3) | 99.33% | 37.09% | 86.80% | 92.73% | 82.77% | 94.95% |
| 5_Features_SFLT, PlGF, KIM1, FGF21, CLEC4A_LR_Loess (Threshold = .2) | 99.48% | 30.47% | 81.70% | 94.77% | 82.77% | 94.95% |

Example 14: Performance of Optimized Multivariate Models in a Time-to-Delivery Performance of the Enet-LR model using the top 5 or 4 biomarkers as features was evaluated in samples from pregnant patients that were 1, 2, 4, or 6 weeks out from delivery. The performance characteristics for the model in each scenario are presented in Table 12. Generally, sensitivity and PPV decreased according to increased time to delivery, whereas specificity and NPV increased with time to delivery.

TABLE 16

Performance of Optimized Multivariate Models in a Time-to-Delivery Analysis

| | NPV | PPV | Spec | Sen | AUP | AUC |
|---|---|---|---|---|---|---|
| 5_Features_SFLT, PlGF, KIM1, FGF21, CLEC4A_LR_Loess vs WTD | | | | | | |
| Within 1 week | 97.68% | 61.63% | 77.43% | 95.30% | 91.04% | 94.01% |
| Within 2 weeks | 97.59% | 59.43% | 82.11% | 93.05% | 87.35% | 93.20% |
| Within 4 weeks | 98.55% | 49.78% | 83.03% | 92.91% | 81.41% | 93.43% |
| Within 6 weeks | 98.90% | 47.29% | 85.00% | 93.11% | 80.83% | 94.09% |
| All Data | 99.14% | 48.79% | 91.91% | 90.23% | 82.77% | 94.95% |
| SFLT/PlGF > 58 | 98.49% | 18.12% | 65.74% | 88.29% | 71.58% | 90.70% |
| 4_Features_SFLT, PlGF, KIM1, CLEC4A_LR_Loess vs WTD | | | | | | |
| Within 1 week | 97.30% | 59.58% | 76.19% | 94.57% | 93.17% | 94.64% |
| Within 2 weeks | 97.39% | 59.40% | 82.22% | 92.41% | 88.71% | 93.06% |
| Within 4 weeks | 98.38% | 50.74% | 84.15% | 92.19% | 83.87% | 93.39% |
| Within 6 weeks | 98.74% | 46.84% | 85.36% | 92.13% | 82.85% | 93.81% |
| All Data | 99.20% | 48.85% | 91.78% | 90.91% | 83.47% | 94.70% |
| SFLT/PlGF > 58 | 98.49% | 18.12% | 65.74% | 88.29% | 71.58% | 90.70% |

Example 15: Interchangeability of High-Signal Markers in Top-Performing Models The top-performing markers discovered in this analysis, sFLT-1, KIM-1, and CLEC-4A were examined to see if combinations of the other lower-signal markers discovered in the study could be substituted for them.

For sFLT-1, it was discovered that a combination of Endoglin, PAPP-A2, and Decorin could produce models with similar performance characteristics to those involving sFLT-1, PlGF, KIM-1, and CLEC-4A. The results in Table 17 demonstrate that a model involving Endoglin, PAPP-A2, and Decorin substituted for sFLT-1 has similar performance characteristics as one involving sFLT-1, with only a minor loss in AUC/AUP.

TABLE 17

Performance of Alternative Model with sFLT-1 substituted for END, PAPP-A2, and DCN

| | NPV | PPV | Spec | Sen | AUP | AUC |
|---|---|---|---|---|---|---|
| No SFLT.1 | | | | | | |
| Model 1_4 Features - SFLT.1, PlGF, KIM1, CLEC4A, | 99.10% | 40.43% | 88.70% | 90.00% | 81.41% | 94.21% |
| 4features, PlGF, KIM, CLEC4A, ENDOGLIN_LR_noSFLT | 98.99% | 43.13% | 90.02% | 88.64% | 79.05% | 93.71% |
| 5features, PlGF, KIM, CLEC4A, ENDOGLIN, PAPP.A2_LR_noSFLT | 99.06% | 39.81% | 88.52% | 89.55% | 76.83% | 93.57% |
| 5features, PlGF, KIM, CLEC4A, ENDOGLIN, DECORIN_LR_noSFLT | 98.97% | 41.94% | 89.59% | 88.41% | 78.56% | 93.59% |

For KIM-1, it was discovered that a substitution with CD274 and/or Decorin had similar performance parameters, although a model involving CD274 alone without Decorin had slightly better AUP than one involving Decorin alone without CD274 (see Table 18).

TABLE 18

Performance of Models with Decorin and/or CD274 Substituted for KIM-1

| | NPV | PPV | Spec | Sen | AUP | AUC |
|---|---|---|---|---|---|---|
| No KIM1 | | | | | | |
| Model 1_4 Features - SFLT.1, PlGF, KIM1, CLEC4A, | 99.10% | 40.43% | 88.70% | 90.00% | 81.41% | 94.21% |
| 4_Features_SFLT, PlGF, CLEC4A, CD274_LR_noKIM | 98.84% | 37.60% | 87.61% | 87.27% | 80.22% | 93.75% |
| 4_Features_SFLT, PlGF, CLEC4A, DECORIN_LR_noKIM | 98.86% | 37.51% | 87.37% | 87.50% | 79.81% | 93.75% |
| 5_Features_SFLT, PlGF, CLEC4A, CD274, DECORIN_LR_noKIM | 98.86% | 37.02% | 87.22% | 87.50% | 79.69% | 93.55% |

For CLEC4A, it was discovered that models substituting CLEC4A for FGF21, TFF2 and/or HGF result in similar performance characteristics (Table 19). Table 19 also demonstrates that, of these models, those using HGF or FGF21 have slightly superior AUP/AUC to those using TFF2.

TABLE 19

Performance of Models with FGF21, TFF2, and/or HGF Substituted for CLEC4A

| | NPV | PPV | Spec | Sen | AUP | AUC |
|---|---|---|---|---|---|---|
| No CLEC4A | | | | | | |
| Model 1_4 Features - SFLT.1, PlGF, KIM1, CLEC4A, | 99.10% | 40.43% | 88.70% | 90.00% | 81.41% | 94.21% |
| 4_Features_SFLT, PlGF, KIM1, FGF21_LR_noCLEC4A | 98.93% | 39.90% | 88.56% | 88.18% | 78.96% | 94.00% |
| 4_Features_SFLT, PlGF, KIM1, HGF_LR_noCLEC4A | 98.84% | 40.81% | 89.22% | 87.05% | 80.54% | 93.37% |
| 4_Features_SFLT, PlGF, KIM1, TFF2_LR_noCLEC4A | 98.90% | 39.57% | 88.59% | 87.73% | 78.39% | 93.60% |
| 6_Features_SFLT, PlGF, KIM1, TFF2, HGF, TFF2_LR_noCLEC4A | 98.97% | 39.02% | 88.09% | 88.64% | 77.54% | 93.66% |

Example 16: Independent Cohort Validation of High Performance Models

An independent cohort of patient samples collected as described in Example 1 and Example 9 was used to validate the performance of the high-performance models developed in the previous examples. These originally consisted of 451 samples, which was reduced to 342 bona fide positive or negative for preeclampsia samples (308 bona fide negative and 34 bona fide positive). After adjudication procedures in which a group of independent-specialist physicians were employed to adjudicate and affirm or modify the initial expanded study classification status of bona fide PreE positive and PreE negative samples (as in Example 12) this cohort was reduced to a final set of 331 patient samples, with 221 being bona-fide negative for preeclampsia and 32 bona-fide positive for preeclampsia. The models selected for validation on the 331 patient sample set are shown in Table 20. In Table 20, where exclusion of data from the training set is indicated, a sample is referred to as False Negative (FN) if the frequency of sample is reported as False Negative by a minimum of two prediction methods is >=0.9, and a sample is referred to as False Positive (FP) if the frequency of the sample is reported as False Positive by a minimum of 3 prediction methods is >=0.8.

TABLE 20

Details for Models Selected for Validation in Independent Cohort

| Model ID | Panel | Algorithm | Score cutoff | Training set data (exclusion of false neg/false pos samples?) | Gest-age adj? |
|---|---|---|---|---|---|
| M_12 | Top4 PC 16 Marker + Interactions | LR-Enet | 0.5 | U-{FN, FP} | LOESS |
| M_2 | sFlt-1, PlGF, KIM1, FGF21, CLEC4A | LR-Enet | 0.5 | U-{FN} | LOESS |
| M_11.1 | sFlt-1, PlGF, KIM1, FGF21, CLEC4A, ENDOGLIN, CD274, DECORIN | LR-Enet | 0.5 | U-{FN} | LOESS |
| M_44 | sFlt-1, PlGF, KIM1, FGF21, CLEC4A, ENDOGLIN | Stacked: LR-Enet-> RF | (0.5, 0.5) | U | LOESS |
| M_44.1 | sFlt-1, PlGF, KIM1, FGF21, CLEC4A, ENDOGLIN | Stacked: LR-Enet-> RF | (0.5, 0.5) | U | N/A |
| M_39 | sFlt-1, PlGF, KIM1, FGF21, CLEC4A, ENDOGLIN, CD274 | RF | 0.5 | U-{FN} | LOESS |
| M_14 | PlGF, KIM1, CLEC4A, ENDOGLIN | LR-Enet | 0.5 | U | LOESS |
| M_29 | sFlt-1, PlGF, KIM1, CLEC4A | LR-Enet | 0.5 | U+{FN-> TN, FP-> TP} | LOESS |
| M_6.1 | PlGF, sFlt-1, KIM1, TFF2, DECORIN, FGF21 | LR-Enet | 0.5 | U-{FN} | LOESS |
| M_2.1 | sFlt-1, PlGF, KIM1, FGF21, CLEC4A | LR-Enet | 0.3 | U-{FN} | LOESS |
| M_39.1 | PlGF, KIM1, DECORIN, PAPA.2, TFF2, FGF21, CD274 | RF | 0.5 | U-{FP} | LOESS |
| M_4.1 | sFlt-1, PlGF, KIM1, ENDOGLIN, CLEC4A | LR-Enet | 0.3 | U-{FP, FN} | LOESS |
| M_33.1 | sFlt-1, PlGF, KIM1, ENDOGLIN, CLEC4A | RF | 0.3 | U-{FP, FN} | LOESS |
| M_1 | sFlt-1, PlGF, KIM1, CLEC4A | LR-Enet | 0.5 | U | N/A |
| M_8 | HGF, SYND1, CD274 (top) sFlt-1, PlGF, KIM1, FGF21, CLEC4A (bottom) | Stacked:LR-Enet-> LR-Enet | (0.7, 0.5) | U | LOESS |

The validation data for the performance parameters of the models built in Table 20 is shown in Table 21. When the models are ranked by performance, the 4.1 model (Enet logistic regression using sFLT-1, PlGF, KIM1, and END using a cutoff of 0.3, with exclusion of false positive and negative samples, and using loess correction for gestational age) has the highest performance. Notably, the AUC of the top 3 models on this independent cohort is consistent with (equivalent or better than) the performance seen in the previous examples

TABLE 21

Performance Parameters for Models Selected for Validation in Independent Cohort

| Model | sen | sp | npv | ppv | AUC |
|---|---|---|---|---|---|
| model4.1_preds | 96.9 | 86.6 | 99.6 | 43.7 | 96.3% |
| model11_preds | 90.6 | 92.6 | 98.9 | 56.9 | 97.1% |
| model12_preds | 81.2 | 96 | 98 | 68.4 | 96.5% |
| model1_preds | 96.9 | 74.9 | 99.6 | 29.2 | — |
| model6.1_preds | 84.4 | 94 | 98.3 | 60 | — |
| model2_preds | 84.4 | 93 | 98.2 | 56.2 | — |
| model14_preds | 87.5 | 89.6 | 98.5 | 47.5 | — |
| model29_preds | 87.5 | 89.6 | 98.5 | 47.5 | — |
| model44_preds | 90.6 | 86 | 98.8 | 40.8 | — |
| model44.1_preds | 90.6 | 84.9 | 98.8 | 39.2 | — |
| model8_preds | 90.6 | 84.9 | 98.8 | 39.2 | — |
| model2.1_preds | 90.6 | 84.6 | 98.8 | 38.7 | — |
| model39_preds | 81.2 | 92.3 | 97.9 | 53.1 | — |
| model39.1_preds | 81.2 | 89 | 97.8 | 44.1 | — |
| model33.1_preds | 87.5 | 82.3 | 98.4 | 34.6 | — |

Based on this positive performance data, an additional 29 models were built (to create a total of 44), for which the performance characteristics on the independent cohort were calculated and are presented in Table 22. The corresponding biomarker/features used in each model, along with the model coefficients ("beta" value for each feature/biomarker in the case of logistic regression, and "feature importance" value for each feature/biomarker in the case of Random Forest or GBM) are presented in Table 23. In the case where "stacked" models are presented, the relevant coefficients for each step are separated into separate rows in Table 23.

TABLE 22

Performance Parameters for Additional Models Against Validation Cohort

| Model | NPV | PPV | Spec | Sen | AUP | AUC |
|---|---|---|---|---|---|---|
| Logistic Regression Models | | | | | | |
| Model1_LR | 99.20% | 48.85% | 91.78% | 90.91% | 83.47% | 94.70% |
| Model2_LR | 99.14% | 48.79% | 91.91% | 90.23% | 82.77% | 94.95% |
| Model3_LR | 99.22% | 48.56% | 91.78% | 91.14% | 83.87% | 94.69% |
| Model4_LR | 99.18% | 47.54% | 91.39% | 90.68% | 83.08% | 94.49% |
| Model5_LR | 99.10% | 47.57% | 91.59% | 89.77% | 81.92% | 94.45% |
| Model6_LR | 99.21% | 49.67% | 92.17% | 90.91% | 81.66% | 95.23% |
| Model7_LR | 99.12% | 47.91% | 91.65% | 90.00% | 82.41% | 94.92% |
| Model8_LR | 99.20% | 46.22% | 90.96% | 90.91% | 83.11% | 94.42% |
| Model9_LR | 99.08% | 45.85% | 91.07% | 89.55% | 81.77% | 94.31% |
| Model10_LR | 99.20% | 48.54% | 91.81% | 90.91% | 82.05% | 95.12% |
| Model11_LR | 99.05% | 45.36% | 90.98% | 89.32% | 81.10% | 94.83% |
| Model13_LR | 99.04% | 48.43% | 91.80% | 89.09% | 80.80% | 93.96% |
| Model14_LR | 98.94% | 46.64% | 91.35% | 87.95% | 80.64% | 93.90% |
| Random Forest Models | | | | | | |
| Model30_RF | 98.73% | 43.05% | 89.94% | 85.68% | 75.78% | 94.49% |
| Model31_RF | 98.75% | 44.07% | 90.39% | 85.91% | 74.38% | 94.88% |
| Model32_RF | 98.77% | 42.95% | 89.78% | 86.14% | 78.40% | 94.42% |
| Model33_RF | 98.62% | 42.95% | 90.19% | 84.32% | 71.18% | 93.94% |
| Model34_RF | 98.77% | 43.67% | 90.06% | 86.14% | 73.30% | 93.70% |
| Model35_RF | 98.71% | 43.33% | 89.98% | 85.45% | 72.09% | 94.12% |
| Model36_RF | 98.78% | 44.56% | 90.54% | 86.14% | 76.23% | 94.73% |
| Model37_RF | 98.77% | 45.93% | 91.04% | 85.91% | 77.42% | 94.07% |
| Model38_RF | 98.68% | 43.67% | 90.11% | 85.00% | 73.78% | 93.58% |
| Model39_RF | 98.77% | 43.15% | 89.78% | 86.14% | 73.44% | 93.93% |
| Model40_RF | 98.72% | 40.77% | 88.89% | 85.68% | 73.43% | 93.24% |
| Stacked Models | | | | | | |
| Model41_LRRF | 99.17% | 40.64% | 88.30% | 90.91% | 82.57% | 95.39% |
| Model42_LRRF | 99.09% | 41.20% | 88.61% | 90.00% | 81.64% | 95.11% |
| Model43_LRRF | 99.17% | 41.17% | 88.50% | 90.91% | 82.07% | 95.28% |
| Model44_LRRF | 99.16% | 41.20% | 88.65% | 90.68% | 80.81% | 95.20% |
| Model45_LRRF | 99.07% | 39.67% | 88.13% | 89.77% | 80.23% | 94.32% |
| GBM Models | | | | | | |
| Model46_GBM | 98.89% | 41.81% | 89.57% | 87.50% | 69.03% | 94.43% |
| Model47_GBM | 98.81% | 43.51% | 90.17% | 86.59% | 69.18% | 94.90% |
| Model48_GBM | 98.83% | 42.98% | 90.02% | 86.82% | 69.11% | 94.43% |
| Model49_GBM | 98.82% | 44.16% | 90.39% | 86.59% | 70.62% | 94.68% |
| Model50_GBM | 98.85% | 44.02% | 90.30% | 87.05% | 70.12% | 93.82% |
| Model51_GBM | 98.82% | 44.68% | 90.65% | 86.59% | 70.40% | 95.00% |
| Model52_GBM | 98.81% | 43.36% | 90.13% | 86.59% | 69.09% | 94.79% |
| Mode53_GBM | 98.88% | 44.19% | 90.26% | 87.27% | 70.72% | 94.55% |
| Mode54_GBM | 98.82% | 44.81% | 90.52% | 86.59% | 70.41% | 94.03% |
| Model55_GBM | 98.83% | 44.52% | 90.46% | 86.82% | 71.10% | 94.89% |
| Model56_GBM | 98.81% | 44.14% | 90.31% | 86.59% | 70.82% | 94.43% |
| Optimization Extra Models | | | | | | |
| Model6.1_LR | 99.04% | 45.06% | 90.76% | 89.09% | 79.26% | 94.41% |
| Model44.1_LRRF | 98.96% | 31.84% | 83.69% | 89.09% | 72.51% | 94.01% |
| Model39_1_RF | 98.80% | 41.85% | 89.46% | 86.59% | 70.79% | 92.33% |
| Model8.1_LRRF | 98.88% | 17.69% | 65.06% | 90.91% | 51.95% | 87.48% |

TABLE 23

Model Coefficients for Models Shown in Table 22

| Model | (Intercept) | PLGF | SFLT.1 | CLEC4A | CD274 | ENDOGLIN | DECORIN |
|---|---|---|---|---|---|---|---|
| Model1_LR | 4.07 | 2.53 | −1.65 | −0.60 | NA | NA | NA |
| Model2_LR | 3.64 | 2.22 | −1.41 | −0.52 | NA | NA | NA |
| Model3_LR | 3.11 | 1.78 | −1.31 | −0.44 | 0.37 | NA | NA |
| Model4_LR | 4.41 | 2.82 | −1.42 | −0.64 | NA | −0.62 | NA |
| Model5_LR | 4.09 | 2.36 | −1.45 | −0.52 | NA | NA | −0.90 |
| Model6_LR | 3.92 | 2.08 | −1.11 | −0.67 | NA | −0.77 | NA |
| Model7_LR | 3.75 | 2.20 | −1.44 | −0.49 | 0.36 | NA | NA |
| Model8_LR | 4.81 | 2.67 | −1.67 | −0.77 | 0.69 | −0.74 | NA |
| Model9_LR | 5.06 | 2.85 | −1.53 | −0.75 | NA | −0.59 | −1.14 |
| Model10_LR | 4.06 | 1.95 | −1.18 | −0.67 | 0.50 | −0.82 | NA |
| Model11_LR | 4.42 | 2.09 | −1.19 | −0.63 | 0.47 | −0.71 | −0.97 |
| Model13_LR | 3.26 | 2.34 | NA | −0.51 | NA | −1.06 | NA |

TABLE 23-continued

Model Coefficients for Models Shown in Table 22

| Model | | | | | | |
|---|---|---|---|---|---|---|
| Model14_LR | 3.14 | 1.94 | NA | −0.43 | NA | −0.90 | −0.72 |
| Model30_RF | NA | 19.63 | 8.25 | 1.21 | NA | NA | NA |
| Model31_RF | NA | 14.16 | 9.36 | 1.56 | NA | NA | NA |
| Model32_RF | NA | 17.32 | 8.94 | 1.13 | 1.09 | NA | NA |
| Model33_RF | NA | 20.61 | 3.46 | 0.80 | NA | 3.11 | NA |
| Model34_RF | NA | 13.89 | 8.98 | 1.42 | NA | NA | 4.25 |
| Model35_RF | NA | 18.31 | 4.00 | 0.80 | NA | 4.68 | NA |
| Model36_RF | NA | 12.70 | 8.92 | 1.49 | 1.84 | NA | NA |
| Model37_RF | NA | 11.35 | 7.12 | 1.38 | 1.63 | 7.32 | NA |
| Model38_RF | NA | 13.65 | 6.30 | 0.95 | NA | 6.73 | 2.04 |
| Model39_RF | NA | 16.20 | 4.60 | 0.77 | 0.49 | 5.57 | NA |
| Model40_RF | NA | 16.73 | 4.17 | 0.60 | 0.39 | 5.11 | 1.31 |
| Model46_GBM | NA | 66.01 | 21.22 | 3.33 | NA | NA | NA |
| Model47_GBM | NA | 65.67 | 20.11 | 2.72 | NA | NA | NA |
| Model48_GBM | NA | 66.14 | 21.00 | 2.64 | 1.52 | NA | NA |
| Model49_GBM | NA | 58.34 | 13.48 | 2.82 | NA | 14.19 | NA |
| Model50_GBM | NA | 65.30 | 20.18 | 2.27 | NA | NA | 5.64 |
| Model51_GBM | NA | 57.23 | 13.62 | 2.40 | NA | 13.37 | NA |
| Model52_GBM | NA | 65.23 | 19.58 | 2.22 | 1.43 | NA | NA |
| Model53_GBM | NA | 58.14 | 13.37 | 2.66 | 1.45 | 14.05 | NA |
| Model54_GBM | NA | 57.57 | 11.59 | 2.12 | NA | 13.36 | 4.59 |
| Model55_GBM | NA | 56.94 | 12.93 | 2.22 | 1.07 | 13.25 | NA |
| Model56_GBM | NA | 56.94 | 11.28 | 1.66 | 0.78 | 12.42 | 3.96 |
| Model_39.1_RF | NA | 19.15 | NA | NA | 0.69 | NA | 2.05 |
| Model40_RF2 | NA | 16.73 | 4.17 | 0.60 | 0.39 | 5.11 | 1.31 |
| Model41_LR_First_Level | 4.07 | 2.53 | −1.65 | −0.60 | NA | NA | NA |
| Model41_RF_Second_Level | NA | 19.63 | 8.25 | 1.21 | NA | NA | NA |
| Model42_LR_First_Level | 3.64 | 2.22 | −1.41 | −0.52 | NA | NA | NA |
| Model42_RF_Second_Level | NA | 14.16 | 9.36 | 1.56 | NA | NA | NA |
| Model43_LR_First_Level | 4.41 | 2.82 | −1.42 | −0.64 | NA | −0.62 | NA |
| Model43_RF_Second_Level | NA | 20.61 | 3.46 | 0.80 | NA | 3.11 | NA |
| Model44_LR_First_Level | 3.92 | 2.08 | −1.11 | −0.67 | NA | −0.77 | NA |
| Model44_RF_Second_Level | NA | 18.31 | 4.00 | 0.80 | NA | 4.68 | NA |
| Model45_LR_First_Level | 4.42 | 2.09 | −1.19 | −0.63 | 0.47 | −0.71 | −0.97 |
| Model45_RF_Second_Level | NA | 16.73 | 4.17 | 0.60 | 0.39 | 5.11 | 1.31 |
| Model_44.1_RF | | 13.94 | 5.65 | 1.36 | NA | 5.79 | NA |
| Model8.1_LR_Second_level | 3.64 | 2.22 | −1.41 | −0.52 | NA | NA | NA |
| Model8.1_LR-First Levels | 0.71 | NA | NA | NA | 0.68 | NA | NA |
| Model_6.1_LR | 4.06 | 2.29 | −1.44 | NA | NA | NA | −0.93 |

| Model | FGF21 | KIM1 | PAPPA.2 | TFF2 | HGF | SYND1 |
|---|---|---|---|---|---|---|
| Model1_LR | NA | −1.24 | NA | NA | NA | NA |
| Model2_LR | −0.47 | −1.04 | NA | NA | NA | NA |
| Model3_LR | NA | −1.01 | NA | NA | NA | NA |
| Model4_LR | NA | −1.24 | NA | NA | NA | NA |
| Model5_LR | NA | −1.12 | NA | NA | NA | NA |
| Model6_LR | −0.80 | −1.10 | NA | NA | NA | NA |
| Model7_LR | −0.47 | −1.14 | NA | NA | NA | NA |
| Model8_LR | NA | −1.58 | NA | NA | NA | NA |
| Model9_LR | NA | −1.33 | NA | NA | NA | NA |
| Model10_LR | −0.77 | −1.26 | NA | NA | NA | NA |
| Model11_LR | −0.88 | −1.26 | NA | NA | NA | NA |
| Model13_LR | NA | −0.78 | NA | NA | NA | NA |
| Model14_LR | NA | −0.76 | NA | NA | NA | NA |
| Model30_RF | NA | 2.51 | NA | NA | NA | NA |
| Model31_RF | 3.29 | 3.00 | NA | NA | NA | NA |
| Model32_RF | NA | 2.75 | NA | NA | NA | NA |
| Model33_RF | NA | 1.99 | NA | NA | NA | NA |
| Model34_RF | NA | 2.62 | NA | NA | NA | NA |
| Model35_RF | 0.91 | 1.74 | NA | NA | NA | NA |
| Model36_RF | 3.30 | 2.86 | NA | NA | NA | NA |
| Model37_RF | NA | 2.43 | NA | NA | NA | NA |
| Model38_RF | NA | 1.59 | NA | NA | NA | NA |
| Model39_RF | 0.97 | 1.57 | NA | NA | NA | NA |
| Model40_RF | 0.66 | 1.29 | NA | NA | NA | NA |
| Model46_GBM | NA | 7.21 | NA | NA | NA | NA |
| Model47_GBM | 2.31 | 6.27 | NA | NA | NA | NA |
| Model48_GBM | NA | 6.48 | NA | NA | NA | NA |
| Model49_GBM | NA | 5.82 | NA | NA | NA | NA |
| Model50_GBM | NA | 5.53 | NA | NA | NA | NA |
| Model51_GBM | 2.38 | 5.08 | NA | NA | NA | NA |
| Model52_GBM | 2.13 | 6.10 | NA | NA | NA | NA |
| Model53_GBM | NA | 5.52 | NA | NA | NA | NA |
| Model54_GBM | NA | 4.94 | NA | NA | NA | NA |
| Model55_GBM | 2.28 | 5.00 | NA | NA | NA | NA |
| Model56_GBM | 2.02 | 4.31 | NA | NA | NA | NA |
| Model_39.1_RF | 0.88 | 1.53 | 5.69 | 1.30 | NA | NA |

TABLE 23-continued

Model Coefficients for Models Shown in Table 22

| | | | | | | |
|---|---|---|---|---|---|---|
| Model40_RF2 | 0.66 | 1.29 | NA | NA | NA | NA |
| Model41_LR_First_Level | NA | −1.24 | NA | NA | NA | NA |
| Model41_RF_Second_Level | NA | 2.51 | NA | NA | NA | NA |
| Model42_LR_First_Level | −0.47 | −1.04 | NA | NA | NA | NA |
| Model42_RF_Second_Level | 3.29 | 3.00 | NA | NA | NA | NA |
| Model43_LR_First_Level | NA | −1.24 | NA | NA | NA | NA |
| Model43_RF_Second_Level | NA | 1.99 | NA | NA | NA | NA |
| Model44_LR_First_Level | −0.80 | −1.10 | NA | NA | NA | NA |
| Model44_RF_Second_Level | 0.91 | 1.74 | NA | NA | NA | NA |
| Model45_LR_First_Level | −0.88 | −1.26 | NA | NA | NA | NA |
| Model45_RF_Second_Level | 0.66 | 1.29 | NA | NA | NA | NA |
| Model_44.1_RF | 1.50 | 2.32 | NA | NA | NA | NA |
| Model8.1_LR_Second_level | −0.47 | −1.04 | NA | NA | NA | NA |
| Model8.1_LR-First Levels | NA | NA | NA | NA | 1.0 | 0.51 |
| Model_6.1_LR | −0.67 | −1.14 | NA | −0.44 | NA | NA |

Ethnicity information for the 331 patient sample set used for validation in this example is provided in Table 24.

TABLE 24

Ethnicity/Race Breakdown for Patients in the 331 Independent Sample Validation Cohort

| | Non-preeclampsia | Preeclampsia | Total |
|---|---|---|---|
| Race | | | |
| AMERICAN INDIAN/ALASKA NATIVE | 0 | 0 | 0 |
| ASIAN | 7 | 0 | 7 |
| BLACK/AFRICAN AMERICAN | 36 | 6 | 42 |
| NATIVE HAWAIIAN/OTHER PACIFIC ISLANDER | 3 | 0 | 3 |
| WHITE | 253 | 26 | 279 |
| Total | 299 | 32 | 331 |
| Ethnicity | | | |
| HISPANIC OR LATINO | 10 | 1 | 11 |
| NOT HISPANIC OR LATINO | 287 | 31 | 318 |
| Unknown | 2 | 0 | 2 |
| Total | 299 | 32 | 331 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claims is:

1. A method for detecting a plurality of proteins in a serum sample from blood of a pregnant human female, the method comprising:
    obtaining a serum sample derived from a pregnant human female;
    contacting the serum sample from the pregnant human female with at least five different probes, each of which has specific affinity for a different protein, wherein the different proteins comprise PLGF, sFlt1, KIM1, FGF21, and CD274; and
    detecting a presence of the different proteins based on binding of the at least five different probes to corresponding proteins;
    wherein the different proteins comprise no more than 10 proteins.

2. The method of claim 1, wherein the at least five different probes further comprise a probe with specific affinity for endoglin.

3. The method of claim 1, wherein the at least five different probes further comprise a probe with specific affinity for decorin.

4. The method of claim 2, wherein the at least five different probes further comprise a probe with specific affinity for decorin.

5. The method of claim 1, wherein one or more of the at least five different probes are antibodies or antibody fragments.

6. The method of claim 1, wherein all of the at least five different probes are antibodies or antibody fragments.

7. The method of claim 1, wherein the serum sample was obtained from the pregnant female after the pregnant human female has shown one or more symptoms of preeclampsia, wherein the symptoms of preeclampsia are selected from (1) high blood pressure and (2) proteinuria.

8. The method of claim 1, wherein the presence of at least one of the different proteins is determined using an enzyme-linked immunosorbent assay (ELISA).

9. The method of claim 1, wherein the serum sample is initially collected from the pregnant human female while in a perinatologist's office, a labor and delivery room, or triage (ER).

10. The method of claim 1, wherein the biological sample is initially collected from the pregnant human female after gestational week 20.

11. The method of claim 1, wherein the at least five different probes contact the biological sample in separate reaction vessels for each protein of the different proteins.

12. The method of claim 1, wherein the contacting the serum sample with the at least five different probes occurs in a single reaction vessel.

13. The method of claim 1, wherein the presence of at least one of the different proteins is determined using a luminescent oxygen channeling immunoassay.

14. The method of claim 1, wherein one or more of the at least five different probes are antibodies or antibody fragments selected from FIG. 18.

15. The method of claim 1, wherein all of the at least five different probes are antibodies or antibody fragments selected from FIG. 18.

* * * * *